(12) United States Patent
Sung et al.

(10) Patent No.: US 10,195,249 B2
(45) Date of Patent: Feb. 5, 2019

(54) ACTIVIN-ACTRII ANTAGONISTS AND USES FOR TREATING BONE AND OTHER DISORDERS

(71) Applicants: CELGENE CORPORATION, Summit, NJ (US); Washington University, St. Louis, MO (US)

(72) Inventors: Victoria Sung, San Francisco, CA (US); Randall Stevens, Plainfield, NJ (US); William Smith, Woodstock, NY (US); Victor Schorr Sloan, Flemington, NJ (US); Keith Hruska, St. Louis, MO (US); Yifu Fang, St. Louis, MO (US)

(73) Assignees: Celgene Corporation, Summit, NJ (US); Washington University, St. Louis, MO (US)

( * ) Notice: Subject to any disclaimer, the term of this patent is extended or adjusted under 35 U.S.C. 154(b) by 0 days.

(21) Appl. No.: 14/438,146

(22) PCT Filed: Nov. 1, 2013

(86) PCT No.: PCT/US2013/068009
§ 371 (c)(1),
(2) Date: Apr. 23, 2015

(87) PCT Pub. No.: WO2014/071158
PCT Pub. Date: May 8, 2014

(65) Prior Publication Data
US 2015/0283209 A1 Oct. 8, 2015

Related U.S. Application Data

(60) Provisional application No. 61/721,898, filed on Nov. 2, 2012, provisional application No. 61/740,665, filed on Dec. 21, 2012.

(51) Int. Cl.
*A61K 38/16* (2006.01)
*A61K 38/17* (2006.01)

(52) U.S. Cl.
CPC ........ *A61K 38/1796* (2013.01); *A61K 38/179* (2013.01)

(58) Field of Classification Search
None
See application file for complete search history.

(56) References Cited

U.S. PATENT DOCUMENTS

| | | |
|---|---|---|
| 4,973,577 A | 11/1990 | Vale, Jr. et al. |
| 5,078,486 A | 1/1992 | Evans |
| 5,118,667 A | 6/1992 | Adams et al. |
| 5,208,219 A | 5/1993 | Ogawa |
| 5,545,616 A | 8/1996 | Woodruff et al. |
| 5,658,876 A | 8/1997 | Crowley et al. |
| 5,703,043 A | 12/1997 | Celeste et al. |
| 5,760,010 A | 6/1998 | Klein |
| 5,808,007 A | 9/1998 | Lee et al. |
| 5,824,637 A | 10/1998 | Crowley et al. |
| 5,847,078 A | 12/1998 | Eto et al. |
| 5,885,794 A | 3/1999 | Mathews et al. |
| 5,914,234 A | 6/1999 | Lee et al. |
| 6,004,780 A | 12/1999 | Soppet et al. |
| 6,034,062 A | 3/2000 | Thies et al. |
| 6,093,547 A | 7/2000 | Jin et al. |
| 6,132,988 A | 10/2000 | Sugino et al. |
| 6,162,896 A | 12/2000 | Mathews et al. |
| 6,287,816 B1 | 9/2001 | Rosen et al. |
| 6,319,499 B1 | 11/2001 | Elliot |
| 6,440,930 B1 | 8/2002 | Rinella, Jr. |
| 6,451,334 B2 | 9/2002 | Perrine |
| 6,537,966 B1 | 3/2003 | Duan et al. |
| 6,548,634 B1 | 4/2003 | Ballinger et al. |
| 6,599,876 B2 | 7/2003 | Kojima |
| 6,605,699 B1 | 8/2003 | Ni et al. |
| 6,632,180 B1 | 10/2003 | Laragh |
| 6,656,475 B1 | 12/2003 | Lee et al. |
| 6,656,708 B1 | 12/2003 | Yu et al. |
| 6,692,925 B1 | 2/2004 | Miyazono et al. |
| 6,696,260 B1 | 2/2004 | Lee et al. |
| 6,777,205 B1 | 8/2004 | Carcagno et al. |
| 6,835,544 B2 | 12/2004 | Mathews et al. |
| 6,891,082 B2 | 5/2005 | Lee et al. |
| 6,914,128 B1 | 7/2005 | Salfeld et al. |
| 7,052,873 B2 | 5/2006 | Tsuchiya |
| 7,192,717 B2 | 3/2007 | Hill et al. |
| 7,202,210 B2 | 4/2007 | Wolfman et al. |
| 7,261,893 B2 | 8/2007 | Veldman et al. |

(Continued)

FOREIGN PATENT DOCUMENTS

| | | |
|---|---|---|
| EP | 1 416 273 A1 | 11/1992 |
| EP | 1174149 A1 | 1/2002 |

(Continued)

OTHER PUBLICATIONS

Boydstun II. Chronic kidney disease in adolescents. Adolesc Med Clin. Feb. 2005;16(1):185-99.*

(Continued)

*Primary Examiner* — Elizabeth C. Kemmerer
(74) *Attorney, Agent, or Firm* — Jones Day

(57) ABSTRACT

Provided herein are methods for the treatment of bone disorders that are associated with kidney disease wherein the methods comprise administration of Activin-ActRIIA inhibitors to a subject in need of the treatment. Also provided herein are methods and compositions for the treatment of low turnover bone disorders wherein the methods comprise administration of Activin-ActRIIA inhibitors to a subject in need of the treatment. Further provided herein are compositions for the treatment of bone disorders that are associated with kidney disease and compositions for the treatment of low turnover bone disorders and vascular calcification.

Figure 1:
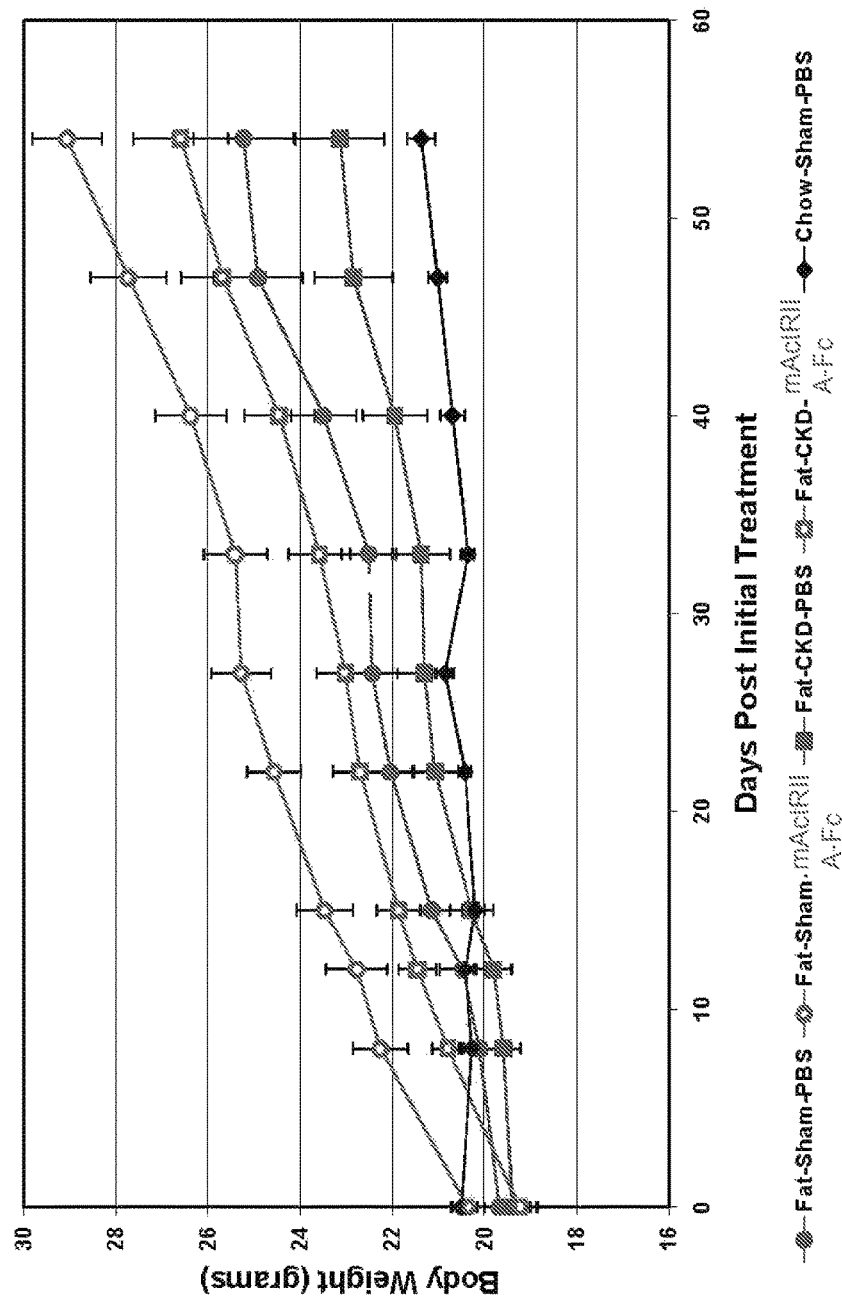

16 Claims, 11 Drawing Sheets
Specification includes a Sequence Listing.

(56) References Cited

U.S. PATENT DOCUMENTS

| | | |
|---|---|---|
| 7,320,789 B2 | 1/2008 | Dunham et al. |
| 7,560,441 B2 | 7/2009 | Wolfman et al. |
| 7,612,041 B2 | 11/2009 | Knopf et al. |
| 7,709,605 B2 | 5/2010 | Knopf et al. |
| 7,842,663 B2 | 11/2010 | Knopf et al. |
| 7,893,213 B2 | 2/2011 | Mathews et al. |
| 7,919,296 B2 | 4/2011 | Wang |
| 7,947,646 B2 | 5/2011 | Sun et al. |
| 7,951,771 B2 | 5/2011 | Knopf et al. |
| 7,960,343 B2 | 6/2011 | Knopf et al. |
| 7,968,091 B2 | 6/2011 | Woolf et al. |
| 7,988,973 B2 | 8/2011 | Sherman |
| 8,007,809 B2 | 8/2011 | Sherman |
| 8,058,229 B2 | 11/2011 | Seehra et al. |
| 8,067,360 B2 | 11/2011 | Knopf et al. |
| 8,110,355 B2 | 2/2012 | Atwood et al. |
| 8,124,830 B2 | 2/2012 | Lee et al. |
| 8,128,933 B2 | 3/2012 | Knopf et al. |
| 8,138,142 B2 | 3/2012 | Seehra et al. |
| 8,173,601 B2 | 5/2012 | Knopf |
| 8,178,488 B2 | 5/2012 | Knopf et al. |
| 8,216,997 B2 | 7/2012 | Seehra et al. |
| 8,252,900 B2 | 8/2012 | Knopf et al. |
| 8,293,236 B2 | 10/2012 | Lin et al. |
| 8,293,881 B2 | 10/2012 | Seehra et al. |
| 8,304,398 B2 | 11/2012 | T Hoen et al. |
| 8,309,082 B2 | 11/2012 | Han et al. |
| 8,343,933 B2 | 1/2013 | Knopf et al. |
| 8,361,957 B2 | 1/2013 | Seehra et al. |
| 8,367,611 B2 | 2/2013 | Knopf et al. |
| 8,388,968 B2 | 3/2013 | Berger et al. |
| 8,410,043 B2 | 4/2013 | Sun et al. |
| 8,435,948 B2 | 5/2013 | Zaidi et al. |
| 8,501,678 B2 | 8/2013 | Sun et al. |
| 8,629,109 B2 | 1/2014 | Knopf et al. |
| 8,637,023 B2 | 1/2014 | Lin et al. |
| 8,637,611 B2 | 1/2014 | Dershem |
| 8,703,694 B2 | 4/2014 | Knopf et al. |
| 8,703,927 B2 | 4/2014 | Seehra et al. |
| 8,710,016 B2 | 4/2014 | Seehra et al. |
| 8,716,459 B2 | 5/2014 | Sun et al. |
| 8,753,627 B2 | 6/2014 | Han et al. |
| 8,765,385 B2 | 7/2014 | Kumar et al. |
| 8,765,663 B2 | 7/2014 | Seehra et al. |
| 8,822,411 B2 | 9/2014 | Lee et al. |
| 8,865,168 B2 | 10/2014 | Lin et al. |
| 8,895,016 B2 | 11/2014 | Sherman et al. |
| 8,987,203 B2 | 3/2015 | Van Leeuwen et al. |
| 8,999,917 B2 | 4/2015 | Sun et al. |
| 9,138,459 B2 | 9/2015 | Knopf et al. |
| 9,163,075 B2 | 10/2015 | Knopf et al. |
| 9,181,533 B2 | 11/2015 | Seerah et al. |
| 9,353,356 B2 | 5/2016 | Knopf et al. |
| 9,399,669 B2 | 7/2016 | Knopf et al. |
| 9,505,813 B2 | 11/2016 | Seerah et al. |
| 9,526,759 B2 | 12/2016 | Knopf et al. |
| 9,572,865 B2 | 2/2017 | Knopf et al. |
| 9,617,319 B2 | 4/2017 | Seehra et al. |
| 9,745,559 B2 | 8/2017 | Seerah et al. |
| 9,790,284 B2 | 10/2017 | Knopf et al. |
| 9,850,298 B2 | 12/2017 | Attie |
| 2001/0027215 A1 | 10/2001 | Perrine |
| 2001/0039036 A1 | 11/2001 | Mathews et al. |
| 2003/0082233 A1 | 5/2003 | Lyons et al. |
| 2003/0083251 A1 | 5/2003 | Westenfelder |
| 2003/0118556 A1 | 6/2003 | Kaspar et al. |
| 2003/0144203 A1 | 7/2003 | Bowen |
| 2003/0215913 A1 | 11/2003 | Alvarez et al. |
| 2003/0224397 A1 | 12/2003 | Lowman et al. |
| 2003/0224501 A1 | 12/2003 | Young et al. |
| 2004/0033511 A1 | 2/2004 | Pfizenmaier et al. |
| 2004/0121008 A1 | 6/2004 | Shiraishi et al. |
| 2004/0132675 A1 | 7/2004 | Kuo et al. |
| 2004/0138129 A1 | 7/2004 | MacLeod |
| 2004/0197828 A1 | 10/2004 | Gaddy |
| 2004/0209805 A1 | 10/2004 | Phillips et al. |
| 2004/0223966 A1 | 11/2004 | Wolfman et al. |
| 2005/0014733 A1 | 1/2005 | Whittemore et al. |
| 2005/0106148 A1 | 5/2005 | Kay et al. |
| 2005/0197292 A1 | 9/2005 | Smithson et al. |
| 2005/0239070 A1 | 10/2005 | Von Knebel-Doeberitz et al. |
| 2005/0244867 A1 | 11/2005 | Soppet et al. |
| 2005/0257278 A1 | 11/2005 | Lee et al. |
| 2006/0068468 A1 | 3/2006 | Knopf et al. |
| 2006/0172347 A1 | 8/2006 | Mellor et al. |
| 2006/0178316 A1 | 8/2006 | Klaus et al. |
| 2006/0208106 A1 | 9/2006 | Boehland et al. |
| 2006/0210657 A1 | 9/2006 | Chou |
| 2007/0048830 A1 | 3/2007 | Gilbert et al. |
| 2007/0117130 A1 | 5/2007 | Han et al. |
| 2007/0149455 A1 | 6/2007 | Wolfman et al. |
| 2007/0172956 A1 | 7/2007 | Magari et al. |
| 2007/0184052 A1 | 8/2007 | Lin et al. |
| 2007/0249022 A1 | 10/2007 | Knopf et al. |
| 2007/0275895 A1 | 11/2007 | Duan et al. |
| 2007/0292885 A1 | 12/2007 | Bejanin et al. |
| 2008/0021104 A1 | 1/2008 | Tarallo |
| 2008/0075692 A1 | 3/2008 | Perrine |
| 2008/0089897 A1 | 4/2008 | Wolfman |
| 2008/0102065 A1 | 5/2008 | Borges et al. |
| 2008/0139590 A1 | 6/2008 | Qian et al. |
| 2008/0261879 A1 | 10/2008 | Melton et al. |
| 2009/0005308 A1 | 1/2009 | Knopf et al. |
| 2009/0017019 A1 | 1/2009 | Shields et al. |
| 2009/0047281 A1 | 2/2009 | Sherman |
| 2009/0074768 A1 | 3/2009 | Knopf et al. |
| 2009/0087433 A1 | 4/2009 | Wolfman et al. |
| 2009/0098113 A1 | 4/2009 | Knopf et al. |
| 2009/0099086 A1 | 4/2009 | Knopf et al. |
| 2009/0118188 A1 | 5/2009 | Knopf et al. |
| 2009/0142333 A1 | 6/2009 | Knopf et al. |
| 2009/0148436 A1 | 6/2009 | LaVallie et al. |
| 2009/0163417 A1 | 6/2009 | Sherman |
| 2009/0202471 A1 | 8/2009 | Khetani et al. |
| 2009/0226460 A1 | 9/2009 | Phillips et al. |
| 2010/0008918 A1 | 1/2010 | Sherman et al. |
| 2010/0015144 A1 | 1/2010 | Sherman et al. |
| 2010/0028331 A1 | 2/2010 | Sherman et al. |
| 2010/0028332 A1 | 2/2010 | Sherman et al. |
| 2010/0068215 A1 | 3/2010 | Seehra et al. |
| 2010/0111852 A1 | 5/2010 | Yoshida |
| 2010/0113327 A1 | 5/2010 | Van Leeuwen et al. |
| 2010/0113932 A1 | 5/2010 | Antich et al. |
| 2010/0125099 A1 | 5/2010 | Hoen et al. |
| 2010/0160220 A1 | 6/2010 | Cao |
| 2010/0183624 A1 | 7/2010 | Seehra et al. |
| 2010/0204092 A1 | 8/2010 | Sherman |
| 2010/0272734 A1 | 10/2010 | Berger et al. |
| 2010/0279409 A1 | 11/2010 | Robson et al. |
| 2010/0316644 A1 | 12/2010 | Seehra et al. |
| 2011/0020372 A1 | 1/2011 | Hill et al. |
| 2011/0038831 A1 | 2/2011 | Seehra et al. |
| 2011/0053930 A1 | 3/2011 | Yu et al. |
| 2011/0070233 A1 | 3/2011 | Seehra et al. |
| 2011/0092670 A1 | 4/2011 | Knopf et al. |
| 2011/0129469 A1 | 6/2011 | Koncarevic et al. |
| 2011/0135638 A1 | 6/2011 | Seehra et al. |
| 2011/0218147 A1 | 9/2011 | Knopf et al. |
| 2011/0281796 A1 | 11/2011 | Han et al. |
| 2011/0286998 A1 | 11/2011 | Gregory et al. |
| 2011/0293526 A1 | 12/2011 | Plikus et al. |
| 2011/0294734 A1 | 12/2011 | Garreta et al. |
| 2012/0003218 A1 | 1/2012 | Sherman et al. |
| 2012/0015877 A1 | 1/2012 | Seehra et al. |
| 2012/0028276 A1 | 2/2012 | Moore et al. |
| 2012/0052067 A1 | 3/2012 | Sherman |
| 2012/0094908 A1 | 4/2012 | Lee et al. |
| 2012/0148588 A1 | 6/2012 | Knopf et al. |
| 2012/0156204 A1 | 6/2012 | Seehra et al. |
| 2012/0232021 A1 | 9/2012 | Martini et al. |
| 2012/0237521 A1 | 9/2012 | Berger et al. |
| 2012/0252884 A1 | 10/2012 | Wolfman et al. |
| 2013/0004489 A1 | 1/2013 | Knopf et al. |
| 2013/0065299 A1 | 3/2013 | Knopf et al. |

(56) References Cited

U.S. PATENT DOCUMENTS

| | | |
|---|---|---|
| 2013/0071393 A1 | 3/2013 | Seehra et al. |
| 2013/0108650 A1 | 5/2013 | Kumar et al. |
| 2013/0177559 A1 | 7/2013 | Seehra et al. |
| 2013/0184210 A1 | 7/2013 | Knopf et al. |
| 2013/0195862 A1 | 8/2013 | Knopf et al. |
| 2013/0225484 A1 | 8/2013 | Sun et al. |
| 2013/0243743 A1 | 9/2013 | Seehra et al. |
| 2013/0244324 A1 | 9/2013 | Seehra et al. |
| 2013/0287765 A1 | 10/2013 | Zaida et al. |
| 2013/0344091 A1 | 12/2013 | Berger et al. |
| 2014/0056902 A1 | 2/2014 | Shimizu et al. |
| 2014/0079700 A1 | 3/2014 | Knopf et al. |
| 2014/0152940 A1 | 6/2014 | Wang et al. |
| 2014/0194355 A1 | 7/2014 | Sun et al. |
| 2014/0220033 A1 | 8/2014 | Han et al. |
| 2014/0303068 A1 | 10/2014 | O'Hehir et al. |
| 2014/0314759 A1 | 10/2014 | Seehra et al. |
| 2014/0348827 A1 | 11/2014 | Sun et al. |
| 2015/0072927 A1 | 3/2015 | Lin et al. |
| 2015/0086526 A1 | 3/2015 | Xie et al. |
| 2015/0086556 A1 | 3/2015 | Han et al. |
| 2015/0111248 A1 | 4/2015 | Bancel et al. |
| 2015/0139983 A1 | 5/2015 | Karni et al. |
| 2015/0183845 A1 | 7/2015 | Sherman et al. |
| 2015/0231206 A1 | 8/2015 | Sun et al. |
| 2015/0258120 A1 | 9/2015 | Zarnitsyn et al. |
| 2015/0266950 A1 | 9/2015 | Sung et al. |
| 2015/0276766 A1 | 10/2015 | Sung et al. |
| 2015/0283209 A1 | 10/2015 | Sung et al. |
| 2015/0328249 A1 | 11/2015 | Gonzalez-Cadavid et al. |
| 2015/0361163 A1 | 12/2015 | Kumar et al. |
| 2016/0039922 A1 | 2/2016 | Attie |
| 2016/0046690 A1 | 2/2016 | Kumar et al. |
| 2016/0108379 A1 | 4/2016 | Knopf et al. |
| 2016/0120939 A1 | 5/2016 | Knopf et al. |
| 2016/0279197 A1 | 9/2016 | Sherman et al. |
| 2016/0279203 A1 | 9/2016 | Sherman et al. |
| 2016/0289286 A1 | 10/2016 | Attie et al. |
| 2016/0318983 A1 | 11/2016 | Koncarevic et al. |
| 2016/0326228 A1 | 11/2016 | Seerah et al. |
| 2017/0037100 A1 | 2/2017 | Kumar |
| 2017/0058016 A1 | 3/2017 | Knopf et al. |
| 2017/0137791 A1 | 5/2017 | Seerah et al. |
| 2017/0145074 A1 | 5/2017 | Knopf et al. |
| 2017/0190784 A1 | 7/2017 | Knopf et al. |
| 2017/0204382 A1 | 7/2017 | Seerah et al. |
| 2017/0274077 A1 | 9/2017 | Kumar et al. |
| 2017/0291935 A1 | 10/2017 | Sherman et al. |
| 2017/0320925 A1 | 11/2017 | Seehra et al. |
| 2017/0327800 A1 | 11/2017 | Seerah et al. |
| 2017/0360887 A1 | 12/2017 | Attie et al. |
| 2018/0009872 A1 | 1/2018 | Sherman et al. |
| 2018/0037622 A1 | 2/2018 | Seerah et al. |
| 2018/0050085 A1 | 2/2018 | Kumar et al. |
| 2018/0080012 A1 | 3/2018 | Seehra et al. |
| 2018/0162954 A1 | 6/2018 | Knopf et al. |
| 2018/0194828 A1 | 7/2018 | Seehra et al. |
| 2018/0194834 A1 | 7/2018 | Attie et al. |

FOREIGN PATENT DOCUMENTS

| | | |
|---|---|---|
| EP | 1 362 062 | 5/2005 |
| EP | 1 884 235 | 2/2008 |
| EP | 2446896 | 5/2012 |
| JP | 2007/99764 | 4/2007 |
| WO | WO 2016/069234 | 5/1916 |
| WO | WO 2016/090077 | 6/1916 |
| WO | WO 2016/090188 | 6/1916 |
| WO | WO 2016/183280 | 11/1916 |
| WO | WO 2016/187378 | 11/1916 |
| WO | WO 1992/004913 A1 | 4/1992 |
| WO | WO 1992/020793 A1 | 11/1992 |
| WO | WO 1993/000432 A1 | 1/1993 |
| WO | WO 1994/015965 A1 | 7/1994 |
| WO | WO 1994/026893 A1 | 11/1994 |
| WO | WO 1995/010611 A1 | 4/1995 |
| WO | WO 1995/029685 A1 | 11/1995 |
| WO | WO 1997/023613 A2 | 7/1997 |
| WO | WO 1998/018926 A1 | 5/1998 |
| WO | WO 1999/006559 A1 | 2/1999 |
| WO | WO 2000/018932 A2 | 4/2000 |
| WO | WO 2000/025807 | 5/2000 |
| WO | WO 2000/043781 A2 | 7/2000 |
| WO | WO 2000/062809 | 10/2000 |
| WO | WO 2001/036001 | 5/2001 |
| WO | WO 2001/043763 A1 | 6/2001 |
| WO | WO 2001/087329 | 11/2001 |
| WO | WO 2002/010214 A2 | 2/2002 |
| WO | WO 2002/022680 A2 | 3/2002 |
| WO | WO 2002/036152 A1 | 5/2002 |
| WO | WO 2002/040501 A2 | 5/2002 |
| WO | WO 2002/043759 A2 | 6/2002 |
| WO | WO 2002/074340 A1 | 9/2002 |
| WO | WO 2002/085306 A2 | 10/2002 |
| WO | WO 2002/094852 A2 | 11/2002 |
| WO | WO 2003/006057 A1 | 1/2003 |
| WO | WO 2003/053219 A2 | 7/2003 |
| WO | WO 2003/072808 A1 | 9/2003 |
| WO | WO 2003/087162 A2 | 10/2003 |
| WO | WO 2004/012759 | 2/2004 |
| WO | WO 2004/016639 A1 | 2/2004 |
| WO | WO 2004/034962 | 4/2004 |
| WO | WO 2004/039948 | 5/2004 |
| WO | WO 2004/064770 | 8/2004 |
| WO | WO 2004/069237 A1 | 8/2004 |
| WO | WO 2004/086953 A2 | 10/2004 |
| WO | WO 2004/092199 | 10/2004 |
| WO | WO 2004/108157 A2 | 12/2004 |
| WO | WO 2005/003158 A2 | 1/2005 |
| WO | WO 2005/009460 A2 | 2/2005 |
| WO | WO 2005/014650 | 2/2005 |
| WO | WO 2005/015003 A2 | 2/2005 |
| WO | WO 2005/028517 A2 | 3/2005 |
| WO | WO 2005/053795 A2 | 6/2005 |
| WO | WO 2005/070967 A2 | 8/2005 |
| WO | WO 2005/094871 A2 | 10/2005 |
| WO | WO 2005/097825 A2 | 10/2005 |
| WO | WO 2005/113590 A2 | 12/2005 |
| WO | WO 2006/002387 A2 | 1/2006 |
| WO | WO 2006/012627 A2 | 2/2006 |
| WO | WO 2006/020884 | 2/2006 |
| WO | WO 2006/039400 A2 | 4/2006 |
| WO | WO 2006/083183 A1 | 8/2006 |
| WO | WO 2006/088972 | 8/2006 |
| WO | WO 2006/115274 A1 | 11/2006 |
| WO | WO 2007/038703 A2 | 4/2007 |
| WO | WO 2007/053775 A1 | 5/2007 |
| WO | WO 2007/062188 | 5/2007 |
| WO | WO 2007/067616 A2 | 6/2007 |
| WO | WO 2007/071023 | 6/2007 |
| WO | WO 2007/075702 | 7/2007 |
| WO | WO 2007/076127 A2 | 7/2007 |
| WO | WO 2007/087505 | 8/2007 |
| WO | WO 2007/101060 | 9/2007 |
| WO | WO 2008/015383 A2 | 2/2008 |
| WO | WO 2008/031061 | 3/2008 |
| WO | WO 2008/060139 | 5/2008 |
| WO | WO 2008/072723 A1 | 6/2008 |
| WO | WO 2008/073292 A2 | 6/2008 |
| WO | WO 2008/076437 A2 | 6/2008 |
| WO | WO 2008/094708 A2 | 8/2008 |
| WO | WO 2008/097541 A2 | 8/2008 |
| WO | WO 2008/100384 A2 | 8/2008 |
| WO | WO 2008/109167 A2 | 9/2008 |
| WO | WO 2008/151078 A1 | 12/2008 |
| WO | WO 2009/009059 A1 | 1/2009 |
| WO | WO 2009/019504 A1 | 2/2009 |
| WO | WO 2009/019505 A2 | 2/2009 |
| WO | WO 2009/021747 | 2/2009 |
| WO | WO 2009/025651 A1 | 2/2009 |
| WO | WO 2008/038745 | 3/2009 |
| WO | WO 2009/058346 | 5/2009 |
| WO | WO 2009/070243 | 6/2009 |
| WO | WO 2009/114180 | 9/2009 |

(56) References Cited

FOREIGN PATENT DOCUMENTS

| | | |
|---|---|---|
| WO | WO 2009/137075 A1 | 11/2009 |
| WO | WO 2009/137613 A2 | 11/2009 |
| WO | WO 2009/146148 | 12/2009 |
| WO | WO 2009/146408 | 12/2009 |
| WO | WO 2009/158015 A2 | 12/2009 |
| WO | WO 2009/158025 A2 | 12/2009 |
| WO | WO 2009/158033 A2 | 12/2009 |
| WO | WO 2010/019261 A1 | 2/2010 |
| WO | WO 2010/083034 A1 | 7/2010 |
| WO | WO 2010/121162 | 10/2010 |
| WO | WO 2010/144452 | 12/2010 |
| WO | WO 2010/151426 | 12/2010 |
| WO | WO 2011/020045 | 2/2011 |
| WO | WO 2011/031901 A1 | 3/2011 |
| WO | WO 2012/027065 | 3/2012 |
| WO | WO 2013/006437 | 1/2013 |
| WO | WO 2013/059347 | 4/2013 |
| WO | WO 2013/063536 | 5/2013 |
| WO | WO 2014/066487 | 1/2014 |
| WO | WO 2014/064292 | 5/2014 |
| WO | WO 2014/066486 | 5/2014 |
| WO | WO 2014/071158 | 8/2014 |
| WO | WO 2015/017576 | 2/2015 |
| WO | WO 2015/022658 | 2/2015 |
| WO | WO 2015/089575 | 6/2015 |
| WO | WO 2015/108972 | 7/2015 |
| WO | WO 2015/111008 | 7/2015 |
| WO | WO 2015/143403 | 9/2015 |
| WO | WO 2015/152183 | 10/2015 |
| WO | WO 2015/162590 | 10/2015 |
| WO | WO 2015/192127 | 12/2015 |

OTHER PUBLICATIONS

Goodman et al. Coronary-artery calcification in young adults with end-stage renal disease who are undergoing dialysis. N Engl J Med. May 18, 2000;342(20):1478-83.*

Milliner et al. Soft tissue calcification in pediatric patients with end-stage renal disease. Kidney Int. Nov. 1990;38(5):931-6.*

Abaza et al., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin", Journal of Protein Chemistry, 11(5):433-444 (1992).

Abbiotec: ACTR-IIA Antibody: Catalog No. 251303 (http://www.abbiotec.com) Jun. 3, 2010.

Acceleron Pharma Presents Positive Phase 1 Results Demonstrating ACE-011 Increases Markers of Bone Formation, Acceleron Pharma, pp. 1-2, retrieved from the Internet, www.acceleronpharma.com/contents/news/press-releases/detail.jsp/q/news-id/47> (2007).

Acta Cryst.,"The CCP4 suite: programs for protein crystallography: Collaborative Computational Project, No. 4," D50: 760-763 (1994). (Abstract only).

Akel et al., "Neutralization of Autocrine Transforming Growth Factor-□□in Human Cord Blood CD34⁺CD38⁻Lin⁻Cells Promotes Stem-Cell-Factor-Mediated Erythropoietin-Independent Early Erythroid Progenitor Development and Reduces Terminal Differentiation." Stem Cells, 21:557-567 (2003).

Akpan et al., "The effects of a soluble activin type IIB receptor on obesity and insulin sensitivity," International Journal of Obesity, 33(11):1265-1273 (2009).

"Anti-human Activin RIIA Antibody," R&D Systems, Catalog No. AF340 (Feb. 14, 2006).

Allendorph, G.P., et al., "Structure of the ternary signaling complex of a TGF-β superfamily member," PNAS, 103(20):7643-7648 (2006).

Anonymous "Iron and Thalassemia," Accessed on the Internet Apr. 3, 2014 at <sickle.bwh.harvard.edu/thaliron.html>. Published Apr. 25, 1997.

Anonymous "Learning about Thalassemia" <http://www.genome.gov/10001221> Accessed on Internet Jul. 9, 2013. Published Jun. 28, 2010.

Anti-ActRIIA Antibodies: Commercial Monoclonal Antibodies Against Human ActRIIA (2010).

Antibodies for ACVR2A: http://www.genecards.org/cgi-bin/carddisp.pl?gene=Acvr2a (Jun. 8, 2010).

Attie et al., "A Single Ascending-Dose Study of Muscle Regulator Ace-031 in Healthy volunteers," Muscle & Nerve, pp. 1-8 (2012).

Banks et al., "The Value of Mammalian Models for Duchenne Muscular Dystrophy in Developing Therapeutic Strategies," Current Topics in Developmental Biology, 84:431-453 (2008).

Benny Klimek et al., "Acute inhibition of myostatin-family proteins preserves skeletal muscle in mouse models of cancer cachexia," Biochemical and Biophysical Research Communications, 391:1548-1554 (2010).

Berenson, "Multiple Myeloma," Multiple Myeloma: Plasma Cell Disorders: Merck Manual Professional, pp. 1-5, Jul. 2008.

Bhatia et al., "Protein Glycosylation: Implications for in Vivo Functions and Therapeutic Applications". Advances in Biochemical Engineering/Biotechnology, vol. 64: 155-201 (1998).

Bodey et al., "Failure of Cancer Vaccines: The Significant Limitations of this Approach to Immunotherapy," Anticancer Research, 20:2665-2676 (2000).

Bogdanovich et al., "Functional improvement of dystrophic muscle by myostatin blockade," Nature, 420:418-421 (2002).

Bork, "Powers and Pitfalls in Sequence Analysis: The 70% Hurdle," Genome Research, 10:398-400 (2000).

Bowie et al., "Deciphering the Message in Protein Sequences: Tolerance to Amino Acid Substitutions," Science, 247:1306-1310 (1990).

Broxmeyer et al., "Selective and indirect modulation of human multipotential and erythroid hematopoietic progenitor cell proliferation by recombinant human activin and inhibin," Proc. Natl. Acad. Sci. USA, 85:9052-9056 (1988).

Burdette et al., "Activin A mediates growth inhibition and cell cycle arrest through Smads in human breast cancer cells." Cancer Research, 65(17):7968-7975; (2005).

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., 111:2129-2138 (1990).

Cadena et al., "Administration of a Soluble Activin Type IIB Receptor Promotes Skeletal Muscle Growth Independent of Fiber Type," Journal of Applied Physiology, 109:635-642 (2010).

Caricasole et al., "Human Growth-Differentiation Factor 3 (HGDF3): Developmental Regulation in Human Teratocarcinoma Cell Lines and Expression in Primary Testicular Germ Cell Tumours," Oncogene, 16:95-103 (1998).

Cannon and Nedergaard, "Neither fat nor flesh," Nature, vol. 454(7207): 947-948 (2008).

Casset et al., "A Peptide mimetic of an anti-CD4 monoclonal antibody by rational design," Biochemical and Biophysical Research Communications, vol. 307:198-205 (2003).

CDR Definitions from Handbook of Therapeutic Antibodies, (2007).

Centrella et al., "Activin-A Binding and Biochemical Effects in Osteoblast-Enriched Cultures from Fetal-Rat Parietal Bone," Molecular and Cellular Biology, 11(1):250-58 (1991).

Chamberlain et al., "Innovations and strategies for the development of anticancer vaccines," Expert Opinion on Pharmacotherapy, 1(4):603-614 (2000).

Chamow and Ashkenazi, "Immunoadhesins: Principles and Applications," TIBTECH, 14: 52-60 (1996).

Chang, "Exploring the Effects of Luteinizing Hormone-Releasing Hormone Agonist Therapy on Bone Health: Implications in the Management of Prostate Cancer," Urology, vol. 52: 29-35 (2003).

Chapman et al., "Effect of intron A from human cytomegalovirus (Towne) immediate-early gene on heterologous expression in mammalian cells," Nucleic Acids Research, 19(14):3979-3986 (1991).

Chantry et al., "Inhibiting Activin-A Signaling Stimulates Bone Formation and Prevents Cancer-Induced Bone Destruction in Vivo," Journal of Bone and Mineral Research, vol. 25(12): 2357-2370 (2010).

(56) References Cited

OTHER PUBLICATIONS

Chardès et al., "Efficient amplification and direct sequencing of mouse variable regions from any immunoglobulin gene family," FEBS Lett. vol. 452(3): 386-394 (1999).
Chavez-Tapia et al., "Insulin sensitizers in treatment of nonalcoholic fatty liver disease: Systematic review," World Journal of Gastroenterology, vol. 12(48): 7826-7831 (2006).
Chen et al., "Selection and Analysis of an Optimized Anti-VEGF Antibody: Crystal Structure of an Affinity-matured Fab in Complex with Antigen," J. Mol. Biol., vol. 293: 865-881 (1999).
Chen et al. "Regulation of Cell Proliferation, Apoptosis, and Carcinogenesis by Activin," Exp. Biol. Med., 227(2):75-87 (2002).
Cirillo et al., "Hematocrit, blood pressure, and hypertension. The Gubbio Population Study," Hypertension, 20(3):319-326 (1992).
Coerver et al., "Activin Signaling through Activin Receptor Type II Causes the Cachexia-Like Symptoms in Inhibin-Deficent Mice," Molecular Endocrinology, 10(5):534-543 (1996).
Collins, "Multidisciplinary Symposium: Haematological Malignancies," Cancer Imaging 5:S119-S126 (2005).
Colman, "Effects of amino acid sequence changes on antibody-antigen interactions," Research of Immunology, 145(1):33-36 (1994).
Crisan et al., "A Reservoir of Brown Adipocyte Progenitors in Human Skeletal Muscle," Stem Cells, vol. 26(9): 2425-2433 (2008).
Daluiski et al., "Bone Morphogenetic Protein-3 is a Negative Regulator of Bone Density," Nature Genetics, 27:84-88 (2001).
Database Geneseq [Online], "Variable heavy chain of anti-human Fas ligand antibody NOK-4," retrieved from EBI accession No. GSP:AAW00829; Database accession No. AAW00829; abstract, sequence (1997).
Database Geneseq [Online]; "Monoclonal antibody 10D4 HMGB1 Vkappa domain," retrieved from EBI accession No. GSP:ADY85028, Database accession No. GSP:ADY85028; abstract, sequence (2005).
Deal, "Potential New Drug Targets for Osteoporosis," Nature Clinical Practice, 5(1):20-27 (2009).
Deconinck et al., "Pathophysiology of Duchenne Muscular Dystrophy: Current Hypotheses," Pediatr. Neurol., 36:1-7 (2007).
Del Re et al., "Reconstitution and Analysis of Soluble Inhibin and Activin Receptor Complexes in a Cell-free System," The Journal of Biological Chemistry, 279(51):53126-53135 (2004).
Delogu et al., "DNA vaccine combinations expressing either tissue plasminogen activator signal sequence fusion proteins or ubiquitin-conjugated antigens induce sustained protective immunity in a mouse model of pulmonary tuberculosis," Infection and Immunity, 70(1):292-302 (2002).
Depaolo et al., "Passive Immunoneutralization with a Monoclonal Antibody Reveals a Role for Endogenous Activin-B in Mediating FSH Hypersecretion during Estrus and Following Ovariectomy of Hypophysectomized, Pituitary-Grafted Rats," Endocrinology, 130(3):1741-1743 (1992).
Donald et al., "SDR: a database of predicted specificity-determining residues in proteins," Nucleic Acids Research, vol. 37: D191-D194 (2009).
Donaldson et al., GenBank: BAA06548.1: activin typeII A receptor precursor [Homo sapiens] (1992).
Donaldson et al., "Activin and inhibin binding to the soluble extracellular domain of activin receptor II", Endocrinology 140(4):1760-1766 (1999).
Donaldson et al., "Molecular Cloning and Binding Properties of the Human Type II Activin Receptor", Biochemical and Biophysical Research Communications, 184(1):310-316 (1992).
Dussiot et al., "An activin receptor IIA ligand trap corrects ineffective erythropoiesis in B-thalassemia," Nature Medicine, vol. 20: 398-407 (2014).
Ear et al., "RAP-011 Efficiently Rescues Erthropoiesis in Zebrafish Models of Diamond Blackfan Anemia," 55 ASH Annual Meeting and Exposition. Abstract #3702 (2013).
Eijken, "The Activin A-Follistatin System: Potent Regulator of Human Extracellular Matrix Mineralization," The FASEB Journal, 21:2949-2960 (2007).

Elliot et al., "Enhancement of therapeutic protein in vivo activities through glycoengineering," Nature Biotechnology, vol. 21: 414-421 (2003).
Supplementary EP Search Report EP 09 80 6981 dated Dec. 7, 2012.
Supplementary EP Search Report EP 10 80 8838 dated Jun. 18, 2013.
Fafioffe et al.,"Activin and inhibin receptor gene expression in the ewe pituitary throughout the oestrous cycle," Journal of Endocrinology, 182:55-68 (2004).
Fajardo et al., "Treatment with a Soluble Receptor for Activin Improves Bone Mass and Structure in the Axial and Appendicular Skeleton of Female Cynomolgus Macaques (Macaca fascicularis)," Bone, 46:64-71 (2010).
Fan et al., "Preclinical evaluation of Hematide, a novel erythropoiesis stimulating agent, for the treatment of anemia," Experimental Hematology 34:1303-1311 (2006).
Farmer, "Brown Fat and Skeletal Muscle: Unlikely Cousins?," Cell, vol. 134(5): 726-727 (2008).
Ferguson et al., "The role of effectors of the activin signalling pathway, activin receptors IIA and IIB, and Smad2, in patterning of tooth development," Development, vol. 128: 4605-4613 (2001).
Foucar, Myelodysplastic/ Myeloproliferative Neoplasms, Am J Clin Pathol, vol. 132: 281-289 (2009).
Fournier et al., "Blockade of the activin receptor IIb activates functional brown adipogenesis and thermogenesis by inducing mitochondrial oxidative metabolism," Mol. Cell. Biol. vol. 32(14): 2871-2879 (2012).
Frankel et al., "Characterization of diphtheria fusion proteins targeted to the human interleukin-3 receptor," Protein Engineering, vol. 13(8): 575-581 (2000).
Frigon, et al, "Regulation of Globin Gene Expression in Human K562 Cells by Recombinant Activin A," Blood, 79(3):765-772 (1992).
Fuller et al., "Activin A Is an Essential Cofactor for Osteoclast Induction," Biochemical and Biophysical Research Communications, 268:2-7 (2000).
Funaba et al., "Expression and Localization of Activin Receptors During Endochondral Bone Development," European Journal of Endocrinology, 144:63-71 (2001).
Gaddy-Kurten et al., "Inhibin Suppresses and Activin Stimulates Osteoblastogenesis and Osteoclastogenesis in Murine Bone Marrow Cultures," Endocrinology, 143(1):74-83 (2002).
Gamer et al., "BMP-3 is a Novel Inhibitor of Both Activin and BMP-4 Signaling in Xenopus Embryos," Developmental Biology, 285:156-168 (2005).
Ge et al., "GDF11 Forms a Bone Morphogenetic Protein 1-Activated Latent Complex That Can Modulate Nerve Growth Factor-Induced Differentiation of PC12 Cells", Molecular and Cellular Biology, 25(14):5846-5858 (2005).
GenBank NM_001106, Homo sapiens activin A receptor, type IIB (ACVR2B), mRNA, http://www.ncbi.nlm.nih.gov/entrez/viewer.fcgi?db=nucleotide&val=116734707 (Downloaded on Jan. 29, 2007).
Gilbert et al., "Prolonged dystrophin expression and functional correction of mdx mouse muscle following gene transfer with a helper-dependent (gutted) adenovirus-encoding murine dystrophin," Human Molecular Genetics, 12(11)1287-1299 (2003).
Gilchrist et al., "Antagonists of the Receptor-G Protein Interface Block Gi-coupled Signal Transduction," The Journal of Biological Chemistry, 273(24):14912-14919 (1998).
Gonzalez-Cadavid et al., "Organization of the human myostatin gene and expression in healthy men and HIV-infected men with muscle wasting," PNAS, 95:14938-14943 (1998).
Gray et al., "Identification of a binding site on the type II activin receptor for activin and inhibin", The Journal of Biological Chemistry, 275(5):3206-3212(2000).
Greenspan et al., "Defining epitopes: It's not as easy as it seems," Nature Biotechnology, 17:936-937 (1999).
Greenwald et al., "Characterization of the Extracellular Ligand-Binding Domain of the Type II Activin Receptor," Biochemistry, 37(47):16711-16718 (1998).
Greenwald et al., "The BMP7/ActRII Extracellular Domain Complex Provides New Insights into the Cooperative Nature of Receptor Assembly," Molecular Cell, 11:605-617 (2003).

(56) References Cited

OTHER PUBLICATIONS

Greenwald et al., "Three-finger toxin fold for the extracellular ligand-binding domain of the type II activin receptor serine kinase," Nature Structural Biology, 6(1):18-22 (1999).
Gregoriadis et al., "Polysialic acids: potential in drug delivery," FEBS, 315(3):271-276 (1993).
Guo et al., Protein Tolerance to Random Amino Acid Change. Proc. Natl. Acad. Sci. USA, 101(25):9205-9210 (Jun. 22, 2004). Epub Jun. 14, 2004.
Gupta et al., "Transforming Growth Factor-beta Superfamily: Evaluation as Breast Cancer Biomarkers and Preventive Agents," Current Cancer Drug Targets, 4:165-182 (2004).
Gura, "Cancer Models: Systems for Identifying New Drugs Are Often Faulty," Science, 278(5340):1041-1042 (1997).
Haidar et al., "Paraspinal extramedullary hematopoiesis in patients with thalassemia intermedia," Eur Spine J., vol. 19: 871-878 (2010).
Hamrick et al., "Bone Mineral Content and Density in the Humerus of Adult Myostatin-Deficient Mice," Calcified Tissue International, 71:63-68 (2002).
Hamrick, "Increased Bone Mineral Density in the Femora of GDF8 Knockout Mice," The Anatomical Record, Part A 272A:388-391 (2003).
Hamrick, et al., "Femoral Morphology and Cross-sectional Geometry of Adult Myostatin-deficient Mice," Bone, 27(3):343-349 (2000).
Harousseau et al., "Multiple Myeloma," American Society of Hematology, pp. 237-256 (2004).
Harrison, et al., "An Activin Mutant with Disrupted ALK4 Binding Blocks Signaling via Type II Receptors," The Journal of Biological Chemistry, 279(27):28036-28044 (2004).
Harrison, et al., "Antagonists of activin signaling: mechanisms and potential biological applications," TRENDS in Endocrinology and Metabolism, 16(2):73-78 (2005).
Hashimoto et al., "Functional Regulation of Osteoblastic Cells by the Interaction of Activin-A with Follistatin," The Journal of Biological Chemistry, 267(7):4999-5004 (1992).
Hemmati-Brivanlou, et al., "A truncated activin receptor inhibits mesoderm induction and formation of axial structures in Xenopus embryos," Nature, 359:609-614 (1992).
Herbert et al., The Dictionary of Immunology, Academic Press, 3rd Edition, London, pp. 58-59 (1985).
Hilden et al., "Expression of Type II Activin Receptor Genes During Differentiation of Human K562 Cells and cDNA Cloning of the Human Type IIB Activin Receptor," Blood, 83(8):2163-2170 (1994).
Hill et al., "Regulation of Myostatin in Vivo by Growth and Differentiation Factor-Associated Serum Protein-1: A Novel Protein with Protease Inhibitor and Follistatin Domains," Molecular Endocrinology, 17(6):1144-1154 (2003).
Holm et al., "Functional mapping and single chain construction of the anti-cytokeratin 8 monoclonal antibody TS1," Molecular Immunology, vol. 44(6): 1075-1084 (2007).
"Human Activin RIIA Antibody," R&D Systems, Tools for Cell Biology Research, Catalog No. MAB340 (Mar. 22, 2011).
Hsieh et al., "HIF-prolyl hydroxylase inhibition results in endogenous erythropoietin induction, erythrocytosis, and modest fetal hemoglobin expression in rhesus macaques," Blood, 110(6):2140-2147 (2007).
International Search Report, PCT/US2010/045509, dated Nov. 23, 2010.
Ito et al., "Presence of activin signal transduction in normal ovarian cells and epithelial ovarian carcinoma," British Journal of Cancer, vol. 82(8): 1415-1420 (2000).
"The Illustrated Guide to Bone Marrow Diagnosis Second Edition," Ed. by G. Kumar. Originally published 2003.
Kaiser, "First Pass at Cancer Genome Reveals Complex Landscape," Science, 313:1370 (2006).
Kanemitsu, "Clinical application of subforms of creatine kinase MM and macro creatine kinases," Journal of Chromatography, vol. 526: 423-438 (1990).
Kaspar, et al., "Retrograde Viral Delivery of IGF-1 Prolongs Survival in a Mouse ALS Model," Science, 301:839-842 (2003).
Kim, et al., "ACE-011, a Soluble Activin Receptor Type IIa IgG—Fc Fusion Protein, Increases Hemoglobin and Hematocrit Levels in Postmenopausal Healthy Women," Blood, 112(11) (2008).
Knight, "Roles of Inhibins, Activins, and Follistatin in the Female Reproductive System," Frontiers in Neuroendocrinology, 17:476-509 (1996).
Koncarevic et al., "A Soluble Activin Receptor Type IIB Prevents the Effects of Androgen Deprivation on Body Composition and Bone Health," Endocrinology, vol. 151(9); 4289-4300 (2010).
Kos et al., "Activin type II receptors in embryonic dorsal root ganglion neurons of the chicken," J. Neurobiol., vol. 47(2): 93-108 (2001).
Kosaki et al., "Left-Right Axis Malformations Associated With Mutations in ACVR2B, the Gene for Human Activin Receptor Type IIB," American Journal of Medical Genetics, 82:70-76 (1999).
Koseki et al., "Role of TGF-beta Family in Osteoclastogenesis Induced by RANKL," Cellular Signaling, 14:31-36 (2002).
Krag et al., "Heregulin ameliorates the dystrophic phenotype in mdx mice," PNAS, 101(38):13856-13860 (2004).
Krneta et al., "Dissociation of Angiogenesis and Tumorigenesis in Follistatin- and Activin-Expressing Tumors," Cancer Research, 66(11):5686-5695 (2006).
Krystal et al., "Transforming Growth Factor 1 Is an Inducer of Erythroid Differentiation". J. Exp. Med. vol. 180 pp. 851-860 (1994).
Kubanek, "Introduction: The Role of the Microenvironment and Cytokines on the Modulation of Erythropoiesis," Annals New York Academy of Sciences, pp. 257-258 (1994).
Kumar et al., "Regulation of FSHbeta and GnRH Receptor Gene Expression in Activin Receptor II Knockout Male Mice," Mol. Cell. Endocrinol., 212:19-27 (2003).
Kunihro et al., "Regulation of Muscle Mass and Hepatic Steatosis by Follistatin-derived Myostatin Inhibitors," Making Muscle in the Embryo and Adult: a joint meeting of Frontiers in Myogenesis and Skeletal Muscle Stem and Satellite Cells, New York, NY, p. 45 (Abstract) (1990).
Kuntz, "Structure-Based Strategies for Drug Design and Discovery," Science, 257:1078-1082 (1992). (Abstract only).
Lazar, "How Now, Brown Fat?" Science, vol. 321(5892): 1048-1049 (2008).
Kwiatkowski et al., "Iron chelation therapy in sickle-cell disease and other transfusion-dependent anemias," Hematol Oncol Clin N Am., vol. 18: 1355-1377 (2004).
Lazar et al., "Transforming Growth Factor α: Mutation of Aspartic Acid 47 and Leucine 48 Results in Different Biological Activities," Molecular and Cellular Biology, 8(3):1247-1252 (1988).
Lebrun et al, "Activin and Inhibin Have Antagonistic Effects on Ligand-Dependent Heteromerization of the Type I and Type II Activin Receptors and Human Erythroid Differentiation," Molecular and Cellular Biology, 17(3):1682-1691 (1997).
Lee et al., "Regulation of Muscle Growth by Multiple Ligands Signaling Through Activin Type II Receptors," PNAS 102(50):18117-18122 (2005).
Lee, et al., "Regulation of Myostatin Activity and Muscle Growth," PNAS, 98(16):9306-9311 (2001).
Leto et al., "Activin A Circulating Levels in Patients with Bone Metastasis from Breast or Prostate Cancer," Clin Exp Metastasis, 23:117-122 (2006).
Li et al., "Prevention of cachexia-like syndrome development and reduction of tumor progression in inhibin-deficient mice following administration of a chimeric activin receptor type II-murine Fc protein," Molecular Human Reproduction, 13(9):675-683 (2007).
Lifespan Biosciences, Activin Receptor Type 2A (ACVR2A) Mouse anti-Human Monoclonal Antibody—LS-C33835—LifeSpan Biosciences, (2010).
Liu et al., "Characterization of isoforms of activin receptor-interacting protein 2 that augment activin signaling," Journal of Endocrinology, vol. 189: 409-421 (2006).
Lotinun et al., "A Soluble Activin Receptor Type IIA Fusion Protein (ACE-011) Increases Bone Mass Via a Dual Anabolic-Antiresorptive Effect in *Cynomolgus* Monkeys," Bone, 46:1082-1088 (2010).

(56) References Cited

OTHER PUBLICATIONS

Lu et al., "Simian Immunodeficiency Virus DNA Vaccine Trial in Macaques," Journal of Virology, 70(6):3978-3991 (1996).
Ludlow et al., "Development of a new antibody to the human inhibin/activin βB subunit and its application to improved inhibin B ELISAs," J. Immunol. Methods, 329:102-111 (2008).
Ma, "Animal Models of Disease," Modern Drug Discovery, 30-36 (2004).
MacCallum et al., "Antibody-antigen Interactions: Contact Analysis and Binding site Topography," J. Mol. Biol, vol. 262: 732-745 (1996).
MacLennan et al., "Multiple Myeloma," BMJ, vol. 308:1033-1036 (1994).
Maguer-Satta et al, "A Novel Role for Fibronectin Type 1 Domain in the Regulation of Human Hematopoietic Cell Adhesiveness Through Binding to Follistatin Domains of FLRG and Follistatin," Experimental Cell Research, 312(4):434-442 (2006).
Maguer-Satta et al, "Regulation of human erythropoiesis by activin A, BMP2, and BMP4, members of the TGFβ family," Experimental Cell Research, 282:110-120 (2003).
Maguer-Satta et al., "FLRG, Member of the Follistatin Family, a New Player in Hematopoiesis," Molecular and Cellular Endocrinology, 225:109-118 (2004).
Marri et al, Human Biochemistry, Moscow, "Mir", vol. 1: 34-35 (1993).
Mathews et al., "Expression Cloning of an Activin Receptor, a Predicted Transmembrane Serine Kinase," Cell, 65(6):973-982 (1991).
Matzuk et al., "Cloning of the human activin receptor cDNA reveals high evolutionary conservation," Biochim Biophys Acta, 1130(1):105-108 (1992).
Matzuk et al., "Different phenotypes for mice deficient in either activins or activin receptor type II," Nature, 374:356-360 (1995).
McCarthy et al., Monoclonal antibodies that recognize the type-2 activin receptor, ACTR2, Hybridoma, vol. 13(3): 199-203 (1994).
McNally, "Powerful Genes—Myostatin Regulation of Human Muscle Mass," N. Engl. J. Med., 350(26):2642-2644 (2004).
McPherron, et al., "GDF-3 and GDF-9: Two New Members of the Transforming Growth Factor-Beta Superfamily Containing a Novel Pattern of Cysteines," Journal of Biological Chemistry, 268(5):3444-3449 (1993).
McPherron, et al., "Regulation of Skeletal Muscle Mass in Mice by a New TGF-beta Superfamily Member," Nature, 387:83-90 (1997).
McPherron and Lee, "Suppression of body fat accumulation in myostatin-deficient mice," The Journal of Clinical Investigation, vol. 109(5): 595-601 (2002).
McPherson et al., "Growth inhibitory response to activin A and B by human prostate tumour cell lines LNCaP and DU145", Journal of Endocrinology, 154:535-545 (1997).
Menstruation: Absent Periods (Amenorrhea), Website downloaded on Jun. 14, 2010, <http://adam.about.com/reports/000101_2.htm?p=1> (11 pages).
Merck Manual. Iron-Utilization Anemias (Sideroblastic Anemias), pp. 1150-1151 (1992).
Merck Manuals Online Medical Library (online). Iron Deficiency Anemia, Jun. 10, 2008. Downloaded from the internet on Jan. 5, 2010. <http://web.archive.org/web/20080610070221/http://www.merck.com/mmpe/sec11/ch130/ch130d.html> pp. 1-4.
Merck Manuals Online Medical Library (online). Anemia of Chronic Disease, Jun. 10, 2008. Downloaded from the internet on Jan. 5, 2010. <http://web.archive.org/web/20080610070226/http://www.merck.com/mmpe/sec11/ch130/ch130d.html> pp. 1-2.
The Merck Manual of Diagnosis and Therapy, 17th Edition. Nyelodysplastic Syndrome, pp. 865 and 963-955 (1999).
Meriggiola et al., "Follistatin Decreases Activin-Stimulated FSH Secretion with No Effect on GnRH-Stimulated FSH Secretion in Prepubertal Male Monkeys," Endocrinology, 134(4):1967-1970 (1994).
Monoclonal Anti-human Activin RII Antibody, R&D Systems, Catalog No. MAB3391 (Feb. 18, 2009).
The website downloaded Oct. 28, 2014 from the Multiple Myeloma Research Foundation, themmrf.org/multiple-myeloma/symptoms/bone-lesions/, 2 pages total.
Mickle et al., "Genotype-Phenotype Relationships in Cystic Fibrosis," Med. Clin. North Am., 84(3):597-607 (2000).
Miller et al., "Ligand Binding to Proteins: The Binding Landscape Model," Protein Science, 6:2166-2179 (1997).
Miura et al., "Utrophin upregulation for treating Duchenne or Becker muscular dystrophy: how close are we?," Trends in Molecular Medicine, 12(3):122-129 (2006).
Moore et al., "Molecular Basis of Bone Morphogenetic Protein-15 Signaling in Granulosa Cells*," The Journal of Biological Chemistry, vol. 278(1): 304-310 (2003).
Morrison et al., "A soluble activin type IIB receptor improves function in a mouse model of amyotrophic lateral sclerosis," Experimental Neurology vol. 217: 258-268 (2009).
Mosekilde et al., "Emerging Anabolic Treatments in Osteoporosis," Current Drug Safety, 6:62-74 (2011).
Murase et al., "Possible Involvement of Protein Kinases and Smad2 Signaling Pathways on Osteoclast Differentiation Enhanced by Activin A," Journal of Cellular Physiology, 188:236-242 (2001).
Murata et al., "Anti-activin A Antibody (IgY) Specifically Neutralizes Various Activin A Activities," Proceedings of the Society for Experimental Biology & Medicine, 211(1):100-107 (1996).
Nagamine et al., "Immunohistochemical Detection of Activin A, Follistatin, and Activin Receptors during Fracture Healing in the Rat," Journal of Orthopaedic Research, 16:314-321 (1998).
Nakamura et al, "Effect of Erythroid Differentiation Factor on Maintenance of Human Hematopoietic Cells in Co-cultures with Allogenic Stromal Cells," Biochemical and Biophysical Research Communications, 194(3):1103-1110 (1993).
Nemeth, "Hepcidin in Beta-thalassemia," Annals of the New York Academy of Sciences, vol. 1202:31-35. Published Aug. 2, 2010.
Ngo et al., "Computational Complexity, Protein Structure Prediction, and the Levinthal Paradox," The Protein Folding Problem and Tertiary Structure Prediction, Merz et al., eds., Birkhauser, Boston, 433 and 492-495 (1994).
"NIH website downloaded May 28, 2014 from: web.archive.org/web/20030409091558/http://www.cc.nih.gov/ccc/patient_education/pepubs/subq.pdf; Patient Information Publications: Giving a Subcutaneous Injection ( 6 pages total)".
Ogawa et al., "Bovine Bone Activin Enhances Bone Morphogenetic Protein-Induced Ectopic Bone Formation," The Journal of Biological Chemistry, 267(20):14233-14237 (1992).
Oh et al., "Activin type IIA and IIB receptors mediate Gdf11 signaling in axial vertebral patterning," Genes & Development, 16:2749-2754 (2002).
Oue et al., "Effect of Local Injection of Activin A on Bone Formation in Newborn Rats," Bone, 15(3):361-366 (1994).
Padlan et al., "Identification of specificity-determining residues in antibodies," The FASEB Journal, vol. 9: 133-139 (1995).
Paulson, "Targeting a new regulator of erythropoiesis to alleviate anemia," Nature Medicine, News and Views, vol. 20(4) (2 pages) (2014).
Pakula and Sauer, "Genetic analysis of protein stability and function," Annu. Rev. Genet., vol. 23: 289-310 (1989).
Patel et al., "The function of Myostatin and strategies of Myostatin blockade—new hope for therapies aimed at promoting growth of skeletal muscle," Neuromuscular Disorders, 15:117-126 (2005).
Paul, Fundamental Immunology, 3rd edition, Raven Press, New York, 1003: 292-295 (1999).
Pearsall et al., An investigative pharmacology study of a GDF-8 (myostatin) inhibitor, ACE-031, in the common Marmoset (Callithrix jacchus), Database Biosis, Biosciences Information Service, Accession No. PREV201200750016; Faseb Journal, vol. 22, Experimental Biology Annual Meeting, San Diego, CA Apr. 5-9, 2008 (Abstract).
Pearsall et al., "A Soluble Activin Receptor Type IIA (ACTRIIA) Acts as a Novel Bone Anabolic Agent," The Official Journal of the European Calcified Tissue Society, 34th European Symposium on Calcified Tissues, May 2007.

(56) References Cited

OTHER PUBLICATIONS

Pearsall et al., "Treatment with a Soluble Activin Type II Receptor Reverses Bone Loss in Ovariectomized Mice," Journal of Bone and Mineral Research 2006 Abstracts, 21(1):s1-s530 (2006).
Pearsall et al., "A soluble activin Type IIA receptor induces bone formation and improves skeletal integrity", PNAS, 105(19):7082-7087 (2008).
Perrien et al., "Inhibin A Is an Endocrine Stimulator of Bone Mass and Strength," Endocrinology, 148(4):1654-1665 (2007).
Phillips, "The challenge of gene therapy and DNA delivery," J. Pharm. Pharmacology, 53:1169-1174 (2001).
Pirollo et al., "Targeted Delivery of Small Interfering RNA: Approaching Effective Cancer Therapies," Cancer Res., 68(5):1247-1250 (2008).
Qi et al., "Blockade of type transforming growth factor signaling prevents liver fibrosis and dysfunction in the rat," PNAS, 96:2345-2349 (1999).
Raju, "Glycosylation in the Fc domain of IgG increases resistance to proteolytic cleavage by papain," Biochemical and Biophysical Research Communications, 341:797-803 (2006).
Rebbapragada et al., "Myostatin Signals Through a Transforming Growth Fact beta-Like Signaling Pathway to Block Adipogenesis," Molecular and Cellular Biology, 23(20):7230-7242 (2003).
"Recombinant Human Activin RIIB/Fc Chimera," R&D Systems 339-RB/CF (Aug. 27, 2003).
"Recombinant Human Activin RIIA/Fc Chimera," R&D Systems 340-R2 (Aug. 27, 2003).
Risbridger et al., "Activins and Inhibins in Endocrine and Other Tumors," Endocrine Reviews, 22(6):836-858 (2001).
Robinson et al., "Inhibins and Activins Regulate Mammary Epithelial Cell Differentiation Through Mesenchymal-epithelial Interactions," Development, 124:2701-2708 (1997).
Rodriquez et al., "Enhanced Osteoclastogenesis Causes Osteopenia in Twisted Gastrulation-Deficient Mice Through Increased BMP Signaling," J. Bone Miner. Res., 24(11):1917-1926 (2009).
Ruckle et al., "Single-Dose, Randomized, Double-Blind, Placebo-Controlled Study of ACE-011 (ActRIIA-IgG1) in Postmenopausal Women," Journal of Bone and Mineral Research, vol. 24(4), pp. 744-752 (2009).
Ruzek et al. "Minimal Effects on Immune Parameters Following Chronic Anti-TGF-Monoclonal Antibody Administration to Normal Mice", Immunopharmacology and Immunotoxicology, 25(2):235-257 (2003).
Sakai et al., "Activin Enhances Osteoclast-Like Cell Formation in Vitro," Biochemical and Biophysical Research Communications, 195(1):39-46 (1993).
Sakai et al., "Activin Increases Bone Mass and Mechanical Strength of Lumbar Vertebrae in Aged Ovariectomized Rats," Bone, 27(1):91-96 (2000).
Sakai et al., "Activin release from bone coupled to bone resorption in organ culture of neonatal mouse calvaria," Bone, 26(3):235-240 (2000).
Sakai et al., "Involvement of Activin in the Regulation of Bone Metabolism," Molecular and Cellular Endocrinology, 180:183-188 (2001).
Sakai et al., "Local Administration of Activin Promotes Fracture Healing in the Rat Fibula Fracture Model," Bone, 25(2):191-196 (1999).
Sakai et al., "The Measurement of Activin/EDF in Mouse Serum: Evidence for Extragonadal Production", Biochecmical and Biophysical Research Communications, 188(2):921-926 (1992).
Sakai et al., "Osteogenic Activity of Activin in Young Normal Rats and Young Adult and Aged Rats after Ovarlectomy," Bone 23:(Suppl.) 467 (1998).
Sako et al., "Characterization of the Ligand Binding Functionality of the Extracellular Domain of Activin Receptor Type IIB," The Journal of Biological Chemistry, 285(27):21037-21048 (2010).
Satoh et al., "Hemodynamic changes by recombinant erythropoietin therapy in hemodialyzed patients," Hypertension, 15(3):262-266 (1990).

Schmelzer et al., "Purification and Characterization of Recombinant Human Activin B," Biochimica et Biophysica Acta, 1039(2):135-141 (1990).
Schuelke et al., "Myostatin Mutation Associated with Gross Muscle Hypertrophy in a Child," New England Journal of Medicine, 350(26):2682-2688 (2004).
Seale et al., "PRDM16 controls a brown fat/skeletal muscle switch," Nature, vol. 454(7207): 961-967 (2008).
Shao et al., "Effect of Activin A on Globin Gene Expression in Purified Human Erythroid Progenitors," Blood, 79(3):773-781 (1992).
Shao et al., "Efficient synthesis of globoside and isogloboside tetrasaccharides by using beta (1—>3) N-acetylgalactosaminyltransferase/UDP-N-acetyglucosamine C4 epimerase fusion protein," Chem Commun.: 1422-1423 (2003).
Shapiro et al., "Side Effects of Adjuvant Treatment of Breast Cancer," New England Journal of Medicine, vol. 344: 1997-2008 (2001).
Shav-Tal et al., "The Role of Activin A in Regulation of Hemopoiesis," Stem Cells, 20:493-500 (2002).
Shi et al., "Energy Balance, Myostatin, and GILZ: Factors Regulating Adipocyte Differentiation in Belly and Bone," PPAR Research, pp. 1-12 (2007).
Shiozaki et al, "Activin A: A Commitment Factor in Erythroid Differentiation," Biochemical and Biophysical Research Communications, 242:631-635 (1998).
Shiozaki et al, "Evidence for the participation of endogenous activin A/erythroid differentiation factor in the regulation of erythropoiesis," Proc. Natl. Acad. Sci. USA, 89:1553-1556 (1992).
Shiozaki et al., "In Vivo Treatment With Erythroid Differentiation Factor (EDF / Activin A) Increases Erythroid Precursors (CFU-E and BFU-E) in Mice," Biochemical and Biophysical Research Communications, 165(3):1155-1161 (1989).
Shoji et al., "Identification and Characterization of a PDZ Protein That Interacts with Activin Type II Receptors," The Journal of Biological Chemistry, vol. 275(8): 5485-5492 (2000).
Shuto et al., "Osteoblasts Express Types I and II Activin Receptors During Early Intramembranous and Endochondral Bone Formation," Journal of Bone Mineral Research, 12(3):403-411 (1997).
Smith et al., "The analysis of doxorubicin resistance in human breast cancer cells using antibody microarrays," Mol. Cancer Therapy, vol. 5: 2115-2120 (2006).
Smith et al., The Status, Quality, and Expansion of the NIH Full-Length cDNA Project: The Mammalian Gene Collection (MGC), Genome Res., vol. 14(10b),: 2127-2127 (2004).
Song et al., "The Type II Activin Receptors Are Essential for Egg Cylinder Growth, Gastrulation, and Rostral Head Development in Mice," Development Biology, 213:157-169 (1999).
Springer et al., "Seventh European Congress on Clinical and Economic Aspects of Osteoporosis and Osteoarthritis," Osteoporosis International, 18(1):S29-S175 (2007).
Sun et al., "FSH Directly Regulates Bone Mass," Cell, 125:247-260 (2006).
Suragani et al., "4236 ACE-536, a Modified Type II Activin Receptor Increases Red Blood Cells in Vivo by Promoting Maturation of Late Stage Erythroblasts," 52nd ASH Annual Meeting and Expositions, Orange County Convention Center, Orlando, FL Dec. 4-7, 2010. (abstract).
Suragani et al., "Transforming growth factor-β superfamily ligand trap ACE-536 corrects anemia by promoting late-stage erythropoiesis," Letters, Nature Medicine, Advance Online Publication (44 pages) (2014).
Swanson et al., "Use of Biosensors to Monitor the Immune Response," Biologics, vol. 109: 71-78 (2000).
Swanson, "New Technologies for the Detection of Antibodies to Therapeutic Proteins," Immunogenicity of Therapeutics Biological Products, vol. 112: 127-133 (2003).
Tanno and Miller, "Iron Loading and Overloading due to Ineffective Erythropoiesis," Advances in Hematology, Article ID 358283, Chapter 2 (Abstract) (2010).
Thompson et al., "Structures of an ActRIIB: activin A complex reveal a novel binding mode for TGF-beta ligand: receptor interactions", EMBO 22(7):1555-1566 (2003).

(56) References Cited

OTHER PUBLICATIONS

Thompson et al., "Beta A versus beta B: is it merely a matter of express?," Molecular and Cellular Endocrinology, 225:9-17 (2004).
Thorpe and Swanson, "Current methods for Detecting Antibodies against Erythropoietin and Other Recombinant Proteins," Clinical and Diagnostic Laboratory Immunology, vol. 12(1): 28-39 (2005).
Tinsley et al., "Expression of full-length utrophin prevents muscular dystrophy in mdx mice," Nature Medicine, 4(12):1441-1444 (1998).
Tisdale, "Cachexia in Cancer Patients," Nat. Rev. Cancer, 2:862-871 (2002).
Tokuriki et al., "Stability effects of mutations and protein evolvability," Current Opinion in Structural Biology, 19:596-604 (2009).
Trivedi et al., "Investigational Anabolic Therapies for Osteoporosis," Expert Opin. Investig. Drugs, 19(8):995-1005 (2010).
Truksa et al., "Bone morphogenetic proteins 2, 4, and 9 stimulate murine hepcidin 1 expression independently of Hfe, transferrin receptor 2 (Tfr2), and IL-6," PNAS, vol. 103(27): 10289-10293 (2006).
Tseng et al., "New role of bone morphogenetic protein 7 in brown adipogenesis and energy expenditure," Nature: International Weekly Journal of Science (and Supplementary Information), vol. 454(7207): 1000-1004 (2008).
Tsuchida et al., "Activin isoforms signal through type I receptor serine/threonine kinase ALK7," Molecular and Cellular Endocrinology, 220:59-65 (2004).
Tu et al., "Genetic Disruption of Myostatin Reduces the Development of Proatherogenic Dyslipidemia and Atherogenic Lesions in Ldlr Null Mice," Diabetes, 58:1739-1748 (2009).
Type 2 Diabetes, PubMed Health, Diseases and Conditions, U.S. National Library of Medicine, Bethesda, MD (online), Jun. 28, 2011 [retrieved on Jun. 6, 2012). Retrieved from the Internet:<URL:http://www.ncbi.nlm.nih.gov/pubmedhealth/PMH0001356/>.
Ukkola et al., "Adiponectin: A Link Between Excess Adiposity and Associated Comorbidities?", Journal of Molecular Medicine, 80(11):696-702 (2002).
Utzschneider et al., Review: The Role of Insulin Resistance in Nonalcoholic Fatty Liver Disease, J. Clin. Endocrinol. Metab., 91(12):4753-4761 (Dec. 2006). Epub Sep. 12, 2006.
US Biological Technical Data Sheet for A0856-10A, accessed on Feb. 20, 2013.
US Biological, Activin Receptor Type IIA (RIIA) A0856-05E www.usbio.net/technicalsheet.php?item=A0856-05E dated Jun. 8, 2010.
Vajdos et al., "Comprehensive Functional Maps of the Antigen-binding Site of an Anti-ErbB2 Antibody Obtained with Shotgun Scanning mutagenesis," J. Mol. Biol., vol. 320(2): 415-428 (2002).
Vallet et al., "Activin A promotes multiple myeloma-induced osteolysis and is a promising target for myeloma bone disease," PNAS, 107(11):5124-5129 (2010).
Vidal et al., "Making sense of antisense," European Journal of Cancer, 41:2812-2818 (2005).
Wagner et al., "A Phase I/II trial of MYO-029 in Adult Subjects with Muscular Dystrophy," Ann. Neurol., 63:561-571 (2008).
Wagner et al., "Loss of Myostatin Attenuates Severity of Muscular Dystrophy in mdx Mice," Ann. Neurol., 52:832-836 (2002).
Wagner et al., "Muscle regeneration in the prolonged absence of myostatin," PNAS, 102(7):2519-2524 (2005).
Walsh et al., "Myostatin: a modulator of skeletal-muscle stems cells," Biochemical Society Transactions, 33(Pt.6):1513-1517 (2005).
Wang et al., "A Single Amino Acid Determines Lysophospholipid Specificity of the $S1P_1$(EDG1) and $LPA_1$ (EDG2) Phospholipid Growth Factor Receptors," The Journal of Biological Chemistry, 276(52):49213-49220 (2001).
Wang et al., "GDF-3 is an adipogenic cytokine under high fat dietary condition," Biochemical and Biophysical Research Comm., 321(4):1024-1031 (2004).
Ware, "How I use hydroxyurea to treat young patients with sickle cell anemia," Blood, vol. 115(26): 5300-5311 (2010).
Ward, "An update on disordered iron metabolism and iron overload," Hematology, vol. 15(5): 311-317 (2010).
Weber et al., A slient H-bond can by mutationally activated for high-affinity interaction of BMP-2 and activin type IIB receptor, BMC Structural Biology, 7(6):1-20 (2007).
Wells, "Additivity of Mutational Effects in Proteins," Biochemistry, 29(37):8509-8517 (1990).
Welt et al., "Activin: an endocrine or panacrine agent?," European Journal of Endocrinology 139:469-471 (1998).
Wiater et al., "Inhibin is an Antagonist of Bone Morphogenetic Protein Signaling," The Journal of Biological Chemistry, 278(10):7934-7941 (2003).
Wolfman et al., "Activation of latent myostatin by the BMP-1/tolloid family of metalloproteinases," PNAS, 100(26):15842-15846 (2003).
Wong et al., "Validation parameters for a novel biosensor assay which simultaneously measures serum concentrations of a humanized monoclonal antibody and detects induced antibodies," Journal of Immunological Methods, vol. 209: 1-15 (1997).
Yamato et al., "Induction of apoptosis in Myeloma Cells with Activin A," Japanese Journal of Clinical Hematology; 37th Annual Meeting, Symposium 3, Apoptosis in Blood Disorders, 37:7, pp. 564-567) (2012). (translated).
Yokota et al., "Isolation and characterization of a mouse cDNA clone that expresses mast-cell growth-factor activity in monkey cells," Proc. Natl. Acad. Sci. USA, 81:1070-1074 (1984).
Yu et al., "Specific roles of activin/inhibin in human erythropoiesis in vitro." Annals New York Academy of Sciences, 20(10):1243-1246 (1991).
Yu et al., "Importance of FSH-releasing protein and inhibin in erythrodifferentiation," Nature, 330:765-767 (1987).
Zatz et al., "Serum creatine-kinase (CK) and pyruvate-kinase (PK) activities in Duchenne (DMD) as compared with Becker (BMD) muscular dystrophy," Journal of the Neurological Sciences, vol. 102: 190-196 (1991).
Zhang et al., Effects of Activin A on the Activities of the Mouse Peritoneal Macrophages, Cellular & Molecular Immunology, vol. 2(1): 63-67 ( 2005).
Zhao et al., "Transgenic expression of myostatin propeptide prevents diet-induced obesity and insulin resistance," Biochemical and Biophysical Research Communications, 337:248-255 (2005).
Agapova et al., 2016, "Ligand trap for the activin type IIA receptor protects against vascular disease and renal fibrosis in mice with chronic kidney disease." Kidney Int., 89(6),1231-1243.
Boydstun II. Chronic Kidney Disease in Adolescents. Adolesc. Med. Clin. 2005, 16(1):185-99.
Fang et al., "Early chronic kidney disease-mineral bone disorder stimulates vascular calcification." Kidney International (Jan. 2014), vol. 85, No. 1, pp. 142-150.
Fang et al., 2014, "Treatment of the CKD-MBD with a Ligand Trap for the Activin Receptor Type 2A." Journal of the American Society of Nephrology, Abstract Supplement, Kidney Week 2014; Abstract FR-PO816.
Goodman et al., 2000, "Coronary-artery calcification in young adults with end-stage renal disease who are undergoing dialysis." N. Engl. J. Med., 342(20):1478-83.
Hruska et al., 2014, "Chronic Kidney Disease (CKD) Stimulates Activin and Endothelial to Mesenchymal Transition (EnMT), which Causes Vascular Calcification and Is Inhibited by an Activin Ligand Trap." Journal of the American Society of Nephrology, Abstract Supplement, Kidney Week 2014; Abstract SA-OR063.
International Search Report dated Feb. 11, 2016 for International Patent Application No. PCT/US2015/054674.
Karwowski et al., 2012, "The mechanism of vascular calcification—a systematic review." Med. Sci. Monit, 18(1):RA1-11.
Malluche et al., 2014, "Sotatercept: Initial Signal-Seeking Quantitative Computed Tomography Results for Bone Mass in Hemodialysis Subjects Treated with Escalating Doses: Interim Analysis of ACE-011-REN-001." Journal of the American Society of Nephrology, Abstract Supplement, Kidney Week 2014; Abstract TH-PO602.
Malluche et al., 2015, "The role of activin signaling in the pathogenesis of renal osteodystrophy of ckd-mbd", ERA EDTA Abstract FP406; https://www.abstracts2view.com/era_archive/view.php?nu=ERA15L1_2789&terms=.

(56) References Cited

OTHER PUBLICATIONS

Milliner et al., 1990, "Soft tissue calcification in pediatric patients with end-stage renal disease." Kidney Int. 38(5):931-6.
Smith et al., 2015, "Long-term effects of 3 dose levels of Sotatercept compared with placebo for correction of anemia in hemodialysis subjects: interim analysis of ACE-011-REN-001", ERA EDTA Abstract FP661; https://www.abstracts2view.com/era_archive/view.php?nu=ERA15L1_971&terms=.
Smith et al., 2015, "Quantitative computed tomography results for bone mass and abdominal aortic vascular calcification in hemodialysis subjects treated with escalating dose levels of Sotatercept: interim analysis of ACE-011-REN-001", ERA EDTA Abstract FP661; https://www.abstracts2view.com/era_archive/view.php?nu=ERA15L1_971&terms=.
Sugatani et al., 2017, "Ligand trap of the activin receptor type IIA inhibits osteoclast stimulation of bone remodeling in diabetic mice with chronic kidney disease." Kidney Int., 91(1):86-95.
Written Opinion of the International Searching Authority dated Feb. 11, 2016 for International Patent Application No. PCT/US2015/054674.
International Search Report and Written Opinion dated May 8, 2015 for PCT/US13/68009.
Supplemental European Search Report dated Apr. 26, 2016 for European Pat. App. No. EP 13851864.
"Anemia of chronic disease (Iron-Reutilization Anemia", Internet Citation, 2008: 1-3; retreived from the internet: http://web.archive.org/web/20080610070226/http://www.merc.com/mmpe/sec11/ch130/ch130.htm; retrieved on Aug. 11, 2011.
Abrahams, B. and Ertel, S., 'Acceleron Pharma at Wells Fargo Healthcare Conference—Final', published on Jun. 17, 2014, Fair Disclosure Wire (Quarterly Earnings Reports), Accession No. 32U3101469591FDW.
Acceleron, 'Corporate Overview', considered published in Jul. 31, 2014, Retrieved on Aug. 20, 2015 from the Internet.
Acceleron, "Review of Data Presented at the European Hematology Association 19th Annual Meeting", Jun. 16, 2014, Retrieved from the internet: <files.shareholder.com/downloads/AMDA-23-MZWJ/0x0x762136/20a51a29-0a0f-4a35-965e-4e299efd7d12/v11.
ACTR-11 (149/1): sc-57022, Santa Cruz Biotechnology, Inc.: http://datasheets.scbt.com/sc-57022.pdf, Dated Jun. 3, 2010.
ACTR-11 (D-15): sc-5669, Santa Cruz Biotechnology, Inc.: http://datasheets.scbt.com/sc-5669.pdf, dated Jun. 3, 2010.
ACTR-11 (H-65): sc-25451, Santa Cruz Biotechnology, Inc.: http://datasheets.scbt.com/sc-25451.pdf, dated Jun. 3, 2010.
ACTR-IIA (A-24): sc-130679, Santa Cruz Biotechnology, Inc.: http://datasheets.scbt.com/sc-130679.pdf, dated Jun. 3, 2010.
ACTR-IIA (N-17): sc-5667, Santa Cruz Biotechnology, Inc.: http://datasheets.scbt.com/sc-5667.pdf, dated Jun. 3, 2010.
Akhtari, M., "When to Treat Myelodysplastic Syndromes," Oncology, vol. 25(6): 480-486 (2011).
Anonymous "Ferritin Blood Test: High vs Low Ferritin Levels" www.webmd.com/a-to-z-guides/ferritin?page=2 originally published 2008.
Anonymous, 2013, "Refractory anaemia with ring sideroblasts (MDS-RARS)", Leukemia Foundation, 3 pages (2013).
Anonymous, 2011, MPN Research Foundation; retrieved from the internet at www.mpnresearchfoundation.org/Primary-myelofibrosis.
Attie, et al., "A Phase 1 Study of ACE-536, a Regulator of Erythroid Differentiation, in Healthy Volunteers," American Journal of Hematology, vol. 89(7): 766-770 (2014).
Attisano et al., "Novel activin receptors: distinct genes and alternative mRNA splicing generate a repertoire of serine/threonine kinase receptors", Cell 68: 97-108 (1992).
Baron et al., "Update on bone anabolics in osteoporosis treatment: rationale, current status, and perspectives", J. Clin. Endocrinol. Metab. 97:311-325 (2012).
Barzi, et al., "Myelodysplastic Syndromes: A Practical Approach to Diagnosis and Treatment," Cleveland Clinic Journal of Medicine, vol. 77(1): 37-44 (2010).

Bejar et al. Validation of a prognostic model and the impact of SF3B1, DNMT3A, and other mutations in 289 genetically characterized lower risk MOS patient samples. Abstract. Blood, vol. 118, No. 21. Abstract No. 969. (Nov. 18, 2011 ).
Bennett, et al., "Proposals for the Classification of the Myelodysplastic Syndromes," British Journal of Hematology, vol. 51: 189-199 (1982).
Beutler et al., Williams Hematoloov, 6th Edition. McGraw Hill, p. 561, published 2001.
Bottomley, et al., "Siderbloastic Anemia: Diagnosis and Management," Hematology Oncology Clinic of North America, vol. 28: 653-670 (2014).
Camaschella, C., "Recent Advances in the Understanding of Inherited Sideroblastic Anemia", British Journal of Haematology, vol. 143:27-38 (2008).
Cao, et al., "Recent Advances in Beta-thalassemias," Pediatric Reports, vol. 3(e17): 65-78 (2011).
Carrancio et al. "An activin receptor IIA ligand trap promotes erythropoiesis resulting in a rapid induction of red blood cells and haemoglobin," British Journal of Haematology, vol. 165: 870-882 (2014).
Casadevall, et al., "Health, Economic, and Quality-of-Life Effects of Erythropoietin and Granulocyte Colony-Stimulating Factor for the Treatment of Myelodysplastic Syndromes: A Randomized, Controlled Trial," Blood, vol. 104(2): 321-327 (2014).
Cazzola, et al., "Quantitative Evaluation of Erythropoietic Activity in Dysmyelopoietic Syndromes," British Journal of Hematology, vol. 50: 55-62 (1982).
Cazzola, et al., "The Genetic Basis of Myelodysplasia and Its Clinical Relevance," Blood, vol. 122(25): 4021-4034 (2013).
Chen et al., "Pharmacokinetics and Exposure-Response of Luspatercept in Patients with Anemia Due to Low- or Intermediate-1-Risk Myelodysplastic Syndromes (MDS): Preliminary Results from Phase 2 Studies", Abstract, Blood, 2016, 128:1990; Published Dec. 1, 2016.
Chen et al. Development of Novel Activin-Targeted Therapeutics. Mol Ther. Mar. 2015;23(3):434-44. (Year: 2015).
Chesnais, et al., "Spliceosome Mutations in Myelodysplastic Syndromes and Chronic Myelomonocytic Leukemia," Impact Journals: Oncotarget, vol. 3(11): 1284-1293 (2012).
Cheson, et al., "Clinical Application and Proposal for Modification of the International Working Group (IWG) Response Criteria in Myelodysplasia," Blood, vol. 108(2): 419-425 (2006).
Cheson, et al., "Report of an International Working Group to Standardize Response Criteria for Myelodysplastic Syndromes," Blood, vol. 96(12): 3671-3674 (2000).
Datta-Mannan et al, Addendum to "An Engineered Human Follistatin Variant: Insights into the Pharmacokinetic and Pharmacodynamic Relationships of a Novel Molecule with Broad Therapeutic Potential," The Journal of Pharmacology and Experimental Therapeutics, 1 page (2013).
Dayyani, et al., "Cause of Death in Patients with Lower-Risk Myelodysplastic Syndrome," Cancer, vol. 116: 2174-2179 (2010).
Dieudonne, et al., "Opposite Effects of Osteogenic Protein and Transforming Growth Factor Beta on Chondrogenesis in Cultured Long Bone Rudiments," Journal of Bone and Mineral Research, vol. 9, No. 6: 771-780 (1994).
Dolatshad, et al., "Disruption of SF3B1 Results in Deregulated Expression and Splicing of Key Genes and Pathways in Myelodysplastic Syndrome Hematopoietic Stem and Progenitor Cells," Leukemia, vol. 29: 1092-1103 (2015).
Dong and Blobe, "Role of transforming growth factor-Pin hematologic malignancies," Blood, vol. 107(12): 4589-4596 (2006).
Dore et al., "Serum erythropoietin levels in thalassemia intermedia," Annals of Hematology, vol. 67:183-186 (1993).
Ebert et al., 2010, "Gastrointestinal and hepatic complications of sickle cell disease", Clinical Gastroenterology and hepatology, 8(6):483-9.
Estey, E. H., "Current Challenges in Therapy of Myelodysplastic Syndromes," Current Opinion in Hematology, vol. 10: 60-67 (2003).
GenBank NP 001607.1, Activin A Type II receptor precursor [*Homo sapiens*], http://www.ncbi.nlm.nih.gov/protein/4501897?sat=34&satkey=10571517 (Apr. 22, 2005); downloaded Nov. 24, 2015).

(56) References Cited

OTHER PUBLICATIONS

GenBank Accession No. AAL96263.1 (Mar. 26, 2002).
Galanello, et al., "Combined Iron Chelation Therapy," Annals of the New York Academy of Sciences, vol. 1202: 79-86 (2010).
Garcia-Manero, et al., "Hypomethylating Agents and Other Novel Strategies in Myelodysplastic Syndromes," Journal of Clinical Oncology, vol. 29(5): 516-523 (2011).
Giagounidis et al., "Luspatercept Treatment Leads to Long Term Increases in Hemoglobin and Reductions in Transfusion Burden in Patients with Low or Intermediate-1 Risk Myelodysplastic Syndromes (MDS): Preliminary Results from the Phase 2 PACE-MDS Extension Study", The 57th Annual American Society of Hematology, Dec. 5-8, 2015.
Giagounidis et al., Luspatercept Increases Hemoglobin and Reduces Transfusion Burden in Patients With Lower-Risk Myelodysplastic Syndromes (MDS): Long-Term Results From the Phase 2 PACE-MDS Study. European Hematology Association Congress. Jun. 22-25, 2017.
Giagounidis et al., "Luspatercept Increases Hemoglobin and Reduces Transfusion Burden in Patients With Lower-Risk Myelodysplastic Syndromes (MDS): Long-Term Results From Phase 2 Pace-MDS Study", Abstract, European Hematology Association, Published May 18, 2017.
Giagounidis et al., "Luspatercept Treatment Leads to Long Term Increases in Hemoglobin and Reductions in Transfusion Burden in Patients with Low or Intermediate-1 Risk Myelodysplastic Syndromes (MDS): Preliminary Results from the Phase 2 PACE-MDS Extension Study", Abstract, Blood, 2015, 126:92; Published Dec. 3, 2015.
Giagounidis, et al., "Outcomes in RBC Transfusion-Dependent Patients with Low-/Intermediate-1-Risk Myelodysplastic Syndromes with Isolated Deletion 5q Treated with Lenalidomide: A Subset Analysis from the MDS-004 Study," European Journal of Hematology, vol. 93: 429-438 (2014).
Glaspy, et al., "Impact of Therapy with Epotin Alfa on Clinical Outcomes in Patients with Nonmyeloid Malignancies During Cancer Chemotherapy in Community Oncology Practice," Journal of Clinical Oncology, vol. 15(3): 1218-1234 (1997).
Glaspy, J. A., "Erythropoietin in Cancer Patients," The Annual Review of Medicine, vol. 60: 181-192 (2009).
Goldberg, et al., "Incidence and Clinical Complications of Myelodysplastic Syndromes Among United States Medicare Beneficiaries," Journal of Clinical Oncology, vol. 28(17): 2847-2852 (2010).
Greenberg, et al., "Myelodysplastic Syndromes: Clinical Practice Guidelines in Oncology," Journal of the National Comprehensive Cancer Network, vol. 9(1): 30-56 (2011).
Greenberg, et al., "Treatment of Myelodysplastic Syndrome Patients with Erythropoietin with or without Granulocyte Colony-Stimulating Factor: Results of a Prospective Randomized Phase 3 Trial by the Eastern Cooperative Oncology Group (E1996)," Blood, vol. 114(12): 2393-2400 (2009).
Hellstrom-Lindberg, et al., "A Validated Decision Model for Treating the Anaemia of Myelodysplastic Syndromes with Erythropoietin + Granulocyte Colony-Stimulating Factor: Significant Effects on Quality of Life," British Journal of Haematology, vol. 120: 1037-1046 (2003).
Heuser & Ganser, 2006, "Recombinant human erythropoietin in the treatment of nonrenal anemia", Ann. Hematology, 85:69-78.
Hori, et al., "European Best Practice Guidelines 14-16 Inadequate Response to Epoetin," Nephrology Dialysis Transplantation, vol. 15(Supp. 4): 43-50 (2000).
Itoh et al. Sideroblastic anemia associated with multiple myeloma in Turner's syndrome. Abstract. Internal medicine Tokyo, Japan, vol. 31, No. 4, pp. 483-485 (Apr. 1992).
Jacobs et al., "European Best Practice Guidelines 5 Target haemoglobin," Nephrology Dialysis Transplaantation, vol. 15[Suppl 4]: 15-19 (2000).
Je, et al., "Mutational Analysis of Splicing Machinery Genes SF3B1, U2AF1 and SRSF2 in Myelodysplasia and Other Common Tumors," International Journal of Cancer, vol. 133: 260-266 (2013).
Jelkmann, et al., "The Erythropoietin Receptor in Normal and Cancer Tissues," Critical Reviews in Oncology/Hematology, vol. 67: 39-61 (2008).
Juneja, et al., "Prevalence and Distribution of Ringed Sideroblasts in Primary Myelodysplastic Syndromes," Journal of Clinical Pathology, vol. 36: 566-569 (1983).
Keutmann et al, "The Role of Follistatin Domains in Follistatin Biological Action," Molecular Endocrinology, Jan.; 18(1) pp. 228-240 (2003).
Kalinowski, et al., "The Evolution of Iron Chelators for the Treatment of Iron Overload Disease and Cancer," Pharmacological Reviews, vol. 57(4): 547-583 (2005).
Kantarjian, et al., "Safety and Efficacy of Romiplostim in Patients With Lower-Risk Myelodysplastic Syndrome and Thrombocytopenia," Journal of Clinical Oncology, vol. 28(3): 437-444 (2010).
Kantarjian, et al., "Survival Advantage with Decitabine Versus Intensive Chemotherapy in Patients with Higher Risk Myelodysplastic Syndrome: Comparison with Historical Experience," Cancer, vol. 109(6): 1133-1137 (2007).
Koury, et al., "Erythropoietin Retards DNA Breakdown and Prevents Programmed Death in Erythroid Progenitor Cells," Science, vol. 248: 378-381 (1990).
Krapf, et al., "Arterial Hypertension Induced by Erythropoietin and Erythropoiesis-Stimulating Agents (ESA)," Clinical Journal of the American Society of Nephrology, vol. 4: 470-480 (2009).
Kumar Mishra and Tiwari, "Iron Overload in Beta Thalassaemia Major and Intermedia Patients," MAEDICA—Journal of Clinical Medicine, vol. 8(4): 328-332 (2013).
Leitch, H. A., "Controversies Surrounding Iron Chelation Therapy for MOS," Blood Reviews, vol. 25: 17-31 (2011).
Liboi, et al., "Erythropoietin Receptor Signals Both Proliferation and Erythroid-Specific Differentiation," Proceedings of the National Academy of Sciences, vol. 90: 11351-11355 (1993).
Lin, et al., "NUP98-HOXD13 Transgenic Mice Develop a Highly Penetrant, Severe Myelodysplastic Syndrome that Progresses to Acute Leukemia," Blood, vol. 106(1 ): 287-295 (2005).
List, et al., "Lenalidomide in the Myelodysplastic Syndrome with Chromosome 5q Deletion," The New England Journal of Medicine, vol. 355(14): 1456-1465 (2006).
Liu, et al., "Suppression of Fas-FasL Coexpression by Erythropoietin Mediates Erythroblast Expansion During the Erythropoietic Stress Response In Vivo," Blood, vol. 108(1): 123-133 (2006).
Ikenoue et al., "Inhibitory Effects of Activin-A on Osteoblast Differentiation During Cultures of Fetal Rat Calvarial Cells," Journal of Cellular Biochemistry, 75:206-214 (1999).
Lyons, et al., "Hematologic Response to Three Alternative Dosing Schedules of Azacitidine in Patients with Myelodysplastic Syndromes," Journal of Clinical Oncology, vol. 27(11): 1850-1856 (2009).
Ludwig et al., 1990, "Erythropoietin treatment of anemia associated with multiple myeloma", NEJM, 332, 1693-9.
Lyons, et al., "Comparison of 24-Month Outcomes in Chelated and Non-Chelated Lower-Risk Patients with Myelodysplastic Syndromes in a Prospective Registry," Leukemia Research, vol. 38: 149-154 (2014).
Malcovati et al. Granulocyte JAK2 (V617F) mutation status in myeloid neoplasms with ringed sideroblasts. Abstract. Blood, vol. 108, No. 11, Part 1, pp. 256A (Nov. 16, 2006).
Malcovati, et al., "Clinical Significance of SF3B1 Mutations in Myelodysplastic Syndromes and Myelodysplastic/Myeloproliferative Neoplasms," Blood, vol. 118(24): 6239-6246 (2011).
Malcovati, et al., "Impact of the Degree of Anemia on the Outcome of Patients with Myelodysplastic Syndrome and its Integration into the WHO classification-based Prognostic Scoring System (WPSS)," Haematologica, vol. 96(10): 1433-1440 (2011).
Malcovati, et al., "Prognostic Factors and Life Expectancy in Myelodysplastic Syndromes Classified According to WHO Criteria: A Basis for Clinical Decision Making," Journal of Clinical Oncology, vol. 23(30): 7594-7603 (2005).

(56) References Cited

OTHER PUBLICATIONS

Malcovati, et al., "Refractory Anemia with Ring Sideroblasts," Best Practice & Research . Clinical Haematology, vol. 26: 377-387 (2013).

Martens et al., "Inhibin Interferes with Activin Signaling at the Level of the Activin Receptor Complex in Chinese Hamster Ovary Cells," Endocrinology, vol. 138(7): 2928-2936 (1997).

Martinez et al., RAP-536 (Murine Analog of ACE-536/ Luspatercept) Inhibits SMAD2/3 Signaling and Promotes Erythroid Differentiation by Restoring GATA-1 Function in a Murine Model of Beta-Thalassemia. 21st Congress of the European Hematology Association. Jun. 10, 2016.

Modell et al., 2007, "Epidemiology of haemoglobin disorders in Europe: an overview." Scand J Clin Lab Invest; 67:39-69.

Modell et al., 2008, "Global epidemiology of haemoglobin disorders and derived service indicators." Bull World Health Organ; 86(6):480-7.

Moyo, et al., "Erythropoiesis-Stimulating Agents in the Treatment of Anemia in Myelodysplastic Syndromes: A Meta-Analysis," Annals of Hematolooy, vol. 87: 527-536 (2008).

Mufti, et al, "Diagnosis and Classification of Myelodysplastic Syndrome: International Working Group on Morphology of Myelodysplastic Syndrome (IWGM-MDS) Consensus Proposals for the Definition and Enumeration of Myeloblasts and Ring Sideroblasts," Haematologica, vol. 93(11):1712-1717 (2008).

Murata M, et al. "Expression of erythroid differentiation factor in Chinese hamster ovary cells." Biochem Biophys Res Commun 1988; 151: 230-5.

Musallam et al. "Non-transfusion-dependent thalassemias," Haematologica, Jun. 1, 2013, vol. 98, pp. 833-844.

NCT02604433: An Efficacy and Safety Study of Luspatercept (ACE-536) Versus Placebo in Adults Who Require Regular Red Blood Cell Transfusions Due to Beta (β) Thalassemia (BELIEVE); First Posted: Nov. 13, 2015; Last Update Posted: Nov. 41, 2017 https://clinicaltrials.gov/ct2/show/NCT02604433?term=luspatercept &cond=thalassemia&rank=4 (last visited Apr. 11, 2018).

NCT01571635: Study to Determine the Safety and Tolerability of Sotatercept (ACE-011) in Adults With Beta (β)-Thalassemia; First Posted: Apr. 5, 2012; Last Update Posted: Oct. 25, 2017 https://clinicaltrials.gov/ct2/show/NCT01571635?term=sotatercept&cond= thalassemia&rank= 1 (last visited Apr. 11, 2018).

NCT01749540: Study to Evaluate the Effects of ACE-536 in Patients With Beta-thalassemia; First Posted: Dec. 13, 2012; Last Update Posted: Dec. 14, 2016; https://clinicaltrials.gov/ct2/show/ NCT01749540?term=luspatercept&cond=thalassemia&rank=3 (last visited Apr. 11, 2018).

NCT02268409: ACE-536 Extension Study—Beta Thalassemia; First Posted: Oct. 20, 2014; Last Update Posted: Jan. 9, 2018; https://clinicaltrials.gov/ct2/show/NCT02268409?term=luspatercept&cond= thalassemia&rank =2 (last visited Apr. 11, 2018).

NCT02626689: To Document the Burden of Illness on the Quality of Life and the Impact on Healthcare Utilization in (Beta) β-thalassemia Subjects Who Are Transfusion Dependent (TD) and Nontransfusion Dependent (NTD) Receiving Standard of Care; First Posted: Dec. 10, 2015; Last Update Posted: Apr. 7, 2017 https://clinicaltrials.gov/ct2/show/NCT02626689?term=luspatercept&cond= thalassemia&rank=5 (last visited Apr. 11, 2018).

NCT03342404: A Study to Determine the Efficacy and Safety of Luspatercept in Adults With Non Transfusion Dependent Beta (β)-Thalassemia (BEYOND); First Posted: Nov. 17, 2017; Last Update Posted: Mar. 26, 2018; https://clinicaltrials.gov/ct2/show/ NCT03342404?term=luspatercept&cond=thalassemia&rank=1 (last visited Apr. 11, 2018).

Negrin, et al., "Maintenance Treatment of the Anemia of Myelodysplastic Syndromes with Recombinant Human Granulocyte Colony-Stimulating Factor and Erythropoietin: Evidence for In Vivo Synergy," Blood, vol. 87(10): 4076-4081 (1996).

Nolan, V.G., et al, 'Sickle Cell Leg Ulcers: Associations with Haemolysis and SNPs in Klotho, TEK and Genes of the TGF-Beta-BMP Pathway: Sickle Cell Leg Ulcers, Genetics and Haemolysis', British Journal of Haematology, 133(5), pp. 570-578 (2006).

Oliva, et al., "A Review of Anemia as a Cardiovascular Risk Factor in Patients with Myelodysplastics Syndromes," American Journal of Blood Research, vol. 1 (2): 160-166 (2011).

Ornstein, et al., "Combination Strategies in Myelodysplastic Syndromes," International Journal of Hematology, vol. 95: 26-33 (2012).

Ozcan et al., "Review of therapeutic options and the management of patients with myelodysplastic syndromes," Expert Review Hematol, vol. 6:165-189 (2013).

Pak et al., "Suppression of hepcidin during anemia requires erythropoietic activity," Blood, vol. 108(12): 3730-3735 (2006).

Papaemmanuil et al., "Somatic SF3B1 Mutation in Myelodysplasia with Ring Sideroblasts" The New England Journal of Medicine, vol. 365(15): 1384-1395 (2011).

Park, et al., "Predictive Factors of Response and Survival in Myelodysplastic Syndrome Treated with Erythropoietin and G-CSF: The GFM Experience," Blood, vol. 111 (2): 574-582 (2008).

Pearsall et al., 2007, "The use of a soluble activin receptor type IIa as a novel anabolic agent for treatment of bone loss." Osteoporos Int., 18(Suppl 1):152.

Pennucci et al., Multiplexed evaluation of a cell-based assay for the detection of antidrug neutralilzing antibodies to Panitumumab in human serum using automated fluorescent microsopy,: J. Biomol. Sceen. vol. 15: 644-652 (2010).

Pereria et al. X-linked sideroblasticanemia (XLSA): Two new mutations identified in males. Abstract. Haematologica, vol. 95, Supp. Suppl. 2, pp. 716-717. Abstract No. 1854 (Jun. 2010).

Platzbecker et al., Biomarkers of Ineffective Erythropoiesis Predict Response to Luspatercept in Patients with Low or Intermediate-1 Risk Myelodysplastic Syndromes (MDS): Final Results from the Phase 2 PACE-MDS Study. The 57th Annual American Society of Hematology. Dec. 5-8, 2015.

Platzbecker et al., Luspatercept Increases Hemoglobin and Reduces Transfusion Burden in Patients with Low or Intermediate-1 Risk MDS: Preliminary Results from the Phase 2 Pace-MDS Study. 20th Congress of the European Hematology Association. Jun. 13, 2015.

Platzbecker et al., Oral Presentation: Luspatercept Increases Hemoglobin and Reduces Transfusion Burden in Patients with Low or Intermediate-1 Risk Myelodysplastic Syndromes (MDS): Preliminary Results from a Phase 2 Study. 13th International Symposium on Myelodysplastic Syndromes (MDS). May 2, 2015.

Platzbecker et al., "Luspatercept Increases Hemoglobin and Reduces Transfusion Burden in Patients with Low-Intermediate Risk Myelodysplastic Syndromes (MDS): Long-Term Results from Phase 2 PACE-MDS Study", 21st Congress of the European Hematology Association. Jun. 9-12, 2016.

Platzbecker et al., Luspatercept Response in New Subpopulations of Patients With Lower-Risk Myelodysplastic Syndromes (MDS): Update of the PACE Study. MDS Symposium 2017. May 3-6, 2017.

Platzbecker et al., Luspatercept for the treatment of anaemia in patients with lower-risk myelodysplastic syndromes (PACE-MDS): a multicentre, open-label phase 2 dose-finding study with long-term extension study. The Lancet Oncology 2017. Published online Sep. 1, 2017.

Platzbecker et al., "Luspatercept Increases Hemoglobin and Reduces Transfusion Burden in Patients with Low-Intermediate Risk Myelodysplastic Syndromes (MDS): Long-Term Results from Phase 2 PACE-MDS Study", Abstract, Blood, 2016, 128:3168; Published online Dec. 1, 2016.

Platzbecker et al., "ACE-536 Increases Hemoglobin and Reduces Transfusion Burden in Patients with Low or Intermediate-1 Risk Myelodysplastic Syndromes (MDS): Preliminary Results from a Phase 2 Study", Abstract, Blood, 2014, 124:411; Published online Dec. 4, 2014.

Platzbecker et al., "Mutational Profile and Analysis of Lower-Risk Myelodysplastic Syndromes (MDS) Patients Treated with Luspatercept: Phase 2 PACE-MDS Study", Abstract, Blood, 2017, 130:2982; Published online Dec. 7, 2017.

Platzbecker et al., "Luspatercept response in new subpopulations of patients with lower-risk myelodysplastic syndromes (MDS): update

(56) References Cited

OTHER PUBLICATIONS of the pace study", Abstract, 14th International Symposium on Myelodysplastic Syndromes / Leukemia Research 55 S1 (2017) S8-S36.
Platzbecker et al., "Luspatercept Increases Hemoglobin and Reduces Transfusion Burden in Patients With Low or Intermediate-1 Risk Myelodysplastic Syndromes (MDS): Preliminary Results From the Phase 2 Pace-MDS Study", Abstract, European Hematology Association, Abstract, Published May 21, 2015.
Platzbecker et al., "Luspatercept Increases Hemoglobin and Reduces Transfusion Burden in Patients With Low or Intermediate-1 Risk Myelodysplastic Syndromes (MDS): Preliminary Results From a Phase 2 Study", Abstract, 13th International Symposium on Myelodyspastic Syndromes / Leukemia Research 39 S1 (2015) S1-S166.
Platzbecker et al., "Biomarkers of Ineffective Erythropoiesis Predict Response to Luspatercept in Patients with Low or Intermediate-1 Risk Myelodysplastic Syndromes (MDS): Final Results from the Phase 2 PACE-MDS Study", Abstract, Blood, 2015, 126:2862; Published online Dec. 3, 2015.
Rawn, J., "The Silent Risks of Blood Transfusion," Current Opinion in Anaethesiology, vol. 21: 664-668 (2008).
Reis et al., "Activin, Inhibin and the Human Breast," Molecular and Cellular Edocrinology, 225:77-82 (2004).
Rosenzweig et al., "Cloning and characterization of a human type II receptor for bone morphogenetic proteins," PNAS, 92:7632-7636 (1995).
Rund and Rachmilewitz, "Medical Progress Beta-Thalassemia," N. England J. Medicine, vol. 35: 1135-1146 (2005).
Scullen et al., 2013, "Lenalidomide in combination with an activin A-neutralizing antibody: preclinical rationale for a novel anti-myeloma strategy", 27: 1715-1721.
Sirskyj et al., Detection of influenza A and B neutralizing antibodies in vaccinated ferrets and macaques using specific biotinstreptavidin conjugated antibodies, J. Virol. Methods. vol. 163: 459-464 (2010).
Sun Shuhan et al., "Section 2: Chromosome 11 and Human Diseases", Chromosome, Gene, and Disease, Science Press (2009).
Santini et al., "Hepcidin Levels and Their Determinants in Different Types of Myelodysplastic Syndromes," PLoS One, vol. 6(8): e23109 (2011).
Santini, V., "Clinical Use of Erythropoietic Stimulating Agents in Myelodysplastic Syndromes," The Oncologist, vol. 16 (Supp. 3): 35-42 (2011).
Santini, V., "Treatment of Low-Risk Myelodysplastic Syndrome: Hematopoietic Growth Factors Erythropoietins and Thrombopoietins," Seminars in Hematology, vol. 49(4): 295-303 (2012).
Shen, et al., "DNA Methylation Predicts Survival and Response to Therapy in Patients with Myelodysplastic Syndromes," Journal of Clinical Oncology, vol. 28(4): 605-613 (2010).
Sherman et al., "Multiple-dose, safety, pharmacokinetic, and pharmacodynamic study of sotatercept (ActRIIA-IgG1), a novel erythropoietic agent, in healthy postmenopausal women" J Clin Pharmacol;53:1121-30 (2013).
Slichter, S. J., "Evidence-Based Platelet Transfusion Guidelines," American Society of Hematology Education Program: 172-178 (2007).
Sloand, et al., "Alemtuzumab Treatment of Intermediate-1 Myelodysplasia Patients is Associated with Sustained Improvement in Blood Counts and Cytogenetic Remissions," Journal of Clinical Oncology, vol. 28(35): 5166-5173 (2010).
Socolovsky, et al., "Ineffective Erythropoiesis in Stat5a$^{-/-}$5b$^{-/-}$ Mice Due to Decreased Survival of Early Erythroblasts," Blood, vol. 98(12): 3261-3273 (2001).
Steensma, D. P., "Hematopoietic Growth Factors in Myelodysplastic Syndromes," Seminars in Oncology, vol. 38(5): 635-647 (2011).
Steensma, et al., "The Myelodysplastic Syndromes: Diagnosis and Treatment," Mayo Clinic Proceedings, vol. 81(1): 104-130 (2006).
Steensma, et al., "When is Iron Overload Deleterious, and When and How Should Iron Chelation Therapy Be Administered in Myelodysplastic Syndromes?," Best Practice & Research Clinical Haematology, vol. 26: 431-444 (2013).
Suragani, et al., "Transforming Growth Factor-β Superfamily Ligand Trap ACE-536 Corrects Anemia by Promoting Late-Stage Erythropoiesis," Nature Medicine, vol. 20(4): 408-417 (2014).
Temraz, et al., "Iron Overload and Chelation Therapy in Myelodysplastic Syndromes," Critical Reviews in Oncology/Hematology, vol. 91: 64-73 (2014).
Terpos et al., "Prolonged Administration of Erythropoietin Increases Response Rate in Myelodysplastic Syndromes: a Phase II Trial in 281 Patients", British Journal of Haematology, vol. 118(1):174-180 (2002).
Thein SL, 2013, "The molecular basis of β-thalassemia", Cold Spring Harb Perspect Med;3(5):a011700.
Vardiman, et al., "The 2008 Revision of the World Health Organization (WHO) Classification of Myeloid Neoplasms and Acute Leukemia: Rationale and Important Changes," Blood, vol. 114(5): 937-951 (2009).
Vogiatzi et al., "Bone Disease in Thalassemia: A Frequent and Still Unresolved Problem," Journal of Bone and Mineral Research, vol. 24: 543-557 (2008).
Walker et al., 2017, "Structural basis for potency differences between GDF8 and GDF11", BMC Biol. 2017, 15(1):19.
Wang, et al., "SF3B1 and Other Novel Cancer Genes in Chronic Lymphocytic Leukemia," The New England Journal of Medicine, vol. 365(26): 2497-2506 (2011).
Weatherall, et al., "Red Cells I: Inherited Anaemias," The Lancet, vol. 355: 1169-1175 (2000).
Webb, et al., "The Development and Application of Small Molecule Modulators of SF3b as Therapeutic Agents for Cancer," Drug Discovery Today, vol. 18(1-2): 43-49 (2013).
Yamashita et al., "Osteogenic protein-1 binds to activin type II receptors and induces certain activin-like effects." J. Cell Biol. 130:217-226 (1995).
Yeo and Whitman, "Nodal signals to SMADs through Cripto-dependent and Cripto-independent mechanisms," Mol. Cell 7: 949-957 (2001).
Zeidan, et al., "There's Risk, and Then There's RISK: the Latest Clinical Prognostic Risk Stratification Models in Myelodysplastic Syndromes," Current Hematologic Malignancy Reports, vol. 8: 351-360 (2013).
The Cancer Genome Atlas Network, "Comprehensive Molecular Portraits of Human Breast Tumours." Nature, vol. 490: 61-70 (2012).
Bejar, et al., "Recent Developments in Myelodysplastic Syndromes," Blood, vol. 124(18): 2793-2803 (2014).
Chen et al., "Pharmacokinetics and Exposure-Response of Luspatercept in Patients With Anemia Due to Low- or Intermediate-1-Risk Myelodysplastic Syndromes (MDS): Preliminary Results From Phase 2 Studies." ASH 2016. Dec. 4, 2016.
Colah et al., 2010; "Global burden, distribution and prevention of β-thalassemias and hemoglobin E disorders." Expert Rev Hematol; 3(1):103-17.
Davidoff, et al., "Patterns of Erythropoiesis-Stimulating Agent Use Among Medicare Beneficiaries with Myelodysplastic Syndromes and Consistency with Clinical Guidelines," Leukemia Research, vol. 37: 675-680 (2013).
Esposito, et al., "Labile Plasma Iron in Iron Overload: Redox Activity and Susceptibility to Chelation," Blood, vol. 102(7): 2670-2677 (2003).
Fenaux, et al., "Efficacy of Azacitidine Compared with that of Conventional Care Regimens in the Treatment of Higher-Risk Myelodysplastic Syndromes: A Randomised, Open-Label, Phase III Study," Lancet: Oncol. vol. 10: 223-232 (2009).
Komaba et al., 2008, "Treatment of chronic kidney disease-mineral and bone disorder (CKD-MBD)", Internal Medicine:989-994; retreived from the internet at <www.jstage.jst.go.jp/article/internalmedicine/47/11/47_11_989/_pdf/-char-en>.
Gregory and Kaiser, 2004, "Regulation of gonadotropins by inhibin and activin", Semin. Reprod. Med., 22(3):253-267.
Klimka et al., 2000, "Human anti-CD30 recombinant antibodies by guided phage antibody selection using cell panning", British J. of Cancer, 83:252-260.

(56) References Cited

OTHER PUBLICATIONS

Malcovati et al., 2009, "Molecular and clinical features of refractory anemia with ringed sideroblasts associated with marked thrombocytosis", Blood, 114(17):3538-3545.
Mariuzza et al, 1987, "The structural basis of antigen-antibody recognition", Ann. Rev. Biophys., 16:139-159.
Martinez et al., RAP-536 (Murine ACE-536/Luspatercept) Inhibits Smad2/3 Signaling and Promotes Erythroid Differentiation by Restoring GATA-1 Function in Murine beta-Thalassemia. The 57th Annual American Society of Hematology. Dec. 7, 2015.
Murphy et al., 2009, "Serum erythropoietin at diagnosis in low grade myelodysplastic syndrome correleates with both redd cell zinc protoporphyrin and serum lactic dehydrogenase (LDH) and may reflect severity of ineffecive erythropeiesis", Leukemia & Lymphoma, 50(6): 1036-1038.
Piga et al., Luspatercept Decreases Transfusion Burden and Liver Iron Concentration in Regularly Transfused Adults with Beta-Thalassemia. 21st Congress of the European Hematology Association. Jun. 12, 2016.
Piga et al., Luspatercept Increases Hemoglobin and Decreases Transfusion Burden in Adults With Beta-Thalassemia. European Hematology Association Congress. Jun. 23, 2017.
Piga et al., Luspatercept (ACE-536) Increases Hemoglobin and Decreases Transfusion Burden and Serum Ferritin in Adults with Beta-Thalassemia: Preliminary Results from a Phase 2 Study. 56th American Society of Hematology Annual Meeting and Exposition. Dec. 7, 2014.
Piga et al., Luspatercept Increases Hemoglobin, Decreases Transfusion Burden, and Improves Patient-Reported Outcomes in Adults with Beta-Thalassemia. ASH 2016. Dec. 5, 2016.
Piga et al., Luspatercept Increases Hemoglobin, Reduces Liver Iron Concentration and Improves Quality of Life in Non-Transfusion Dependent Adults with Beta-Thalassemia. Congress of the European Hematology Association. Jun. 11, 2016.
Suragani et al., 2014, "Modified ActRIIb-mFc Fusion Protein (murine ortholog of Luspatercept) Mitigates Sickling and Red Cell Pathology in a Murine Model of Sickle Cell Disease", retrieved from the internet: http://acceleronpharma.com/wp-content/uploads/2017/03/20141208-RAP-536-SCD-ASH-2014-Final-poster1-2.jpg.
Poulaki et al., 2004, "Activin A in the regulation of corneal neovascularization and vascular endothelial growth factor expression", Amer. J. of Pathology, 164(4):1293-1302.
R&D Systems, "Antibody Reference Guide and Catalog Instructions," [retrieved on Feb. 13, 2013]; retrieved from the internet at http://web.archive.org/web/20090220022132/https://rndsystems.com/DAM_public/5658.pdf published Mar. 14, 2009 as per the Wayback Engine. See, in particular: p. 3.
Raya et al., 2008, "Refractory anemia with ringed sideroblasts associated with thrombocytosis: comparative analysis of marked with non-marked thromobocytosis, and relationship with JAK2 V617F mutational status." Int. J. Hematol. 88:387-395.
Rudikoff et al., 1982, "Single amino acid substitution altering antigen-binding specificity", Proc. Natl. Acad. Sci., 79:1979-1983.
Sapitro et al., 2010, "Suppression of transforming growth factor-beta effects in rabbit subconjunctival fibroblasts by activin receptor-like kinase 5 inhibitor", Molecular Vision, 16:1880-1892.
Tanno et al., 2007, "High levels of GDF15 in thalassemia suppress expression of the iron regulatory protein hepcidin", Nat. Med. 13:1096-1101.
YIP, 2000, "Significance of an abnormally low or high hemoglobin concentration during pregnancy: special consideration of iron nutrition", Am J Clin Nutr, 72(Suppl):272S-9S.
Andrades, et al., "Selection and amplification of a bone marrow cell population and its induction to the chondro-ostenogenic lineage by rhOP-1: an in vitro and in vivo study," Int. J. Dev. Biol. 45: 689-693 (2001).
Beiboer et al., 2000, "Guided selection of a Pan Carcinoma Specific Antibody Reveals Similar Binding Characteristics yet Structural Divergence between the Original Murine Antibody and its Human Equivalent", J. Mol. Biol., 296(833-849).
Bradley et al., 2008, "Visions & Reflections (minireview) myostatin as a therapeutic target for muscoloskeletal disease", Cellular and Molecular Life Sciences, 65: 2119-2124.
Cesari et al., 2005, "Bone density and hemoglobin levels in older person: results from the InCHIANTI study", Osteoporosis Int., 16:691-699.
Iancu-Rubin et al, 2013, "Stromal cell-mediated inhibition of erythropoiesis can be attentuated by Sotatercept (ACE-011), an activin receptor type II ligand trap", Exp. Hematol., 41:155-166.
Li et al., "Transgenic overexpression of bone morphogenetic protein 11 propeptide in skeleton enhances bone formation", Biochem. Biophys. Res. Comm. 416:289-292 (2011).
Makanji et al., "Generation of a specific activin antagonist by modification of the activin A propeptide", Endocrinol. 152:3758-3768 (2011).
Marks-Bluth et al., "Cell signalling pathways that mediate haematopoietic stem cell specification", Int. J. Biochem. Cell Biol. 44:2175-2184 (2012).
O'Neill et al., 2010, "Recent progress in the treatment of vascular calcification", Kidney International, 78(12):1232-1239.
Platzbecker et al., "Mutational Profile and Analysis of Lower-Risk Myelodysplastic Syndromes (MDS) Patients Treated with Luspatercept: Phase 2 PACE-MDS Study." American Society of Hematology . Dec. 9-12, 2017.
Platzbecker et al., "Luspatercept Increases Hemoglobin and Reduces Transfusion Burden in Patients With Low-Intermediate Risk Myelodysplastic Syndromes (Mds): Long-Term Results From Phase 2 Pace?Mds Study", Abstract, European Hematology Association, Published May 19, 2016.
Ribeil et al., 2013, "Ineffective erythropoiesis in beta-thalassemia", Scientific World J., 2013:394295.
Stark et al., 2007, "Polycythemia and increased erythropoietin in a patient with chronic kidney disease", Nat Clin Pract Nephrol, 3(4):222-226.
Suragani et al., 2014, "Modified ACTRIIB-Fc Fusion Protein (ACE-536) Decreases Irreversible Sickle Cells in a Murine Model of Sickle Cell Disease", retreived from the internet: <acceleronpharma.com/wp-content/uploads/2017/03/20140614-ACE-536-20140613-modified-AcctRIIB-Fc-Fusion-Protein-Decreases-Irreversible-Sickle-Cells-in-a-Murine-Model-of-1.pdf.
Siah, et al., "Normal Iron Metabolism and the Pathophysiology of Iron Overload Disorders," The Clinical Biochemist Reviews, vol. 27: 5-16 (2006).
Steinbicker et al., "Inhibition of bone morphogenetic protein signaling attenuates anemia associated with inflammation", Blood 117:4915-4923 (2011).
Whatley, et al., "C-Terminal Deletions in the ALAS2 Gene Lead to Gain of Function and Cause XLinked Dominant Protoporphyria Without Anemia or Iron Overload", American Journal of Human Genetics, vol. 83:408-414 (2008).
Yamawaki et al., "Adult-specific systemic over-expression reveals novel in vivo effects of the soluble forms of ActRIIA, ActRIIB and BMPRII", PLoS One 8(10):e78076 (2013).
Platzbecker et al., Luspatercept Increases Hemoglobin and Reduces Transfusion Burden in Patients with Low-Intermediate Risk Myelodysplastic Syndromes (MDS): Long-Term Results from Phase 2 PACE-MDS Study. ASH 2016. Dec. 6, 2016.
Longo et al., "Therapeutic approaches to myeloma bone disease: an evolving story", Cancer Treat Rev. 38:787-797 (2012).
Suragani et al., Modified Activin Receptor IIB Ligand Trap Mitigates Ineffective Erythropoiesis and Disease Complications in Murine Beta-Thalassemia. Blood 2014. vol. 123 No. 25, Jun. 19, 2014.
Demetri, et al., "Quality-of-life Benefit in Chemotherapy Patients Treated With Epoetin Alfa Is Independent of Disease Response or Tumor Type: Results From a Prospective Community Oncology Study," Journal of Clinical Oncology, vol. 16(10): 3412-3425 (1998).
Djaldetti et al., 1975, "Erythropoietin effects on fetal mouse erythroud cells. II. Nucleic acid synthesis and the erythropeietin-sensitive cell", J. Biol. Chem. 247:731-735.
Ferrara et al., 2015, "Recombinant renewable polyclonal antibodies", mAbs 7:1, 32-41.

(56) References Cited

OTHER PUBLICATIONS

Weatherall DJ, 2001, "Phenotype-genotype relationships in monogenic disease: lessons from the thalassaemias", Nature Reviews Genetics; 2(4):245-255.

Wooldridge et al., 2012, "The pharmacokinetics and safety of a single dose of sottercept (ACE-011), in subjects on hemodialysis and the effects of its murine analog (RAP-011) on anemia and in preventing bone loss in C57B/6 mice with 5/6 nephrectomy", J. Am Soc Nephrol, 23:page abstract SA-OR87.

Mallat et al., "Potential mechanisims for renal demage in beta-thalassemia," J. Nephrol, vol. 26(5): 821-828 (2013).

Piga et al., "ACE-536 Increases Hemoglobin and Decreases Transfusion Burden and Serum Ferritin in Adults with Beta-Thalassemia: Preliminary Results from a Phase 2 Study", Blood, vol. 124(21): p. 53 (2014).

Biankin, et al., "Pancreatic Cancer Genomes Reveal Aberrations in Axon Guidance Pathway Genes," Nature, vol. 491: 399-405 (2012).

Halpern et al., 2006, "Anemia, costs and mortality in chronic obstructive pulmonary disease", Cost Effectiveness and Resource Allocation, 4:17-24.

Kirsch et al., 2000, "BMP-2 antagonists emerge from alterations in the low-affinity binding epitope for receptor BMPR-II", Embo (EP molecular biology organization) Journal, Wiley, DE, 19(13):3314-3324.

McPHERRON, "Metabolic Functions of Myostatin and GDF11", Immunol. Endocr. Metab. Agents Med. Chem. 10:217-231 (2010).

Mulivor et al., "RAP-011, a soluble activin receptor type IIa murine IgG-Fc fusion protein, prevents chemotherapy induced anemia", 51st ASH Annual Meeting, Dec. 6, 2009.

NCT01190644 "A phase 2 open-label, pharmacodynamic study to evaluate the effect of Sotatercept (ACE-011) on red blood cell mass and plasma volume in subjects with solid tumors", Aug. 14, 2012.

NCT01712308 A phase 2, prospective, open-label study to determine the safety and efficacy of Sotatercept (ACE-011) in subjects with myeloproliferative neoplasm (MPN)-associated myelofibrosis and anemia. Oct. 22, 2012.

Furney, et al., "SF3B1 Mutations Are Associated with Alternative Splicing in Uveal Melanoma," Cancer Discovery, vol. 3(10): 1122-1129 (2013).

Dussiot et al., "Modulation of activin signaling by RAP-011 (ActRIIA-IgG1) improves anemia, increases hemoglobin levels and corrects ineffective erythropoiesis in beta-thelassemia", 54th ASH Annual Meeting, Dec. 10, 2012.

Quinglie et al., 2007, "Prevention of cachexia-like syndrome development and reduction of tumor progression in inhibin-deficient mice following administration of a chimeric activin receptor type-II-murine Fc protein", Molecular Human Reproduction, 13(9):675-683.

Cappellini et al., A Phase 2a, Open-Label, Dose-Finding Study to Determine the Safety and Tolerability of Sotatercept (ACE-011) in Adults With Beta-Thalassemia: Interim Results. Blood 2013. vol. 122, Dec. 9, 2013.

* cited by examiner

ACTIVIN-ACTRII ANTAGONISTS AND USES FOR TREATING BONE AND OTHER DISORDERS

This application is a national stage entry of International Patent Application No. PCT/US2013/068009, filed Nov. 1, 2013, which claims priority benefit of U.S. Provisional Patent Application No. 61/721,898, filed Nov. 2, 2012 and U.S. Provisional Patent Application No. 61/740,665, filed Dec. 21, 2012, the disclosures of each of which are herein incorporated by reference in their entireties.

This invention was made with Government support under Grant Nos. DK070790 and DK089137, awarded by the National Institutes of Health. The Government has certain rights in the invention.

1. INTRODUCTION

Provided herein are methods for the treatment of bone disorders that are associated with kidney disease, such as chronic kidney disease-mineral and bone disorder ("CKD-MBD"), wherein the methods comprise administration of Activin-ActRII inhibitors to a subject in need of the treatment. Also provided herein are methods and compositions for the treatment of low turnover bone disorders wherein the methods comprise administration of Activin-ActRII inhibitors to a subject in need of the treatment. Also provided herein are compositions for the treatment of bone disorders that are associated with kidney disease and compositions for the treatment of low turnover bone disorders and vascular calcification.

2. BACKGROUND

Bone growth and mineralization are dependent on the activities of two cell types, osteoclasts and osteoblasts, although chondrocytes and cells of the vasculature also participate in critical aspects of these processes. Developmentally, bone formation occurs through two mechanisms, endochondral ossification and intramembranous ossification, with the former responsible for longitudinal bone formation and the later responsible for the formation of topologically flat bones, such as the bones of the skull. Endochondral ossification requires the sequential formation and degradation of cartilaginous structures in the growth plates that serve as templates for the formation of osteoblasts, osteoclasts, the vasculature and subsequent mineralization. During intramembranous ossification, bone is formed directly in the connective tissues. Both processes require the infiltration of osteoblasts and subsequent matrix deposition.

Chronic kidney disease is associated with a progressive deterioration in mineral homeostasis, with a disruption of normal serum and tissue concentrations of phosphorus and calcium, and changes in circulating hormones, such as parathyroid hormone, 25-hydroxyvitamin D, 1,25-dihydroxyvitamin D, other vitamin D metabolites, fibroblast growth factor-23, and growth hormone. See, Chronic Kidney Disease-Mineral and Bone Disorder (CKD-MBD), Kidney Disease: Improving Global Outcomes (KDIGO) CKD-MBD Work Group, In: Kidney Int Suppl. (2009) 76 (Suppl 113):S1-130, page S3. The mineral and hormone homeostasis that is disrupted in chronic kidney disease is critical for initial bone formation during growth (bone modeling) and bone structure and function during adulthood (bone remodeling). As a result, bone abnormalities are found in patients with chronic kidney disease. In addition, similarly due to the disruption in mineral and endocrine functions, extraskeletal calcification may be found in patients with chronic kidney disease. These syndromes are termed chronic kidney disease-related mineral and bone disorders ("CDK-MBD").

Bone undergoes continuous turnover. Bone turnover is the process of resorption followed by replacement of bone. Osteoblasts and osteoclasts are the cells necessary for bone turnover. Low turnover and adynamic bone diseases are characterized by reduced or absent resorption and replacement of bone. CKD-MBD can be characterized by low turnover or adynamic bone. (Chronic Kidney Disease-Mineral and Bone Disorder (CKD-MBD), Kidney Disease: Improving Global Outcomes (KDIGO) CKD-MBD Work Group, In: Kidney Int Suppl. (2009) 76 (Suppl 113):S1-130, page S34).

Increased calcium levels in the vasculature can lead to vascular calcification, a condition characterized by increased vessel stiffening. Patients with vascular calcification have an increased risk of myocardial infarction, and vascular calcification is particularly prevalent in patients suffering from kidney disease, e.g., CKD-MBD. See, e.g., Shanahan et al., 2011, Circ. Res. 109:697-711.

Two related type II receptors, ActRIIA and ActRIIB, have been identified as the type II receptors for activins (Mathews and Vale, 1991, Cell 65:973-982; Attisano et al., 1992, Cell 68: 97-108). Besides activins, ActRIIA and ActRIIB can biochemically interact with several other TGF-beta family proteins, including BMP7, Nodal, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell 7: 949-957; Oh et al., 2002, Genes Dev. 16:2749-54). ALK4 is the primary type I receptor for activins, particularly for activin A, and ALK-7 may serve as a receptor for activins as well, particularly for activin B.

3. SUMMARY

In certain embodiments, provided herein are methods for treating an adynamic bone disorder in a subject, wherein the method comprises administering a therapeutically effective amount of an ActRII inhibitor to a subject in need of treatment of the adynamic bone disorder. Further provided herein are methods for treating an adynamic bone disorder form of CKD-MBD in a subject, wherein the method comprises administering a therapeutically effective amount of an ActRII inhibitor to a subject in need of treatment of the adynamic bone disorder form of CKD-MBD.

In certain more specific embodiments, the adynamic bone disorder is characterized by absence of tetracycline incorporation into mineralized bone.

In certain embodiments, provided herein are methods for treating a low bone turnover form of CKD-MBD in a subject, wherein the method comprises administering a therapeutically effective amount of an ActRII inhibitor to a subject in need of treatment of the low bone turnover form of CKD-MBD. In a more specific embodiment, the low bone turnover form of CKD-MBD is osteomalacia.

In certain embodiments, provided herein are methods for treating a bone disorder characterized by hyperphosphatemia in a subject, wherein the method comprises administering a therapeutically effective amount of an ActRII inhibitor to a subject in need of treatment of the bone disorder characterized by hyperphosphatemia.

In certain embodiments, provided herein are methods for treating atherosclerotic calcification in a subject, wherein the method comprises administering a therapeutically effective amount of an ActRII inhibitor to a subject in need of treatment of atherosclerotic calcification.

In certain embodiments, provided herein are methods for treating a renal disease in a subject, wherein the method comprises administering a therapeutically effective amount of an ActRII inhibitor to a subject in need of treatment of the renal disease. In a more specific embodiment, the renal disease is renal fibrosis.

In a specific embodiment, provided herein is a method for treating extraskeletal calcification in a subject, wherein said method comprises administering a therapeutically effective amount of an ActRII inhibitor to the subject. In another specific embodiment, provided herein is a method for preventing extraskeletal calcification in a subject, wherein said method comprises administering a therapeutically effective amount of an ActRII inhibitor to the subject. In specific embodiments, the extraskeletal calcification treated or prevented in a subject by the methods described herein is vascular calcification, i.e., the accumulation of calcium salts in the vasculature of the subject, e.g., calcification of arteries of the subject.

In certain embodiments, the ActRII inhibitor that can be used with the methods provided herein is a polypeptide comprising an amino acid sequence selected from the group consisting of: 90% identical to SEQ ID NO:2; 95% identical to SEQ ID NO:2; 98% identical to SEQ ID NO:2; SEQ ID NO:2; 90% identical to SEQ ID NO:3; 95% identical to SEQ ID NO:3; 98% identical to SEQ ID NO:3; SEQ ID NO:3; 90% identical to SEQ ID NO:6; 95% identical to SEQ ID NO:6; 98% identical to SEQ ID NO:6; SEQ ID NO:6; 90% identical to SEQ ID NO:7; 95% identical to SEQ ID NO:7; 98% identical to SEQ ID NO:7; SEQ ID NO:7; 90% identical to SEQ ID NO:12; 95% identical to SEQ ID NO:12; 98% identical to SEQ ID NO:12; SEQ ID NO:12; 90% identical to SEQ ID NO:17; 95% identical to SEQ ID NO:17; 98% identical to SEQ ID NO:17; SEQ ID NO:17; 90% identical to SEQ ID NO:20; 95% identical to SEQ ID NO:20; 98% identical to SEQ ID NO:20; SEQ ID NO:20; 90% identical to SEQ ID NO:21; 95% identical to SEQ ID NO:21; 98% identical to SEQ ID NO:21; and SEQ ID NO:21. In a more specific embodiment, the ActRII inhibitor is a polypeptide comprising the amino acid sequence of SEQ ID NO:7. In a more specific embodiment, the ActRII inhibitor is administered parentally.

In a specific embodiment, the ActRII inhibitor that can be used with the methods provided herein is an ActRIIA inhibitor, wherein the ActRIIA inhibitor comprises or consists of a polypeptide selected from the group consisting of: a. a polypeptide at least 90% identical to SEQ ID NO:2; b. a polypeptide at least 95% identical to SEQ ID NO:2; c. a polypeptide at least 98% identical to SEQ ID NO:2; d. SEQ ID NO:2; e. a polypeptide at least 90% identical to SEQ ID NO:3; f. a polypeptide at least 95% identical to SEQ ID NO:3; g. a polypeptide at least 98% identical to SEQ ID NO:3; h. SEQ ID NO:3; i. a polypeptide at least 90% identical to SEQ ID NO:6; j. a polypeptide at least 95% identical to SEQ ID NO:6; k. a polypeptide at least 98% identical to SEQ ID NO:6; l. SEQ ID NO:6; m. a polypeptide at least 90% identical to SEQ ID NO:7; n. a polypeptide at least 95% identical to SEQ ID NO:7; o. a polypeptide at least 98% identical to SEQ ID NO:7; p. SEQ ID NO:7; q. a polypeptide at least 90% identical to SEQ ID NO:12; r. a polypeptide at least 95% identical to SEQ ID NO:12; s. a polypeptide at least 98% identical to SEQ ID NO:12; and t. SEQ ID NO:12. In a specific embodiment, the ActRIIA inhibitor is a polypeptide comprising or consisting of the amino acid sequence of SEQ ID NO:7.

In another specific embodiment, the ActRII inhibitor that can be used with the methods provided herein is an ActRIIB inhibitor, wherein the ActRIIB inhibitor comprises or consists of a polypeptide selected from the group consisting of: a. a polypeptide at least 90% identical to SEQ ID NO:17, 18, 23, 26, 27, 29, 30, 31, 32, 33, 36, 37, 42, or 43; b. a polypeptide at least 95% identical to SEQ ID NO:17, 18, 23, 26, 27, 29, 30, 31, 32, 33, 36, 37, 42, or 43; c. a polypeptide at least 98% identical to SEQ ID NO:17, 18, 23, 26, 27, 29, 30, 31, 32, 33, 36, 37, 42, or 43; d. SEQ ID NO:17, 18, 23, 26, 27, 29, 30, 31, 32, 33, 36, 37, 42, or 43; e. a polypeptide 90% identical to SEQ ID NO:20, 21, 24, 25, 34, 35, 38, 39, 40, 41, 44, 46, or 47; f. a polypeptide 95% identical to SEQ ID NO:20, 21, 24, 25, 34, 35, 38, 39, 40, 41, 44, 46, or 47; g. a polypeptide 98% identical to SEQ ID NO:20, 21, 24, 25, 34, 35, 38, 39, 40, 41, 44, 46, or 47; and h. SEQ ID NO:20, 21, 24, 25, 34, 35, 38, 39, 40, 41, 44, 46, or 47. In a specific embodiment, the ActRIIB inhibitor is a polypeptide comprising or consisting of SEQ ID NO:23. In another specific embodiment, the ActRIIB inhibitor is a polypeptide comprising or consisting of SEQ ID NO:25.

In another specific embodiment, an ActRIIA inhibitor and an ActRIIB inhibitor can be used in the methods provided herein (e.g., a composition comprising an ActRIIA inhibitor and an ActRIIB inhibitor can be used; or an ActRIIA inhibitor and an ActRIIB inhibitor can both be administered, separately, to a subject being treated in accordance with the methods described herein), wherein the ActRIIA inhibitor comprises or consists of a polypeptide selected from the group consisting of: a. a polypeptide at least 90% identical to SEQ ID NO:2; b. a polypeptide at least 95% identical to SEQ ID NO:2; c. a polypeptide at least 98% identical to SEQ ID NO:2; d. SEQ ID NO:2; e. a polypeptide at least 90% identical to SEQ ID NO:3; f. a polypeptide at least 95% identical to SEQ ID NO:3; g. a polypeptide at least 98% identical to SEQ ID NO:3; h. SEQ ID NO:3; i. a polypeptide at least 90% identical to SEQ ID NO:6; j. a polypeptide at least 95% identical to SEQ ID NO:6; k. a polypeptide at least 98% identical to SEQ ID NO:6; l. SEQ ID NO:6; m. a polypeptide at least 90% identical to SEQ ID NO:7; n. a polypeptide at least 95% identical to SEQ ID NO:7; o. a polypeptide at least 98% identical to SEQ ID NO:7; p. SEQ ID NO:7; q. a polypeptide at least 90% identical to SEQ ID NO:12; r. a polypeptide at least 95% identical to SEQ ID NO:12; s. a polypeptide at least 98% identical to SEQ ID NO:12; and t. SEQ ID NO:12; and wherein the ActRIIB inhibitor comprises or consists of a polypeptide selected from the group consisting of: a. a polypeptide at least 90% identical to SEQ ID NO:17, 18, 23, 26, 27, 29, 30, 31, 32, 33, 36, 37, 42, or 43; b. a polypeptide at least 95% identical to SEQ ID NO:17, 18, 23, 26, 27, 29, 30, 31, 32, 33, 36, 37, 42, or 43; c. a polypeptide at least 98% identical to SEQ ID NO:17, 18, 23, 26, 27, 29, 30, 31, 32, 33, 36, 37, 42, or 43; d. SEQ ID NO:17, 18, 23, 26, 27, 29, 30, 31, 32, 33, 36, 37, 42, or 43; e. a polypeptide 90% identical to SEQ ID NO:20, 21, 24, 25, 34, 35, 38, 39, 40, 41, 44, 46, or 47; f. a polypeptide 95% identical to SEQ ID NO:20, 21, 24, 25, 34, 35, 38, 39, 40, 41, 44, 46, or 47; g. a polypeptide 98% identical to SEQ ID NO:20, 21, 24, 25, 34, 35, 38, 39, 40, 41, 44, 46, or 47; and h. SEQ ID NO:20, 21, 24, 25, 34, 35, 38, 39, 40, 41, 44, 46, or 47. In a specific embodiment, the ActRIIA inhibitor is a polypeptide comprising or consisting of SEQ ID NO:7 and the ActRIIB inhibitor is a polypeptide comprising or consisting of SEQ ID NO:23. In another specific embodiment, the ActRIIA inhibitor is a polypeptide comprising or consisting of SEQ ID NO:7 and the ActRIIB inhibitor is a polypeptide comprising or consisting of SEQ ID NO:25.

In certain embodiments, the subject to be treated with the methods provided herein is less than 18 years old. In certain embodiments, the subject to be treated with the methods provided herein has end stage renal disease. In certain embodiments, the subject to be treated with the methods provided herein undergoes dialysis. In certain embodiments, provided herein is a method to increase the height of the subject.

In certain embodiments, provided herein are methods for treating or preventing hyperphosphatemia, secondary hyperparathyroidism (due to increase in phosphorus), extraskeletal calcification, e.g., vascular calcification, and adynamic bone disorder in a subject, wherein the method comprises administering a therapeutically effective amount of an ActRII inhibitor to a subject in need of treatment of hyperphosphatemia, secondary hyperparathyroidism (due to increase in phosphorus), extraskeletal calcification, e.g., vascular calcification, and adynamic bone.

4. BRIEF DESCRIPTION OF THE FIGURES

FIG. 1: Mouse body weight following partial nephrectomy.

Figure 2:
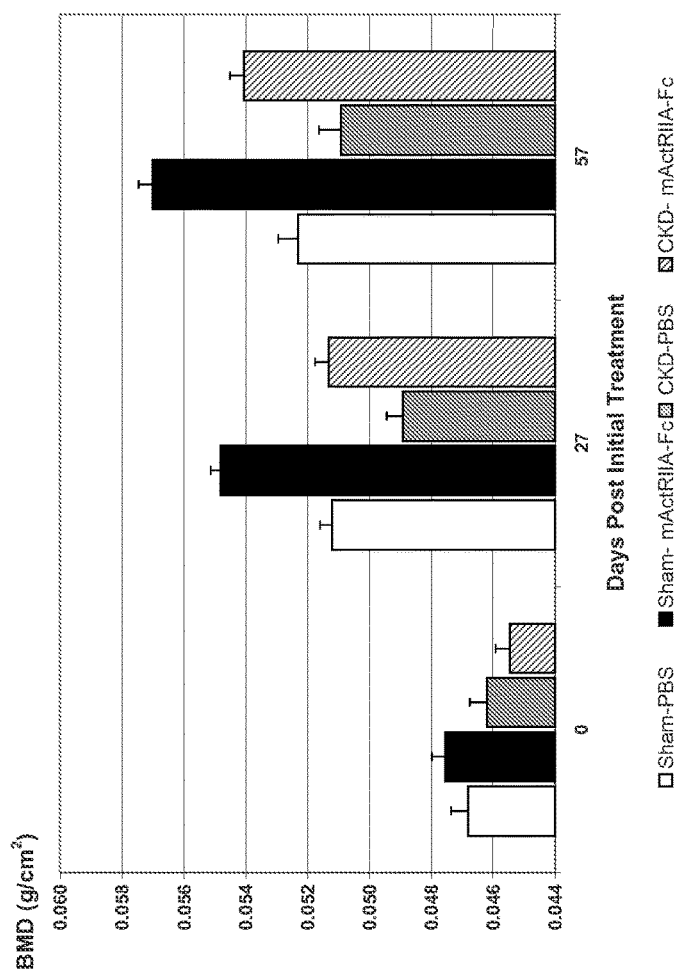

FIG. 2: Changes in BMD by DEXA Scan following partial nephrectomy in mice.

Figure 3:
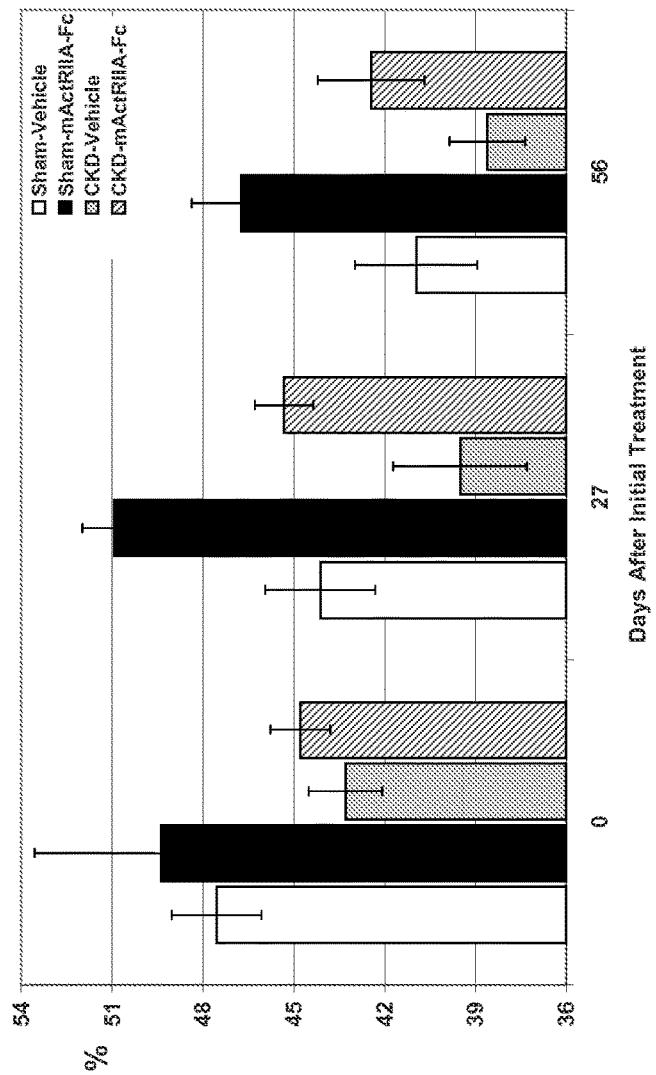

FIG. 3: The murine counterpart of SEQ ID NO 7 ("mActRIIA-Fc") hematocrit changes following partial nephrectomy in mice.

Figure 4:
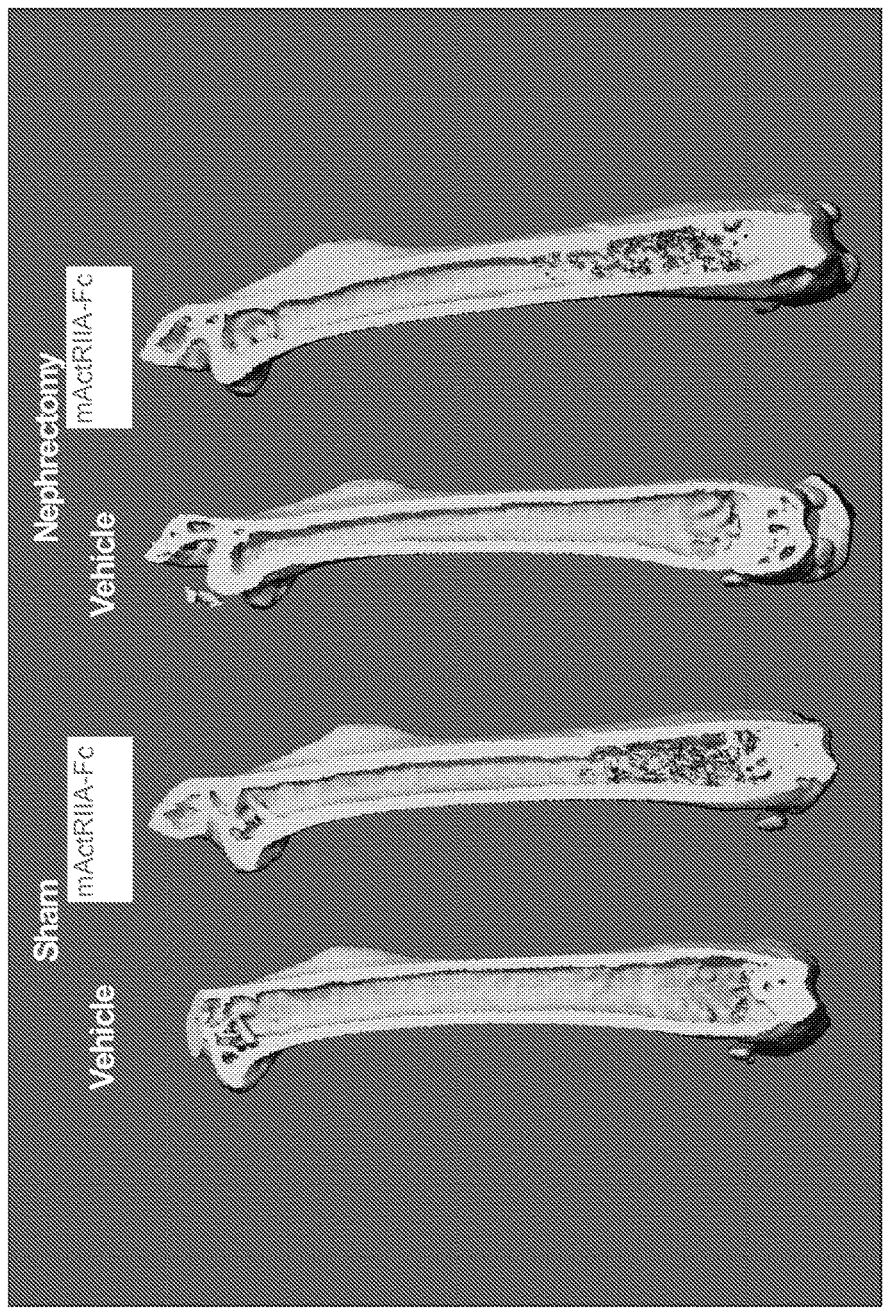

FIG. 4: MicroCT 3D image of representative bones following partial nephrectomy in mice.

Figure 5:
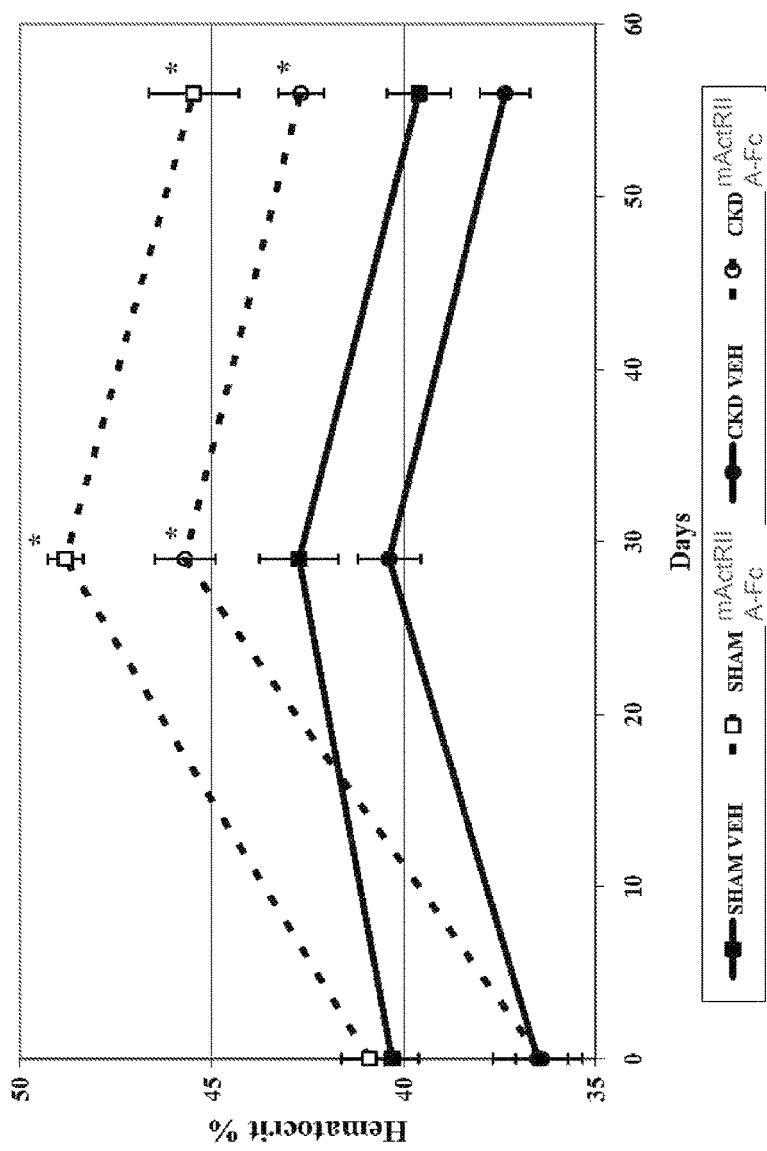

FIG. 5: mActRIIA-Fc treatment Increases Hematocrit.

Figure 6:
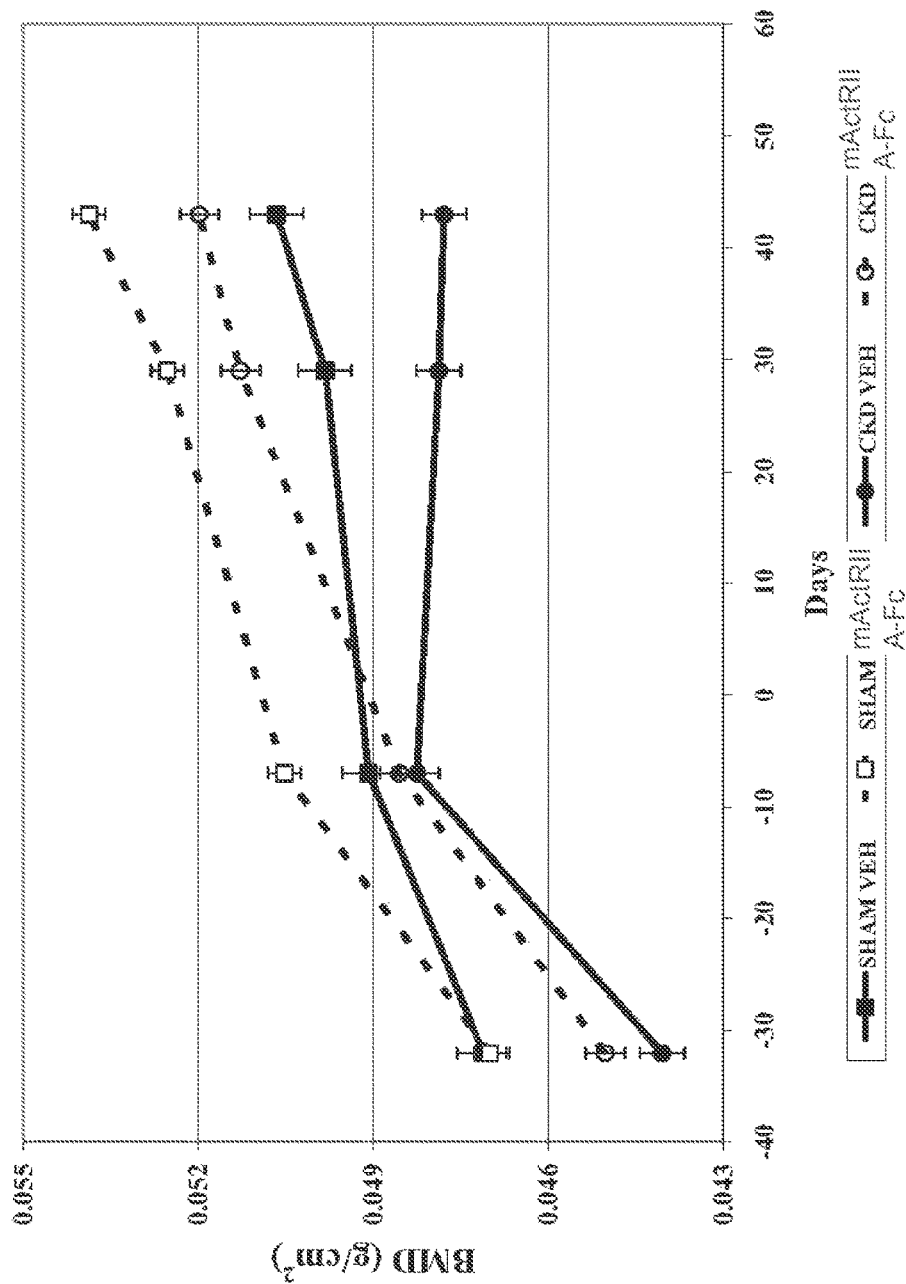

FIG. 6: mActRIIA-Fc increases Bone Mineral Density.

Figure 7:
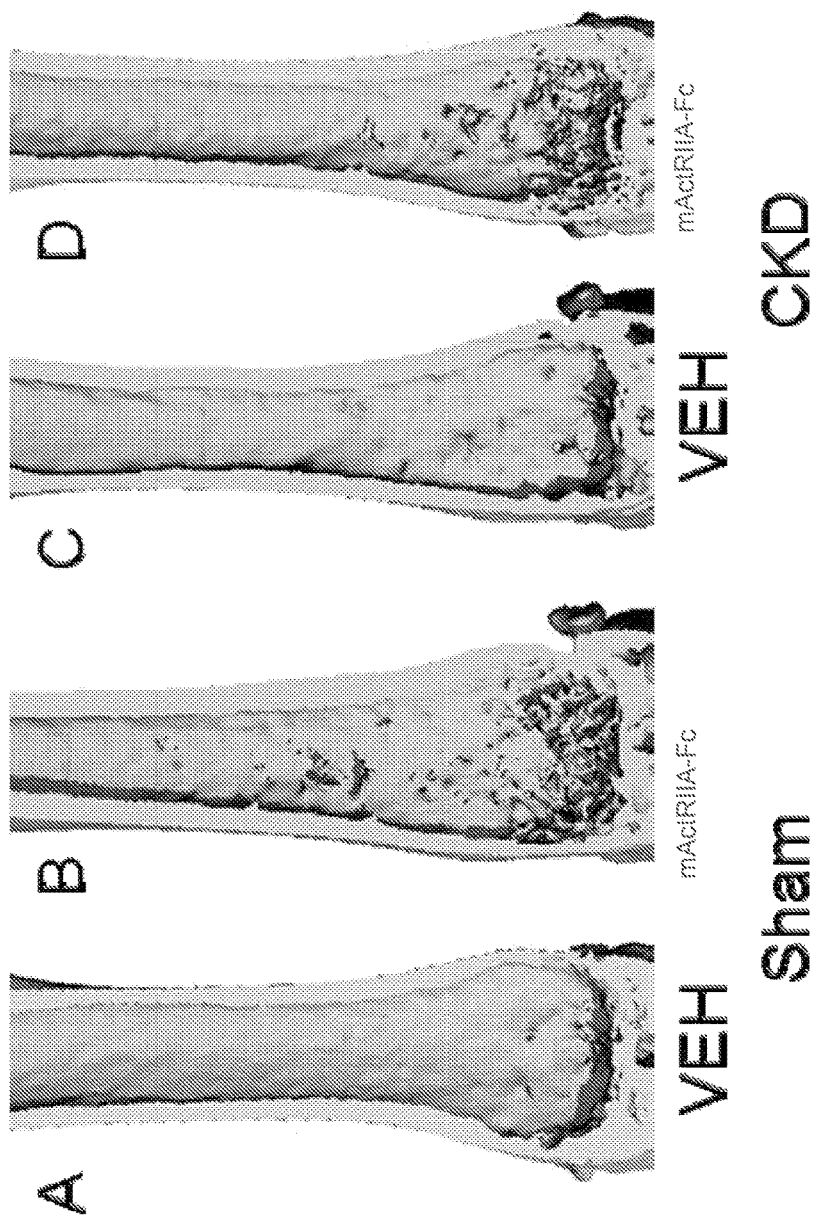

FIG. 7: Representative microCT Scans of Femurs.

Figure 8:
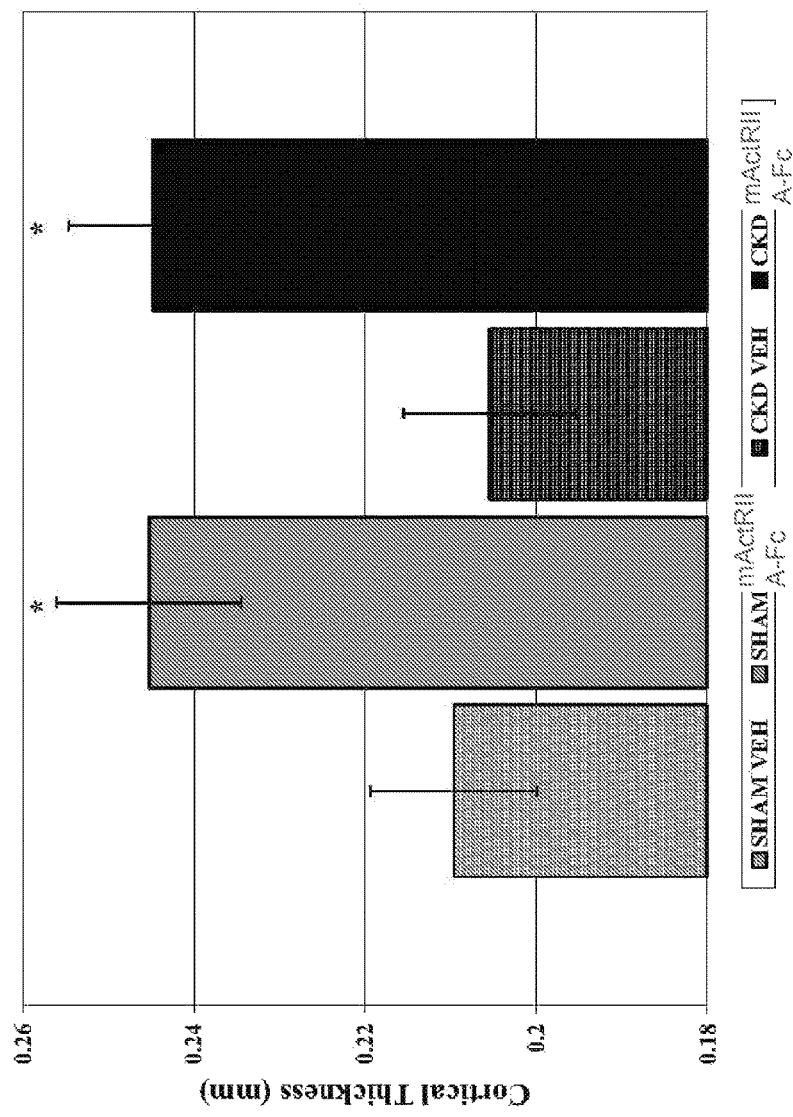

FIG. 8: mActRIIA-Fc increases Cortical Thickness of the Femur Mid-Shaft.

Figure 9:
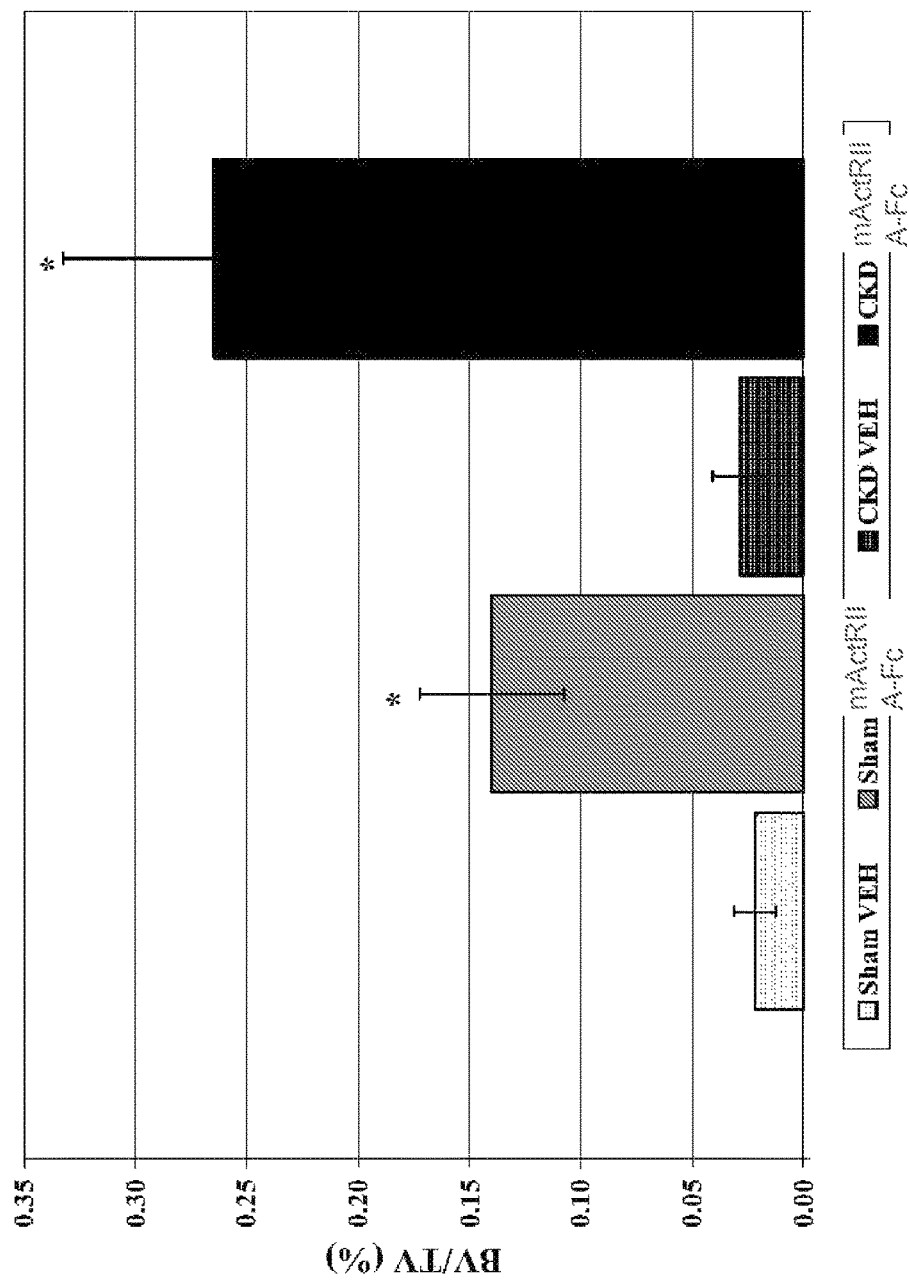

FIG. 9: mActRIIA-Fc Increases Trabecular Bone Volume.

Figure 10:
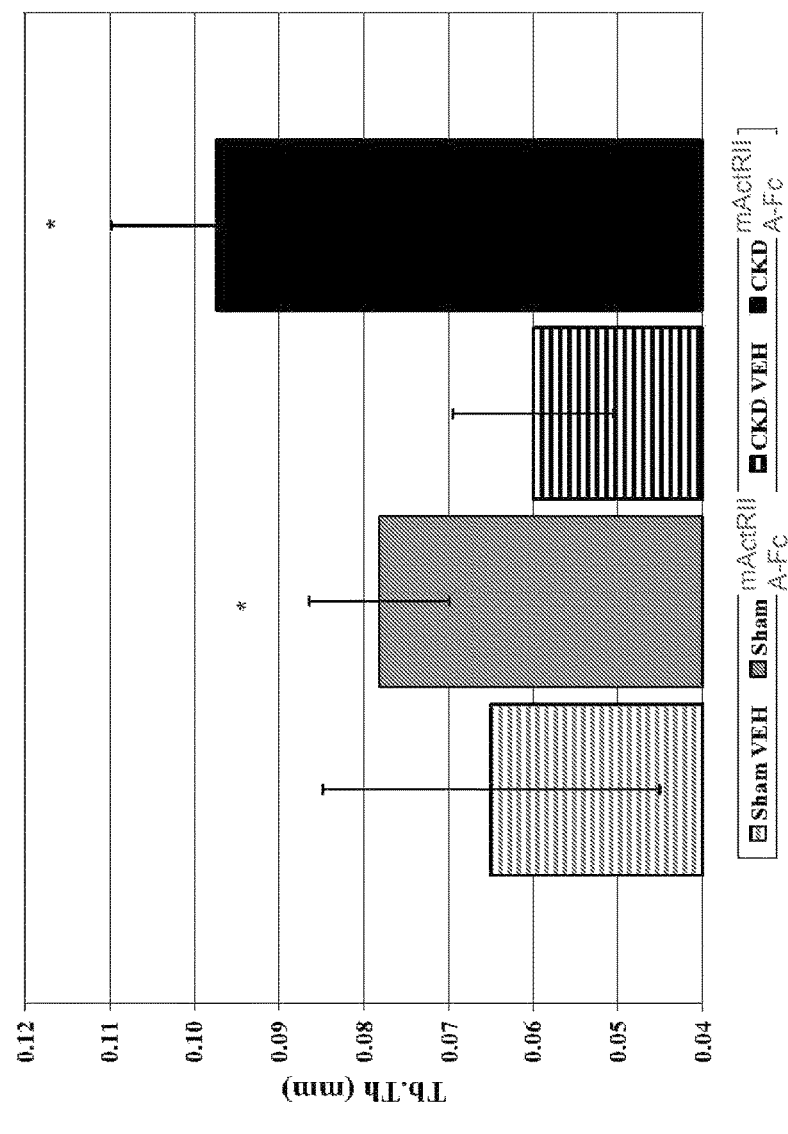

FIG. 10: mActRIIA-Fc Increases Trabecular Thickness in the Distal Femur.

Figure 11:
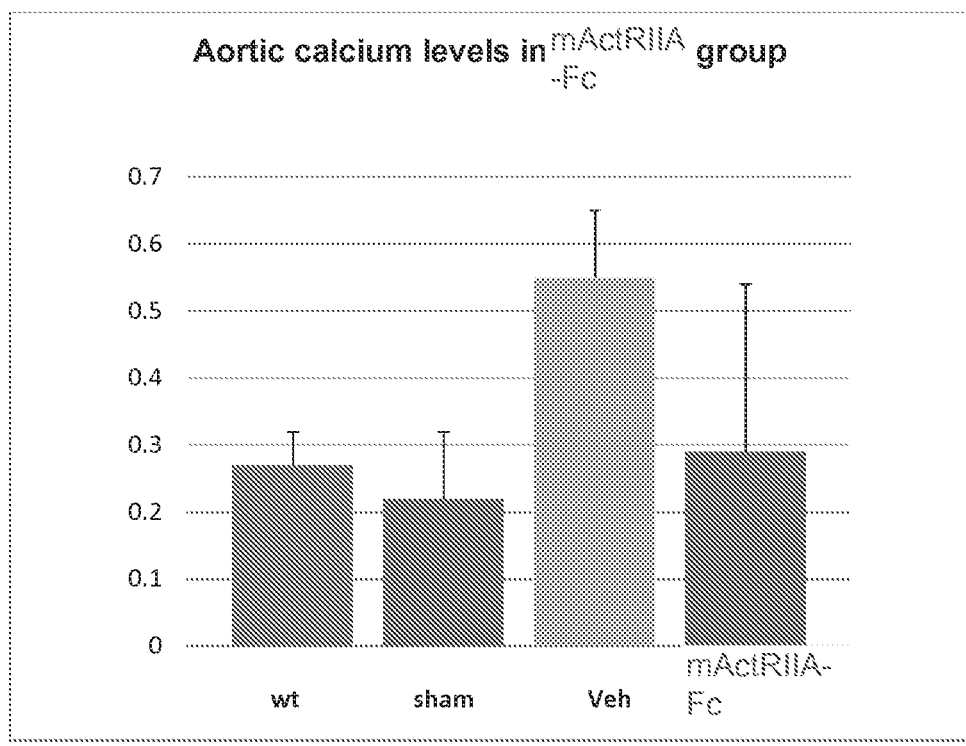

FIG. 11: mActRIIA-Fc causes a reduction in the levels of aortic calcium in a CKD mouse model.

5. DETAILED DESCRIPTION

5.1 Overview

Provided herein, in one aspect, is a method for the treatment of Chronic Kidney Disease-Mineral and Bone Disorders (CKD-MBD) wherein the method comprises administering an inhibitor of ActRII to a patient in need of treatment. The inhibitor of ActRII can be an inhibitor of ActRIIA and/or ActRIIB.

CKD-MBD can be diagnosed as a systemic disorder of mineral and bone metabolism due to chronic kidney disease and manifested by either one or a combination of (1) abnormalities of calcium; phosphorus; calcium×phosphorus product; alkaline phosphatases (total or bone specific); bicarbonate; parathyroid hormone ("PTH"); 1-84 PTH, 1-84-PTH/7-84 PTH ratio; osteocalcin; osteoprotegrin; tartrate-resistant acid phosphatase isoform 5b ("TRAP-5b"); pyridinoline and deoxypyridinoline; procollagen type 1 amino-terminal extension peptides; C-terminal crosslinks; C-terminal crosslinks of collagen; fibroblast growth factor 23 ("FGF23"); Fetulin-A; or vitamin D metabolism; (2) abnormalities of bone turnover, mineralization, volume, linear growth, or strength; and (3) vascular or other soft tissue calcification. See Nickolas, 2008, Kidney International 74:721-731; and Moe et al., 2006, Kidney International 69:1945-1953. Guidelines for the diagnosis of CKD-MBD can be found, e.g., in KDIGO clinical practice guidelines for the prevention, diagnosis, evaluation, and treatment of Chronic Kidney Disease-Mineral and Bone Disorder (CKD-MBD), Kidney Disease: Improving Global Outcomes (KDIGO) CKD-MBD Work Group, In: Kidney Int Suppl. (2009) 76 (Suppl 113):S1-130.

In certain embodiments, provided herein are methods for the treatment of low bone turnover forms of CKD-MBD wherein the method comprises administering an inhibitor of ActRII to a patient in need of treatment. In certain embodiments, provided herein are methods for the treatment of CKD-MBD characterized by hyperphosphatemia and/or hypercalcemia. In certain embodiments, provided herein are methods for the treatment of CKD-MBD characterized by extraskeletal calcification, such as, but not limited to atherosclerotic calcification.

In certain embodiments, provided herein are methods for the treatment of CKD-MBD, wherein the chronic kidney disease has reached stage 3, stage 4, stage 5, or stage 5D. In a specific embodiment, the kidney disease is end stage kidney disease. In certain embodiments, provided herein are methods for the treatment of CKD-MBD characterized by a glomerular filtration rate of less than 60 ml/min/1.73 m$^2$ in adults or less than 89 ml/min/1.73 m$^2$ in pediatric patients. See, Moe et al., 2006, Kidney International 69:1945-1953. In certain embodiments, provided herein are methods for the treatment in adults of CKD-MBD characterized by a glomerular filtration rate of less than 50 ml/min/1.73 m$^2$, 40 ml/min/1.73 m$^2$, 30 ml/min/1.73 m$^2$, 20 ml/min/1.73 m$^2$, or less than 10 ml/min/1.73 m$^2$. In certain embodiments, provided herein are methods for the treatment in pediatric patients of CKD-MBD characterized by a glomerular filtration rate of less than 80 ml/min/1.73 m$^2$, 70 ml/min/1.73 m$^2$, 60 ml/min/1.73 m$^2$, 50 ml/min/1.73 m$^2$, 40 ml/min/1.73 m$^2$, 30 ml/min/1.73 m$^2$, 20 ml/min/1.73 m$^2$, or less than 10 ml/min/1.73 m$^2$.

Without being bound by theory, a glomerular filtration rate of less than 60 ml/min/1.73 m$^2$ in adult patients and less than 89 ml/min/1.73 m$^2$ in pediatric patients results in detectable abnormalities in calcium levels, phosphorus levels, PTH levels, and vitamin D metabolism; and abnormal levels of these markers result in bone disease.

In certain embodiments, provided herein are methods for the treatment of a bone pathology associated with chronic kidney disease, i.e., CKD-MBD. See Moe et al., 2006, Kidney International 69:1945-1953. In certain embodiments, the CKD-MBD is low-turnover CKD-MBD. Low-turnover CKD-MBD can be diagnosed by the histological features set forth in Table 1 below. See National Kidney Foundation, Kidney Disease Outcomes Quality Initiative Guidelines at the website of the National Kidney Foundation.

TABLE 1

| Histological Features of Low-Turnover CKD-MBD | | |
|---|---|---|
| Feature | Adynamic | Osteomalacia |
| Bone Formation | | |
| Trabecular bone volume | Normal, low | Variable Low, normal or high |
| Osteoid volume | Normal, low | High-very high |
| Osteoid seam thickness | Normal, low | High-very high |

TABLE 1-continued

Histological Features of Low-Turnover CKD-MBD

| Feature | Adynamic | Osteomalacia |
|---|---|---|
| Number of osteoblasts | Low | Low |
| Bone formation rate | Low-very low | Low-very low |
| Mineralization lag time | Normal | Prolonged |
| Bone Resorption | | |
| Eroded bone perimeter | Normal, low | Variable |
| | | Often low, may be high |
| Number of osteoclasts | Low | Low, may be normal or high |
| Marrow fibrosis | Absent | Absent |

In a specific embodiment, provided herein is a method for treating extraskeletal calcification in a subject, wherein said method comprises administering a therapeutically effective amount of an ActRII inhibitor to the subject. In another specific embodiment, provided herein is a method for preventing extraskeletal calcification in a subject, wherein said method comprises administering a therapeutically effective amount of an ActRII inhibitor to the subject. In specific embodiments, the extraskeletal calcification treated or prevented in a subject by the methods described herein is vascular calcification, i.e., the accumulation of calcium salts in the vasculature of the subject, e.g., calcification of arteries of the subject.

In certain embodiments, the methods of treatment or prevention of extraskeletal calcification, e.g., vascular calcification, provided herein are performed on a subject that is at risk of suffering from extraskeletal calcification, e.g., vascular calcification (i.e., the at risk subject is administered an ActRII inhibitor in accordance with the methods described herein). In a specific embodiment, the subject at risk of suffering from extraskeletal calcification, e.g., vascular calcification, has hypercholesterolemia. In another specific embodiment, the subject at risk of suffering from extraskeletal calcification, e.g., vascular calcification, has hypertension. In another specific embodiment, the subject at risk of suffering from extraskeletal calcification, e.g., vascular calcification, has diabetes. In another specific embodiment, the subject at risk of suffering from extraskeletal calcification, e.g., vascular calcification, has renal disease (e.g., end-stage renal disease). In another specific embodiment, the subject at risk of suffering from extraskeletal calcification, e.g., vascular calcification, has chronic kidney disease. In another specific embodiment, the subject at risk of suffering from extraskeletal calcification, e.g., vascular calcification, has increased oxidative stress, e.g., an imbalance between oxidant production and antioxidant activity in the vasculature. In another specific embodiment, the subject at risk of suffering from extraskeletal calcification, e.g., vascular calcification, has a calcification inhibitor deficiency (e.g., a deficiency in one or more of fetuin-A, matrix gla protein (MGP), and osteoprotegerin (OPG)).

In certain embodiments, the subjects suffering from vascular calcification treated in accordance with the methods described herein have Media calcification (also known as Mönckeberg's sclerosis or media calcinosis). Media calcification is characterized by diffuse mineral deposits within the arterial tunica media. In a specific embodiment, the subjects suffering from media calcification are elderly. In a specific embodiment, the subjects suffering from media calcification have a disorder that causes the Media calcification, e.g., diabetes, renal disease (e.g., CKD).

In certain embodiments, the subjects suffering from vascular calcification treated in accordance with the methods described herein have Intima calcification. Intima calcification is associated with atherosclerosis and progresses as atherosclerotic plaques progress.

In certain embodiments, a subject suffering from, or at risk of suffering from, a form of CKD-MBD and/or extraskeletal calcification, e.g., vascular calcification, has increased levels of FGF23, a hormone produced by osteocytes in response to decreased mechanical loading, decreases in bone formation and to excess phosphorus in the exchangable pool (see, e.g., Hruska and Mathew, 2011, Advances in Chronic Kidney Disease 18(2):98-104), relative to FGF23 levels in subjects that are not suffering from, or not at risk of suffering from, a form of CKD-MBD and/or extraskeletal calcification, e.g., vascular calcification. Levels of FGF23 can be detected using methods known in the art, e.g., ELISA, using samples from the subjects, e.g, blood, serum. In a specific embodiment, the level of FGF23 (e.g., the level detectable in the serum) in a subject suffering from, or at risk of suffering from, a form of CKD-MBD and/or extraskeletal calcification, e.g., vascular calcification, is about 5%, 10%, 15%, 20%, 25%, 30%, 35%, 40%, 45%, 50%, or greater than 50%, greater than the level of FGF23 (e.g., the level detectable in the serum) in a subject not suffering from, or not at risk of suffering from, a form of CKD-MBD and/or extraskeletal calcification, e.g., vascular calcification. In another specific embodiment, the level of FGF23 (e.g., the level detectable in the serum) in a subject suffering from, or at risk of suffering from, a form of CKD-MBD and/or extraskeletal calcification, e.g., vascular calcification, is about 5-10%, 10-20%, 20-30%, 30-40%, 40-50%, 50-60%, 50-75%, or 75-100%, greater than the level of FGF23 (e.g., the level detectable in the serum) in a subject not suffering from, or not at risk of suffering from, a form of CKD-MBD and/or extraskeletal calcification, e.g., vascular calcification.

In certain embodiments, levels of FGF23 in a subject suffering from, or at risk of suffering from, a form of CKD-MBD and/or extraskeletal calcification, e.g., vascular calcification, can be used to monitor the effectiveness of a method described herein, e.g., a method of treating a form of CKD-MBD and/or a method of treating extraskeletal calcification (e.g., vascular calcification), wherein such methods comprise administration of a therapeutically effective amount of an ActRII inhibitor described herein. In a specific embodiment, a subject treated in accordance with one or more of the methods described herein has a decreased level of FGF23 (e.g., as detected in the serum of the subject) as compared to the level of FGF23 detected in the subject prior to being treated with a method described herein. In another specific embodiment, the level of FGF23 (e.g., the level detectable in the serum) in a subject suffering from, or at risk of suffering from, a form of CKD-MBD and/or extraskeletal calcification, e.g., vascular calcification, treated with a method described herein is decreased by about 5%, 10%, 15%, 20%, 25%, 30%, 35%, 40%, 45%, 50%, or greater than 50%, relative to the level of FGF23 (e.g., the level detectable in the serum) detected in the subject prior to treatment with a method described herein. In another specific embodiment, the level of FGF23 (e.g., the level detectable in the serum) in a subject suffering from, or at risk of suffering from, a form of CKD-MBD and/or extraskeletal calcification, e.g., vascular calcification, is decreased by about 5-10%, 10-20%, 20-30%, 30-40%, 40-50%, 50-60%, 50-75%, or 75-100%, relative to the level of FGF23 (e.g., the level detectable in the serum) detected in the subject prior to treatment with a method described herein.

In a specific embodiment, provided herein is a method of treating a form of CKD-MBD and/or extraskeletal calcification, e.g., vascular calcification, comprising: (i) administering an ActRII inhibitor to an individual having a form of CKD-MBD and/or extraskeletal calcification, e.g., vascular calcification; (ii) determining an amount of FGF23 in a tissue sample (e.g., serum) of said individual after the administration of the ActRII inhibitor; and (iii) if the amount of FGF23 in said tissue sample is decreased by no more than about 5%, 10%, 15%, 20%, or 25%, or by about 5-10%, 10-20%, 20-30%, as compared to the amount of FGF23 determined in a sample of the same tissue type from said individual (e.g., a different sample of serum from the same individual) prior to administration of the ActRII inhibitor, repeating the administration of the ActRII inhibitor. In certain embodiments, if the amount of FGF23 is not decreased following administration of the ActRII inhibitor, the dose of the ActRII inhibitor administered can be increased. In certain embodiments, if the amount of FGF23 is not decreased following administration of the ActRII inhibitor, the frequency of administration of the ActRII inhibitor administered can be increased.

In certain embodiments, a subject suffering from, or at risk of suffering from, a form of CKD-MBD and/or extraskeletal calcification, e.g., vascular calcification, has increased levels of sclerostin, a protein increased in subjects suffering from, or at risk of suffering from, CKD-MBD (see, e.g., Graciolli et al., 2010, J Am Soc Nephrol 21:774A), relative to sclerostin levels in subjects that are not suffering from, or not at risk of suffering from, a form of CKD-MBD and/or extraskeletal calcification, e.g., vascular calcification. Levels of sclerostin can be detected using methods known in the art, e.g., ELISA, using samples from the subjects, e.g, blood, serum. In a specific embodiment, the level of sclerostin (e.g., the level detectable in the serum) in a subject suffering from, or at risk of suffering from, a form of CKD-MBD and/or extraskeletal calcification, e.g., vascular calcification, is about 5%, 10%, 15%, 20%, 25%, 30%, 35%, 40%, 45%, 50%, or greater than 50%, greater than the level of sclerostin (e.g., the level detectable in the serum) in a subject not suffering from, or not at risk of suffering from, a form of CKD-MBD and/or extraskeletal calcification, e.g., vascular calcification. In another specific embodiment, the level of sclerostin (e.g., the level detectable in the serum) in a subject suffering from, or at risk of suffering from, a form of CKD-MBD and/or extraskeletal calcification, e.g., vascular calcification, is about 5-10%, 10-20%, 20-30%, 30-40%, 40-50%, 50-60%, 50-75%, or 75-100%, greater than the level of sclerostin (e.g., the level detectable in the serum) in a subject not suffering from, or not at risk of suffering from, a form of CKD-MBD and/or extraskeletal calcification, e.g., vascular calcification.

In certain embodiments, levels of sclerostin in a subject suffering from, or at risk of suffering from, a form of CKD-MBD and/or extraskeletal calcification, e.g., vascular calcification, can be used to monitor the effectiveness of a method described herein, e.g., a method of treating a form of CKD-MBD and/or a method of treating extraskeletal calcification (e.g., vascular calcification), wherein such methods comprise administration of a therapeutically effective amount of an ActRII inhibitor described herein. In a specific embodiment, a subject treated in accordance with one or more of the methods described herein has a decreased level of sclerostin (e.g., as detected in the serum of the subject) as compared to the level of sclerostin detected in the subject prior to being treated with a method described herein. In another specific embodiment, the level of sclerostin (e.g., the level detectable in the serum) in a subject suffering from, or at risk of suffering from, a form of CKD-MBD and/or extraskeletal calcification, e.g., vascular calcification, treated with a method described herein is decreased by about 5%, 10%, 15%, 20%, 25%, 30%, 35%, 40%, 45%, 50%, or greater than 50%, relative to the level of sclerostin (e.g., the level detectable in the serum) detected in the subject prior to treatment with a method described herein. In another specific embodiment, the level of sclerostin (e.g., the level detectable in the serum) in a subject suffering from, or at risk of suffering from, a form of CKD-MBD and/or extraskeletal calcification, e.g., vascular calcification, is decreased by about 5-10%, 10-20%, 20-30%, 30-40%, 40-50%, 50-60%, 50-75%, or 75-100%, relative to the level of sclerostin (e.g., the level detectable in the serum) detected in the subject prior to treatment with a method described herein.

In a specific embodiment, provided herein is a method of treating a form of CKD-MBD and/or extraskeletal calcification, e.g., vascular calcification, comprising: (i) administering an ActRII inhibitor to an individual having a form of CKD-MBD and/or extraskeletal calcification, e.g., vascular calcification; (ii) determining an amount of sclerostin in a tissue sample (e.g., serum) of said individual after the administration of the ActRII inhibitor; and (iii) if the amount of sclerostin in said tissue sample is decreased by no more than about 5%, 10%, 15%, 20%, or 25%, or by about 5-10%, 10-20%, 20-30%, as compared to the amount of sclerostin determined in a sample of the same tissue from said individual (e.g., a different sample of serum from the same individual) prior to administration of the ActRII inhibitor, repeating the administration of the ActRII inhibitor. In certain embodiments, if the amount of sclerostin is not decreased following administration of the ActRII inhibitor, the dose of the ActRII inhibitor administered can be increased. In certain embodiments, if the amount of sclerostin is not decreased following administration of the ActRII inhibitor, the frequency of administration of the ActRII inhibitor administered can be increased.

In certain embodiments, the subject suffering from vascular calcification treated in accordance with the methods described herein is less than 18 years old. In a specific embodiment, the subject suffering from vascular calcification treated in accordance with the methods described herein is less than 13 years old. In another specific embodiment, the subject suffering from vascular calcification treated in accordance with the methods described herein is less than 12, less than 11, less than 10, less than 9, less than 8, less than 7, less than 6, or less than 5 years old. In another specific embodiment, the subject suffering from vascular calcification treated in accordance with the methods described herein is 1-3 years old, 3-5 years old, 5-7 years old, 7-9 years old, 9-11 years old, 11-13 years old, 13-15 years old, 15-20 years old, 20-25 years old, 25-30 years old, or greater than 30 years old. In another specific embodiment, the subject suffering from vascular calcification treated in accordance with the methods described herein is 30-35 years old, 35-40 years old, 40-45 years old, 45-50 years old, 50-55 years old, 55-60 years old, or greater than 60 years old. In another specific embodiment, the subject suffering from vascular calcification treated in accordance with the methods described herein is 60-65 years old, 65-70 years old, 70-75 years old, 75-80 years old, or greater than 80 years old.

In certain embodiments, the subject suffering from vascular calcification treated in accordance with the methods described herein has end stage renal disease. In certain embodiments, the subject suffering from vascular calcification treated in accordance with the methods described herein undergoes dialysis.

In certain embodiments, the effectiveness of treatment or prevention of extraskeletal calcification, e.g., vascular calcification, is assessed using one or more assays known to those of skill in the art. Exemplary assays are described in Section 5.3(a)(iv). In accordance with such embodiments, one of skill in the art will understand that a subject being treated with an ActRII inhibitor as described herein may have their treatment regimen adjusted based on the outcome of the assays. For example, a subject being treated by a method described herein that displays increases in levels of calcium, e.g., vascular calcium (e.g., arterial calcium) may be administered an increased dose of ActRII inhibitor, or a may be administered an ActRII inhibitor more frequently (i.e., the time between dose administrations may be decreased). Conversely, a subject being treated by a method described herein that displays decreases in levels of calcium, e.g., vascular calcium (e.g., arterial calcium) may be administered a decreased dose of ActRII inhibitor, or a may be administered an ActRII inhibitor less frequently (i.e., the time between dose administrations may be increased).

In certain embodiments, the methods provided herein result in the improvement of the symptoms of one or more of the following: hyperphosphatemia, secondary hyperparathyroidism (due to increase in phosphorus), and extraskeletal calcification, e.g., vascular calcification. Any method known to the skilled artisan to determine the degree of these symptoms can be used with the methods provided herein. In specific embodiments, the methods described herein result in the improvement of one or more symptoms of vascular calcification. Exemplary symptoms include, without limitation, increases in the levels of vascular (e.g., arterial) calcium, increased apoptosis of vascular smooth muscle cells, loss of arterial elasticity, an increase in PWV (pulse wave velocity), development of left ventricular hypertrophy, decrease in coronary artery perfusion, and myocardial ischaemia.

In certain embodiments, the methods described herein result in a decrease in the levels of vascular calcium, e.g., arterial calcium, in a subject by at least 5%, 10%, 15%, 20%, 25%, 30%, 35%, 40%, 45% or 50%. In certain embodiments, the methods described herein result in a decrease in the levels of vascular calcium, e.g., arterial calcium, in a subject by 5%-10%, 10%-15%, 15%-20%, 20%-25%, 25%-30%, 30%-35%, 35%-40%, 40%-45%, or 45%-50%.

In a specific embodiment, provided herein is a method of reducing the levels of vascular calcium in a subject, comprising: (i) administering an ActRII inhibitor to a subject in need of reduction vascular calcium levels (e.g., a subject having a form of CKD-MBD and/or extraskeletal calcification, e.g., vascular calcification); (ii) determining an amount of vascular calcium in a tissue sample (e.g., serum) of said subject after the administration of the ActRII inhibitor; and (iii) if the amount of vascular calcium in said tissue sample is decreased by no more than about 5%, 10%, 15%, 20%, or 25%, or by about 5-10%, 10-20%, 20-30%, as compared to the amount of vascular calcium determined in a sample of the same tissue from said subject (e.g., a different sample of serum from the same individual) prior to administration of the ActRII inhibitor, repeating the administration of the ActRII inhibitor. In certain embodiments, if the amount of vascular calcium is not decreased following administration of the ActRII inhibitor, the dose of the ActRII inhibitor administered can be increased. In certain embodiments, if the amount of vascular calcium is not decreased following administration of the ActRII inhibitor, the frequency of administration of the ActRII inhibitor administered can be increased.

In certain embodiments, the methods described herein result in a decrease in the progression of the Agatston score of a subject having or at risk of developing vascular calcification. In a specific embodiment, the methods described herein result in a 5%, 10%, 15%, 20%, 25%, 30%, or greater than 30% decrease in the Agatston score of a subject having or at risk of developing vascular calcification as compared to the Agatston score of the subject prior to administration of an ActRII inhibitor in accordance with the methods described herein (see, e.g., Section 5.3(a)(iv)). In another specific embodiment, the methods described herein result in a 5%-10%, 10%-15%, 15%-20%, 20%-25%, 25%-30%, 30%-35%, 35%-40%, 40%-45%, or 45%-50% decrease in the Agatston score of a subject having or at risk of developing vascular calcification as compared to the Agatston score of the subject prior to administration of an ActRII inhibitor in accordance with the methods described herein (see, e.g., Section 5.3(a)(iv)).

In another specific embodiment, the methods described herein result in a decrease in the levels of calcium in the vasculature of a subject, e.g., a decrease in the levels of calcium in one or more arteries of the subject, e.g., a subject having or at risk of developing vascular calcification. In another specific embodiment, the methods described herein result in a decrease in the levels of phosphorus in the vasculature of a subject, e.g., a decrease in the levels of phosphorus in one or more arteries of the subject, e.g., a subject having or at risk of developing vascular calcification.

In certain embodiments, provided herein are methods for the treatment of low turnover bone disorders. Low bone turnover can be diagnosed using the tests set forth in Section 5.3(a) below. Biochemical markers of bone turnover include: serum or urine collagen cross-links (N-telopeptide or C-telopeptide), bone-specific alkaline phosphatase, serum osteocalcin and/or propeptide type 1 collagen, 25 hydroxyvitamin D, and parathyroid hormone ("PTH"). In a specific embodiment, the low turnover bone disorder is adynamic bone disorder. In certain embodiments, a patient to be treated with the methods provided herein has a reduction in bone-turnover of at least 10%, 20%, 25%, 30%, 40%, 50%, 60%, 70%, 75%, 80%, 85%, 90%, 95%, 98%, 99% or of 100%. In certain embodiments, a patient to be treated with the methods provided herein has a reduction in bone-turnover of at most 10%, 20%, 25%, 30%, 40%, 50%, 60%, 70%, 75%, 80%, 85%, 90%, 95%, 98%, 99% or of 100%. In certain embodiments, a patient to be treated with the methods provided herein has a reduction in bone-turnover of at between 10% and 25%, 20% and 35%, 30% and 45%, 40% and 55%, 50% and 65%, 60% and 75%, 70% and 85%, 80% and 95%, 90% and 100%. In certain embodiments, the reduction in bone turnover is compared to historical data of the same patient. In other embodiments, the reduction in bone turnover is compared to the average bone turnover in a population without bone disorders. The population without bone disorders can be of the same age and/or same sex as the patient.

In a specific embodiment, provided herein is a method of treating a low turnover bone disorder, e.g., adynamic bone disorder, comprising: (i) administering an ActRII inhibitor to a subject having a low turnover bone disorder; (ii) determining the level of bone-turnover in said subject after the administration of the ActRII inhibitor (e.g., by using one or more of the tests set forth in Section 5.3(a) below and/or by measuring one or more biochemical markers of bone turnover); and (iii) if the level of bone turnover in the subject is decreased by no more than about 5%, 10%, 15%, 20%, or 25%, or by about 5-10%, 10-20%, 20-30%, as compared to the level of bone turnover in the subject prior to administration of the ActRII inhibitor, repeating the administration of the ActRII inhibitor. In certain embodiments, if the level of bone turnover is not decreased following administration of the ActRII inhibitor, the dose of the ActRII inhibitor administered can be increased. In certain embodiments, if the level of bone turnover is not decreased following administration of the ActRII inhibitor, the frequency of administration of the ActRII inhibitor administered can be increased.

5.2 Inhibitors of ActRII (a) Inhibitors of ActRIIA

As used herein, the term "ActRIIA" refers to a family of activin receptor type IIa (ActRIIA) proteins from any species and variants derived from such ActRIIA proteins by mutagenesis or other modification. Reference to ActRIIA herein is understood to be a reference to any one of the currently identified forms. Members of the ActRIIA family are generally transmembrane proteins, composed of a ligand-binding extracellular domain with a cysteine-rich region, a transmembrane domain, and a cytoplasmic domain with predicted serine/threonine kinase activity.

ActRIIA inhibitors to be used in the compositions and methods described herein include, without limitation, activin-binding soluble ActRIIA polypeptides; antibodies that bind to activin (particularly the activin A or B subunits, also referred to as βA or βB) and disrupt ActRIIA binding; antibodies that bind to ActRIIA and disrupt activin binding; non-antibody proteins selected for activin or ActRIIA binding (see e.g., WO/2002/088171, WO/2006/055689, WO/2002/032925, WO/2005/037989, US 2003/0133939, and US 2005/0238646, each of which is incorporated herein by reference in its entirety, for examples of such proteins and methods for design and selection of same); and randomized peptides selected for activin or ActRIIA binding, which can be conjugated to an Fc domain.

In certain embodiments, two or more different proteins (or other moieties) with activin or ActRIIA binding activity, especially activin binders that block the type I (e.g., a soluble type I activin receptor) and type II (e.g., a soluble type II activin receptor) binding sites, respectively, may be linked together to create a bifunctional or multifunctional binding molecule that inhibits ActRIIA and thus can be used in the compositions and methods described herein. In certain embodiments, Activin-ActRIIA signaling axis antagonists that inhibit ActRIIA include nucleic acid aptamers, small molecules and other agents are used in the compositions and methods described herein include.

(i) ActRIIA Inhibitors Comprising ActRIIA Polypeptides

The term "ActRIIA polypeptide" includes polypeptides comprising any naturally occurring polypeptide of an ActRIIA family member as well as any variants thereof (including mutants, fragments, fusions, and peptidomimetic forms) that retain a useful activity. For example, ActRIIA polypeptides include polypeptides derived from the sequence of any known ActRIIA having a sequence at least about 80% identical to the sequence of an ActRIIA polypeptide, and optionally at least 85%, 90%, 95%, 97%, 98%, 99% or greater identity. For example, an ActRIIA polypeptide may bind to and inhibit the function of an ActRIIA protein and/or activin. An ActRIIB polypeptide may be selected for its ability to promote bone growth and bone mineralization. Examples of ActRIIA polypeptides include human ActRIIA precursor polypeptide (SEQ ID NO: 1) and soluble human ActRIIA polypeptides (e.g., SEQ ID NOs: 2, 3, 7 and 12). With respect to the ActRIIA precursor polypeptide whose amino acid sequence is depicted at SEQ ID NO:1, the signal peptide of the human ActRIIA precursor polypeptide located at amino acid positions 1 to 20; the extracellular domain is located at amino acid positions 21 to 135 and the N-linked glycosylation sites of the human ActRIIA precursor polypeptide (SEQ ID NO: 1) are located at amino acid positions 43 and 56 of SEQ ID NO:1. The nucleic acid sequence encoding the human ActRIIB precursor polypeptide of SEQ ID NO:1 is disclosed as SEQ ID NO:4 (nucleotides 164-1705 of Genbank entry NM 001616). The nucleic acid sequence encoding the soluble human ActRIIA polypeptide of SEQ ID NO:2 is disclosed as SEQ ID NO:5. See Table 6 for a description of the sequences.

In specific embodiments, the ActRIIA polypeptides used in the compositions and methods described herein are soluble ActRIIA polypeptides. An extracellular domain of an ActRIIA protein can bind to activin and is generally soluble, and thus can be termed a soluble, activin-binding ActRIIA polypeptide. Thus, as used herein, the term "soluble ActRIIA polypeptide" generally refers to polypeptides comprising an extracellular domain of an ActRIIA protein, including any naturally occurring extracellular domain of an ActRIIA protein as well as any variants thereof (including mutants, fragments and peptidomimetic forms). Soluble ActRIIA polypeptides can bind to activin; however, the wild type ActRIIA protein does not exhibit significant selectivity in binding to activin versus GDF8/11. Native or altered ActRIIA proteins may be given added specificity for activin by coupling them with a second, activin-selective binding agent. Examples of soluble, activin-binding ActRIIA polypeptides include the soluble polypeptides illustrated in SEQ ID NOs: 2, 3, 7, 12 and 13. Other examples of soluble, activin-binding ActRIIA polypeptides comprise a signal sequence in addition to the extracellular domain of an ActRIIA protein, for example, the honey bee mellitin leader sequence (SEQ ID NO: 8), the tissue plasminogen activator (TPA) leader (SEQ ID NO: 9) or the native ActRIIA leader (SEQ ID NO: 10). The ActRIIA-hFc polypeptide illustrated in SEQ ID NO:13 uses a TPA leader.

In certain embodiments, the inhibitors of ActRIIA used in the compositions and methods described herein comprise a conjugate/fusion protein comprising an activin-binding domain of ActRIIA linked to an Fc portion of an antibody. In certain embodiments, the activin-binding domain is linked to an Fc portion of an antibody via a linker, e.g., a peptide linker. Optionally, the Fc domain has one or more mutations at residues such as Asp-265, lysine 322, and Asn-434. In certain cases, the mutant Fc domain having one or more of these mutations (e.g., an Asp-265 mutation) has a reduced ability to bind to the Fcγ receptor relative to a wild-type Fc domain. In other cases, the mutant Fc domain having one or more of these mutations (e.g., an Asn-434 mutation) has an increased ability to bind to the MHC class I-related Fc-receptor (FcRN) relative to a wild-type Fc domain. Exemplary fusion proteins comprising a soluble extracellular domain of ActRIIA fused to an Fc domain are set forth in SEQ ID NOs: 6, 7, 12, and 13.

In a specific embodiment, the ActRIIA inhibitors used in the compositions and methods described herein comprise the extracellular domain of ActRIIA, or a portion thereof, linked to an Fc portion of an antibody, wherein said ActRIIA inhibitor comprises an amino acid sequence that is at least 75% identical to an amino acid sequence selected from SEQ ID NOs: 6, 7, 12, and 13. In another specific embodiment, the ActRIIA inhibitors used in the compositions and methods described herein comprise the extracellular domain of ActRIIA, or a portion thereof, linked to an Fc portion of an antibody, wherein said ActRIIA inhibitor comprises an amino acid sequence that is at least 80%, 85%, 90%, 95%, 96%, 97%, 98%, or 99% identical to an amino acid sequence selected from SEQ ID NOs: 6, 7, 12, and 13.

In certain embodiments, the inhibitors of ActRIIA used in the compositions and methods described herein comprise a truncated form of an extracellular domain of ActRIIA. The truncation can be at the carboxy terminus and/or the amino terminus of the ActRIIA polypeptide. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 amino acids long relative to the mature ActRIIB polypeptide extracellular domain. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 N-terminal amino acids of the mature ActRIIA polypeptide extracellular domain. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 C-terminal amino acids of the mature ActRIIA polypeptide extracellular domain. For example, truncated forms of ActRIIA include polypeptides with amino acids 20-119; 20-128; 20-129; 20-130; 20-131; 20-132; 20-133; 20-134; 20-131; 21-131; 22-131; 23-131; 24-131; and 25-131, wherein the amino acid positions refer to the amino acid positions in SEQ ID NO:1.

In certain embodiments, the inhibitors of ActRIIA used in the compositions and methods described herein comprise an extracellular domain of ActRIIA with one or more amino acid substitutions. In certain embodiments, the inhibitors of ActRIIA used in the compositions and methods described herein comprise a truncated form of an ActRIIA extracellular domain that also carries an amino acid substitution.

In a specific embodiment, the ActRIIA inhibitor to be used in the compositions and methods described herein is a fusion protein between the extracellular domain of the human ActRIIA receptor and the Fc portion of IgG1. In another specific embodiment, the ActRIIA inhibitor to be used in the compositions and methods described herein is a fusion protein between a truncated extracellular domain of the human ActRIIA receptor and the Fc portion of IgG1. In another specific embodiment, the ActRIIA inhibitor to be used in the compositions and methods described herein is a fusion protein between a truncated extracellular domain of the human ActRIIA receptor and the Fc portion of IgG1, wherein the truncated extracellular domain of the human ActRIIA receptor possesses one or more amino acid substitutions.

Functionally active fragments of ActRIIA polypeptides can be obtained, for example, by screening polypeptides recombinantly produced from the corresponding fragment of the nucleic acid encoding an ActRIIA polypeptide. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRIIA protein or signaling mediated by activin.

In addition, functionally active variants of ActRIIA polypeptides can be obtained, for example, by screening libraries of modified polypeptides recombinantly produced from the corresponding mutagenized nucleic acids encoding an ActRIIA polypeptide. The variants can be produced and tested to identify those that can function as antagonists (inhibitors) of ActRIIA protein or signaling mediated by activin. In certain embodiments, a functional variant of the ActRIIA polypeptides comprises an amino acid sequence that is at least 75% identical to an amino acid sequence selected from SEQ ID NOs: 2 or 3. In certain cases, the functional variant has an amino acid sequence at least 80%, 85%, 90%, 95%, 97%, 98%, 99% or 100% identical to an amino acid sequence selected from SEQ ID NOs: 2 or 3.

Functional variants may be generated, for example, by modifying the structure of an ActRIIA polypeptide for such purposes as enhancing therapeutic efficacy, or stability (e.g., ex vivo shelf life and resistance to proteolytic degradation in vivo). Such modified ActRIIA polypeptides when selected to retain activin binding, can be considered functional equivalents of the naturally-occurring ActRIIA polypeptides. Modified ActRIIA polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRIIA polypeptide results in a functional homolog can be readily determined by assessing the ability of the variant ActRIIA polypeptide to produce a response in cells in a fashion similar to the wild-type ActRIIA polypeptide.

In certain embodiments, the ActRIIA inhibitor to be used in the compositions and methods described herein may comprise an ActRIIA polypeptide having one or more specific mutations that can alter the glycosylation of the polypeptide. Such mutations may introduce or eliminate one or more glycosylation sites, such as O-linked or N-linked glycosylation sites. Asparagine-linked glycosylation recognition sites generally comprise a tripeptide sequence, asparagine-X-threonine (or asparagines-X-serine) (where "X" is any amino acid) which is specifically recognized by appropriate cellular glycosylation enzymes. The alteration may also be made by the addition of, or substitution by, one or more serine or threonine residues to the sequence of the wild-type ActRIIA polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRIIA polypeptide is by chemical or enzymatic coupling of glycosides to the ActRIIA polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on an ActRIIA polypeptide may be accomplished chemically and/or enzymatically. Chemical deglycosylation may involve, for example, exposure of the ActRIIA polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ActRIIA polypeptides can be achieved by the use of a variety of endo- and exo-glycosidases as described by Thotakura et al. (1987) Meth. Enzymol. 138:350. The sequence of an ActRIIA polypeptide may be adjusted, as appropriate, depending on the type of expression system used, as mammalian, yeast, insect and plant cells may all introduce differing glycosylation patterns that can be affected by the amino acid sequence of the peptide. In general, ActRIIA proteins for use in humans can be expressed in a mammalian cell line that provides proper glycosylation, such as HEK293 or CHO cell lines, although other expression systems, such as other mammalian expression cell lines, yeast cell lines with engineered glycosylation enzymes and insect cells, are expected to be useful as well.

Further provided herein are methods of generating mutants, particularly sets of combinatorial mutants of an ActRIIA polypeptide, as well as truncation mutants; pools of combinatorial mutants are especially useful for identifying functional variant sequences. The purpose of screening such combinatorial libraries may be to generate, for example, ActRIIA polypeptide variants which can act as either agonists or antagonist, or alternatively, which possess novel activities all together. A variety of screening assays are provided below, and such assays may be used to evaluate variants. For example, an ActRIIA polypeptide variant may be screened for ability to bind to an ActRIIA ligand, to prevent binding of an ActRIIA ligand to an ActRIIA polypeptide or to interfere with signaling caused by an ActRIIA ligand.

Combinatorially-derived variants can be generated which have a selective or generally increased potency relative to a naturally occurring ActRIIA polypeptide. Likewise, mutagenesis can give rise to variants which have intracellular half-lives dramatically different than the corresponding a wild-type ActRIIA polypeptide. For example, the altered protein can be rendered either more stable or less stable to proteolytic degradation or other cellular processes which result in destruction of, or otherwise inactivation of a native ActRIIA polypeptide. Such variants, and the genes which encode them, can be utilized to alter ActRIIA polypeptide levels by modulating the half-life of the ActRIIA polypeptides. For instance, a short half-life can give rise to more transient biological effects and can allow tighter control of recombinant ActRIIA polypeptide levels within the patient. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential ActRIIA polypeptide sequences. For instance, a mixture of synthetic oligonucleotides can be enzymatically ligated into gene sequences such that the degenerate set of potential ActRIIA polypeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, ActRIIA polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of ActRIIA polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRIIA polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include activin binding assays and activin-mediated cell signaling assays.

In certain embodiments, ActRIIA polypeptides used in the inhibitors of the methods and compositions described herein may further comprise post-translational modifications in addition to any that are naturally present in the ActRIIA polypeptides. Such modifications may include, but are not limited to, acetylation, carboxylation, glycosylation, phosphorylation, lipidation, and acylation. As a result, the modified ActRIIA polypeptides may contain non-amino acid elements, such as polyethylene glycols, lipids, poly- or mono-saccharide, and phosphates. Effects of such non-amino acid elements on the functionality of a ActRIIA polypeptide may be tested by any method known to the skilled artisan. When an ActRIIA polypeptide is produced in cells by cleaving a nascent form of the ActRIIA polypeptide, post-translational processing may also be important for correct folding and/or function of the protein. Different cells (such as CHO, HeLa, MDCK, 293, W138, NIH-3T3 or HEK293) have specific cellular machinery and characteristic mechanisms for such post-translational activities and may be chosen to ensure the correct modification and processing of the ActRIIA polypeptides.

In certain aspects, functional variants or modified forms of the ActRIIA polypeptides used in the inhibitors of the methods and compositions described herein include fusion proteins having at least a portion of the ActRIIA polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS6) fusion partners. As another example, a fusion domain may be selected so as to facilitate detection of the ActRIIA polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus hemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRIIA polypeptide is fused with a domain that stabilizes the ActRIIA polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of bone growth or muscle growth, as desired).

It is understood that different elements of the fusion proteins may be arranged in any manner that is consistent with the desired functionality. For example, an ActRIIA polypeptide may be placed C-terminal to a heterologous domain, or, alternatively, a heterologous domain may be placed C-terminal to an ActRIIA polypeptide. The ActRIIA polypeptide domain and the heterologous domain need not be adjacent in a fusion protein, and additional domains or amino acid sequences may be included C- or N-terminal to either domain or between the domains.

In certain embodiments, the ActRIIA polypeptides used in the inhibitors of the methods and compositions described herein may contain one or more modifications that are capable of stabilizing the ActRIIA polypeptides. For example, such modifications may enhance the in vitro half life of the ActRIIA polypeptides, enhance circulatory half life of the ActRIIA polypeptides or reduce proteolytic degradation of the ActRIIA polypeptides. Such stabilizing modifications may include, but are not limited to, fusion proteins (including, for example, fusion proteins comprising an ActRIIA polypeptide and a stabilizer domain), modifications of a glycosylation site (including, for example, addition of a glycosylation site to an ActRIIA polypeptide), and modifications of carbohydrate moiety (including, for example, removal of carbohydrate moieties from an ActRIIA polypeptide). In the case of fusion proteins, an ActRIIA polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, isolated and/or purified forms of ActRIIA polypeptides, which are isolated from, or otherwise substantially free of, other proteins can be used with the methods and compositions described herein. ActRIIA polypeptides can generally be produced by expression from recombinant nucleic acids.

In certain aspects, the ActRIIA polypeptides used in the compositions and methods described herein are generated using isolated and/or recombinant nucleic acids encoding any of the ActRIIA polypeptides (e.g., soluble ActRIIA polypeptides), including fragments, functional variants and fusion proteins disclosed herein. For example, SEQ ID NO: 4 encodes the naturally occurring human ActRIIA precursor polypeptide, while SEQ ID NO: 5 encodes the processed extracellular domain of ActRIIA. Such nucleic acids may be single-stranded or double stranded. Such nucleic acids may be DNA or RNA molecules. These nucleic acids may be used, for example, in methods for making ActRIIA polypeptides or as direct therapeutic agents (e.g., in a gene therapy approach).

In certain aspects, nucleic acids encoding ActRIIA polypeptides may include nucleic acids that are variants of SEQ ID NO: 4 or 5. Variant nucleotide sequences include sequences that differ by one or more nucleotide substitutions, additions or deletions, such as allelic variants.

In certain embodiments, isolated or recombinant nucleic acid sequences encoding ActRIIA polypeptides may be least 80%, 85%, 90%, 95%, 97%, 98%, 99% or 100% identical to SEQ ID NO: 4 or 5. One of ordinary skill in the art will appreciate that nucleic acid sequences complementary to SEQ ID NO: 4 or 5, and variants of SEQ ID NO: 4 or 5 may be used in the production of ActRIIA polypeptides suitable for use in the methods and compositions described herein. In further embodiments, such nucleic acid sequences can be isolated, recombinant, and/or fused to a heterologous nucleotide sequence, or be from a DNA library.

In other embodiments, nucleic acids used in the production of ActRIIA polypeptides suitable for use in the methods and compositions described herein may include nucleotide sequences that hybridize under highly stringent conditions to the nucleotide sequence designated in SEQ ID NO: 4 or 5, complement sequence of SEQ ID NO: 4 or 5, or fragments thereof. One of ordinary skill in the art will understand that appropriate stringency conditions which promote DNA hybridization can be varied. For example, one can perform the hybridization at 6.0 times sodium chloride/sodium citrate (SSC) at about 45 degree Celsius, followed by a wash of 2.0 times SSC at 50 degree Celsius. For example, the salt concentration in the wash step can be selected from a low stringency of about 2.0 times SSC at 50 degree Celsius to a high stringency of about 0.2 times SSC at 50 degree Celsius. In addition, the temperature in the wash step can be increased from low stringency conditions at room temperature, about 22 degree Celsius, to high stringency conditions at about 65 degree Celsius. Both temperature and salt may be varied, or temperature or salt concentration may be held constant while the other variable is changed. In one embodiment, nucleic acids which hybridize under low stringency conditions of 6 times SSC at room temperature followed by a wash at 2 times SSC at room temperature can be used with the methods and compositions described herein.

Isolated nucleic acids which differ from the nucleic acids as set forth in SEQ ID NOs: 4 or 5 due to degeneracy in the genetic code also can be used in the production of ActRIIA polypeptides suitable for use in the methods and compositions described herein. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation.

In certain embodiments, the recombinant nucleic acids may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated herein. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects, the a nucleic acid used in the production of ActRIIA polypeptides suitable for use in the methods and compositions described herein can be provided in an expression vector comprising a nucleotide sequence encoding an ActRIIA polypeptide and operably linked to at least one regulatory sequence. Regulatory sequences are art-recognized and are selected to direct expression of the ActRIIA polypeptide. Accordingly, the term regulatory sequence includes promoters, enhancers, and other expression control elements. Exemplary regulatory sequences are described in Goeddel; Gene Expression Technology: Methods in Enzymology, Academic Press, San Diego, Calif. (1990). For instance, any of a wide variety of expression control sequences that control the expression of a DNA sequence when operatively linked to it may be used in these vectors to express DNA sequences encoding an ActRIIA polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid used in the production of ActRIIA polypeptides suitable for use in the methods and compositions described herein can be produced by ligating the cloned gene, or a portion thereof, into a vector suitable for expression in either prokaryotic cells, eukaryotic cells (yeast, avian, insect or mammalian), or both. Expression vehicles for production of a recombinant ActRIIA polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Vectors can be designed for production of the subject ActRIIA polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRIIA polypeptides in cells propagated in culture, e.g., to produce proteins, including fusion proteins or variant proteins, for purification.

Host cells transfected with a recombinant gene including a coding sequence (e.g., SEQ ID NO: 4 or 5) for one or more of the subject ActRIIA polypeptides can be used in the production of ActRIIA polypeptides suitable for use in the methods and compositions described herein. The host cell may be any prokaryotic or eukaryotic cell. For example, an ActRIIA polypeptide provided herein may be expressed in bacterial cells such as E. coli, insect cells (e.g., using a baculovirus expression system), yeast, or mammalian cells. Other suitable host cells are known to those skilled in the art.

Accordingly, provided herein are methods of producing the ActRIIA polypeptides. For example, a host cell transfected with an expression vector encoding an ActRIIA polypeptide can be cultured under appropriate conditions to allow expression of the ActRIIA polypeptide to occur. The ActRIIA polypeptide may be secreted and isolated from a mixture of cells and medium containing the ActRIIA polypeptide. Alternatively, the ActRIIA polypeptide may be retained cytoplasmically or in a membrane fraction and the cells harvested, lysed and the protein isolated. A cell culture includes host cells, media and other byproducts. Suitable media for cell culture are well known in the art. The subject ActRIIA polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRIIA polypeptides and affinity purification with an agent that binds to a domain fused to the ActRIIA polypeptide (e.g., a protein A column may be used to purify an ActRIIA-Fc fusion). In a preferred embodiment, the ActRIIA polypeptide is a fusion protein containing a domain which facilitates its purification. In one embodiment, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. As demonstrated herein, ActRIIA-hFc protein was purified to a purity of >98% as determined by size exclusion chromatography and >95% as determined by SDS PAGE. This level of purity was sufficient to achieve desirable effects on bone in mice and an acceptable safety profile in mice, rats and non-human primates.

In another embodiment, a fusion gene coding for a purification leader sequence, such as a poly-(His)/enterokinase cleavage site sequence at the N-terminus of the desired portion of a recombinant ActRIIA polypeptide, can allow purification of the expressed fusion protein by affinity chromatography using a Ni2+ metal resin. The purification leader sequence can then be subsequently removed by treatment with enterokinase to provide the purified ActRIIA polypeptide (e.g., see Hochuli et al., (1987) J. Chromatography 411:177; and Janknecht et al., PNAS USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al., John Wiley & Sons: 1992).

ActRIIA-Fc fusion protein can be expressed in stably transfected CHO-DUKX B11 cells from a pAID4 vector (SV40 ori/enhancer, CMV promoter), using a tissue plasminogen leader sequence of SEQ ID NO:9. The Fc portion is a human IgG1 Fc sequence, as shown in SEQ ID NO:7. In certain embodiments, upon expression, the protein contained has, on average, between about 1.5 and 2.5 moles of sialic acid per molecule of ActRIIA-Fc fusion protein.

In certain embodiments, the long serum half-life of an ActRIIA-Fc fusion can be 25-32 days in human patients. Additionally, the CHO cell expressed material can have a higher affinity for activin B ligand than that reported for an ActRIIA-hFc fusion protein expressed in human 293 cells (del Re et al., J Biol Chem. 2004 Dec. 17; 279(51):53126-35). Additionally, without being bound by theory, the use of the TPA leader sequence provided greater production than other leader sequences and, unlike ActRIIA-Fc expressed with a native leader, may provide a highly pure N-terminal sequence. Use of the native leader sequence may result in two major species of ActRIIA-Fc, each having a different N-terminal sequence.

(b) Inhibitors of ActRIIB

As used herein, the term "ActRIIB" refers to a family of activin receptor type IIB (ActRIIB) proteins from any species and variants derived from such ActRIIB proteins by mutagenesis or other modification. Reference to ActRIIB herein is understood to be a reference to any one of the currently identified forms of the receptor. Members of the ActRIIB family are generally transmembrane proteins, composed of a ligand-binding extracellular domain with a cysteine-rich region, a transmembrane domain, and a cytoplasmic domain with predicted serine/threonine kinase activity.

ActRIIB inhibitors to be used in the compositions and methods described herein include, without limitation, activin-binding soluble ActRIIB polypeptides; antibodies that bind to activin (particularly the activin A or B subunits, also referred to as BA or BB) and disrupt ActRIIB binding; antibodies that bind to ActRIIB and disrupt activin binding; non-antibody proteins selected for activin or ActRIIB binding; and randomized peptides selected for activin or ActRIIB binding, which can be conjugated to an Fc domain.

In certain embodiments, two or more different proteins (or other moieties) with activin or ActRIIB binding activity, especially activin binders that block the type I (e.g., a soluble type I activin receptor) and type II (e.g., a soluble type II activin receptor) binding sites, respectively, may be linked together to create a bifunctional or multifunctional binding molecule that inhibits ActRIIB and thus can be used in the compositions and methods described herein include. In certain embodiments, Activin-ActRIIB signaling axis antagonists that inhibit ActRIIB include nucleic acid aptamers, small molecules and other agents are used in the compositions and methods described herein include.

(i) ActRIIB Inhibitors Comprising ActRIIB Polypeptides

As used herein, the term "ActRIIB polypeptide" refers to polypeptides comprising any naturally occurring polypeptide of an ActRIIB family member as well as any variants thereof (including mutants, fragments, fusions, and peptidomimetic forms) that retain a useful activity. For example, ActRIIB polypeptides include polypeptides derived from the sequence of any known ActRIIB receptor having a sequence at least about 80% identical to the sequence of an ActRIIB polypeptide, and optionally at least 85%, 90%, 95%, 96%, 97%, 98%, 99% or greater identity. For example, an ActRIIB polypeptide may bind to and inhibit the function of an ActRIIB protein and/or activin. An example of an ActRIIB polypeptide includes the human ActRIIB precursor polypeptide (SEQ ID NO:16 or SEQ ID NO:28). With respect to the ActRIIB precursor polypeptide whose amino acid sequence is depicted as SEQ ID NO:16 or SEQ ID NO:28 (i.e., the human ActRIIB precursor polypeptide), the signal peptide of the ActRIIB precursor polypeptide is located at amino acids 1 to 18; the extracellular domain is located at amino acids 19 to 134 and the potential N-linked glycosylation sites are located at amino acid positions 42 and 65. The nucleic acid sequence encoding the human ActRIIB precursor polypeptide of SEQ ID NO:16 is disclosed as SEQ ID NO:19 (SEQ ID NO:19 provides an alanine at the codon corresponding to amino acid position 64, but could be readily modified by one of skill in the art using methods known in the art to provide an arginine at the codon corresponding to amino acid position 64 instead). See Table 6 for a description of the sequences.

The numbering of amino acids for all of the ActRIIB-related polypeptides described herein is based on the amino acid numbering for SEQ ID NO:16 and SEQ ID NO:28 (which only differ in the amino acid expressed at position 64), unless specifically designated otherwise. For example, if an ActRIIB polypeptide is described as having a substitution/mutation at amino acid position 79, then it is to be understood that position 79 refers to the 79th amino acid in SEQ ID NO:16 or SEQ ID NO:28, from which the ActRIIB polypeptide is derived. Likewise, if an ActRIIB polypeptide is described as having an alanine or an arginine at amino acid position 64, then it is to be understood that position 64 refers to the 64th amino acid in SEQ ID NO:16 or SEQ ID NO:28, from which the ActRIIB polypeptide is derived.

In certain embodiments, the inhibitors of ActRIIB used in the compositions and methods described herein comprise polypeptides comprising an activin-binding domain of ActRIIB. In some embodiments, the activin-binding domains of ActRIIB comprise the extracellular domain of ActRIIB, or a portion thereof. In specific embodiments, the extracellular domain or portion thereof of ActRIIB is soluble. Illustrative modified forms of ActRIIB polypeptides are disclosed in U.S. Patent Application Publication Nos. 20090005308 and 20100068215, the disclosures of which are incorporated herein by reference in their entireties.

In specific embodiments, the ActRIIB polypeptides used in the compositions and methods described herein are soluble ActRIIB polypeptides. The term "soluble ActRIIB polypeptide" generally refers to polypeptides comprising an extracellular domain of an ActRIIB protein, including any naturally occurring extracellular domain of an ActRIIB protein as well as any variants thereof (including mutants, fragments and peptidomimetic forms). Soluble ActRIIB polypeptides can bind to activin; however, the wild type ActRIIB protein does not exhibit significant selectivity in binding to activin versus GDF8/11. In certain embodiments, altered forms of ActRIIB with different binding properties can be used in the methods provided herein. Such altered forms are disclosed, e.g., in international patent application publication Nos. WO 2006/012627 and WO 2010/019261, the disclosures of which are incorporated herein by reference in their entireties. Native or altered ActRIIB proteins may be given added specificity for activin by coupling them with a second, activin-selective binding agent. Exemplary soluble ActRIIB polypeptides include the extracellular domain of a human ActRIIB polypeptide (e.g., SEQ ID NOs: 17, 18, 23, 26, 27, 29, 30, 31, 32, 33, 36, 37, 42, and 43).

An Fc fusion protein having the ActRIIB extracellular sequence disclosed by Hilden et al. (Blood, 1994, 83(8): 2163-70), which has an alanine at the position corresponding to amino acid 64 of the ActRIIB precursor amino acid sequence, i.e., SEQ ID NO: 16 (herein referred to as "A64"), has been demonstrated to possess a relatively low affinity for activin and GDF-11. By contrast, an Fc fusion protein with an arginine at position 64 of the ActRIIB precursor amino acid sequence (herein referred to as "R64") has an affinity for activin and GDF-11 in the low nanomolar to high picomolar range (see, e.g., U.S. Patent Application Publication No. 20100068215, the disclosure of which is herein incorporated in its entirety). An ActRIIB precursor amino acid sequence with an arginine at position 64 is presented in SEQ ID NO:28. As such, in certain embodiments, the ActRIIB polypeptides used in accordance with the compositions and methods described herein may comprise either (i) an alanine at the position corresponding to amino acid 64 of the ActRIIB precursor amino acid sequence, i.e., SEQ ID NO: 16; or (ii) an arginine at position 64 of the ActRIIB precursor amino acid sequence, i.e., SEQ ID NO: 28. In other embodiments, the ActRIIB polypeptides used in accordance with the compositions and methods described herein may comprise an amino acid that is not alanine or arginine at the position corresponding to amino acid 64 of the ActRIIB precursor amino acid sequence, i.e., SEQ ID NO: 16 or SEQ ID NO:28.

It has been shown that a deletion of the proline knot at the C-terminus of the extracellular domain of ActRIIB reduces the affinity of the receptor for activin (see, e.g., Attisano et al., Cell, 1992, 68(1):97-108). An ActRIIB-Fc fusion protein containing amino acids 20-119 of SEQ ID NO: 28 (i.e., SEQ ID NO:32), "ActRIIB(20-119)-Fc" has reduced binding to GDF-11 and activin relative to an ActRIIB-Fc fusion protein containing amino acids 20-134 of SEQ ID NO: 28 (i.e., SEQ ID NO:31), "ActRIIB(20-134)-Fc", which includes the proline knot region and the complete juxtamembrane domain. However, an ActRIIB-Fc fusion protein containing amino acids 20-129 of SEQ ID NO: 28, "ActRIIB(20-129)-Fc" retains similar but somewhat reduced activity relative to the non-truncated extracellular domain of ActRIIB, even though the proline knot region is disrupted. Thus, ActRIIB polypeptides comprising extracellular domains that stop at amino acid 134, 133, 132, 131, 130 and 129 of SEQ ID NO: 28 (or SEQ ID NO:16) are all expected to be active, but constructs stopping at amino acid 134 or 133 may be most active. Similarly, mutations at any of residues 129-134 are not expected to alter ligand binding affinity by large margins, as indicated by the fact that mutations of P129 and P130 of SEQ ID NO: 28 do not substantially decrease ligand binding. Therefore, the ActRIIB polypeptides used in accordance with the methods and compositions described herein may end as early as amino acid 109 (i.e., the final cysteine) of SEQ ID NO:28 (or SEQ ID NO:16), however, forms ending at or between amino acid positions 109 and 119 of SEQ ID NO:28 (or SEQ ID NO:16) are expected to have reduced ligand binding ability.

Amino acid 29 of SEQ ID NO:16 and SEQ ID NO:28 represents the initial cysteine in the ActRIIB precursor sequence. It is expected that an ActRIIB polypeptide beginning at amino acid 29 of the N-terminus of SEQ ID NO:16 or SEQ ID NO:28, or before these amino acid positions, will retain ligand binding activity. An alanine to asparagine mutation at position 24 of SEQ ID NO:16 or SEQ ID NO:28 introduces an N-linked glycosylation sequence without substantially affecting ligand binding. This confirms that mutations in the region between the signal cleavage peptide and the cysteine cross-linked region, corresponding to amino acids 20-29 of SEQ ID NO:16 or SEQ ID NO:28, are well tolerated. In particular, ActRIIB polypeptides beginning at amino acid position 20, 21, 22, 23 and 24 of SEQ ID NO:16 or SEQ ID NO:28 will retain activity, and ActRIIB polypeptides beginning at amino acid positions 25, 26, 27, 28 and 29 of SEQ ID NO:16 or SEQ ID NO:28 are also expected to retain activity. An ActRIIB polypeptide beginning at amino acid position 22, 23, 24 or 25 of SEQ ID NO:16 or SEQ ID NO:28 will have the most activity.

Taken together, the active portions (i.e., ActRIIB polypeptides) of the ActRIIB precursor protein (i.e., SEQ ID NO:16 or SEQ ID NO:28) to be used in accordance with the methods and compositions described herein will generally comprise amino acids 29-109 of SEQ ID NO:16 or SEQ ID NO:28, and such ActRIIB polypeptides may, for example, begin at a residue corresponding to any one of amino acids 19-29 of SEQ ID NO:16 or SEQ ID NO:28 and end at a position corresponding to any one of amino acids 109-134 of SEQ ID NO:16 or SEQ ID NO:28. Specific examples of ActRIIB polypeptides encompassed herein include those that begin at an amino acid position from 19-29, 20-29 or 21-29 of SEQ ID NO:16 or SEQ ID NO:28 and end at an amino acid position from 119-134, 119-133 or 129-134, 129-133 of SEQ ID NO:16 or SEQ ID NO:28. Other specific examples of ActRIIB polypeptides encompassed herein include those that begin at an amino acid position from 20-24 (or 21-24, or 22-25) of SEQ ID NO:16 or SEQ ID NO:28 and end at an amino acid position from 109-134 (or 109-133), 119-134 (or 119-133) or 129-134 (or 129-133) of SEQ ID NO:16 or SEQ ID NO:28. Variant ActRIIB polypeptides falling within these ranges are also contemplated, particularly those having at least 80%, 85%, 90%, 91%, 92%, 93%, 94%, 95%, 96%, 97%, 98%, or 99% sequence identity or sequence homology to the corresponding portion of SEQ ID NO:16 or SEQ ID NO:28.

In certain embodiments, the inhibitors of ActRIIB used in the compositions and methods described herein comprise a truncated form of an extracellular domain of ActRIIB. The truncation can be at the carboxy terminus and/or the amino terminus of the ActRIIB polypeptide. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 amino acids long relative to the mature ActRIIB polypeptide extracellular domain. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 N-terminal amino acids of the mature ActRIIB polypeptide extracellular domain. In certain embodiments, the truncation can be 1, 2, 3, 4, 5, 6, 7, 8, 9, 10, 11, 12, 13, 14, 15, 16, 17, 18, 19, 20, 21, 22, 23, 24, or 25 C-terminal amino acids of the mature ActRIIB polypeptide extracellular domain. For example, truncated forms of ActRIIB include polypeptides with amino acids 20-119; 20-128; 20-129; 20-130; 20-131; 20-132; 20-133; 20-134; 20-131; 21-131; 22-131; 23-131; 24-131; and 25-131, wherein the amino acid positions refer to the amino acid positions in SEQ ID NO:16 or SEQ ID NO:28.

Additional exemplary truncated forms of ActRIIB include (i) polypeptides beginning at amino acids at any of amino acids 21-29 of SEQ ID NO:16 or SEQ ID NO:28 (optionally beginning at 22-25 of SEQ ID NO:16 or SEQ ID NO:28) and ending at any of amino acids 109-134 of SEQ ID NO:16 or SEQ ID NO:28; (ii) polypeptides beginning at any of amino acids 20-29 of SEQ ID NO:16 or SEQ ID NO:28 (optionally beginning at 22-25 of SEQ ID NO:16 or SEQ ID NO:28) and ending at any of amino acids 109-133 of SEQ ID NO:16 or SEQ ID NO:28; (iii) polypeptides beginning at any of amino acids 20-24 of SEQ ID NO:16 or SEQ ID NO:28 (optionally beginning at 22-25 of SEQ ID NO:16 or SEQ ID NO:28) and ending at any of amino acids 109-133 of SEQ ID NO:16 or SEQ ID NO:28; (iv) polypeptides beginning at any of amino acids 21-24 of SEQ ID NO:16 or SEQ ID NO:28 and ending at any of amino acids 109-134 of SEQ ID NO:16 or SEQ ID NO:28; (v) polypeptides beginning at any of amino acids 20-24 of SEQ ID NO:16 or SEQ ID NO:28 and ending at any of amino acids 118-133 of SEQ ID NO:16 or SEQ ID NO:28; (vi) polypeptides beginning at any of amino acids 21-24 of SEQ ID NO:16 or SEQ ID NO:28 and ending at any of amino acids 118-134 of SEQ ID NO:16 or SEQ ID NO:28; (vii) polypeptides beginning at any of amino acids 20-24 of SEQ ID NO:16 or SEQ ID NO:28 and ending at any of amino acids 128-133 of SEQ ID NO:16 or SEQ ID NO:28; (viii) polypeptides beginning at any of amino acids 20-24 of SEQ ID NO:16 or SEQ ID NO:28 and ending at any of amino acids 128-133 of SEQ ID NO:16 or SEQ ID NO:28; (ix) polypeptides beginning at any of amino acids 21-29 of SEQ ID NO:16 or SEQ ID NO:28 and ending at any of amino acids 118-134 of SEQ ID NO:16 or SEQ ID NO:28; (x) polypeptides beginning at any of amino acids 20-29 of SEQ ID NO:16 or SEQ ID NO:28 and ending at any of amino acids 118-133 of SEQ ID NO:16 or SEQ ID NO:28; (xi) polypeptides beginning at any of amino acids 21-29 of SEQ ID NO:16 or SEQ ID NO:28 and ending at any of amino acids 128-134 of SEQ ID NO:16 or SEQ ID NO:28; and (xii) polypeptides beginning at any of amino acids 20-29 of SEQ ID NO:16 or SEQ ID NO:28 and ending at any of amino acids 128-133 of SEQ ID NO:16 or SEQ ID NO:28. In a specific embodiment, an ActRIIB polypeptides comprises, consists essentially of, or consists of, an amino acid sequence beginning at amino acid position 25 of SEQ ID NO:16 or SEQ ID NO:28 and ending at amino acid position 131 of SEQ ID NO:16 or SEQ ID NO:28. In another specific embodiment, an ActRIIB polypeptide consists of, or consists essentially of, the amino acid sequence of SEQ ID NO:17, 18, 23, 26, 27, 29, 30, 31, 32, 33, 36, 37, 42, or 43.

Any of the ActRIIB polypeptides used in the compositions and methods described herein may be produced as a homodimer. Any of the ActRIIB polypeptides used in the compositions and methods described herein may be formulated as a fusion protein having a heterologous portion that comprises a constant region from an IgG heavy chain, such as an Fc domain. Any of the ActRIIB polypeptides used in the compositions and methods described herein may comprise an acidic amino acid at the position corresponding to position 79 of SEQ ID NO:16 or SEQ ID NO:28, optionally in combination with one or more additional amino acid substitutions, deletions or insertions relative to SEQ ID NO:16 or SEQ ID NO:28.

In specific embodiments, the inhibitors of ActRIIB used in the compositions and methods described herein comprise an extracellular domain of ActRIIB with one or more amino acid substitutions/mutations. Such an amino acid substitution/mutation can be, for example, an exchange from the leucine at amino acid position 79 of SEQ ID NO:16 or SEQ ID NO:28 to an acidic amino acid, such as aspartic acid or glutamic acid. For example, position L79 of SEQ ID NO:16 or SEQ ID NO:28 may be altered in ActRIIB extracellular domain polypeptides to confer altered activin-myostatin (GDF-11) binding properties. L79A and L79P mutations reduce GDF-11 binding to a greater extent than activin binding. L79E and L79D mutations retain GDF-11 binding, while demonstrating greatly reduced activin binding.

In certain embodiments, the inhibitors of ActRIIB used in the compositions and methods described herein comprise a truncated form of an ActRIIB extracellular domain that also carries an amino acid substitution, e.g., an exchange from the leucine at amino acid position 79 of SEQ ID NO:16 or SEQ ID NO:28 to an acidic amino acid, such as aspartic acid or glutamic acid. In a specific embodiment, the truncated form of an extracellular domain of ActRIIB polypeptide that also carries an amino acid substitution used in the compositions and methods described herein is SEQ ID NO:23. Forms of ActRIIB that are truncated and/or carry one or more amino acid substitutions can be linked to an Fc domain of an antibody as discussed above.

Functionally active fragments of ActRIIB polypeptides can be obtained, for example, by screening polypeptides recombinantly produced from the corresponding fragment of the nucleic acid encoding an ActRIIB polypeptide. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRIIB protein or signaling mediated by activin.

In addition, functionally active variants of ActRIIB polypeptides can be obtained, for example, by screening libraries of modified polypeptides recombinantly produced from the corresponding mutagenized nucleic acids encoding an ActRIIB polypeptide. The variants can be produced and tested to identify those that can function as antagonists (inhibitors) of ActRIIB protein or signaling mediated by activin. In certain embodiments, a functional variant of the ActRIIB polypeptides comprises an amino acid sequence that is at least 75% identical to an amino acid sequence selected from SEQ ID NO:17, 18, 23, 26, 27, 29, 30, 31, 32, 33, 36, 37, 42, and 43. In certain embodiments, the functional variant has an amino acid sequence at least 80%, 85%, 90%, 95%, 96%, 97%, 98%, or 99% identical to an amino acid sequence selected from SEQ ID NO:17, 18, 23, 26, 27, 29, 30, 31, 32, 33, 36, 37, 42, and 43.

Functional variants may be generated, for example, by modifying the structure of an ActRIIB polypeptide for such purposes as enhancing therapeutic efficacy, or stability (e.g., ex vivo shelf life and resistance to proteolytic degradation in vivo). Such modified ActRIIB polypeptides when selected to retain activin binding, are considered functional equivalents of the naturally-occurring ActRIIB polypeptides. Modified ActRIIB polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRIIB polypeptide results in a functional homolog can be readily determined by assessing the ability of the variant ActRIIB polypeptide to produce a response in cells in a fashion similar to the wild-type ActRIIB polypeptide.

ActRIIB polypeptide mutants, particularly sets of combinatorial mutants of an ActRIIB polypeptide, as well as truncation mutants; pools of combinatorial mutants are especially useful for identifying functional variant sequences can be used in the methods and compositions described herein. The purpose of screening such combinatorial libraries may be to generate, for example, ActRIIB polypeptide variants which can act as either agonists or antagonist, or alternatively, which possess novel activities all together.

It has been demonstrated that the ligand binding pocket of ActRIIB is defined by residues Y31, N33, N35, L38 through T41, E47, E50, Q53 through K55, L57, H58, Y60, S62, K74, W78 through N83, Y85, R87, A92, and E94 through F101 of SEQ ID NO:16 or SEQ ID NO:28. At these positions, it is expected that conservative mutations will be tolerated, although a K74A mutation is well-tolerated, as are R40A, K55A, F82A and mutations at position L79. R40 is a K in Xenopus, indicating that basic amino acids at this position will be tolerated. Q53 is R in bovine ActRIIB and K in Xenopus ActRIIB, and therefore amino acids including R, K, Q, N and H will be tolerated at this position. Thus, a general formula for an ActRIIB polypeptide for use in the methods and compositions described herein is one that comprises amino acids 29-109 of SEQ ID NO:16 or SEQ ID NO:28, but optionally beginning at an amino acid position ranging from 20-24 or 22-25 of SEQ ID NO:16 or SEQ ID NO:28 and ending at an amino acid position ranging from 129-134 of SEQ ID NO:16 or SEQ ID NO:28, and comprising no more than 1, 2, 5, or 15 conservative amino acid changes in the ligand binding pocket, and zero, one or more non-conservative alterations at amino acid positions 40, 53, 55, 74, 79 and/or 82 of SEQ ID NO:16 or SEQ ID NO:28 in the ligand binding pocket. Such an ActRIIB polypeptide may retain greater than 80%, 90%, 95% or 99% sequence identity or sequence homology to the sequence of amino acids 29-109 of SEQ ID NO:16 or SEQ ID NO:28. Sites outside the binding pocket, at which variability may be particularly well tolerated, include the amino and carboxy termini of the extracellular domain of ActRIIB, and positions 42-46 and 65-73. An asparagine to alanine alteration at position 65 of SEQ ID NO:16 or SEQ ID NO:28 (N65A) actually improves ligand binding in the A64 background, and is thus expected to have no detrimental effect on ligand binding in the R64 background. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64.

As a specific example of an ActRIIB polypeptide with a mutation in the ligand binding domain, the positively-charged amino acid residue Asp (D80) of the ligand-binding domain of ActRIIB can be mutated to a different amino acid residue such that the variant ActRIIB polypeptide preferentially binds to GDF8, but not activin. In a specific embodiment, the D80 residue is changed to an amino acid residue selected from the group consisting of: an uncharged amino acid residue, a negative amino acid residue, and a hydrophobic amino acid residue. As a further specific example, the hydrophobic residue L79 can be altered to the acidic amino acids aspartic acid or glutamic acid to greatly reduce activin binding while retaining GDF11 binding. As will be recognized by one of skill in the art, most of the described mutations, variants or modifications may be made at the nucleic acid level or, in some cases, by post translational modification or chemical synthesis. Such techniques are well known in the art.

In specific embodiments, the inhibitors of ActRIIB used in the compositions and methods described herein comprise a conjugate/fusion protein comprising an extracellular domain (e.g., an activin-binding domain) of an ActRIIB receptor linked to an Fc portion of an antibody. Such conjugate/fusion proteins may comprise any of the ActRIIB polypeptides disclosed herein (e.g., any of SEQ ID NOs:17, 18, 23, 26, 27, 29, 30, 31, 32, 33, 36, 37, 42, or 43), any ActRIIB polypeptides known in the art, or any ActRIIB polypeptides generated using methods known in the art and/or provided herein.

In certain embodiments, the extracellular domain is linked to an Fc portion of an antibody via a linker, e.g., a peptide linker. Exemplary linkers include short polypeptide sequences such as 2-10, 2-5, 2-4, 2-3 amino acid residues (e.g., glycine residues), such as, for example, a Gly-Gly-Gly linker. In a specific embodiment, the linker comprises the amino acid sequence Gly-Gly-Gly (GGG). In another specific embodiment, the linker comprises the amino acid sequence Thr-Gly-Gly-Gly (TGGG). Optionally, the Fc domain has one or more mutations at residues such as Asp-265, lysine 322, and Asn-434. In certain cases, the mutant Fc domain having one or more of these mutations (e.g., an Asp-265 mutation) has a reduced ability to bind to the Fcγ receptor relative to a wild-type Fc domain. In other cases, the mutant Fc domain having one or more of these mutations (e.g., an Asn-434 mutation) has an increased ability to bind to the MHC class I-related Fc-receptor (FcRN) relative to a wild-type Fc domain. Exemplary fusion proteins comprising a soluble extracellular domain of ActRIIB fused to an Fc domain are set forth in SEQ ID NOs:20, 21, 24, 25, 34, 35, 38, 39, 40, 41, 44, 46, and 47.

In a specific embodiment, the ActRIIB inhibitors used in the compositions and methods described herein comprise the extracellular domain of ActRIIB, or a portion thereof, linked to an Fc portion of an antibody, wherein said ActRIIB inhibitor comprises an amino acid sequence that is at least 75% identical to an amino acid sequence selected from SEQ ID NOs:20, 21, 24, 25, 34, 35, 38, 39, 40, 41, 44, 46, and 47. In another specific embodiment, the ActRIIB inhibitors used in the compositions and methods described herein comprise the extracellular domain of ActRIIB, or a portion thereof, linked to an Fc portion of an antibody, wherein said ActRIIB inhibitor comprises an amino acid sequence that is at least 80%, 85%, 90%, 95%, 96%, 97%, 98%, or 99% identical to an amino acid sequence selected from SEQ ID NOs:20, 21, 24, 25, 34, 35, 38, 39, 40, 41, 44, 46, and 47.

In a specific embodiment, the ActRIIB inhibitor to be used in the compositions and methods described herein is a fusion protein between the extracellular domain of the human ActRIIB receptor and the Fc portion of IgG1. In another specific embodiment, the ActRIIB inhibitor to be used in the compositions and methods described herein is a fusion protein between a truncated extracellular domain of the human ActRIIB receptor and the Fc portion of IgG1. In another specific embodiment, the ActRIIB inhibitor to be used in the compositions and methods described herein is a fusion protein between a truncated extracellular domain of the human ActRIIB receptor and the Fc portion of IgG1, wherein the truncated extracellular domain of the human ActRIIB receptor possesses an amino acid substitution at the amino acid position corresponding to amino acid 79 of SEQ ID NO:16 or SEQ ID NO:28. In one embodiment, the amino acid substitution at the amino acid position corresponding to amino acid 79 of SEQ ID NO:16 or SEQ ID NO:28 is substitution of Leucine for Aspartic Acid (i.e., an L79D mutation).

In a specific embodiment, the ActRIIB inhibitor to be used in the compositions and methods described herein is SEQ ID NO:24 or 25, which represents a fusion protein between the extracellular domain of the human ActRIIB receptor and the Fc portion of IgG1, wherein said ActRIIB extracellular domain comprises amino acids 25-131 of SEQ ID NO:28 with an L79D mutation. The nucleic acid sequence encoding the ActRIIB-Fc fusion protein of SEQ ID NO:24 is presented in SEQ ID NO:45.

In another specific embodiment, the ActRIIB inhibitor to be used in the compositions and methods described herein is SEQ ID NO:34 or 35, which represents a fusion protein between the extracellular domain of the human ActRIIB receptor and the Fc portion of IgG1, wherein said ActRIIB extracellular domain comprises amino acids 25-131 of SEQ ID NO:16 with an L79D mutation.

Asparagine-linked glycosylation recognition sites generally comprise a tripeptide sequence, asparagine-X-threonine (or asparagine-X-serine) (where "X" is any amino acid) which is specifically recognized by appropriate cellular glycosylation enzymes. The alteration may also be made by the addition of, or substitution by, one or more serine or threonine residues to the sequence of the wild-type ActRIIB polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRIIB polypeptide is by chemical or enzymatic coupling of glycosides to the ActRIIB polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in International Patent Application No. WO 87/05330 published Sep. 11, 1987, and in Aplin and Wriston (1981) CRC Crit. Rev. Biochem., pp. 259-306, incorporated by reference herein. Removal of one or more carbohydrate moieties present on an ActRIIB polypeptide may be accomplished chemically and/or enzymatically. Chemical deglycosylation may involve, for example, exposure of the ActRIIB polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ActRIIB polypeptides can be achieved by the use of a variety of endo- and exo-glycosidases as described by Thotakura et al. (1987) Meth. Enzymol. 138:350. The sequence of an ActRIIB polypeptide may be adjusted, as appropriate, depending on the type of expression system used, as mammalian, yeast, insect and plant cells may all introduce differing glycosylation patterns that can be affected by the amino acid sequence of the peptide. In general, ActRIIB proteins for use in humans will be expressed in a mammalian cell line that provides proper glycosylation, such as HEK293 or CHO cell lines, although other expression systems, such as other mammalian expression cell lines, yeast cell lines with engineered glycosylation enzymes and insect cells, are expected to be useful as well.

In specific embodiments, mutated ActRIIB polypeptides comprising the addition of a further N-linked glycosylation site (N—X—S/T) that increases the serum half-life of an ActRIIB-Fc fusion protein, relative to the ActRIIB(R64)-Fc form can be used in the methods and compositions described herein. In a specific embodiment, introduction of an asparagine at position 24 of SEQ ID NO:16 or SEQ ID NO:28 (A24N) results in the creation of an NXT sequence that confers a longer half-life. Other NX(T/S) sequences can be found at 42-44 (NQS) and 65-67 (NSS), although the latter may not be efficiently glycosylated with the R at position 64 (i.e., in R64 polypeptides). N—X—S/T sequences may be generally introduced at positions outside the ligand binding pocket of ActRIIB, which is detailed above. Particularly suitable sites for the introduction of non-endogenous N—X—S/T sequences include amino acids 20-29, 20-24, 22-25, 109-134, 120-134 or 129-134 of SEQ ID NO:16 or SEQ ID NO:28. N—X—S/T sequences may also be introduced into the linker between the ActRIIB sequence and the Fc or other fusion component. Such a site may be introduced with minimal effort by introducing an N in the correct position with respect to a pre-existing S or T, or by introducing an S or T at a position corresponding to a pre-existing N. Thus, desirable alterations that would create an N-linked glycosylation site are: A24N, R64N, S67N (possibly combined with an N65A alteration), E106N, R112N, G120N, E123N, P129N, A132N, R112S and R112T (with all amino acid positions corresponding to the positions they can be found in SEQ ID NO:16 or SEQ ID NO:28). Any S that is predicted to be glycosylated may be altered to a T without creating an immunogenic site, because of the protection afforded by the glycosylation. Likewise, any T that is predicted to be glycosylated may be altered to an S. Thus the alterations S67T and S44T are encompassed herein. Likewise, in an A24N variant, an S26T alteration may be used. Accordingly, an ActRIIB polypeptide may include one or more additional, non-endogenous N-linked glycosylation consensus sequences.

A variety of screening assays may be used to evaluate ActRIIB polypeptide variants. For example, an ActRIIB polypeptide variant may be screened for ability to bind to an ActRIIB ligand, to prevent binding of an ActRIIB ligand to an ActRIIB polypeptide or to interfere with signaling caused by an ActRIIB ligand. The activity of an ActRIIB polypeptide or its variants may also be tested in a cell-based or in vivo assay.

Combinatorially-derived variants can be generated which have a selective or generally increased potency relative to a naturally occurring ActRIIB polypeptide. Likewise, mutagenesis can give rise to variants which have intracellular half-lives dramatically different than the corresponding wild-type ActRIIB polypeptide. For example, the altered protein can be rendered either more stable or less stable to proteolytic degradation or other cellular processes which result in destruction of, or otherwise inactivation of a native ActRIIB polypeptide. Such variants, and the genes which encode them, can be utilized to alter ActRIIB polypeptide levels by modulating the half-life of the ActRIIB polypeptides. For instance, a short half-life can give rise to more transient biological effects and can allow tighter control of recombinant ActRIIB polypeptide levels within the patient. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential ActRIIB polypeptide sequences. For instance, a mixture of synthetic oligonucleotides can be enzymatically ligated into gene sequences such that the degenerate set of potential ActRIIB polypeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, ActRIIB polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of ActRIIB polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRIIB polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include activin binding assays and activin-mediated cell signaling assays.

In certain embodiments, ActRIIB polypeptides used in the methods and compositions described herein may further comprise post-translational modifications in addition to any that are naturally present in the ActRIIB polypeptides. Such modifications include, but are not limited to, acetylation, carboxylation, glycosylation, phosphorylation, lipidation, and acylation. As a result, the modified ActRIIB polypeptides may contain non-amino acid elements, such as polyethylene glycols, lipids, poly- or mono-saccharide, and phosphates. Effects of such non-amino acid elements on the functionality of a ActRIIB polypeptide may be tested by any method known to the skilled artisan. When an ActRIIB polypeptide is produced in cells by cleaving a nascent form of the ActRIIB polypeptide, post-translational processing may also be important for correct folding and/or function of the protein. Different cells (such as CHO, HeLa, MDCK, 293, W138, NIH-3T3 or HEK293) have specific cellular machinery and characteristic mechanisms for such post-translational activities and may be chosen to ensure the correct modification and processing of the ActRIIB polypeptides.

In certain aspects, functional variants or modified forms of the ActRIIB polypeptides include fusion proteins having at least a portion of the ActRIIB polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS6) fusion partners. As another example, a fusion domain may be selected so as to facilitate detection of the ActRIIB polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus hemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRIIB polypeptide is fused with a domain that stabilizes the ActRIIB polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of bone growth or muscle growth, as desired).

It is understood that different elements of the fusion proteins may be arranged in any manner that is consistent with the desired functionality. For example, an ActRIIB polypeptide may be placed C-terminal to a heterologous domain, or, alternatively, a heterologous domain may be placed C-terminal to an ActRIIB polypeptide. The ActRIIB polypeptide domain and the heterologous domain need not be adjacent in a fusion protein, and additional domains or amino acid sequences may be included C- or N-terminal to either domain or between the domains.

In certain embodiments, the ActRIIB polypeptides used in the methods and compositions described herein contain one or more modifications that are capable of stabilizing the ActRIIB polypeptides. For example, such modifications enhance the in vitro half life of the ActRIIB polypeptides, enhance circulatory half life of the ActRIIB polypeptides or reduce proteolytic degradation of the ActRIIB polypeptides. Such stabilizing modifications include, but are not limited to, fusion proteins (including, for example, fusion proteins comprising an ActRIIB polypeptide and a stabilizer domain), modifications of a glycosylation site (including, for example, addition of a glycosylation site to an ActRIIB polypeptide), and modifications of carbohydrate moiety (including, for example, removal of carbohydrate moieties from an ActRIIB polypeptide). In the case of fusion proteins, an ActRIIB polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol.

In certain embodiments, the methods and compositions described herein use isolated or purified ActRIIB polypeptides, i.e., ActRIIB polypeptides which are isolated from, or otherwise substantially free of, other proteins can be used with the methods and compositions described herein. ActRIIB polypeptides will generally be produced by expression from recombinant nucleic acids.

In certain aspects, the ActRIIB polypeptides used in the methods and compositions described herein are encoded by isolated and/or recombinant nucleic acids, including fragments, functional variants and fusion proteins disclosed herein. For example, SEQ ID NO:19 encodes the naturally occurring human ActRIIB precursor polypeptide. The subject nucleic acids may be single-stranded or double stranded. Such nucleic acids may be DNA or RNA molecules. These nucleic acids may be used, for example, in methods for making ActRIIB polypeptides or as direct therapeutic agents (e.g., in a gene therapy approach).

In certain aspects, the nucleic acids that can be used to produce ActRIIB polypeptides suitable for use in the methods and compositions described herein are further understood to include nucleic acids that are variants of SEQ ID NO: 19 as well as variants of those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43). Variant nucleotide sequences include sequences that differ by one or more nucleotide substitutions, additions or deletions, such as allelic variants.

In certain embodiments, the isolated or recombinant nucleic acid sequences that can be used to produce ActRIIB polypeptides suitable for use in the methods and compositions described herein are at least 80%, 85%, 90%, 95%, 97%, 98%, 99% or 100% identical to SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43). One of ordinary skill in the art will appreciate that nucleic acid sequences complementary to SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43), and variants of SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43) can be used with the methods and compositions described herein. In further embodiments, the nucleic acid sequences can be isolated, recombinant, and/or fused with a heterologous nucleotide sequence, or in a DNA library.

In other embodiments, nucleic acids that can be used to produce ActRIIB polypeptides suitable for use in the methods and compositions described herein include nucleotide sequences that hybridize under highly stringent conditions to the nucleotide sequence designated in SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43), complement sequence of SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43), or fragments thereof. One of ordinary skill in the art will understand that appropriate stringency conditions which promote DNA hybridization can be varied. For example, one can perform the hybridization at 6.0 times sodium chloride/sodium citrate (SSC) at about 45 degree Celsius, followed by a wash of 2.0 times SSC at 50 degree Celsius. For example, the salt concentration in the wash step can be selected from a low stringency of about 2.0 times SSC at 50 degree Celsius to a high stringency of about 0.2 times SSC at 50 degree Celsius. In addition, the temperature in the wash step can be increased from low stringency conditions at room temperature, about 22 degree Celsius, to high stringency conditions at about 65 degree Celsius. Both temperature and salt may be varied, or temperature or salt concentration may be held constant while the other variable is changed. In one embodiment, nucleic acids which hybridize under low stringency conditions of 6 times SSC at room temperature followed by a wash at 2 times SSC at room temperature can be used with the methods and compositions described herein.

Isolated nucleic acids which differ from the nucleic acids as set forth in SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43) due to degeneracy in the genetic code can also be used to produce ActRIIB polypeptides suitable for use in the methods and compositions described herein. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms can be used with the methods and compositions described herein.

In certain embodiments, the recombinant nucleic acids that can be used to produce ActRIIB polypeptides suitable for use in the methods and compositions described herein may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art can be used with the methods and compositions described herein. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects, the nucleic acids that can be used to produce ActRIIB polypeptides suitable for use in the methods and compositions described herein are provided in an expression vector comprising a nucleotide sequence encoding an ActRIIB polypeptide and operably linked to at least one regulatory sequence. Regulatory sequences are art-recognized and are selected to direct expression of the ActRIIB polypeptide. Accordingly, the term regulatory sequence includes promoters, enhancers, and other expression control elements. Exemplary regulatory sequences are described in Goeddel; Gene Expression Technology: Methods in Enzymology, Academic Press, San Diego, Calif. (1990). For instance, any of a wide variety of expression control sequences that control the expression of a DNA sequence when operatively linked to it may be used in these vectors to express DNA sequences encoding an ActRIIB polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant ActRIIB polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In one embodiment, a vector can be designed for production of the ActRIIB polypeptides used in the methods and compositions described herein in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRIIB polypeptides in cells propagated in culture, e.g., to produce proteins, including fusion proteins or variant proteins, for purification.

Host cells transfected with a recombinant gene including a coding sequence (e.g., SEQ ID NO:19 or those nucleic acid sequences that encode soluble ActRIIB polypeptides (e.g., nucleic acids that encode SEQ ID NOs: 17, 18, 23, 26, 27, 29, 30, 31, 32, 33, 36, 37, 42, and 43)) for one or more of the subject ActRIIB polypeptides can be used to produce ActRIIB polypeptides suitable for use in the methods and compositions described herein. The host cell may be any prokaryotic or eukaryotic cell. For example, an ActRIIB polypeptide may be expressed in bacterial cells such as E. coli, insect cells (e.g., using a baculovirus expression system), yeast, or mammalian cells. Other suitable host cells are known to those skilled in the art.

Accordingly, provided herein are methods of producing the ActRIIB polypeptides used in the methods and compositions described herein. For example, a host cell transfected with an expression vector encoding an ActRIIB polypeptide can be cultured under appropriate conditions to allow expression of the ActRIIB polypeptide to occur. The ActRIIB polypeptide may be secreted and isolated from a mixture of cells and medium containing the ActRIIB polypeptide. Alternatively, the ActRIIB polypeptide may be retained cytoplasmically or in a membrane fraction and the cells harvested, lysed and the protein isolated. A cell culture includes host cells, media and other byproducts. Suitable media for cell culture are well known in the art. The subject ActRIIB polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRIIB polypeptides and affinity purification with an agent that binds to a domain fused to the ActRIIB polypeptide (e.g., a protein A column may be used to purify an ActRIIB-Fc fusion). In a preferred embodiment, the ActRIIB polypeptide is a fusion protein containing a domain which facilitates its purification. In a preferred embodiment, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. As demonstrated herein, ActRIIB-hFc protein was purified to a purity of >98% as determined by size exclusion chromatography and >95% as determined by SDS PAGE. This level of purity was sufficient to achieve desirable effects on bone in mice and an acceptable safety profile in mice, rats and non-human primates.

In another embodiment, a fusion gene coding for a purification leader sequence, such as a poly-(His)/enterokinase cleavage site sequence at the N-terminus of the desired portion of the recombinant ActRIIB polypeptide, can allow purification of the expressed fusion protein by affinity chromatography using a Ni2+ metal resin. The purification leader sequence can then be subsequently removed by treatment with enterokinase to provide the purified ActRIIB polypeptide (e.g., see Hochuli et al., (1987) J. Chromatography 411:177; and Janknecht et al., PNAS USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al., John Wiley & Sons: 1992).

ActRIIB-Fc fusion protein can be expressed in stably transfected CHO-DUKX B1 1 cells from a pAID4 vector (SV40 ori/enhancer, CMV promoter), using a tissue plasminogen leader sequence of SEQ ID NO:8. The Fc portion can comprise a human IgG1 Fc sequence, as shown in SEQ ID NO:7. In certain embodiments, upon expression, the protein contained has, on average, between about 1.5 and 2.5 moles of sialic acid per molecule of ActRIIB-Fc fusion protein.

In certain embodiments, the long serum half-life of an ActRIIB-Fc fusion can be 25-32 days in human patients. Additionally, the CHO cell expressed material can have a higher affinity for activin B ligand than that reported for an ActRIIB-hFc fusion protein expressed in human 293 cells (del Re et al., J Biol Chem. 2004 Dec. 17; 279(51):53126-35). Additionally, without being bound by theory, the use of the TPA leader sequence provided greater production than other leader sequences and, unlike ActRIIB-Fc expressed with a native leader, may provide a highly pure N-terminal sequence. Use of the native leader sequence may result in two major species of ActRIIB-Fc, each having a different N-terminal sequence.

(ii) Other ActRII Receptor Inhibitors

In certain embodiments, the inhibitors of ActRII receptors used in the compositions and methods described herein are nucleic acid compounds.

Examples of categories of nucleic acid compounds that inhibit ActRII receptors include antisense nucleic acids, siRNA or RNAi constructs and catalytic nucleic acid constructs. A nucleic acid compound may be single- or double-stranded. A double-stranded compound may also include regions of overhang or non-complementarity, where one or the other of the strands is single-stranded. A single-stranded compound may include regions of self-complementarity, meaning that the compound may form a so-called "hairpin" or "stem-loop" structure, with a region of double helical structure.

In certain embodiments, the nucleic acid compounds that inhibit ActRII receptors may comprise a nucleotide sequence that is complementary to a region consisting of no more than 1000, no more than 500, no more than 250, no more than 100 or no more than 50, 35, 30, 25, 22, 20 or 18 nucleotides of the full-length ActRII receptor nucleic acid sequence or activin nucleic acid sequence (e.g., the nucleic acid sequence of an activin A or activin B subunit, also referred to as βA or βB). In specific embodiments, the region of complementarity will be at least 8 nucleotides, and optionally at least 10 or at least 15 nucleotides, and optionally between 15 and 25 nucleotides. A region of complementarity may fall within an intron, a coding sequence or a noncoding sequence of the target transcript, such as the coding sequence portion. Generally, a nucleic acid compound that inhibits an ActRII receptor will have a length of about 8 to about 500 nucleotides or base pairs in length, and optionally the length will be about 14 to about 50 nucleotides. A nucleic acid compound that inhibits an ActRII receptor may be a DNA (particularly for use as an antisense), an RNA, or an RNA:DNA hybrid. Any one strand may include a mixture of DNA and RNA, as well as modified forms that cannot readily be classified as either DNA or RNA. Likewise, a double stranded nucleic acid compound may be DNA:DNA, DNA:RNA, or RNA:RNA, and any one strand may also include a mixture of DNA and RNA, as well as modified forms that cannot readily be classified as either DNA or RNA.

The nucleic acid compounds that inhibit an ActRII receptor may include any of a variety of modifications, including one or modifications to the backbone (the sugar-phosphate portion in a natural nucleic acid, including internucleotide linkages) or the base portion (the purine or pyrimidine portion of a natural nucleic acid). In certain embodiments, an antisense nucleic acid compound will have a length of about 15 to about 30 nucleotides and will often contain one or more modifications to improve certain characteristics, such as stability in the serum, stability in a cell, or stability in a place where the compound is likely to be delivered, such as, e.g., the stomach in the case of orally delivered compounds and the lung for inhaled compounds. In the case of an RNAi construct, the strand complementary to the target transcript will generally be RNA or modifications thereof. The other strand may be RNA, DNA, or any other variation. The duplex portion of double stranded or single stranded "hairpin" RNAi construct may, in certain embodiments, have a length of 18 to 40 nucleotides in length and optionally about 21 to 23 nucleotides in length, so long as it serves as a Dicer substrate. Catalytic or enzymatic nucleic acids may be ribozymes or DNA enzymes and may also contain modified forms. In certain embodiments, nucleic acid compounds that inhibit ActRII receptors may inhibit expression of their target by about 50%, 60%, 70%, 75%, 80%, 85%, 90%, 95%, 99%, or more under physiological conditions and at a concentration where a nonsense or sense control has little or no effect. Concentrations for testing the effect of nucleic acid compounds include 1, 5, 10 micromolar, or more.

In other embodiments, the inhibitors of ActRII receptors used in the compositions and methods described herein are antibodies. Such antibodies include antibodies that bind to activin (particularly the activin A or B subunits, also referred to as βA or βB) and disrupt ActRII receptor binding; and antibodies that bind to ActRII receptor polypeptides (e.g., a soluble ActRIIA or soluble ActRIIB polypeptide) and disrupt activin binding.

By using immunogens derived from an ActRII receptor polypeptide or an activin polypeptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the ActRII receptor polypeptide, an antigenic fragment which is capable of eliciting an antibody response, or a fusion protein. Techniques for conferring immunogenicity on a protein or peptide include conjugation to carriers or other techniques well known in the art. An immunogenic portion of an ActRII receptor or activin polypeptide can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of an ActRII receptor polypeptide, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an ActRII receptor polypeptide and monoclonal antibodies isolated from a culture comprising such hybridoma cells.

The term "antibody" as used herein is intended to include fragments thereof which are also specifically reactive with a subject polypeptide. Antibodies can be fragmented using conventional techniques and the fragments screened for utility in the same manner as described above for whole antibodies. For example, F(ab)2 fragments can be generated by treating antibody with pepsin. The resulting F(ab)2 fragment can be treated to reduce disulfide bridges to produce Fab fragments. An antibody is further intended to include bispecific, single-chain, chimeric, humanized and fully human molecules having affinity for an ActRII receptor or activin polypeptide conferred by at least one CDR region of the antibody. An antibody may further comprise a label attached thereto and able to be detected (e.g., the label can be a radioisotope, fluorescent compound, enzyme or enzyme co-factor).

In certain embodiments, the antibody is a recombinant antibody, which term encompasses any antibody generated in part by techniques of molecular biology, including CDR-grafted or chimeric antibodies, human or other antibodies assembled from library-selected antibody domains, single chain antibodies and single domain antibodies (e.g., human VH proteins or camelid VHH proteins). In certain embodiments, an antibody can be a monoclonal antibody, and in certain embodiments. For example, a method for generating a monoclonal antibody that binds specifically to an ActRII receptor polypeptide or activin polypeptide may comprise administering to a mouse an amount of an immunogenic composition comprising the antigen polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the antigen. Once obtained, a hybridoma can be propagated in a cell culture, optionally in culture conditions where the hybridoma-derived cells produce the monoclonal antibody that binds specifically to the antigen. The monoclonal antibody may be purified from the cell culture.

The adjective "specifically reactive with" as used in reference to an antibody is intended to mean, as is generally understood in the art, that the antibody is sufficiently selective between the antigen of interest (e.g., an ActRII receptor polypeptide) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody: antigen interaction is the affinity of the antibody for the antigen. Although the desired specificity may be reached with a range of different affinities, generally preferred antibodies will have an affinity (a dissociation constant) of about 10-6, 10-7, 10-8, 10-9 or less. Given the extraordinarily tight binding between activin and an ActRII receptor, it is expected that a neutralizing anti-activin or anti-ActRII receptor antibody would generally have a dissociation constant of 10-10 or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Biacore AB, Uppsala, Sweden), sandwich assays (e.g., the paramagnetic bead system of IGEN International, Inc., Gaithersburg, Md.), Western blots, immunoprecipitation assays, and immunohistochemistry.

In certain embodiments, ActRII receptor inhibitors to be used in the compositions and methods described herein include alternative forms of activin, particularly those with alterations in the type I receptor binding domain can bind to type II receptors and fail to form an active ternary complex. In certain embodiments, nucleic acids, such as antisense molecules, siRNAs or ribozymes that inhibit activin A, B, C or E, or, particularly, ActRII receptor expression, can be used in the compositions and methods described herein.

In other embodiments, the inhibitors of ActRII receptors used in the compositions and methods described herein are non-antibody proteins with ActRII receptor antagonist activity, including inhibin (i.e., inhibin alpha subunit), follistatin (e.g., follistatin-288 and follistatin-315), Cerberus, follistatin related protein ("FSRP"), endoglin, activin C, alpha(2)-macroglobulin, and an M108A (methionine to alanine change at position 108) mutant activin A.

In a specific embodiment, the ActRII receptor inhibitor to be used in the compositions and methods described herein is a follistatin polypeptide that antagonizes activin bioactivity and/or binds to activin. The term "follistatin polypeptide" includes polypeptides comprising any naturally occurring polypeptide of follistatin as well as any variants thereof (including mutants, fragments, fusions, and peptidomimetic forms) that retain a useful activity, and further includes any functional monomer or multimer of follistatin. Variants of follistatin polypeptides that retain activin binding properties can be identified based on previous studies involving follistatin and activin interactions. For example, WO2008/030367, which is included by reference herein in its entirety, discloses specific follistatin domains ("FSDs") that are shown to be important for activin binding. Follistatin polypeptides include polypeptides derived from the sequence of any known follistatin having a sequence at least about 80% identical to the sequence of a follistatin polypeptide, and optionally at least 85%, 90%, 95%, 96%, 97%, 98%, 99% or greater identity. Examples of follistatin polypeptides include the mature follistatin polypeptide or shorter isoforms or other variants of the human follistatin precursor polypeptide as described, for example, in WO2005/025601, which is included by reference herein in its entirety.

In a specific embodiment, the ActRII receptor inhibitor to be used in the compositions and methods described herein is a follistatin-like related gene (FLRG) that antagonizes activin bioactivity and/or binds to activin. The term "FLRG polypeptide" includes polypeptides comprising any naturally occurring polypeptide of FLRG as well as any variants thereof (including mutants, fragments, fusions, and peptidomimetic forms) that retain a useful activity. Variants of FLRG polypeptides that retain activin binding properties can be identified using routine methods to assay FLRG and activin interactions. See, for example, U.S. Pat. No. 6,537,966, which is included by reference herein in its entirety. FLRG polypeptides include polypeptides derived from the sequence of any known FLRG having a sequence at least about 80% identical to the sequence of an FLRG polypeptide, and optionally at least 85%, 90%, 95%, 96%, 97%, 98%, 99% or greater identity.

In certain embodiments, functional variants or modified forms of the follistatin polypeptides and FLRG polypeptides include fusion proteins having at least a portion of the follistatin polypeptides or FLRG polypeptides and one or more fusion domains, such as, for example, domains that facilitate isolation, detection, stabilization or multimerization of the polypeptide. Suitable fusion domains are discussed in detail above with reference to the ActRIIA and ActRIIB polypeptides. In one embodiment, an ActRII receptor inhibitor is a fusion protein comprising an activin binding portion of a follistatin polypeptide fused to an Fc domain. In another embodiment, an ActRII receptor inhibitor is a fusion protein comprising an activin binding portion of an FLRG polypeptide fused to an Fc domain.

5.3 Assays (a) Diagnostic Assays (i) Bone Turnover

Various circulating markers of bone turnover can be used to diagnose bone disorders, such as low bone turnover. Circulating markers of bone turnover are markers of bone formation such as bone specific alkaline phosphatase (bAP), osteocalcin, procollagen type I C-terminal propeptide (PICP) and insulin-like growth factor-1 (IGF-1), some being markers of bone resorption such as pyridinoline, deoxypyridinoline, tartrate-resistant acid phosphatase (TRAP), TRAP type 5b, pyridinoline, deoxypyridinoline and procollagen type I C-terminal telopeptide (ICTP), serum or urine collagen cross-links (N-telopeptide or C-telopeptide), and 25 hydroxyvitamin D. Assays to measure the entire parathyroid hormone (PTH) molecule can also be used. The skilled artisan is aware of imaging methods allowing the assessment of bone mineral density (BMD). See, e.g., Tilman B. Drueke and Sharon M. Moe, Disturbances of bone and mineral metabolism in chronic kidney disease: an international initiative to improve diagnosis and treatment, Nephrol Dial Transplant (2004) 19: 534-536; Okuno S, Inaba M., Biochemical markers of bone turnover. New aspect. Dialysis and bone metabolic marker, Clin Calcium. 2009 August; 19(8):1084-91; Herberth J, Monier-Faugere M C, Mawad H W, Branscum A J, Herberth Z, Wang G, Cantor T, Malluche H H, The five most commonly used intact parathyroid hormone assays are useful for screening but not for diagnosing bone turnover abnormalities in CKD-5 patients, Clin Nephrol. 2009 July; 72(1):5-14; Lehmann G, Ott U, Kaemmerer D, Schuetze J, Wolf G., Bone histomorphometry and biochemical markers of bone turnover in patients with chronic kidney disease Stages 3-5, Clin Nephrol. 2008 October; 70(4):296-305; Drüeke T B., Is parathyroid hormone measurement useful for the diagnosis of renal bone disease?, Kidney Int. 2008 March; 73(6):674-6; Yamada S, Inaba M, Kurajoh M, Shidara K, Imanishi Y, Ishimura E, Nishizawa Y., Utility of serum tartrate-resistant acid phosphatase (TRACP5b) as a bone resorption marker in patients with chronic kidney disease: independence from renal dysfunction., Clin Endocrinol (Oxf). 2008 August; 69(2):189-96. Epub 2008 Jan. 23. See also, Paul D. Miller, Diagnosis and Treatment of Osteoporosis in Chronic Renal Disease, 2009.

Another marker for monitoring bone resorption in CKD patients with mild renal dysfunction is serum concentration of type I collagen N-telopeptide (S-NTX). See, e.g., Hamano T, Fujii N, Nagasawa Y, Isaka Y, Moriyama T, Okada N, Imai E, Horio M, Ito T., Serum NTX is a practical marker for assessing antiresorptive therapy for glucocorticoid treated patients with chronic kidney disease., Bone. 2006 November; 39(5):1067-72. Epub 2006 Jun. 16.

Quantitative computed tomography (QCT) can also be used to determine bone turnover.

(ii) Adynamic Bone Disorder Model

A mouse model for adynamic bone disease in a renal setting is to use a mouse nephrectomy model, such as the 5/6 nephrectomy model used in Sections 6.2 and 6.3, wherein the mice are fed a low phosphate diet.

In another mouse model, mice are subjected to electrocautery of one kidney and nephrectomy of the other kidney. The mice are fed low-phosphate chow supplemented with calcitriol. See, e.g., Lund et al., 2004, J Am Soc Nephrol 15:349-369.

(iii) Tetracycline Labeling of Bone

A diagnostic test that can be used to determine the type of bone disease associated with CKD is iliac crest bone biopsy with double tetracycline labeling and bone histomorphometric analysis. See, e.g., National Kidney Foundation: NKF KDOQI Guidelines.

(iv) Vascular Calcification

Non-contrast computed tomography (CT) for imaging the extent of coronary artery calcification (CAC) and contrast CT for noninvasive coronary angiography (CTA) are developments generally used to diagnose obstructive coronary disease. Radionuclide stress testing, coronary artery calcium scanning, and noninvasive coronary angiography for diagnostic and prognostic cardiac assessment can also be used. See: Berman D S, Shaw L J, Hachamovitch R, Friedman J D, Polk D M, Hayes S W, Thomson L E, Germano G, Wong N D, Kang X, Rozanski A., Comparative use of radionuclide stress testing, coronary artery calcium scanning, and noninvasive coronary angiography for diagnostic and prognostic cardiac assessment, Semin Nucl Med. 2007 January; 37(1): 2-16.

Coronary calcium screening results from asymptomatic patients can be used as a comparison. For example, calcium screening results obtained prior to the onset of kidney disease can be used as a comparison when vascular calcification is related to the kidney disease.

Possible methods of detecting and quantifying coronary artery calcification (CAC) include, but are not limited to, x-ray computed tomography and myocardial perfusion single photon emission computed tomography (SPECT). Moser K W, O'Keefe J H Jr, Bateman™, McGhie I A., Coronary calcium screening in asymptomatic patients as a guide to risk factor modification and stress myocardial perfusion imaging, J Nucl Cardiol. 2003 November-December; 10(6):590-8. Multi-detector computed tomography (MDCT) also can be used to detect vascular calcification (see, e.g., Burrill et al., 2007, Postgrad. Med. J. 83(985): 698-704).

Another diagnostic method for vascular calcification is fluorine 18 fluorodeoxyglucose (FDG) uptake in the thoracic aortic wall at combined positron emission tomography (PET)/computed tomography (CT). See: Tatsumi M, Cohade C, Nakamoto Y, Wahl R L., Fluorodeoxyglucose uptake in the aortic wall at PET/CT: possible finding for active atherosclerosis, Radiology. 2003 December; 229(3):831-7. Epub 2003 Oct. 30.

In even another embodiment, ultrafast CT can be used to detect the presence of atherosclerotic coronary disease. See, e.g., Breen J F, Sheedy P F 2nd, Schwartz R S, Stanson A W, Kaufmann R B, Moll P P, Rumberger J A, Coronary artery calcification detected with ultrafast CT as an indication of coronary artery disease, Radiology. 1992 November; 185 (2):435-9.

Electron-beam computed tomography scanning can also be used to diagnose coronary artery disease. See: Schmermund A, Baumgart D, Sack S, Mohlenkamp S, Gronemeyer D, Seibel R, Erbel R., Assessment of coronary calcification by electron-beam computed tomography in symptomatic patients with normal, abnormal or equivocal exercise stress test, Eur Heart J. 2000 October; 21(20):1674-82.

Another test for vascular calcification regards the plaque composition in plexogenic and thromboembolic pulmonary hypertension. Chronic thromboembolic pulmonary hypertension is associated with atherosclerotic plaques with glycophorin-rich pultaceous cores, and plexogenic pulmonary hypertension with fibrous plaques. Thromboembolic material plays a critical role in the formation of pultaceous cores, of which erythrocyte membrane derived glycophorin is a major component. Thereby, chronic thromboembolic and plexogenic pulmonary hypertension (primary and secondary (Eisenmenger syndrome)) are investigated. See: Arbustini E, Morbini P, D'Armini A M, Repetto A, Minzioni G, Piovella F, Viganó M, Tavazzi L, Plaque composition in plexogenic and thromboembolic pulmonary hypertension: the critical role of thrombotic material in pultaceous core formation, Heart. 2002 August; 88(2):177-82.

Agatston scoring, a calcium scoring system based on density measurements of deposited calcium plaques, can be used to quantify vascular calcification. In this system, levels of vascular calcification can be measured by multi-detector computed tomography (MDCT) and attenuations in the rate of progression in the Agatston score can be assessed (see, e.g., Sharma et al., 2010, Vasc. Health Risk Manag. 6:603-611).

Further, vascular calcification can be assessed using the methods described in Adragao et al., 2004, Nephrol. Dial. Transplant 19:1480-1488.

Another assay for use in quantifying vascular calcification in a subject is the lesion-specific calcium score, which comprises a method of calcium measurement that results from a CT test for coronary artery calcification. This method is described by, e.g., Akram and Voros, 2008, Int. J. cardiovac. Imaging 14:743-749.

(v) Kidney Disease

Glomerular filtration rate can be determined by any method known to the skilled artisan to determine kidney disease. See website of the National Kidney Foundation.

(vi) Secondary Parathyroidism

Secondary hyperparathyroidism occurs when the parathyroid glands produce too much parathyroid hormone (PTH) because of too low calcium levels or increased phosphorus levels. Calcium, phosphorus, and PTH levels can be determined from blood samples.

(vii) Hyperphosphatemia

Abnormally elevated levels of phosphate in the blood can be determined by any method known to the skilled artisan.

(b) Screening Assays

Various ActRII polypeptide variants, or soluble ActRII polypeptide variants, may be tested for their ability to inhibit ActRII. In addition, compounds can be tested for their ability to inhibit ActRII. Once inhibitors of ActRII activity are confirmed, these compounds can be used with the methods provided herein. ActRII can be ActRIIA or ActRIIB. The assays below are described for ActRIIA but can be performed analogously for ActRIIB.

For example, the effect of an ActRIIA polypeptide variant on the expression of genes involved in bone production or bone destruction may be assessed. This may, as needed, be performed in the presence of one or more recombinant ActRIIA ligand proteins (e.g., activin), and cells may be transfected so as to produce an ActRIIA polypeptide and/or variants thereof, and optionally, an ActRIIA ligand. Likewise, an ActRIIA polypeptide may be administered to a mouse or other animal, and one or more bone properties, such as density or volume may be assessed. The healing rate for bone fractures may also be evaluated. Dual-energy x-ray absorptiometry (DEXA) is a well-established, non-invasive, quantitative technique for assessing bone density in an animal. In humans central DEXA systems may be used to evaluate bone density in the spine and pelvis. These are the best predictors of overall bone density. Peripheral DEXA systems may be used to evaluate bone density in peripheral bones, including, for example, the bones of the hand, wrist, ankle and foot. Traditional x-ray imaging systems, including CAT scans, may be used to evaluate bone growth and fracture healing. In addition, bone density can be measured using quantitative computed tomography (qCT). The mechanical strength of bone may also be evaluated.

In certain aspects, provided herein is the use of ActRIIA polypeptides (e.g., soluble ActRIIA polypeptides) and activin polypeptides to identify compounds (agents) which are agonist or antagonists of the activin-ActRIIA signaling pathway. Compounds identified through this screening can be tested to assess their ability to modulate bone growth or mineralization in vitro. Optionally, these compounds can further be tested in animal models to assess their ability to modulate tissue growth in vivo.

There are numerous approaches to screening for therapeutic agents for modulating tissue growth by targeting activin and ActRIIA polypeptides. In certain embodiments, high-throughput screening of compounds can be carried out to identify agents that perturb activin or ActRIIA-mediated effects on bone. In certain embodiments, the assay is carried out to screen and identify compounds that specifically inhibit or reduce binding of an ActRIIA polypeptide to activin. Alternatively, the assay can be used to identify compounds that enhance binding of an ActRIIA polypeptide to activin. In a further embodiment, the compounds can be identified by their ability to interact with an activin or ActRIIA polypeptide.

A variety of assay formats will suffice and, in light of the present disclosure, those not expressly described herein will nevertheless be comprehended by one of ordinary skill in the art. As described herein, the test compounds (agents) used herein may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated herein include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRIIA polypeptide and activin.

Merely to illustrate, in an exemplary screening assay, the compound of interest is contacted with an isolated and purified ActRIIA polypeptide which is ordinarily capable of binding to activin. To the mixture of the compound and ActRIIA polypeptide is then added a composition containing an ActRIIA ligand. Detection and quantification of ActRIIA/activin complexes provides a means for determining the compound's efficacy at inhibiting (or potentiating) complex formation between the ActRIIA polypeptide and activin. The efficacy of the compound can be assessed by generating dose response curves from data obtained using various concentrations of the test compound. Moreover, a control assay can also be performed to provide a baseline for comparison. For example, in a control assay, isolated and purified activin is added to a composition containing the ActRIIA polypeptide, and the formation of ActRIIA/activin complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the ActRIIA polypeptide and activin may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ActRIIA polypeptide or activin, by immunoassay, or by chromatographic detection.

In certain embodiments, contemplated herein is the use of fluorescence polarization assays and fluorescence resonance energy transfer (FRET) assays in measuring, either directly or indirectly, the degree of interaction between an ActRIIA polypeptide and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments described herein.

Moreover, an interaction trap assay, also known as the "two hybrid assay," can be used for identifying agents that disrupt or potentiate interaction between an ActRIIA polypeptide and its binding protein. See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, contemplated herein is the use of reverse two hybrid systems to identify compounds (e.g., small molecules or peptides) that dissociate interactions between an ActRIIA polypeptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with an ActRIIA or activin polypeptide. The interaction between the compound and the ActRIIA or activin polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to an activin or ActRIIA polypeptide. This may include a solid phase or fluid phase binding event. Alternatively, the gene encoding an activin or ActRIIA polypeptide can be transfected with a reporter system (e.g., β-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, provided herein are methods and agents for modulating (stimulating or inhibiting) bone formation and increasing bone mass. Therefore, any compound identified can be tested in whole cells or tissues, in vitro or in vivo, to confirm their ability to modulate bone growth or mineralization. Various methods known in the art can be utilized for this purpose. In particular, the compounds can be tested for their ability to increase bone turnover.

For example, the effect of the ActRIIA or activin polypeptides or test compounds on bone or cartilage growth can be determined by measuring induction of Msx2 or differentiation of osteoprogenitor cells into osteoblasts in cell based assays (see, e.g., Daluiski et al., Nat Genet. 2001, 27(1):84-8; Hino et al., Front Biosci. 2004, 9:1520-9). Another example of cell-based assays includes analyzing the osteogenic activity of the subject ActRIIA or activin polypeptides and test compounds in mesenchymal progenitor and osteoblastic cells. To illustrate, recombinant adenoviruses expressing an activin or ActRIIA polypeptide can be constructed to infect pluripotent mesenchymal progenitor C3H10T1/2 cells, preosteoblastic C2C12 cells, and osteoblastic TE-85 cells. Osteogenic activity is then determined by measuring the induction of alkaline phosphatase, osteocalcin, and matrix mineralization (see, e.g., Cheng et al., J bone Joint Surg Am. 2003, 85-A(8): 1544-52).

Also provided herein are in vivo assays to measure bone or cartilage growth. For example, Namkung-Matthai et al., Bone, 28:80-86 (2001) discloses a rat osteoporotic model in which bone repair during the early period after fracture is studied. Kubo et al., Steroid Biochemistry & Molecular Biology, 68:197-202 (1999) also discloses a rat osteoporotic model in which bone repair during the late period after fracture is studied. Andersson et al., J. Endocrinol. 170:529-537 describe a mouse osteoporosis model in which mice are ovariectomized, which causes the mice to lose substantial bone mineral content and bone mineral density, with the trabecular bone losing roughly 50% of bone mineral density. Bone density could be increased in the ovariectomized mice by administration of factors such as parathyroid hormone. In certain aspects, fracture healing assays that are known in the art can be used. These assays include fracture technique, histological analysis, and biomechanical analysis, which are described in, for example, U.S. Pat. No. 6,521,750, which is incorporated by reference in its entirety for its disclosure of experimental protocols for causing as well as measuring the extent of fractures, and the repair process.

5.4 Dose

Provided herein are methods for the treatment of CKD-MBD and/or low turnover bone disease, wherein the methods comprise administering to a patient in need of treatment a therapeutically effective amount of an inhibitor of ActRII (see Section 5.2). In certain embodiments, an ActRII inhibitor is an inhibitor of ActRIIA as set forth in Section 5.2(a). In other embodiments, an ActRII inhibitor is an inhibitor of ActRIIB as set forth in Section 5.2(b). In certain embodiments, an ActRII inhibitor is a combination of an ActRIIA inhibitor and an ActRIIB inhibitor.

In certain embodiments, a therapeutically effective amount of an ActRII inhibitor is sufficient to ameliorate one symptom of CKD-MBD. In certain embodiments, a therapeutically effective amount of an ActRII inhibitor is sufficient to prevent at least one symptom of CKD-MBD from worsening.

In certain embodiments, a therapeutically effective amount of an ActRII inhibitor improves or stabilizes kidney function. Kidney function can be measured by glomerular filtration rate. See, e.g., Section 5.4(a)(iv). In certain embodiments, a therapeutically effective amount of an ActRII inhibitor is a daily dose that is sufficient to stabilize the glomerular filtration rate of a CKD-MBD patient for the duration of treatment with ActRII inhibitor and for at least 3 months, 6 months, 9 months, or 12 months. In certain embodiments, a therapeutically effective amount of an ActRIIA inhibitor is a daily dose that is sufficient to increase the glomerular filtration rate by at least 5%, 10%, 15%, 20%, 25%, 30%, 35%, 40%, 45%, or at least 50%.

In certain embodiments, a therapeutically effective amount of an ActRII inhibitor increases the red blood cell level and/or hemoglobin levels in the patient.

In certain embodiments, a therapeutically effective amount of an ActRII inhibitor is effective to (a) increase red blood cell and/or hemoglobin levels in the patient; (b) improvement in bone quality and/or bone mineral density in the patient; and (c) improve kidney function in the patient.

In certain embodiments, a therapeutically effective amount of an ActRII inhibitor is effective to (a) increase red blood cell and/or hemoglobin levels in the patient; (b) increase the bone turnover in the patient; and (c) improve kidney function in the patient.

In certain embodiments, the ActRII inhibitor is dosed at intervals and amounts sufficient to achieve serum concentrations of 0.2 microgram/kg or greater, and serum levels of 1 microgram/kg or 2 microgram/kg or greater are desirable for achieving significant effects on bone density and strength. Dosing regimens may be designed to reach serum concentrations of between 0.2 and 15 microgram/kg, and optionally between 1 and 5 microgram/kg. In humans, serum levels of 0.2 microgram/kg may be achieved with a single dose of 0.1 mg/kg or greater and serum levels of 1 microgram/kg may be achieved with a single dose of 0.3 mg/kg or greater. The observed serum half-life of the molecule is between about 20 and 30 days, substantially longer than most Fc fusion proteins, and thus a sustained effective serum level may be achieved, for example, by dosing with 0.2-0.4 mg/kg on a weekly or biweekly basis, or higher doses may be used with longer intervals between dosings. For example, doses of 1-3 mg/kg might be used on a monthly or bimonthly basis, and the effect on bone may be sufficiently durable that dosing is necessary only once every 3, 4, 5, 6, 9, 12 or more months.

5.5 Pharmaceutical Compositions

In certain embodiments, activin-ActRII antagonists (e.g., ActRII polypeptides) are formulated with a pharmaceutically acceptable carrier for use with the methods described herein. For example, an ActRII polypeptide can be administered alone or as a component of a pharmaceutical formulation (therapeutic composition). The subject compounds may be formulated for administration in any convenient way for use in human or veterinary medicine. ActRII can be ActRIIA or ActRIIB.

In certain embodiments, the therapeutic methods described herein include administering the composition systemically, or locally as an implant or device. When administered, the therapeutic compositions used herein can be in a pyrogen-free, physiologically acceptable form. Therapeutically useful agents other than the ActRIIA antagonists which may also optionally be included in the composition as described above, may be administered simultaneously or sequentially with the subject compounds (e.g., ActRII polypeptides, such as ActRIIA and/or ActRIIB polypeptides (see Section 5.2)).

Typically, ActRIIA antagonists will be administered parenterally. Pharmaceutical compositions suitable for parenteral administration may comprise one or more ActRII polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions used in the methods described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Further, the composition may be encapsulated or injected in a form for delivery to a target tissue site (e.g., bone). In certain embodiments, compositions used in the methods described herein may include a matrix capable of delivering one or more therapeutic compounds (e.g., ActRIIA polypeptides) to a target tissue site (e.g., bone), providing a structure for the developing tissue and optimally capable of being resorbed into the body. For example, the matrix may provide slow release of the ActRIIA polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, the compositions used in the methods described herein can be administered orally, e.g., in the form of capsules, cachets, pills, tablets, lozenges (using a flavored basis, usually sucrose and *acacia* or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and *acacia*) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds used in the methods described herein may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or *acacia*; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions used in the methods described herein may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds used in the methods described herein (e.g., ActRII polypeptides, such as ActRIIA and/or ActRIIB polypeptides (see Section 5.2)). The various factors include, but are not limited to, amount of bone weight desired to be formed, the degree of bone density loss, the site of bone damage, the condition of the damaged bone, the patient's age, sex, and diet, the severity of any disease that may be contributing to bone loss, time of administration, and other clinical factors. Optionally, the dosage may vary with the type of matrix used in the reconstitution and the types of compounds in the composition. The addition of other known growth factors to the final composition, may also affect the dosage. Progress can be monitored by periodic assessment of bone growth and/or repair, for example, X-rays (including DEXA), histomorphometric determinations, and tetracycline labeling.

In certain embodiments, the methods described herein comprise gene therapy for the in vivo production of ActRII polypeptides. Such therapy would achieve its therapeutic effect by introduction of the ActRII polynucleotide sequences into cells or tissues having the disorders as listed above. Delivery of ActRII polynucleotide sequences can be achieved using a recombinant expression vector such as a chimeric virus or a colloidal dispersion system. Preferred for therapeutic delivery of ActRII polynucleotide sequences is the use of targeted liposomes. The ActRII polypeptides can be ActRIIA and/or ActRIIB polypeptides (see Section 5.2)).

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the ActRIIA polynucleotide. In a preferred embodiment, the vector is targeted to bone or cartilage.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for ActRIIA polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. One colloidal system that can be used is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

In certain embodiments, the ActRIIA inhibitor is substantially pure in a pharmaceutical composition. Specifically, at most 20%, 10%, 5%, 2.5%, 1%, 0.1%, or at most 0.05% of the compounds in the pharmaceutical composition are compounds other than the ActRII inhibitor and the pharmaceutical acceptable carrier.

6. EXAMPLES

6.1 Example 1

(a) ActRIIA-Fc Fusion Proteins

A soluble ActRIIA fusion protein that has the extracellular domain of human ActRIIA fused to a human or mouse Fc domain with a minimal linker is described. The constructs are referred to as ActRIIA-hFc and mActRIIA-Fc, respectively. ActRIIA-hFc is provided as SEQ ID NO:7. mActRIIA-Fc is the murine counterpart to SEQ ID NO:7.

The ActRIIA-hFc and mActRIIA-Fc proteins were expressed in CHO cell lines.
Three different leader sequences were considered:
(i) Honey bee mellitin (HBML): SEQ ID NO: 8
(ii) Tissue Plasminogen Activator (TPA): SEQ ID NO: 9
(iii) Native ActRIIA: SEQ ID NO: 10

The selected form employs the TPA leader and has the following unprocessed amino acid sequence is set forth in SEQ ID NO: 13. This polypeptide is encoded by SEQ ID NO: 14.

(b) ActRIIB-Fc Fusion Proteins

Co-crystal structure of an extracellular domain of human ActRIIB fused to a human Fc domain and Activin did not show any role for the final (C-terminal) 15 amino acids (referred to as the "tail" herein) of the extracellular domain in ligand binding. This sequence failed to resolve on the crystal structure, suggesting that these residues are present in a flexible loop that did not pack uniformly in the crystal. Thompson et al. EMBO J. 2003 Apr. 1; 22(7):1555-66. This sequence is also poorly conserved between ActRIIB and ActRIIA. Accordingly, these residues were omitted in the basic, or background, ActRIIB-Fc fusion construct. Additionally, position 64 in the background form is occupied by an alanine, which is generally considered the "wild type" form, although a A64R allele occurs naturally. Thus, the background ActRIIB-Fc fusion has the sequence disclosed as SEQ ID NO:21.

Surprisingly, the C-terminal tail was found to enhance activin and GDF-11 binding, thus a preferred version of ActRIIB-Fc has a sequence SEQ ID NO:20.

A variety of ActRIIB a variants that may be used according to the methods described herein are described in the International Patent Application published as WO2006/012627 (see e.g., pp. 59-60), incorporated herein by reference in its entirety.

6.2 Effects of mActRIIA Inhibition in a Mouse Model of Chronic Kidney Disease This study was designed to study the effects of soluble mouse ActRIIA fused with mouse Fc via a minimal linker (SEQ ID NO:15) on treatment of blood and bone parameters in a mouse model of chronic kidney disease and CKD-MBD.

Patients with chronic kidney disease (CKD) can become anemic and also become osteopenic. Mice with partial renal ablation (⅚ nephrectomy) were used as a model of CKD to test the effects of the polypeptide with the amino acid sequence of SEQ ID NO:15 in this model. Mice received two surgeries to 1) remove one kidney completely and 2) to ligate 2 of the 3 renal arteries in the remaining kidney. Sham operated mice were also included as controls. The sham or ⅚ nephrectomy surgeries were performed at Jackson Laboratories.

After mice were received they were placed on high fat diet for the duration of the study. Two weeks after the final surgery mice were divided into groups (both SHAM and CKD) and began dosing with vehicle (PBS) or mActRIIA-Fc at 10 mg/kg twice per week for 8 weeks. Complete blood counts (CBC) were taken periodically during the study to assess for anemia.

Bone mineral density was determined using dual energy x-ray absorptiometry (DEXA, PIXIMus). At the conclusion of the study necropsies were conducted to collect the long bones of the hind limbs and major organs. The remnant kidney was sent for histology processing and staining with H&E or Trichrome stain. Femurs were scanned by uCT (Scanco) to determine bone microarchitecture.

Mice appeared normal and healthy throughout the study period and put on weight as the study progressed (FIG. 1). Bone mineral density increased in all four groups of mice, but mActRIIA-Fc treated mice (SHAM and CKD) had greater increases than either vehicle treated group (FIG. 2). mActRIIA-Fc treatment in CKD mice had bone mineral densities that equaled or exceeded SHAM-VEH treated mice by the end of the study. CKD mice also became anemic by the end of the study (HCT<40%), but mActRIIA-Fc treatment prevented anemia in the CKD group (HCT>40%; FIG. 3). mActRIIA-Fc treated mice in the SHAM group also showed increases in HCT when compared to VEH controls. Micro CT analysis of femurs after dissection showed increases in trabecular bone in the mActRIIA-Fc treated mice, but there were no major differences between the SHAM and CKD vehicle treated groups at this time in the disease progression. At necropsy, no major differences in organ weights were observed, although mActRIIA-Fc treated mice had a slight increase in fat pad weights. Trichrome stained histological sections of the remnant kidney did not indicate widespread fibrosis at this point in the study in the CKD mice.

6.3 mActRIIA Inhibition Prevents Anemia and Bone Loss in a Therapeutic Model of Established Kidney Disease The ⅚ nephrectomy surgery in rodents is a commonly performed experimental protocol used to model chronic kidney disease. In this two-phase surgery ⅔ of one kidney and the complete kidney on the contralateral side are removed using aseptic surgical procedures. As a result of the surgery the animal experiences impaired kidney function and exhibits physiologic behavior analogous to humans with chronic kidney disease.

Sham or ⅚ nephrectomy surgery was performed at Jackson Laboratories according to standard operating procedures. Animals were allowed to recover from surgery and then shipped. Animals were acclimated to laboratory conditions for a minimum of 48 hours prior to the first measurements being made. During this period all animals were observed for any signs of clinical abnormalities that would exclude them from study. Animals were assigned a study number on their cage cards and uniquely identified by ear notching.

ActRIIA-mIgG2aFc was diluted using Sterile PBS to a concentration of 2.0 mg/ml. The dosing concentration: was 2.0 mg/ml. ActRIIA-mIgG2aFc was stored at −65° C.±15° C., material may be thawed at room temperature, or overnight at 4° C. Thawed protein was kept on wet ice until use.

Thirty C57BL/6 female mice (10 weeks old) underwent a 5/6 nephrectomy surgery in which one kidney is completely removed followed by ligation of 2 of 3 renal veins ligated in the remaining kidney two weeks later. Sham surgeries were also performed on thirty C57BL/6 females in which the animals are subject to the same abdominal surgical procedure without removal of the kidneys. After recovery from the second surgery animals were shipped and allowed to acclimate to laboratory conditions for a minimum of 48 hours. Two months after the second surgery mice were randomly assigned to one of four treatment groups with 15 mice per group (Table 2). Mice were weighed and dosed with either mActRIIA-Fc or PBS twice per week for a total of 8 weeks. Longitudinal measurements of bone mineral density (BMD) and hematological parameters were made at baseline, an interim time point and at the conclusion of the study. At necropsy bones were collected and stored for histological examination or for analysis by microCT scanning.

(a) Experimental Procedures (i) Surgical Modification

Female C57BL/6 mice aged 10 weeks were given a two-stage surgery to accomplish a ⅚ nephrectomy or the equivalent sham surgery.

(ii) Animal Dosing

Dosing in the current study commenced one month after the completion of the ⅚ nephrectomy surgery. Mice were weighed and administered either PBS or mActRIIA-Fc at 10 mg/kg twice per week by subcutaneous injection.

(iii) DXA Scanning

Longitudinal measurements of BMD were made monthly on anesthetized mice using DXA scanning (Lunar PIXIMus, GE Medical Systems). During DXA scan analysis of BMD the mouse head was eliminated from the region of interest prevent quantification artifacts associated with the skull.

(iv) Blood Collection

Longitudinal measurements of complete blood counts (HM2, VetScan) were made on blood collected by monthly submandibular bleeding. At the termination of the study a terminal bleed was performed, blood was collected and divided into either an EDTA containing tube for CBC analysis or into a serum separation tube for serum collection. Serum was frozen at −80° for future analyses.

(v) Serum Analyses

Frozen serum was defrosted and 100 microliter were analyzed using a Vetscan VS2 analyzer (Abaxis, Inc.). A comprehensive diagnostic rotor was used to analyzes the samples for serum albumin (ALB), alkaline phosphatase (ALP), alanine aminotransferase (ALT), amylase (AMY), total bilirubin (TBIL), blood urea nitrogen (BUN), total calcium (Ca++), Phosphorus (PHOS), creatinine (CRE), glucose (GLU), sodium (NA+), potassium (K+), total protein (TP) and globulin (GLOB).

(vi) Necropsy

At the conclusion of the study mice were euthanized by $CO_2$ inhalation. The kidneys and spleens were removed, weighed and stored in 10% formalin. The tibiae and femurs were collected and stored in 70% ethanol.

(vii) microCT Analysis

At the termination of the experiment the left femur and tibia from each mouse were dissected and fixed in 70% ethanol. Bones were scanned using a Scanco microCT (VivaCT75, Scanco) at 55 kV, 145 microA and a voxel size of 20 microm. Scanned images were reconstructed using the incorporated Scanco software. Trabecular bone volume (BV/TV) and trabecular thickness (Tb.Th) were assessed in a 400 microm section of bone which was positioned 200 microm from the distal tip of the femur. Cortical thickness was measured in a 200 microm section of bone centered at the mid-line of the femur.

(viii) Data Analysis

Comparisons between mActRIIA-Fc and vehicle treated mice and tissues were performed by Student's t-Test using Microsoft Excel. Data are expressed as mean±SEM.

TABLE 2

| Group | N Mice | Diet | Treatment | Surgery | Concentration | Route |
|---|---|---|---|---|---|---|
| 1 | 15 C57BL/6 | Chow | PBS | Sham | volume | S.C. |
| 2 | 15 C57BL/6 | Chow | mActRIIA-Fc | Sham | 10 mg/kg | S.C. |
| 3 | 15 C57BL/6 | Chow | PBS | 5/6 Nephr. | volume | S.C. |
| 4 | 15 C57BL/6 | Chow | mActRIIA-Fc | 5/6 Nephr. | 10 mg/kg | S.C. |

(b) Results

We investigated the ability of mActRIIA-Fc to prevent anemia and bone loss in a mouse model of chronic kidney disease. After 2 months of disease progression following the ⅚ nephrectomy surgery (Day 0), ⅚ nephrectomized mice (CKD) exhibited a significant decrease in hematocrit compared to the sham cohorts (−5.4%, P<0.01). Longitudinal blood sampling and subsequent CBC analysis showed that mActRIIA-Fc treated mice in both the CKD and sham cohorts displayed significant increases in hematocrit compared to their VEH treated counterparts after 4 and 8 weeks of treatment (FIG. 5).

After 2 months of disease progression following the ⅚ nephrectomy surgery (Day 0), ⅚ nephrectomized mice (CKD) exhibited a significant decrease in BMD compared to the sham cohorts (−5.4%, P<0.01). Through 6 weeks of treatment the mActRIIA-Fc treated sham and CKD cohorts had significantly greater BMD compared to their VEH treated counterparts (FIG. 6).

At the conclusion of the study the hind limbs were collected and fixed in 70% ethanol. The right femur was microCT scanned (VivaCT 75, Scanco) to quantify cortical and trabecular bone structure. FIG. 7 shows cross-sectional images of femurs from each treatment group. Nephrectomized mice exhibited decreased cortical thickness and no obvious changes to trabecular bone structure.

mActRIIA-Fc treated mice exhibited increases in both cortical thickness and trabecular bone volume. Analyses of the femur mid-shaft were used to quantify the mean cortical thickness in each cohort (FIG. 8). The CKD mice had thinner cortical bones than their sham counterparts in both the VEH (P<0.01) and mActRIIA-Fc (P<0.01) cohorts. mActRIIA-Fc treated mice had a significant increase in cortical thickness in both the sham (+17%, P<0.01) and CKD (+19.2%, P<0.01) cohorts compared to their respective VEH-treated mice. As evidenced by the sample images in FIG. 7, analyses of the distal femur revealed dramatic increases in trabecular bone volume and thickness in mActRIIA-Fc treated mice. mActRIIA-Fc was able to significantly increase trabecular bone volume (FIG. 9) and trabecular thickness (FIG. 10) over VEH treated mice in both the sham and CKD cohorts. Measurements of trabecular bone volume demonstrated at week 8 that mActRIIA-Fc treated mice had a significant increase in trabecular bone volume in both the sham (+549%, P<0.001) and CKD (+827%, P<0.001) cohorts compared to their respective VEH-treated mice. Measurements of trabecular thickness demonstrated at week 8 that mActRIIA-Fc treated mice had a significant increase in trabecular thickness in the CKD (+62%, P<0.001) cohorts compared to their respective VEH-treated mice.

At terminal sacrifice whole blood was taken from all animals and processed for serum. Serum samples were analyzed using a Vetscan VS2 analyzer (Abaxis, Inc) using a comprehensive profile rotor. Mean values for the analyates from each group are shown in Table 3. Comparison of the SHAM and CKD vehicle control groups showed increases in blood urea nitrogen (BUN) and creatinine (CRE) as expected due to impaired renal function. Additionally the ALT and amylase (AMY) were increased in CKD mice due to altered kidney function or suggestive of the nephrectomy also altering liver function. Calcium (CA++) and total alkaline phosphates (ALP) levels also increased as expected due to increased bone turnover. mActRIIA-Fc treatment increased ALP levels in both the SHAM and CKD mice due to the bone anabolic properties of the drug. In CKD mice mActRIIA-Fc treatment decreased albumin (ALB), total protein (TP) and CRE levels compared to CKD-VEH controls, but were not different than SHAM mice. These changes are not thought to be relevant to the model or the treatment at this point.

TABLE 3

|      |        | SHAM VEH | SHAM mActRIIA-Fc | CKD VEH | CKD mActRIIA-Fc |
|------|--------|----------|------------------|---------|-----------------|
| AMY  | U/L    | 865.45 ± 39.41 | 803.38 ± 66.06 | 1486.18 ± 53.82 | 1418.42 ± 36.68 |
| TBIL | mg/dL  | 0.25 ± 0.02 | 0.23 ± 0.02 | 0.23 ± 0.01 | 0.27 ± 0.01a |
| BUN  | mg/dL  | 27.92 ± 1.39 | 29.20 ± 1.26 | 52.75 ± 2.66 | 51.50 ± 2.10 |
| CA++ | mg/dL  | 10.18 ± 0.16 | 10.38 ± 0.12 | 11.00 ± .13 | 11.33 ± 0.13 |
| PHOS | mg/dL  | 8.58 ± 0.17 | 8.96 ± 0.28 | 8.28 ± 0.36 | 7.96 ± 0.26 |
| CRE  | mg/dL  | 0.33 ± 0.05 | 0.40 ± 0.05 | 0.44 ± 0.05 | 0.31 ± 0.02a |
| GLU  | mg/dL  | 198.50 ± 6.52 | 260.90 ± 28.79* | 223.67 ± 13.53 | 260.86 ± 14.98 |
| NA+  | mmol/L | 156.50 ± 0.77 | 157.60 ± 0.73 | 158.58 ± 2.37 | 155.64 ± 0.34 |
| K+   | mmol/L | 7.65 ± 0.14 | 7.85 ± 0.15 | 7.98 ± 0.14 | 7.77 ± 0.13 |
| TP   | g/dL   | 5.66 ± 0.05 | 5.42 ± 0.057* | 5.73 ± 0.08 | 5.47 ± 0.07a |
| GLOB | g/dL   | 1.79 ± 0.08 | 1.67 ± 0.06 | 1.73 ± 0.07 | 1.97 ± 0.06a |

*= p < 0.05 vs SHAM VEH;
++= p < 0.05 vs CKD VEH

(c) Conclusions

Treatment with mActRIIA-Fc was able to prevent anemia and bone loss in a ⅚ nephrectomy model of chronic kidney disease. CKD mice were anemic, had lower BMD and thinner cortical bone structure in the femur when compared to the sham counterparts. mActRIIA-Fc treatment of CKD mice increased the hematocrit, BMD and cortical bone structure significantly over the VEH treated mice. Furthermore, mActRIIA-Fc was able to increase trabecular bone volume and trabecular thickness in the CKD mice to values greater than the VEH treated mice in both the sham and CKD cohorts. These data demonstrate that blocking Activin receptor IIA signaling by mActRIIA-Fc administration can prevent anemia and bone loss in the ⅚ nephrectomy model of chronic kidney disease.

6.4 Prophetic Example—mActRIIa Inhibition to Treat Adynamic Bone Disease in Cdk Context Mice are subjected to electrocautery of one kidney and nephrectomy of the other kidney. The mice are fed low-phosphate chow supplemented with calcitriol. See, e.g., Lund et al., 2004, J Am Soc Nephrol 15:349-369.

This study is designed to study the effects of soluble mouse ActRIIA that is fused with mouse Fc via a minimal linker (SEQ ID NO:15) on treatment of blood and bone parameters in a mouse model of adynamic bone disorder.

Mice with electrocautery of one kidney and nephrectomy of the other kidney are used as a model of adynamic bone in CKD ("ADB") context to test the effects of the polypeptide with the amino acid sequence of SEQ ID NO:15 in this model. Mice receive two surgeries to 1) remove one kidney completely and 2) electrocautery of the other kidney. Sham operated mice are also included as controls. The surgeries can be conducted as described in Lund et al., 2004, J Am Soc Nephrol 15:349-369.

One group of mice is placed on low-phosphate chow supplemented with calcitriol diet. Another group of mice is placed on normal chow diet. Two weeks after the final surgery mice are divided into groups (both SHAM and ADB) and administration begins with vehicle (PBS) or mActRIIA-Fc at 10 mg/kg twice per week for 8 weeks. Complete blood counts (CBC) are taken periodically during the study to assess for anemia.

Bone mineral density is determined using dual energy x-ray absorptiometry (DEXA, PIXIMus). At the conclusion of the study necropsies are conducted to collect the long bones of the hind limbs and major organs. The remnant kidney is sent for histology processing and staining with H&E or Trichrome stain. Femurs are scanned by uCT (Scanco) to determine bone microarchitecture. Quantitative computed tomography (QCT) can also be used to determine bone turnover.

6.5 Effects of ActRIIA Inhibition on Vascular Calcification

This Example demonstrates that inhibiting ACTRIIA is effective in reducing calcium levels in the vasculature of subjects, and thus represents a means for treating vascular calcification.

Stage 3 chronic kidney disease (CKD) was induced in 14-week old ldlr$^{-/-}$ mice (C57Bl/6J background; Jackson Laboratory) that were fed high fat diets ("CKD mice"). Low-density lipoprotein receptor (ldlr) is known to be involved in lipid clearance, and ldlr knockout mice represent a model of atherosclerosis. The ldlr deficient mice that are fed high fat/cholesterol diets develop atherosclerosis, and aortic plaque associated calcification that is stimulated by CKD induced by renal ablation. CKD was induced in the ldlr$^{-/-}$ mice by 5/6 nephrectomy (see above). As described above, the 5/6 nephrectomy comprises complete removal of one kidney followed by ligation of 2 of the 3 renal veins in the remaining kidney.

By week 22, vascular calcification is established in the CKD mice, as confirmed by chemical calcification quantitation. Briefly, hearts and aorta from the mice are dissected at sacrifice, and all extraneous tissue is removed by blunt dissection under a dissecting microscope. Tissues are desiccated for 20-24 hours at 55° C., weighed and crushed to a powder with a pestle and mortar. Calcium is eluted in 10% formic acid (10:1 v/w) for 24 hours at 4° C. Calcium content of eluate is assayed using a cresolphthalein complexone method (Sigma, St Louis), according to manufacturers instructions, and results are corrected for dry tissue weight.

The CKD mice were divided into two experimental groups (i) mActRIIA-Fc treated mice; and (ii) CKD-3-Vehicle mice, which were administered the vehicle portion only of the mActRIIA-Fc composition (i.e., the mice were administered a saline composition without mActRIIA-Fc). mActRIIA-Fc-treated mice (n=5) were administered 10 mg/kg of mActRIIA-Fc twice per week for 6 weeks. CKD-3-Vehicle mice (n=6; vehicle=saline) were administered vehicle only on the same days that mActRIIA-Fc was administered to the mActRIIA-Fc-treated mice. Wild-type mice (n=6; C57Bl/6J background) and SHAM mice (n=8; C57Bl/6J background) were used as negative controls. SHAM mice consisted of ldlr$^{-/-}$ mice that were operated on, but in which CKD was not induced (e.g., nephrectomy was not conducted). All mice were euthanized at week 28 for assessment of aortic calcium levels in each of the four treatment groups (CKD-3-Vehicle; mActRIIA-Fc-treated; SHAM; and wild-type).

Table 4, below, provides the aortic calcium levels observed in each mouse used in the study (column 2), as well as the average calcium levels for each of the SHAM, CKD-3-Vehicle, mActRIIA-Fc, and wild-type study groups (column 3). The results are presented in graph form in FIG. 11. As demonstrated by the data, a clear reduction in aortic calcium was observed in the mice belonging to the mActRIIA-Fc treated group compared to the vehicle-treated group. In 4 of the 5 CKD mice that were treated with mActRIIA-Fc, levels of aortic calcium were comparable to levels observed in the two negative control groups (wild-type and SHAM mice).

Elevated vascular (e.g., arterial) calcium levels are known to be associated with vascular calcification (see, e.g., Raggi P et al., Clin J Am Soc Nephrol 2008; 3: 836-843). Thus, the foregoing results indicate that ActRIIA inhibition represents a suitable approach for the treatment and prevention of vascular calcification.

TABLE 4

| Aortic Calcium Levels | | |
|---|---|---|
| Experimental Group | Subject Specific Ca$^{2+}$ Levels (mg/g) | Average Ca$^{2+}$ mg/g |
| Wild-type (n = 6) | 0.25, 0.11, 0.26, 0.36, 0.31, 0.35 | 0.27 ± 0.09 |
| Sham (n = 8) | 0.28, 0.18, 0.24, 0.16, 0.13, 0.25, 0.26, 0.27 | 0.22 ± 0.06 |
| CKD-3-Vehicle (n = 6) | 0.58, 0.17, 0.51, 0.56, 0.31, 0.99 | 0.52 ± 0.28 |
| mActRIIA-Fc (n = 5) | 0.83, 0.28, 0.19, 0.13, 0.04 | 0.29 ± 0.31 |

6.6 Effects of ActRIIA Inhibition on Vascular Calcification

This Example describes a study of the effect of ActRII inhibition on vascular calcification in subjects with chronic kidney disease.

The mouse model of early CKD-MBD described in the preceding examples can be used. In this model, renal ablation is added to genetic deficiency of the LDL receptor, ldlr, and mice are fed a high fat high cholesterol diet. In stage 3 CKD, the animals have CKD induced stimulation of vascular calcification, decreases in bone formation, elevated FGF23 levels, hyperphosphatemia, and elevated PTH levels.

(a) Materials and Methods

Animals and Diets:

LDL receptor null (LDLR$^{-/-}$) mice on a C57Bl/6J background or wild type C57Bl/6J mice can be purchased from Jackson Laboratory (Bar Harbor, Me.) and bred in a pathogen-free environment. Animals can be weaned at three weeks to a chow diet having 6.75% calories as fat. At 10 weeks, some animals can be initiated on a high cholesterol (0.15%) diet containing 42% calories as fat (Harlan Teklad, Madison Wis., Product No. TD88137), a diet that has been shown to generate atherosclerosis with vascular calcification in this genetic background (see, e.g., Towler et al., 1998, J Biol Chem 273:30427-30434). Calcium content in all diets can be 0.6%. Animals can be given access to water ad libitum, and maintained according to local and national animal care guidelines. mActRIIA-Fc can be administered IP (10 mg/kg) twice weekly.

Surgical Procedures:

A two-step procedure can be utilized to create CKD as previously described (see, e.g., Davies et al., 2003, J Am Soc Nephrol 14:1559-1567; and Davies et al., 2005, J Am Soc Nephrol 16:917-928). Briefly, electrocautery can be applied to the right kidney through a 2 cm flank incision at 10 weeks post-natal, followed by left total nephrectomy through a similar incision 2 weeks later. Control animals can receive sham operations in which the appropriate kidney is exposed and mobilized but not treated in any other way. Intraperitoneal anesthesia (xylazine 13 mg/kg and ketamine 87 mg/kg) can be used for all procedures. Saphenous vein blood samples can be taken at 1 week following the second surgery to assess baseline post-surgical renal function. Animals can be sacrificed under anesthesia at 20 weeks, or 26 weeks depending on the group after blood is taken by intracardiac stab. The heart and aorta can be dissected en bloc.

Tissue Preparation:

Resected specimens can be fixed in formalin, and then divided as follows: the heart, ascending aorta and aortic arch can be separated from the descending aorta, and bisected sagittally through the aortic outflow tract. The descending aorta can be bisected coronally, approximately halfway along its length. All four pieces can be embedded in the same wax block. Slices (5 μm thick) can be cut and stained with hematoxilin and eosin, trichrome, Alizarin Red and von Kossa.

Immunohistochemistry:

Tissue sections can be prepared as above, deparaffinized in xylene, and rehydrated in graded ethanols. Endogenous peroxidase activity can be blocked by incubation in 3% hydrogen peroxide (Sigma, St Louis Mo.), and non-specific binding can be blocked with a 10-minute incubation with a proprietary solution of casein in PBS ('Background SNIPER', BioCare Medical, Walnut Creek Calif.). Antigen retrieval can be performed with a 5-minute incubation with citrate buffer ('Decloaker' BioCare Medical, Walnut Creek Calif.) at 100° C. Sections can be incubated with affinity-purified goat polyclonal antibody against mouse osteocalcin (OC) (Biogenesis Inc, Brentwood N.H.) overnight, then incubated with biotinylated mouse anti-goat secondary antibody for 10 minutes prior to streptavidin-conjugated peroxidase staining (all reagents, BioCare Medical, Walnut Creek Calif.), and counterstained with 0.1% Hematoxylin (Sigma).

RT-PCR:

RNA can be extracted from tissue samples using the RNAqueous-4PCR kit (Ambion), according to the manufacturer's instructions. RT-PCR can be performed using the One-step RT-PCR Kit (Qiagen, Valencia Calif.) according to manufacturer's instructions. Conditions can be: 50° C. for 30 min, 95° C. for 15 min, then 35-40 cycles of 94° C. for 1 min, 60° C. for 1 min & 72° C. for 1 min, then 72° C. for 10 min. Primer specific to murine osteocalcin and murin GAPDH can be selected.

Chemical Calcification Quantitation:

Hearts and aorta can be dissected at sacrifice, and all extraneous tissue removed by blunt dissection under a dissecting microscope. Tissues can be desiccated for 20-24 hours at 55° C., weighed and crushed to a powder with a pestle and mortar. Calcium can be eluted in 10% formic acid (10:1 v/w) for 24 hours at 4° C. Calcium content of eluate can be assayed using a cresolphthalein complexone method (Sigma, St Louis), according to manufacturers instructions, and results can be corrected for dry tissue weight.

Bone Histomorphometry:

Bone formation rate can be determined by double fluorescence labeling. All mice can receive intraperitoneal calcein (20 mg/kg) 7 d and 2 d before they are sacrificed. Both femurs can be dissected at the time the animals are sacrificed and placed in 70% ethanol. The specimens can be implanted undecalcified in a plastic embedding kit H7000 (Energy Beam Sciences). Bones can be sectioned longitudinally through the frontal plane in 10-μm sections with JB-4 microtome (Energy Beam Sciences). Unstained sections can be used for calcein-labeled fluorescence analysis. Slides can be examined at ×400 magnification with a Leitz microscope attached to an Osteomeasure Image Analyzer (Osteometrics, Atlanta Ga.). Ten contiguous 0.0225-mm$^2$ fields of the distal femur, 150 μm proximal to the growth plate, can be examined per animal.

Measurements of Parathyroid Hormone and Serum Chemistry:

Blood samples can be obtained at 2 and 8 weeks of CKD by capillary tube aspiration of the saphenous vein, and with a different procedure (intracardiac puncture) at the time of sacrifice (12 weeks CKD) and transferred to heparinized tubes. After centrifugation (400×g for 5 minutes), plasma can be removed, aliquoted and frozen at −80° C. Intact PTH levels (performed only at sacrifice because of the volume of blood required) can be measured by two-site immunoradiometric assay (IRMA) using a commercially available kit (Immutopics, San Clemente, Calif.). Blood urea nitrogen (BUN), serum calcium and phosphorus can be measured using standard multichannel analyzer techniques.

Measurements of FGF23:

An FGF23 murine ELISA assay can be purchased from the Kainos company.

Measurements of DKK1 and Osteocalcin:

Commercial ELISA assays for DKK1 and undercarboxylated osteocalcin can be used.

Measurements of OPG and sRANKL:

The ratio of OPG to RANKL can be determined in serum assays. These assays have been shown to correlate well with bone turnover and excess bone resorption (see, e.g., Geusens et al., 2006, Arthritis & Rheumatism 54:1772-17775). The levels of sRANKL in the serum can be determined by a radioimmunoassay (Linco Research, St. Louis Mo.). Levels of serum OPG can be measured by an ELISA method (OSTEOmedical NL, Marishof, N L). The intra- and inter-assay coefficients of variation (CV) are less than 10% for both tests, according to the manufacturers. The detection limit for sRANKL is 0.08 pmol/l, and for OPG is 0.14 pmol/l.

Measurements of Markers of Bone Turnover:

Serum P1NP and osteocalcin can be used as markers of osteoblast activity and tartrate resistant acid phosphatase form 5b (TRACP 5b) (mouseTRAP, IDS Ltd, Bolden, UK) can be used as a marker of osteoclast levels.

Measurements of Markers of Inflammation:

Serum assays for TNF alpha, and c reactive protein can be used to follow the levels of inflammation and the response to mActRIIA-Fc.

Statistical Analysis:

Data can be analyzed for statistical significance (P<0.05) using ANOVA. Comparison can be made between animals treated with vehicle (control group) and those treated with mActRIIA-Fc. Comparison can also be made between sham-operated mice and CKD mice treated with Vehicle and mActRIIA-Fc. These analyses can be performed with the SPSS 11.0 statistical package (Needham Heights, Mass.).

(b) Study Parameters

Mice used in the study can be placed into one of eight groups as shown in Table 5, below.

TABLE 5

| Group | Description of Group | # Animals |
|---|---|---|
| A | Wild type | 10 |
| B | LDLR High Fat/CKD vehicle treated euth 22 wks | 10 |
| C | LDLR High Fat/CKD RAP-011 treated euth 22 wks | 10 |
| D | LDLR High Fat/CKD vehicle teated euth 28 wks | 10 |
| E | LDLR High Fat/CKD RAP-011 treated euth 28 wks | 10 |
| F | LDLR High Fat/sham operation euth 28 wks | 10 |
| G | LDLR High Fat/sham operation euth 20 wks | 10 |
| H | LDLR High Fat/CKD euth at 14 weeks | 10 |

One group of animals (Group H in Table 5) can be sacrificed at 14 weeks to measure the baseline vascular calcification and histomorphometry at the time of instituting therapy. Groups C and E can be used to assess the efficacy of treatment with mActRIIA-Fc compared to vehicle treated groups (Groups B and D) over variable periods of CKD. Groups F and G are age matched sham operated high fat fed animals that can be used as the control for the CKD effects. Group sizes of 10 animals per group after randomization into the treatment groups can be sufficient to obtain statistical significance.

At 16-18 weeks, glomerular filtration rate (GFR) can be measured by injection of inulin into the mice and measurement of its disappearance. At euthanasia, blood can be drawn by intracardiac stab, and serum DKK1, FGF23, osteocalcin, PTH and calcitriol levels can be determined, along with serum calcium, Pi, blood urea nitrogen (BUN), glucose, and cholesterol levels.

Aortas from the ldlr-/- high fat fed CKD animals can be analyzed. Total aortic calcium levels and von Kossa stained microscopic sections can be obtained. Aortas can be processed to obtain RNA for analysis of aortic gene expression. Aortas can be processed for immunohistochemistry. At 22 weeks in the model of CKD described above, the euthanasia age for groups B and C, vascular calcification is established and adynamic bone disorder is present despite secondary hyperparathyroidism. Between 22 and 28 weeks, vascular calcification is progressive and the effects of the presence of parathyroid hormone begin to increase osteoblast surfaces.

The study described in this example can be used to determine the effects of ActRII inhibition on vascular calcification, bone remodeling rates, and secondary hyperparathyroidism observed in subjects having CKD.

TABLE 6

Sequence Information

| SEQ ID NO: | Description | Sequence |
|---|---|---|
| 1 | human ActRIIA precursor polypeptide | MGAAAKLAFAVFLISCSSGAILGRSETQECLFFNANWEKDRTNQTGVEPC YGDKDKRRHCFATWKNISGSIEIVKQGCWLDDINCYDRTDCVEKKDSPEV YFCCCEGNMCNEKFSYFPEMEVTQPTSNPVTPKPPYYNILLYSLVPLMLI AGIVICAFWVYRHHKMAYPPVLVPTQDPGPPPPSPLLGLKPLQLLEVKAR GRFGCVWKAQLLNEYVAVKIFPIQDKQSWQNEYEVYSLPGMKHENILQFI GAEKRGTSVDVDLWLITAFHEKGSLSDFLKANVVSWNELCHIAETMARGL AYLHEDIPGLKDGHKPAISHRDIKSKNVLLKNNLTACIADFGLALKFEAG KSAGDTHGQVGTRRYMAPEVLEGAINFQRDAFLRIDMYAMGLVLWELASR CTAADGPVDEYMLPFEEEIGQHPSLEDMQEVVVHKKKRPVLRDYWQKHAG MAMLCETIEECWDHDAEARLSAGCVGERITQMQRLTNIITTEDIVTVVTM VTNVDFPPKESSL |
| 2 | human ActRIIA soluble (extracellular), processed polypeptide sequence | ILGRSETQECLFFNANWEKDRTNQTGVEPCYGDKDKRRHCFATWKNISGS IEIVKQGCWLDDINCYDRTDCVEKKDSPEVYFCCCEGNMCNEKFSYFPEM EVTQPTSNPVTPKPP |
| 3 | human ActRIIA soluble (extracellular), processed polypeptide sequence with the C-terminal 15 amino acids deleted | ILGRSETQECLFFNANWEKDRTNQTGVEPCYGDKDKRRHCFATWKNISGS IEIVKQGCWLDDINCYDRTDCVEKKDSPEVYFCCCEGNMCNEKFSYFPEM |
| 4 | nucleic acid sequence encoding human ActRIIA precursor protein | ATGGGAGCTGCTGCAAAGTTGGCGTTTGCCGTCTTTCTTATCTCCTGTTC TTCAGGTGCTATACTTGGTAGATCAGAAACTCAGGAGTGTCTTTTCTTTA ATGCTAATTGGGAAAAAGACAGAACCAATCAAACTGGTGTTGAACCGTGT TATGGTGACAAAGATAAACGGCGGCATTGTTTTGCTACCTGGAAGAATAT TTCTGGTTCCATTGAAATAGTGAAACAAGGTTGTTGGCTGGATGATATCA ACTGCTATGACAGGACTGATTGTGTAGAAAAAAAAGACAGCCCTGAAGTA TATTTTTGTTGCTGTGAGGGCAATATGTGTAATGAAAGTTTTCTTATTT TCCAGAGATGGAAGTCACACAGCCCACTTCAAATCCAGTTACACCTAAGC CACCCTATTACAACATCCTGCTCTATTCCTTGGTGCCACTTATGTTAATT GCGGGGATTGTCATTTGTGCATTTTGGGTGTACAGGCATCACAAGATGGC CTACCCTCCTGTACTTGTTCCAACTCAAGACCCAGGACCACCCCCACCTT CTCCATTACTAGGGTTGAAACCACTGCAGTTATTAGAAGTGAAAGCAAGG GGAAGATTTGGTTGTGTCTGGAAAGCCCAGTTGCTTAACGAATATGTGGC TGTCAAAATATTTCCAATACAGGACAAACAGTCATGGCAAAATGAATACG |

TABLE 6-continued

Sequence Information

| SEQ ID NO: | Description | Sequence |
|---|---|---|
| | | AAGTCTACAGTTTGCCTGGAATGAAGCATGAGAACATATTACAGTTCATT GGTGCAGAAAAACGAGGCACCAGTGTTGATGTGGATCTTTGGCTGATCAC AGCATTTCATGAAAAGGGTTCACTATCAGACTTTCTTAAGGCTAATGTGG TCTCTTGGAATGAACTGTGTCATATTGCAGAAACCATGGCTAGAGGATTG GCATATTTACATGAGGATATACCTGGCCTAAAAGATGGCCACAAACCTGC CATATCTCACAGGGACATCAAAAGTAAAAATGTGCTGTTGAAAAACAACC TGACAGCTTGCATTGCTGACTTTGGGTTGGCCTTAAAATTTGAGGCTGGC AAGTCTGCAGGCGATACCCATGGACAGGTTGGTACCCGGAGGTACATGGC TCCAGAGGTATTAGAGGGTGCTATAAACTTCGAAAGGGATGCATTTTTGA GGATAGATATGTATGCCATGGGATTAGTCCTATGGGAACTGGCTTCTCGC TGTACTGCTGCAGATGGACCTGTAGATGAATACATGTTGCCATTTGAGGA GGAAATTGGCCAGCATCCATCTCTTGAAGACATGCAGGAAGTTGTTGTGC ATAAAAAAAGAGGCCTGTTTTAAGAGATTATTGGCAGAAACATGCTGGA ATGGCAATGCTCTGTGAAACCATTGAAGAATGTTGGGATCACGACGCAGA AGCCAGGTTATCAGCTGGATGTGTAGGTGAAAGAATTACCCAGATGCAGA GACTAACAAATATTATTACCACAGAGGACATTGTAACAGTGGTCACAATG GTGACAAATGTTGACTTTCCTCCCAAAGAATCTAGTCTATGA |
| 5 | nucleic acid sequence encoding a human ActRIIA soluble (extracellular) polypeptide | ATACTTGGTAGATCAGAAACTCAGGAGTGTCTTTTCTTTAATGCTAATTG GGAAAAAGACAGAACCAATCAAACTGGTGTTGAACCGTGTTATGGTGACA AGATAAACGGCGGCATTGTTTTGCTACCTGGAAGAATATTTCTGGTTCC ATTGAAATAGTGAAACAAGGTTGTTGGCTGGATGATATCAACTGCTATGA CAGGACTGATTGTGTAGAAAAAAAAGACAGCCCTGAAGTATATTTTTGTT GCTGTGAGGGCAATATGTGTAATGAAAAGTTTTCTTATTTTCCAGAGATG GAAGTCACACAGCCCACTTCAAATCCAGTTACACCTAAGCCACCC |
| 6 | fusion protein comprising a soluble extracellular domain of ActRIIA fused to an Fc domain | THTCPPCPAPELLGGPSVFLFPPKPKDTLMISRTPEVTCVVVD(A)VSHE DPEVKFNWYVDGVEVHNAKTKPREEQYNSTYRVVSVLTVLHQDWLNGKEY KCK(A)VSNKALPVPIEKTISKAKGQPREPQVYTLPPSREEMTKNQVSLT CLVKGFYPSDIAVEWESNGQPENNYKTTPPVLDSDGPFFLYSKLTVDKSR WQQGNVFSCSVMHEALHN(A)HYTQKSLSLSPGK* |
| 7 | Extracellular domain of human ActRIIA fused to a human Fc domain | ILGRSETQECLFFNANWEKDRTNQTGVEPCYGDKDKRRHCFATWKNISGS IEIVKQGCWLDDINCYDRTDCVEKKDSPEVYFCCCEGNMCNEKFSYFPEM EVTQPTSNPVTPKPPTGGGTHTCPPCPAPELLGGPSVFLFPPKPKDTLMI SRTPEVTCVVVDVSHEDPEVKFNWYVDGVEVHNAKTKPREEQYNSTYRVV SVLTVLHQDWLNGKEYKCKVSNKALPVPIEKTISKAKGQPREPQVYTLPP SREEMTKNQVSLTCLVKGFYPSDIAVEWESNGQPENNYKTTPPVLDSDGS FFLYSKLTVDKSRWQQGNVFSCSVMHEALHNHYTQKSLSLSPGK |
| 8 | Leader sequence of Honey bee mellitin (HBML) | MKFLVNVALVFMVVYISYIYA |
| 9 | Leader sequence of Tissue Plasminogen Activator (TPA) | MDAMKRGLCCVLLLCGAVFVSP |
| 10 | Native ActRIIA leader | MGAAAKLAFAVFLISCSSGA |
| 11 | ActRIIA-hFc and ActRIIA-mFc N-terminal sequence | ILGRSETQE |
| 12 | ActRIIA-Fc Protein with deletion of the C-terminal 15 amino acids of the extracellular domain of ActRIIA | ILGRSETQECLFFNANWEKDRTNQTGVEPCYGDKDKRRHCFATWKNISGS IEIVKQGCWLDDINCYDRTDCVEKKDSPEVYFCCCEGNMCNEKFSYFPEM TGGGTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKE YKCKVSNKALPVPIEKTISKAKGQPREPQVYTLPPSREEMTKNQVSLTCL VKGFYPSDIAVEWESNGQPENNYKTTPPVLDSDGSFFLYSKLTVDKSRWQ QGNVFSCSVMHEALHNHYTQKSLSLSPGK |
| 13 | Unprocessed ActRIIA-hFc with TPA leader sequence | MDAMKRGLCCVLLLCGAVFVSPGAAILGRSETQECLFFNANWEKDRTNQT GVEPCYGDKDKRRHCFATWKNISGSIEIVKQGCWLDDINCYDRTDCVEKK DSPEVYFCCCEGNMCNEKFSYFPEMEVTQPTSNPVTPKPPTGGGTHTCPP CPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKAL PVPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVM HEALHNHYTQKSLSLSPGK |

TABLE 6-continued

Sequence Information

| SEQ ID NO: | Description | Sequence |
|---|---|---|
| 14 | Nucleic acid sequence encoding Unprocessed ActRIIA-hFc with TPA leader sequence | ATGGATGCAATGAAGAGAGGGCTCTGCTGTGTGCTGCTGCTGTGTGGAGC AGTCTTCGTTTCGCCCGGCGCCGCTATACTTGGTAGATCAGAAACTCAGG AGTGTCTTTTTTTAATGCTAATTGGGAAAAAGACAGAACCAATCAAACTG GTGTTGAACCGTGTTATGGTGACAAAGATAAACGGCGGCATTGTTTTGCT ACCTGGAAGAATATTTCTGGTTCCATTGAATAGTGAAACAAGGTTGTTGG CTGGATGATATCAACTGCTATGACAGGACTGATTGTGTAGAAAAAAAAGA CAGCCCTGAAGTATATTTCTGTTGCTGTGAGGGCAATATGTGTAATGAAA AGTTTTCTTATTTTCCGGAGATGGAAGTCACACAGCCCACTTCAAATCCA GTTACACCTAAGCCACCCACCGGTGGTGGAACTCACACATGCCCACCGTG CCCAGCACCTGAACTCCTGGGGGGACCGTCAGTCTTCCTCTTCCCCCCAA AACCCAAGGACACCCTCATGATCTCCCGGACCCCTGAGGTCACATGCGTG GTGGTGGACGTGAGCCACGAAGACCCTGAGGTCAAGTTCAACTGGTACGT GGACGGCGTGGAGGTGCATAATGCCAAGACAAAGCCGCGGGAGGAGCAGT ACAACAGCACGTACCGTGTGGTCAGCGTCCTCACCGTCCTGCACCAGGAC TGGCTGAATGGCAAGGAGTACAAGTGCAAGGTCTCCAACAAAGCCCTCCC AGTCCCCATCGAGAAAACCATCTCCAAAGCCAAAGGGCAGCCCCGAGAAC CACAGGTGTACACCCTGCCCCCATCCCGGGAGGAGATGACCAAGAACCAG GTCAGCCTGACCTGCCTGGTCAAAGGCTTCTATCCCAGCGACATCGCCGT GGAGTGGGAGAGCAATGGGCAGCCGGAGAACAACTACAAGACCACGCCTC CCGTGCTGGACTCCGACGGCTCCTTCTTCCTCTATAGCAAGCTCACCGTG GACAAGAGCAGGTGGCAGCAGGGGAACGTCTTCTCATGCTCCGTGATGCA TGAGGCTCTGCACAACCACTACACGCAGAAGAGCCTCTCCCTGTCTCCGG GTAAATGAGAATTC |
| 15 | human ActRIIB soluble (extracellular), processed polypeptide sequence with the N-terminal 6 amino acids of the EC domain deleted and the C-terminal 4 amino acids of the EC domain deleted (amino acids 25-130 of SEQ ID NO: 28) and with an L79D mutation | ETRECIYYNANWELERTNQSGLERCEGEQDKRLHCYASWRNSSGTIELV KKGCWDDDFNCYDRQECVATEENPQVYFCCCEGNFCNERFTHLPEAGGP EVTYEPPP |
| 16 | human ActRIIB precursor protein sequence (A64) | MTAPWVALALLWGSLW PGSGRGEAETRECIYY NANWELERTNQSGLER CEGEQDKRLHCYASWA NSSGTIELVKKGCWLD DFNCYDRQECVATEEN PQVYFCCCEGNFCNER FTHLPEAGGPEVTYEP PPTAPTLLTVLAYSLL PIGGLSLIVLLAFWMY RHRKPPYGHVDIHEDP GPPPPSPLVGLKPLQL LEIKARGRFGCVWKAQ LMNDFVAVKIFPLQDK QSWQSEREIFSTPGMK HENLLQFIAAEKRGSN LEVELWLITAFHDKGS LTDYLKGNIITWNELC HVAETMSRGLSYLHED VPWCRGEGHKPSIAHR DFKSKNVLLKSDLTAV LADFGLAVRFEPGKPP GDTHGQVGTRRYMAPE VLEGAINFQRDAFLRI DMYAMGLVLWELVSRC KAADGPVDEYMLPFEE EIGQHPSLEELQEVVV HKKMRPTIKDHWLKHP GLAQLCVTIEECWDHD AEARLSAGCVEERVSL IRRSVNGTTSDCLVSL VTSVTNVDLPPKESSI |
| 17 | human ActRIIB soluble (extracellular), processed polypeptide sequence (amino acids 19-134 of SEQ ID NO: 16) | SGRGEAETRECIYYNANWELERTNQSGLERCEGEQDKRLHCYASWANSSG TIELVKKGCWLDDFNCYDRQECVATEENPQVYFCCCEGNFCNERFTHLPE AGGPEVTYEPPPTAPT |
| 18 | human ActRIIB soluble (extracellular), processed polypeptide sequence with the C-terminal 15 amino acids deleted (amino acids 19-119 of SEQ ID NO: 16) | SGRGEAETRECIYYNANWELERTNQSGLERCEGEQDKRLHCYASWANSSG TIELVKKGCWLDDFNCYDRQECVATEENPQVYFCCCEGNFCNERFTHLPE A |
| 19 | nucleic acid sequence encoding a human ActRIIB (A64) precursor protein | ATGACGGCGCCCTGGGTGGCCCTCGCCCTCCTCTGGGGATCGCTGTGGCC CGGCTCTGGGCGTGGGGAGGCTGAGACACGGGAGTGCATCTACTACAACG CCAACTGGGAGCTGGAGCGCACCAACCAGAGCGGCCTGGAGCGCTGCGAA GGCGAGCAGGACAAGCGGCTGCACTGCTACGCCTCCTGGGCCAACAGCTC TGGCACCATCGAGCTCGTGAAGAAGGCTGCTGGTAGATGACTTCAACT GCTACGATAGGCAGGAGTGTGTGGCCACTGAGGAGAACCCCCAGGTGTAC TTCTGCTGCTGTGAAGGCAACTTCTGCAACGAGCGCTTCACTCATTTGCC AGAGGCTGGGGGCCCGGAAGTCACGTACGAGCCACCCCCGACAGCCCCCA CCCTGCTCACGGTGCTGGCCTACTCACTGCTGCCCATCGGGGGCCTTTCC CTCATCGTCCTGCTGGCCTTTTGGATGTACCGGCATCGCAAGCCCCCCTA |

TABLE 6-continued

Sequence Information

| SEQ ID NO: | Description | Sequence |
|---|---|---|
| | | CGGTCATGTGGACATCCATGAGGACCCTGGGCCTCCACCACCATCCCCTC<br>TGGTGGGCCTGAAGCCACTGCAGCTGCTGGAGATCAAGGCTCGGGGCGC<br>TTTTGGCTGTGTCTGGAAGGCCCAGCTCATGAATGACTTTGTAGCTGTCAA<br>GATCTTCCCACTCCAGGACAAGCAGTCGTGGCAGAGTGAACGGGAGATCT<br>TCAGCACACCTGGCATGAAGCACGAGAACCTGCTACAGTTCATTGCTGCC<br>GAGAAGCGAGGCTCCAACCTCGAAGTAGAGCTGTGGCTCATCACGGCCTT<br>CCATGACAAGGGCTCCCTCACGGATTACCTCAAGGGGAACATCATCACAT<br>GGAACGAACTGTGTCATGTAGCAGAGACGATGTCACGAGGCCTCTCATAC<br>CTGCATGAGGATGTGCCCTGGTGCCGTGGCGAGGGCCACAAGCCGTCTAT<br>TGCCCACAGGGACTTTAAAAGTAAGAATGTATTGCTGAAGAGCGACCTCA<br>CAGCCGTGCTGGCTGACTTTGGCTTGGCTGTTCGATTTGAGCCAGGGAAA<br>CCTCCAGGGGACACCCACGGACAGGTAGGCACGAGACGGTACATGGCTCC<br>TGAGGTGCTCGAGGGAGCCATCAACTTCCAGAGAGATGCCTTCCTGCGCA<br>TTGACATGTATGCCATGGGGTTGGTGCTGTGGGAGCTTGTGTCTCGCTGC<br>AAGGCTGCAGACGGACCCGTGGATGAGTACATGCTGCCCTTTGAGGAAGA<br>GATTGGCCAGCACCCTTCGTTGGAGGAGCTGCAGGAGGTGGTGGTGCACA<br>AGAAGATGAGGCCCACCATTAAAGATCACTGGTTGAAACACCCGGGCCTG<br>GCCCAGCTTTGTGTGACCATCGAGGAGTGCTGGGACCATGATGCAGAGGC<br>TCGCTTGTCCGCGGGCTGTGTGGAGGAGCGGGTGTCCCTGATTCGGAAGGT<br>CGGTCAACGGCACTACCTCGGACTGTCTCGTTTCCCTGGTGACCTCTGTC<br>ACCAATGTGGACCTGCCCCCTAAAGAGTCAAGCATCTAA |
| 20 | fusion protein comprising a soluble extracellular domain of ActRIIB (A64; SEQ ID NO: 17) fused to an Fc domain | SGRGEAETRECIYYNANWELERTNQSGLERCEGEQDKRLHCYASWANSSG<br>TIELVKKGCWLDDFNCYDRQECVATEENPQVYFCCCEGNFCNERFTHLPE<br>AGGPEVTYEPPPTAPTGGGTHTCPPCPAPELLGGPSVFLFPPKPKDTLMI<br>SRTPEVTCVVVDVSHEDPEVKFNWYVDGVEVHNAKTKPREEQYNSTYRVV<br>SVLTVLHQDWLNGKEYKCKVSNKALPVPIEKTISKAKGQPREPQVYTLPP<br>SREEMTKNQVSLTCLVKGFYPSDIAVEWESNGQPENNYKTTPPVLDSDGS<br>FFLYSKLTVDKSRWQQGNVFSCSVMHEALHNHYTQKSLSLSPGK |
| 21 | fusion protein comprising a soluble extracellular domain of ActRIIB (A64) with the C-terminal 15 amino acids deleted (SEQ ID NO: 18) fused to an Fc domain | SGRGEAETRECIYYNANWELERTNQSGLERCEGEQDKRLHCYASWANSSG<br>TIELVKKGCWLDDFNCYDRQECVATEENPQVYFCCCEGNFCNERFTHLPE<br>AGGGTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKE<br>YKCKVSNKALPVPIEKTISKAKGQPREPQVYTLPPSREEMTKNQVSLTCL<br>VKGFYPSDIAVEWESNGQPENNYKTTPPVLDSDGSFFLYSKLTVDKSRWQ<br>QGNVFSCSVMHEALHNHYTQKSLSLSPGK |
| 22 | human ActRIIB soluble (extracellular), processed polypeptide sequence with the N-terminal 6 amino acids of the EC domain deleted and the C-terminal 5 amino acids of the EC domain deleted (amino acids 25-129 of SEQ ID NO: 28) and with an L79D mutation | ETRECIYYNANWELERTNQSGLERCEGEQDKRLHCYASWRNSSGTIELV<br>KKGCWDDDFNCYDRQECVATEENPQVYFCCCEGNFCNERFTHLPEAGGP<br>EVTYEPP |
| 23 | human ActRIIB soluble (extracellular), processed polypeptide sequence with the N-terminal 6 amino acids of the EC domain deleted and the C-terminal 3 amino acids of the EC domain deleted (amino acids 25-131 of SEQ ID NO: 28) and with an L79D mutation | ETRECIYYNANWELERTNQSGLERCEGEQDKRLHCYASWRNSSGTIELV<br>KKGCWDDDFNCYDRQECVATEENPQVYFCCCEGNFCNERFTHLPEAGGP<br>EVTYEPPPT |
| 24 | Unprocessed ActRIIB-Fc fusion protein with the N-terminal 6 amino acids of the EC domain deleted and the C-terminal 3 amino acids of the EC domain | MDAMKRGLCCVLLLCGAVFVSPGAAETRECIYYNANWELERTNQSGLERC<br>EGEQDKRLHCYASWRNSSGTIELVKKGCWDDDFNCYDRQECVATEENPQV<br>YFCCCEGNFCNERFTHLPEAGGPEVTYEPPPTGGGTHTCPPCPAPELLGG<br>PSVFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKTIS<br>KAKGQPREPQVYTLPPSREEMTKNQVSLTCLVKGFYPSDIAVEWESNGQP<br>ENNYKTTPPVLDSDGSFFLYSKLTVDKSRWQQGNVFSCSVMHEALHNHYT |

TABLE 6-continued

Sequence Information

| SEQ ID NO: | Description | Sequence |
|---|---|---|
| | deleted (amino acids 25-131 of SEQ ID NO: 28) and with an L79D mutation and with TPA leader sequence | QKSLSLSPGK* |
| 25 | Processed ActRIIB-Fc fusion protein with the N-terminal 6 amino acids of the EC domain deleted and the C-terminal 3 amino acids of the EC domain deleted (amino acids 25-131 of SEQ ID NO: 28) and with an L79D mutation | ETRECIYYNANWELERTNQSGLERCEGEQDKRLHCYASWRNSSGTIELVK KGCWDDDFNCYDRQECVATEENPQVYFCCCEGNFCNERFTHLPEAGGPEV TYEPPPTGGGTHTCPPCPAPELLGGPSVFLFPPKPKDTLMISRTPEVTCV VVDVSHEDPEVKFNWYVDGVEVHNAKTKPREEQYNSTYRVVSVLTVLHQD WLNGKEYKCKVSNKALPAPIEKTISKAKGQPREPQVYTLPPSREEMTKNQ VSLTCLVKGFYPSDIAVEWESNGQPENNYKTTPPVLDSDGSFFLYSKLTV DKSRWQQGNVFSCSVMHEALHNHYTQKSLSLSPGK* |
| 26 | human ActRIIB soluble (extracellular), processed polypeptide sequence (amino acids 20-134 of SEQ ID NO: 16) | GRGEAETRECIYYNANWELERTNQSGLERCEGEQDKRLHCYASWANSSG TIELVKKGCWLDDFNCYDRQECVATEENPQVYFCCCEGNFCNERFTHLPE AGGPEVTYEPPPTAPT |
| 27 | human ActRIIB soluble (extracellular), processed polypeptide sequence with the C-terminal 15 amino acids deleted (amino acids 20-119 of SEQ ID NO: 16) | GRGEAETRECIYYNANWELERTNQSGLERCEGEQDKRLHCYASWANSSG TIELVKKGCWLDDFNCYDRQECVATEENPQVYFCCCEGNFCNERFTHLPE A |
| 28 | human ActRIIB precursor protein sequence (R64) | MTAPWVALALLWGSLW PGSGRGEAETRECIYY NANWELERTNQSGLER CEGEQDKRLHCYASWR NSSGTIELVKKGCWLD DFNCYDRQECVATEEN PQVYFCCCEGNFCNER FTHLPEAGGPEVTYEP PPTAPTLLTVLAYSLL PIGGLSLIVLLAFWMY RHRKPPYGHVDIHEDP GPPPPSPLVGLKPLQL LEIKARGRFGCVWKAQ LMNDFVAVKIFPLQDK QSWQSEREIFSTPGMK HENLLQFIAAEKRGSN LEVELWLITAFHDKGS LTDYLKGNIITWNELC HVAETMSRGLSYLHED VPWCRGEGHKPSIAHR DFKSKNVLLKSDLTAV LADPFGLAVRFEPGKPP GDTHGQVGTRRYMAPE VLEGAINFQRDAFLRI DMYAMGLVLWELVSRC KAADGPVDEYMLPFEE EIGQHPSLEELQEVVV HKKMRPTIKDHWLKHP GLAQLCVTIEECWDHD AEARLSAGCVEERVSL IRRSVNGTTSDCLVSL VTSVTNVDLPPKESSI |
| 29 | human ActRIIB soluble (extracellular), processed polypeptide sequence (amino acids 19-134 of SEQ ID NO: 28) | SGRGEAETRECIYYNANWELERTNQSGLERCEGEQDKRLHCYASWRNSSG TIELVKKGCWLDDFNCYDRQECVATEENPQVYFCCCEGNFCNERFTHLPE AGGPEVTYEPPPTAPT |
| 30 | human ActRIIB soluble (extracellular), processed polypeptide sequence with the C-terminal 15 amino acids deleted (amino acids 19-119 of SEQ ID NO: 28) | SGRGEAETRECIYYNANWELERTNQSGLERCEGEQDKRLHCYASWRNSSG TIELVKKGCWLDDFNCYDRQECVATEENPQVYFCCCEGNFCNERFTHLPE A |
| 31 | human ActRIIB soluble (extracellular), processed polypeptide sequence (amino acids 20-134 of SEQ ID NO: 28) | GRGEAETRECIYYNANWELERTNQSGLERCEGEQDKRLHCYASWRNSSG TIELVKKGCWLDDFNCYDRQECVATEENPQVYFCCCEGNFCNERFTHLPE AGGPEVTYEPPPTAPT |
| 32 | human ActRIIB soluble (extracellular), processed polypeptide sequence with the C-terminal 15 amino acids deleted (amino acids 20-119 of SEQ ID NO: 28) | GRGEAETRECIYYNANWELERTNQSGLERCEGEQDKRLHCYASWRNSSG TIELVKKGCWLDDFNCYDRQECVATEENPQVYFCCCEGNFCNERFTHLPE A |

TABLE 6-continued

Sequence Information

| SEQ ID NO: | Description | Sequence |
|---|---|---|
| 33 | human ActRIIB soluble (extracellular), processed polypeptide sequence with the N-terminal 6 amino acids of the EC domain deleted and the C-terminal 3 amino acids of the EC domain deleted (amino acids 25-131 of SEQ ID NO: 16) and with an L79D mutation | ETRECIYYNANWELERTNQSGLERCEGEQDKRLHCYASWANSSGTIELV KKGCWDDDFNCYDRQECVATEENPQVYFCCCEGNFCNERFTHLPEAGGP EVTYEPPPT |
| 34 | Unprocessed ActRIIB-Fc fusion protein with the N-terminal 6 amino acids of the EC domain deleted and the C-terminal 3 amino acids of the EC domain deleted (amino acids 25-131 of SEQ ID NO: 16) and with an L79D mutation and with TPA leader sequence | MDAMKRGLCCVLLLCGAVFVSPGAAETRECIYYNANWELERTNQSGLERC EGEQDKRLHCYASWANSSGTIELVKKGCWDDDFNCYDRQECVATEENPQV YFCCCEGNFCNERFTHLPEAGGPEVTYEPPPTGGGTHTCPPCPAPELLGG PSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTIS KAKGQPREPQVYTLPPSREEMTKNQVSLTCLVKGFYPSDIAVEWESNGQP ENNYKTTPPVLDSDGSFFLYSKLTVDKSRWQQGNVFSCSVMHEALHNHYT QKSLSLSPGK* |
| 35 | Processed ActRIIB-Fc fusion protein with the N-terminal 6 amino acids of the EC domain deleted and the C-terminal 3 amino acids of the EC domain deleted (amino acids 25-131 of SEQ ID NO: 16) and with an L79D mutation | ETRECIYYNANWELERTNQSGLERCEGEQDKRLHCYASWANSSGTIELVK KGCWDDDFNCYDRQECVATEENPQVYFCCCEGNFCNERFTHLPEAGGPEV TYEPPPTGGGTHTCPPCPAPELLGGPSVFLFPPKPKDTLMISRTPEVTCV VVDVSHEDPEVKFNWYVDGVEVHNAKTKPREEQYNSTYRVVSVLTVLHQD WLNGKEYKCKVSNKALPAPIEKTISKAKGQPREPQVYTLPPSREEMTKNQ VSLTCLVKGFYPSDIAVEWESNGQPENNYKTTPPVLDSDGSFFLYSKLTV DKSRWQQGNVFSCSVMHEALHNHYTQKSLSLSPGK* |
| 36 | human ActRIIB soluble (extracellular), processed polypeptide sequence (amino acids 20-134 of SEQ ID NO: 28) with L79D mutation | GRGEAETRECIYYNANWELERTNQSGLERCEGEQDKRLHCYASWRNSSG TIELVKKGCWDDDFNCYDRQECVATEENPQVYFCCCEGNFCNERFTHLPE AGGPEVTYEPPPTAPT |
| 37 | human ActRIIB soluble (extracellular), processed polypeptide sequence (amino acids 20-134 of SEQ ID NO: 16) with L79D mutation | GRGEAETRECIYYNANWELERTNQSGLERCEGEQDKRLHCYASWANSSG TIELVKKGCWDDDFNCYDRQECVATEENPQVYFCCCEGNFCNERFTHLPE AGGPEVTYEPPPTAPT |
| 38 | human ActRIIB soluble (extracellular), processed polypeptide sequence (amino acids 20-134 of SEQ ID NO: 28) with L79D mutation fused to an Fc domain with a GGG linker | GRGEAETRECIYYNANWELERTNQSGLERCEGEQDKRLHCYASWRNSSG TIELVKKGCWDDDFNCYDRQECVATEENPQVYFCCCEGNFCNERFTHLPE AGGPEVTYEPPPTAPTGGGTHTCPPCPAPELLGG PSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTIS KAKGQPREPQVYTLPPSREEMTKNQVSLTCLVKGFYPSDIAVEWESNGQP ENNYKTTPPVLDSDGSFFLYSKLTVDKSRWQQGNVFSCSVMHEALHNHYT QKSLSLSPGK* |
| 39 | human ActRIIB soluble (extracellular), processed polypeptide sequence (amino acids 20-134 of SEQ ID NO: 16) with L79D mutation fused to an Fc domain | GRGEAETRECIYYNANWELERTNQSGLERCEGEQDKRLHCYASWANSSG TIELVKKGCWDDDFNCYDRQECVATEENPQVYFCCCEGNFCNERFTHLPE AGGPEVTYEPPPTAPTGGGTHTCPPCPAPELLGG PSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTIS KAKGQPREPQVYTLPPSREEMTKNQVSLTCLVKGFYPSDIAVEWESNGQP ENNYKTTPPVLDSDGSFFLYSKLTVDKSRWQQGNVFSCSVMHEALHNHYT QKSLSLSPGK* |

TABLE 6-continued

Sequence Information

| SEQ ID NO: | Description | Sequence |
|---|---|---|
| 40 | human ActRIIB soluble (extracellular), processed polypeptide sequence (amino acids 20-134 of SEQ ID NO: 28) with L79D mutation fused to an Fc domain and with TPA leader sequence | MDAMKRGLCCVLLLCGAVFVSPGASGRGEAETRECIYYNANWELERTNQSG LERCEGEQDKRLHCYASWRNSSG TIELVKKGCWDDDFNCYDRQECVATEENPQVYFCCCEGNFCNERFTHLPE AGGPEVTYEPPPTAPTGGGTHTCPPCPAPELLGG PSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTIS KAKGQPREPQVYTLPPSREEMTKNQVSLTCLVKGFYPSDIAVEWESNGQP ENNYKTTPPVLDSDGSFFLYSKLTVDKSRWQQGNVFSCSVMHEALHNHYT QKSLSLSPGK* |
| 41 | human ActRIIB soluble (extracellular), processed polypeptide sequence (amino acids 20-134 of SEQ ID NO: 16) with L79D mutation fused to an Fc domain and with TPA leader sequence | MDAMKRGLCCVLLLCGAVFVSPGASGRGEAETRECIYYNANWELERTNQSG LERCEGEQDKRLHCYASWANSSG TIELVKKGCWDDDFNCYDRQECVATEENPQVYFCCCEGNFCNERFTHLPE AGGPEVTYEPPPTAPTGGGTHTCPPCPAPELLGG PSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTIS KAKGQPREPQVYTLPPSREEMTKNQVSLTCLVKGFYPSDIAVEWESNGQP ENNYKTTPPVLDSDGSFFLYSKLTVDKSRWQQGNVFSCSVMHEALHNHYT QKSLSLSPGK* |
| 42 | human ActRIIB soluble (extracellular), processed polypeptide sequence having a variant C-terminal sequence (disclosed in WO2007/053775) | GRGEAETRECIYYNANWELERTNQSGLERCEGEQDKRLHCYASWRNSSGT IELVKKGCWLDDFNCYDRQECVATEENPQVYFCCCEGNFCNERFTHLPEA GGPEGPWASTTIPSGGPEATAAAGDQGSGALWLCLEGPAHE |
| 43 | human ActRIIB soluble (extracellular), processed polypeptide sequence having a variant C-terminal sequence (disclosed in WO2007/053775) having an L79D mutation | GRGEAETRECIYYNANWELERTNQSGLERCEGEQDKRLHCYASWRNSSGT IELVKKGCWDDDFNCYDRQECVATEENPQVYFCCCEGNFCNERFTHLPEA GGPEGPWASTTIPSGGPEATAAAGDQGSGALWLCLEGPAHE |
| 44 | human ActRIIB soluble (extracellular), processed polypeptide sequence having a variant C-terminal sequence (disclosed in WO2007/053775) having an L79D mutation fused to an Fc domain with a TGGG linker | GRGEAETRECIYYNANWELERTNQSGLERCEGEQDKRLHCYASWRNSSGT IELVKKGCWDDDFNCYDRQECVATEENPQVYFCCCEGNFCNERFTHLPEA GGPEGPWASTTIPSGGPEATAAAGDQGSGALWLCLEGPAHE TGGGTHTCPPCPAPELLGG PSVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTIS KAKGQPREPQVYTLPPSREEMTKNQVSLTCLVKGFYPSDIAVEWESNGQP ENNYKTTPPVLDSDGSFFLYSKLTVDKSRWQQGNVFSCSVMHEALHNHYT QKSLSLSPGK* |
| 45 | Nucleic Acid Sequence Encoding SEQ ID NO: 24 | ATGGATGCAA TGAAGAGAGG GCTCTGCTGT GTGCTGCTGC TGTGTGGAGC AGTCTTCGTT TCGCCCGGCG CCGCCGAAAC CCGCGAATGT ATTTATTACA ATGCTAATTG GGAACTCGAA CGGACGAACC AATCCGGGCT CGAACGGTGT GAGGGGGAAC AGGATAAACG CCTCCATTGC TATGCGTCGT GGAGGAACTC CTCCGGGACG ATTGAACTGG TCAAGAAAGG TGCTGGGAC GACGATTTCA ATTGTTATGA CCGCCAGGAA TGTGTCGCGA CCGAAGAGAA TCCGCAGGTC TATTTCTGTT GTTGCGAGGG GAATTTCTGT AATGAACGGT TTACCCACCT CCCCGAAGCC GGCGGGCCCG AGGTGACCTA TGAACCCCCG CCCACCGGTG GTGGAACTCA CACATGCCCA CCGTGCCCAG CACCTGAACT CCTGGGGGGA CCGTCAGTCT TCCTCTTCCC CCCAAAACCC AAGGACACCC TCATGATCTC CCGGACCCCT GAGGTCACAT GCGTGGTGGT GGACGTGAGC CACGAAGACC CTGAGGTCAA GTTCAACTGG TACGTGGACG GCGTGGAGGT GCATAATGCC AAGACAAAGC CGCGGGAGGA GCAGTACAAC AGCACGTACC GTGTGGTCAG CGTCCTCACC GTCCTGCACC AGGACTGGCT GAATGGCAAG GAGTACAAGT GCAAGGTCTC CAACAAAGCC CTCCCAGCCC CCATCGAGAA AACCATCTCC AAAGCCAAAG |

TABLE 6-continued

Sequence Information

| SEQ ID NO: | Description | Sequence |
|---|---|---|
| | | GGCAGCCCCG AGAACCACAG GTGTACACCC TGCCCCCATC<br>CCGGGAGGAG ATGACCAAGA ACCAGGTCAG CCTGACCTGC<br>CTGGTCAAAG GCTTCTATCC CAGCGACATC GCCGTGGAGT<br>GGGAGAGCAA TGGGCAGCCG GAGAACAACT ACAAGACCAC<br>GCCTCCCGTG CTGGACTCCG ACGGCTCCTT CTTCCTCTAT<br>AGCAAGCTCA CCGTGGACAA GAGCAGGTGG CAGCAGGGGA<br>ACGTCTTCTC ATGCTCCGTG ATGCATGAGG CTCTGCACAA<br>CCACTACACG CAGAAGAGCC TCTCCCTGTC CCCGGGTAAA TGA |
| 46 | fusion protein comprising a soluble extracellular domain of ActRIIB (R64; SEQ ID NO: 29) fused to an Fc domain | SGRGEAETRECIYYNANWELERTNQSGLERCEGEQDKRLHCYASWRNSSG<br>TIELVKKGCWLDDFNCYDRQECVATEENPQVYFCCCEGNFCNERFTHLPE<br>AGGPEVTYEPPPTAPTGGGTHTCPPCPAPELLGGPSVFLFPPKPKDTLMI<br>SRTPEVTCVVVDVSHEDPEVKFNWYVDGVEVHNAKTKPREEQYNSTYRVV<br>SVLTVLHQDWLNGKEYKCKVSNKALPVPIEKTISKAKGQPREPQVYTLPP<br>SREEMTKNQVSLTCLVKGFYPSDIAVEWESNGQPENNYKTTPPVLDSDGS<br>FFLYSKLTVDKSRWQQGNVFSCSVMHEALHNHYTQKSLSLSPGK |
| 47 | fusion protein comprising a soluble extracellular domain of ActRIIB (R64) with the C-terminal 15 amino acids deleted (SEQ ID NO: 30) fused to an Fc domain | SGRGEAETRECIYYNANWELERTNQSGLERCEGEQDKRLHCYASWRNSSG<br>TIELVKKGCWLDDFNCYDRQECVATEENPQVYFCCCEGNFCNERFTHLPE<br>AGGGTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKE<br>YKCKVSNKALPVPIEKTISKAKGQPREPQVYTLPPSREEMTKNQVSLTCL<br>VKGFYPSDIAVEWESNGQPENNYKTTPPVLDSDGSFFLYSKLTVDKSRWQ<br>QGNVFSCSVMHEALHNHYTQKSLSLSPGK |
| 48 | full-length, unprocessed precursor protein GDF11, i.e., GDF11 preproprotein | MVLAAPLLLGFLLLALELRPRGEAAEGPAAAAAAAAAAAAAGVGGERSSRPAP<br>SVAPEPDGCPVCVWRQHSRELRLESIKSQILSKLRLKEAPNISREVVKQLLPK<br>APPLQQILDLHDFQGDALQPEDFLEEDEYHATTETVISMAQETDPAVQTDGSP<br>LCCHFHFSPKVMFTKVLKAQLWVYLRPVPRPATVYLQILRLKPLTGEGTAGGG<br>GGGRRHIRIRSLKIELHSRSGHWQSIDFKQVLHSWFRQPQSNWGIEINAFDPS<br>GTDLAVTSLGPGAEGLHPFMELRVLENTKRSRRNLGLDCDEHSSESRCCRYPL<br>TVDFEAFGWDWIIAPKRYKANYCSGQCEYMFMQKYPHTHLVQQANPRGSAGPC<br>CTPTKMSPINMLYFNDKQQIIYGKIPGMVVDRCGCS |
| 49 | Nucleic acid sequence encoding SEQ ID NO: 48 | ATGGTGCTCGCGGCCCCGCTGCTGCTGGGCTTCCTGCTCCTCGCCCTG<br>GAGCTGCGGCCCCGGGGGAGGCGGCCGAGGGCCCCGCGGCGGCGGCG<br>GCGGCGGCGGCGGCGGCAGCGGCGGGGGTCGGGGGGGAGCGCTCC<br>AGCCGGCCAGCCCCGTCCGTGGCGCCCGAGCCGGACGGCTGCCCCGTG<br>TGCGTTTGGCGGCAGCACAGCCGCGAGCTGCGCCTAGAGAGCATCAAG<br>TCGCAGATCTTGAGCAAACTGCGGCTCAAGGAGGCGCCCAACATCAGC<br>CGCGAGGTGGTGAAGCAGCTGCTGCCCAAGGCGCCGCCGCTGCAGCAG<br>ATCCTGGACCTACACGACTTCCAGGGCGACGCGCTGCAGCCCGAGGAC<br>TTCCTGGAGGAGGACGAGTACCACGCCACCACCGAGACCGTCATTAGC<br>ATGGCCCAGGAGACGGACCCAGCAGTACAGACAGATGGCAGCCCTCTC<br>TGCTGCCATTTTCACTTCAGCCCCAAGGTGATGTTCACAAAGGTACTG<br>AAGGCCCAGCTGTGGGTGTACCTACGGCCTGTACCCCGCCCAGCCACA<br>GTCTACCTGCAGATCTTGCGACTAAAACCCCTAACTGGGGAAGGGACC<br>GCAGGGGAGGGGCGGAGGCCGGCGTCACATCCGTATCCGCTCACTG<br>AAGATTGAGCTGCACTCACGCTCAGGCCATTGGCAGAGCATCGACTTC<br>AAGCAAGTGCTACACAGCTGGTTCCGCCAGCCACAGAGCAACTGGGGC<br>ATCGAGATCAACGCCTTTGATCCCAGTGGCACAGACCTGGCTGTCACC<br>TCCCTGGGGCCGGGAGCCGAGGGGCTGCATCCATTCATGGAGCTTCGA<br>GTCCTAGAGAACACAAAACGTTCCCGGCGGAACCTGGGTCTGGACTGC<br>GACGAGCACTCAAGCGAGTCCCGCTGCTGCCGATATCCCCTCACAGTG<br>GACTTTGAGGCTTTCGGCTGGGACTGGATCATCGCACCTAAGCGCTAC<br>AAGGCCAACTACTGCTCCGGCCAGTGCGAGTACATGTTCATGCAAAAA<br>TATCCGCATACCCATTTGGTGCAGCAGGCCAATCCAAGAGGCTCTGCT<br>GGGCCCTGTTGTACCCCCACCAAGATGTCCCCAATCAACATGCTCTAC<br>TTCAATGACAAGCAGCAGATTATCTACGGCAAGATCCCTGGCATGGTG<br>GTGGATCGCTGTGGCTGCTCT |
| 50 | GDF11 propeptide of human GDF11 protein | AEGPAAAAAAAAAAAAAGVGGERSSRPAPSVAPEPDGCPVCVWRQHSR<br>ELRLESIKSQILSKLRLKEAPNISREVVKQLLPKAPPLQQILDLHDFQ<br>GDALQPEDFLEEDEYHATTETVISMAQETDPAVQTDGSPLCCHFHFSP<br>KVMFTKVLKAQLWVYLRPVPRPATVYLQILRLKPLTGEGTAGGGGGGR<br>RHIRIRSLKIELHSRSGHWQSIDFKQVLHSWFRQPQSNWGIEINAFDP<br>SGTDLAVTSLGPGAEGLHPFMELRVLENTKRSRR |
| 51 | Nucleic acid sequence encoding SEQ ID NO: 50 | GCCGAGGGCCCCGCGGCGGCGGCGGCGGCGGCGGCGGCGGCAGCG<br>GCGGGGGTCGGGGGGAGCGCTCCAGCCGGCCAGCCCCGTCCGTGGCG<br>CCCGAGCCGGACGGCTGCCCCGTGTGCGTTTGGCGGCAGCACAGCCGC<br>GAGCTGCGCCTAGAGAGCATCAAGTCGCAGATCTTGAGCAAACTGCGG<br>CTCAAGGAGGCGCCCAACATCAGCCGCGAGGTGGTGAAGCAGCTGCTG |

TABLE 6-continued

Sequence Information

| SEQ ID NO: | Description | Sequence |
|---|---|---|
| | | CCCAAGGCGCCGCCGCTGCAGCAGATCCTGGACCTACACGACTTCCAG<br>GGCGACGCGCTGCAGCCCGAGGACTTCCTGGAGGAGGACGAGTACCAC<br>GCCACCACCGAGACCGTCATTAGCATGGCCCAGGAGACGGACCCAGCA<br>GTACAGACAGATGGCAGCCCTCTCTGCTGCCATTTTCACTTCAGCCCC<br>AAGGTGATGTTCACAAAGGTACTGAAGGCCCAGCTGTGGGTGTACCTA<br>CGGCCTGTACCCCGCCCAGCCACAGTCTACCTGCAGATCTTGCGACTA<br>AAACCCCTAACTGGGGAAGGGACCGCAGGGGGAGGGGGCGGAGGCCGG<br>CGTCACATCCGTATCCGCTCACTGAAGATTGAGCTGCACTCACGCTCA<br>GGCCATTGGCAGAGCATCGACTTCAAGCAAGTGCTACACAGCTGGTTC<br>CGCCAGCCACAGAGCAACTGGGGCATCGAGATCAACGCCTTTGATCCC<br>AGTGGCACAGACCTGGCTGTCACCTCCCTGGGGCCGGGAGCCGAGGGG<br>CTGCATCCATTCATGGAGCTTCGAGTCCTAGAGAACACAAAACGTTCC<br>CGGCGG |
| 52 | Mature human GDF11 protein | NLGLDCDEHSSESRCCRYPLTVDFEAFGWDWIIAPKRYKANYCSGQCE<br>YMFMQKYPHTHLVQQANPRGSAGPCCTPTKMSPINMLYFNDKQQIIYG<br>KIPGMVVDRCGCS |
| 53 | Nucleic acid sequence encoding SEQ ID NO: 52 | AACCTGGGTCTGGACTGCGACGAGCACTCAAGCGAGTCCCGCTGCTGC<br>CGATATCCCCTCACAGTGGACTTTGAGGCTTTCGGCTGGGACTGGATC<br>ATCGCACCTAAGCGCTACAAGGCCAACTACTGCTCCGGCCAGTGCGAG<br>TACATGTTCATGCAAAAATATCCGCATACCCATTTGGTGCAGCAGGCC<br>AATCCAAGAGGCTCTGCTGGGCCCTGTTGTACCCCCACCAAGATGTCC<br>CCAATCAACATGCTCTACTTCAATGACAAGCAGCAGATTATCTACGGC<br>AAGATCCCTGGCATGGTGGTGGATCGCTGTGGCTGCTCT |
| 54 | Extracellular domain of murine ActRIIA fused to a murine Fc domain ("mActRIIA-Fc") | Murine counterpart of SEQ ID NO: 7. Comprises murine IgG2a fused to the extracellular domain of AcrRIIA. |

EQUIVALENTS

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference in their entireties.

SEQUENCE LISTING

```
<160> NUMBER OF SEQ ID NOS: 53

<210> SEQ ID NO 1
<211> LENGTH: 513
<212> TYPE: PRT
<213> ORGANISM: Homo sapiens
<220> FEATURE:
<223> OTHER INFORMATION: human ActRIIA precursor polypeptide

<400> SEQUENCE: 1

Met Gly Ala Ala Ala Lys Leu Ala Phe Ala Val Phe Leu Ile Ser Cys
 1               5                  10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60
```

-continued

```
Lys Asn Ile Ser Gly Ser Ile Glu Ile Val Lys Gln Gly Cys Trp Leu
 65                  70                  75                  80

Asp Asp Ile Asn Cys Tyr Asp Arg Thr Asp Cys Val Glu Lys Lys Asp
                 85                  90                  95

Ser Pro Glu Val Tyr Phe Cys Cys Glu Gly Asn Met Cys Asn Glu
            100                 105                 110

Lys Phe Ser Tyr Phe Pro Glu Met Glu Val Thr Gln Pro Thr Ser Asn
            115                 120                 125

Pro Val Thr Pro Lys Pro Pro Tyr Tyr Asn Ile Leu Leu Tyr Ser Leu
            130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
            195                 200                 205

Ala Gln Leu Leu Asn Glu Tyr Val Ala Val Lys Ile Phe Pro Ile Gln
210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
            275                 280                 285

Leu Cys His Ile Ala Glu Thr Met Ala Arg Gly Leu Ala Tyr Leu His
            290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
            355                 360                 365

Glu Val Leu Glu Gly Ala Ile Asn Phe Gln Arg Asp Ala Phe Leu Arg
            370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
            420                 425                 430

Val His Lys Lys Lys Arg Pro Val Leu Arg Asp Tyr Trp Gln Lys His
            435                 440                 445

Ala Gly Met Ala Met Leu Cys Glu Thr Ile Glu Glu Cys Trp Asp His
            450                 455                 460

Asp Ala Glu Ala Arg Leu Ser Ala Gly Cys Val Gly Glu Arg Ile Thr
465                 470                 475                 480
```

```
Gln Met Gln Arg Leu Thr Asn Ile Ile Thr Thr Glu Asp Ile Val Thr
                485                 490                 495
Val Val Thr Met Val Thr Asn Val Asp Phe Pro Pro Lys Glu Ser Ser
            500                 505                 510
Leu
```

<210> SEQ ID NO 2
<211> LENGTH: 115
<212> TYPE: PRT
<213> ORGANISM: Homo sapiens
<220> FEATURE:
<223> OTHER INFORMATION: human ActRIIA soluble (extracellular),
      processed polypeptide

<400> SEQUENCE: 2

```
Ile Leu Gly Arg Ser Glu Thr Gln Glu Cys Leu Phe Phe Asn Ala Asn
 1               5                  10                  15
Trp Glu Lys Asp Arg Thr Asn Gln Thr Gly Val Glu Pro Cys Tyr Gly
            20                  25                  30
Asp Lys Asp Lys Arg Arg His Cys Phe Ala Thr Trp Lys Asn Ile Ser
        35                  40                  45
Gly Ser Ile Glu Ile Val Lys Gln Gly Cys Trp Leu Asp Asp Ile Asn
    50                  55                  60
Cys Tyr Asp Arg Thr Asp Cys Val Glu Lys Lys Asp Ser Pro Glu Val
65                  70                  75                  80
Tyr Phe Cys Cys Cys Glu Gly Asn Met Cys Asn Glu Lys Phe Ser Tyr
                85                  90                  95
Phe Pro Glu Met Glu Val Thr Gln Pro Thr Ser Asn Pro Val Thr Pro
            100                 105                 110
Lys Pro Pro
        115
```

<210> SEQ ID NO 3
<211> LENGTH: 100
<212> TYPE: PRT
<213> ORGANISM: Artificial Sequence
<220> FEATURE:
<223> OTHER INFORMATION: human ActRIIA soluble (extracellular),
      processed polypeptide with the C-terminal 15 amino acids deleted

<400> SEQUENCE: 3

```
Ile Leu Gly Arg Ser Glu Thr Gln Glu Cys Leu Phe Phe Asn Ala Asn
 1               5                  10                  15
Trp Glu Lys Asp Arg Thr Asn Gln Thr Gly Val Glu Pro Cys Tyr Gly
            20                  25                  30
Asp Lys Asp Lys Arg Arg His Cys Phe Ala Thr Trp Lys Asn Ile Ser
        35                  40                  45
Gly Ser Ile Glu Ile Val Lys Gln Gly Cys Trp Leu Asp Asp Ile Asn
    50                  55                  60
Cys Tyr Asp Arg Thr Asp Cys Val Glu Lys Lys Asp Ser Pro Glu Val
65                  70                  75                  80
Tyr Phe Cys Cys Cys Glu Gly Asn Met Cys Asn Glu Lys Phe Ser Tyr
                85                  90                  95
Phe Pro Glu Met
            100
```

<210> SEQ ID NO 4
<211> LENGTH: 1542
<212> TYPE: DNA

<213> ORGANISM: Homo sapiens
<220> FEATURE:
<223> OTHER INFORMATION: human ActRIIA precursor

<400> SEQUENCE: 4

```
atgggagctg ctgcaaagtt ggcgtttgcc gtctttctta tctcctgttc ttcaggtgct    60
atacttggta gatcagaaac tcaggagtgt cttttcttta atgctaattg ggaaaaagac   120
agaaccaatc aaactggtgt tgaaccgtgt tatggtgaca agataaacg gcggcattgt    180
tttgctacct ggaagaatat ttctggttcc attgaaatag tgaaacaagg ttgttggctg   240
gatgatatca actgctatga caggactgat tgtgtagaaa aaaagacag ccctgaagta    300
tattttgtt gctgtgaggg caatatgtgt aatgaaaagt tttcttattt tccagagatg    360
gaagtcacac agcccacttc aaatccagtt acacctaagc caccctatta caacatcctg   420
ctctattcct tggtgccact tatgttaatt gcggggattg tcatttgtgc attttgggtg   480
tacaggcatc acaagatggc ctaccctcct gtacttgttc aactcaaga cccaggacca    540
cccccaccct tctccattact agggttgaaa ccactgcagt tattagaagt gaaagcaagg   600
ggaagatttg ttgtgtctg aaagcccag ttgcttaacg aatatgtggc tgtcaaaata    660
tttccaatac aggacaaaca gtcatggcaa atgaatacg aagtctacag tttgcctgga    720
atgaagcatg agaacatatt acagttcatt ggtgcagaaa acgaggcac cagtgttgat    780
gtggatcttt ggctgatcac agcatttcat gaaaagggtt cactatcaga ctttcttaag   840
gctaatgtgg tctcttggaa tgaactgtgt catattgcag aaaccatggc tagaggattg   900
gcatatttac atgaggatat acctggccta aagatggcc acaaacctgc catatctcac   960
agggacatca aaagtaaaaa tgtgctgttg aaaaacaacc tgacagcttg cattgctgac  1020
tttgggttgg ccttaaaatt tgaggctggc aagtctgcag cgatacccca tggacaggtt  1080
ggtacccgga ggtacatggc tccagaggta ttagagggtg ctataaactt cgaaagggat  1140
gcattttga ggatagatat gtatgccatg ggattagtcc tatgggaact ggcttctcgc  1200
tgtactgctg cagatggacc tgtagatgaa tacatgttgc catttgagga ggaaattggc  1260
cagcatccat ctcttgaaga catgcaggaa gttgttgtgc ataaaaaaaa gaggcctgtt  1320
ttaagagatt attggcagaa acatgctgga atggcaatgc tctgtgaaac cattgaagaa  1380
tgttgggatc acgacgcaga agccaggtta tcagctggat gtgtaggtga agaattacc   1440
cagatgcaga gactaacaaa tattattacc acagaggaca ttgtaacagt ggtcacaatg  1500
gtgacaaatg ttgactttcc tcccaaagaa tctagtctat ga                    1542
```

<210> SEQ ID NO 5
<211> LENGTH: 345
<212> TYPE: DNA
<213> ORGANISM: Homo sapiens
<220> FEATURE:
<223> OTHER INFORMATION: human ActRIIA soluble (extracellular)
      polypeptide

<400> SEQUENCE: 5

```
atacttggta gatcagaaac tcaggagtgt cttttcttta atgctaattg ggaaaaagac    60
agaaccaatc aaactggtgt tgaaccgtgt tatggtgaca agataaacg gcggcattgt   120
tttgctacct ggaagaatat ttctggttcc attgaaatag tgaaacaagg ttgttggctg   180
gatgatatca actgctatga caggactgat tgtgtagaaa aaaagacag ccctgaagta    240
tattttgtt gctgtgaggg caatatgtgt aatgaaaagt tttcttattt tccagagatg    300
```
gaagtcacac agcccacttc aaatccagtt acacctaagc caccc                345

<210> SEQ ID NO 6
<211> LENGTH: 225
<212> TYPE: PRT
<213> ORGANISM: Artificial Sequence
<220> FEATURE:
<223> OTHER INFORMATION: Synthetic construct - fusion protein comprising
      a soluble extracellular domain of ActRIIA fused to an Fc domain
<220> FEATURE:
<221> NAME/KEY: MOD_RES
<222> LOCATION: (43)..(43)
<223> OTHER INFORMATION: Asp or Ala
<220> FEATURE:
<221> NAME/KEY: MOD_RES
<222> LOCATION: (100)..(100)
<223> OTHER INFORMATION: Lys or Ala
<220> FEATURE:
<221> NAME/KEY: MOD_RES
<222> LOCATION: (212)..(212)
<223> OTHER INFORMATION: Asn or Ala

<400> SEQUENCE: 6

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Xaa Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Xaa Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Xaa His Tyr Thr Gln Lys Ser Leu Ser Leu Ser Pro Gly
    210                 215                 220

Lys
225

<210> SEQ ID NO 7
<211> LENGTH: 344
<212> TYPE: PRT
<213> ORGANISM: Artificial Sequence
<220> FEATURE:
<223> OTHER INFORMATION: Synthetic construct - Extracellular domain of
      human ActRIIA fused to a human Fc domain

<400> SEQUENCE: 7

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr Gly Gly Thr His Thr Cys Pro Pro Cys Pro Ala
            115                 120                 125

Pro Glu Leu Leu Gly Gly Pro Ser Val Phe Leu Phe Pro Pro Lys Pro
        130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 8
<211> LENGTH: 21
<212> TYPE: PRT
<213> ORGANISM: Apis mellifera
<220> FEATURE:
<223> OTHER INFORMATION: Leader sequence of Honey bee mellitin

<400> SEQUENCE: 8

Met Lys Phe Leu Val Asn Val Ala Leu Val Phe Met Val Val Tyr Ile

```
                1               5                    10                   15

Ser Tyr Ile Tyr Ala
                20

<210> SEQ ID NO 9
<211> LENGTH: 22
<212> TYPE: PRT
<213> ORGANISM: Unknown
<220> FEATURE:
<223> OTHER INFORMATION: Leader sequence of Tissue Plasminogen Activator
      (TPA)

<400> SEQUENCE: 9

Met Asp Ala Met Lys Arg Gly Leu Cys Cys Val Leu Leu Leu Cys Gly
1               5                   10                  15

Ala Val Phe Val Ser Pro
                20

<210> SEQ ID NO 10
<211> LENGTH: 20
<212> TYPE: PRT
<213> ORGANISM: Unknown
<220> FEATURE:
<223> OTHER INFORMATION: Native ActRIIA leader

<400> SEQUENCE: 10

Met Gly Ala Ala Ala Lys Leu Ala Phe Ala Val Phe Leu Ile Ser Cys
1               5                   10                  15

Ser Ser Gly Ala
            20

<210> SEQ ID NO 11
<211> LENGTH: 9
<212> TYPE: PRT
<213> ORGANISM: Artificial Sequence
<220> FEATURE:
<223> OTHER INFORMATION: Synthetic construct - ActRIIA-hFc and
      ActRIIA-mFc N-terminal sequence

<400> SEQUENCE: 11

Ile Leu Gly Arg Ser Glu Thr Gln Glu
1               5

<210> SEQ ID NO 12
<211> LENGTH: 329
<212> TYPE: PRT
<213> ORGANISM: Artificial Sequence
<220> FEATURE:
<223> OTHER INFORMATION: Synthetic construct - ActRIIA-Fc Protein with
      deletion of the C-terminal 15 amino acids of the extracellular
      domain of ActRIIA

<400> SEQUENCE: 12

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Val Glu Lys Lys Asp Ser Pro Glu Val
65                  70                  75                  80
```

```
Tyr Phe Cys Cys Cys Glu Gly Asn Met Cys Asn Glu Lys Phe Ser Tyr
                85                  90                  95

Phe Pro Glu Met Thr Gly Gly Thr His Thr Cys Pro Pro Cys Pro
            100                 105                 110

Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
            165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
            195                 200                 205

Ala Leu Pro Val Pro Ile Glu Lys Thr Ile Ser Lys Ala Lys Gly Gln
            210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 13
<211> LENGTH: 369
<212> TYPE: PRT
<213> ORGANISM: Artificial Sequence
<220> FEATURE:
<223> OTHER INFORMATION: Synthetic construct - Unprocessed ActRIIA-hFc
      with TPA leader sequence

<400> SEQUENCE: 13

Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
            35                  40                  45

Gln Thr Gly Val Glu Pro Cys Tyr Gly Asp Lys Asp Lys Arg Arg His
        50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
                85                  90                  95

Val Glu Lys Lys Asp Ser Pro Glu Val Tyr Phe Cys Cys Cys Glu Gly
            100                 105                 110
```

Asn Met Cys Asn Glu Lys Phe Ser Tyr Phe Pro Glu Met Glu Val Thr
            115                 120                 125
Gln Pro Thr Ser Asn Pro Val Thr Pro Lys Pro Pro Thr Gly Gly Gly
        130                 135                 140
Thr His Thr Cys Pro Pro Cys Pro Ala Pro Glu Leu Leu Gly Gly Pro
145                 150                 155                 160
Ser Val Phe Leu Phe Pro Pro Lys Pro Lys Asp Thr Leu Met Ile Ser
                165                 170                 175
Arg Thr Pro Glu Val Thr Cys Val Val Val Asp Val Ser His Glu Asp
            180                 185                 190
Pro Glu Val Lys Phe Asn Trp Tyr Val Asp Gly Val Glu Val His Asn
        195                 200                 205
Ala Lys Thr Lys Pro Arg Glu Glu Gln Tyr Asn Ser Thr Tyr Arg Val
    210                 215                 220
Val Ser Val Leu Thr Val Leu His Gln Asp Trp Leu Asn Gly Lys Glu
225                 230                 235                 240
Tyr Lys Cys Lys Val Ser Asn Lys Ala Leu Pro Val Pro Ile Glu Lys
                245                 250                 255
Thr Ile Ser Lys Ala Lys Gly Gln Pro Arg Glu Pro Gln Val Tyr Thr
            260                 265                 270
Leu Pro Pro Ser Arg Glu Glu Met Thr Lys Asn Gln Val Ser Leu Thr
        275                 280                 285
Cys Leu Val Lys Gly Phe Tyr Pro Ser Asp Ile Ala Val Glu Trp Glu
    290                 295                 300
Ser Asn Gly Gln Pro Glu Asn Asn Tyr Lys Thr Thr Pro Pro Val Leu
305                 310                 315                 320
Asp Ser Asp Gly Ser Phe Phe Leu Tyr Ser Lys Leu Thr Val Asp Lys
                325                 330                 335
Ser Arg Trp Gln Gln Gly Asn Val Phe Ser Cys Ser Val Met His Glu
            340                 345                 350
Ala Leu His Asn His Tyr Thr Gln Lys Ser Leu Ser Leu Ser Pro Gly
        355                 360                 365
Lys

<210> SEQ ID NO 14
<211> LENGTH: 1114
<212> TYPE: DNA
<213> ORGANISM: Artificial Sequence
<220> FEATURE:
<223> OTHER INFORMATION: Synthetic construct - Unprocessed ActRIIA-hFc
      with TPA leader sequence

<400> SEQUENCE: 14
atggatgcaa tgaagagagg ctctgctgt gtgctgctgc tgtgtggagc agtcttcgtt      60
tcgcccggcg ccgctatact tggtagatca gaaactcagg agtgtctttt tttaatgcta    120
attgggaaaa agacagaacc aatcaaactg gtgttgaacc gtgttatggt gacaaagata    180
aacggcggca ttgttttgct acctggaaga atatttctgg ttccattgaa tagtgaaaca    240
aggttgttgg ctggatgata tcaactgcta tgacaggact gattgtgtag aaaaaaaaga    300
cagccctgaa gtatatttct gttgctgtga gggcaatatg tgtaatgaaa gttttctta    360 ttttccggag atggaagtca cacagcccac ttcaaatcca gttacaccta agccacccac    420
cggtggtgga actcacacat gcccaccgtg cccagcacct gaactcctgg ggggaccgtc    480
agtcttcctc ttccccccaa aacccaagga caccctcatg atctcccgga cccctgaggt    540

```
cacatgcgtg gtggtggacg tgagccacga agaccctgag gtcaagttca actggtacgt    600
ggacggcgtg gaggtgcata atgccaagac aaagccgcgg gaggagcagt acaacagcac    660
gtaccgtgtg gtcagcgtcc tcaccgtcct gcaccaggac tggctgaatg caaggagta    720 caagtgcaag gtctccaaca aagccctccc agtccccatc gagaaaacca tctccaaagc    780
caaagggcag ccccgagaac acaggtgta caccctgccc ccatcccggg aggagatgac    840
caagaaccag gtcagcctga cctgcctggt caaaggcttc tatcccagcg acatcgccgt    900
ggagtgggag agcaatgggc agccggagaa caactacaag accacgcctc ccgtgctgga    960
ctccgacggc tccttcttcc tctatagcaa gctcaccgtg gacaagagca ggtggcagca   1020
ggggaacgtc ttctcatgct ccgtgatgca tgaggctctg cacaaccact acacgcagaa   1080
gagcctctcc ctgtctccgg gtaaatgaga attc                               1114
```

<210> SEQ ID NO 15
<211> LENGTH: 106
<212> TYPE: PRT
<213> ORGANISM: Artificial Sequence
<220> FEATURE:
<223> OTHER INFORMATION: Synthetic construct - human ActRIIB soluble
      (extracellular), processed polypeptide sequence with the
      N-terminal 6 amino acid of the EC domain deleted and the
      C-terminal 4 amino acids of the EC domain deleted

<400> SEQUENCE: 15

```
Glu Thr Arg Glu Cys Ile Tyr Tyr Asn Ala Asn Trp Glu Leu Glu Arg
 1               5                  10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro
            100                 105
```

<210> SEQ ID NO 16
<211> LENGTH: 512
<212> TYPE: PRT
<213> ORGANISM: Homo sapiens
<220> FEATURE:
<223> OTHER INFORMATION: human ActRIIB precursor protein

<400> SEQUENCE: 16

```
Met Thr Ala Pro Trp Val Ala Leu Ala Leu Leu Trp Gly Ser Leu Trp
 1               5                  10                  15

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Ala
    50                  55                  60

Asn Ser Ser Gly Thr Ile Glu Leu Val Lys Lys Gly Cys Trp Leu Asp
65                  70                  75                  80
```

```
Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
            115                 120                 125

Pro Pro Thr Ala Pro Thr Leu Leu Thr Val Leu Ala Tyr Ser Leu Leu
130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
            195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
            275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
            355                 360                 365

Val Leu Glu Gly Ala Ile Asn Phe Gln Arg Asp Ala Phe Leu Arg Ile
370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
            435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495
```

```
Val Thr Ser Val Thr Asn Val Asp Leu Pro Pro Lys Glu Ser Ser Ile
            500                 505                 510
```

```
<210> SEQ ID NO 17
<211> LENGTH: 116
<212> TYPE: PRT
<213> ORGANISM: Homo sapiens
<220> FEATURE:
<223> OTHER INFORMATION: human ActRIIB soluble (extracellular),
      processed polypeptide

<400> SEQUENCE: 17

Ser Gly Arg Gly Glu Ala Glu Thr Arg Glu Cys Ile Tyr Tyr Asn Ala
  1               5                  10                  15

Asn Trp Glu Leu Glu Arg Thr Asn Gln Ser Gly Leu Glu Arg Cys Glu
             20                  25                  30

Gly Glu Gln Asp Lys Arg Leu His Cys Tyr Ala Ser Trp Ala Asn Ser
         35                  40                  45

Ser Gly Thr Ile Glu Leu Val Lys Lys Gly Cys Trp Leu Asp Asp Phe
     50                  55                  60

Asn Cys Tyr Asp Arg Gln Glu Cys Val Ala Thr Glu Glu Asn Pro Gln
 65                  70                  75                  80

Val Tyr Phe Cys Cys Cys Glu Gly Asn Phe Cys Asn Glu Arg Phe Thr
                 85                  90                  95

His Leu Pro Glu Ala Gly Gly Pro Glu Val Thr Tyr Glu Pro Pro Pro
            100                 105                 110

Thr Ala Pro Thr
        115
```

```
<210> SEQ ID NO 18
<211> LENGTH: 101
<212> TYPE: PRT
<213> ORGANISM: Artificial Sequence
<220> FEATURE:
<223> OTHER INFORMATION: human ActRIIB soluble (extracellular),
      processed polypeptide sequence with the C-terminal 15 amino acids
      deleted

<400> SEQUENCE: 18

Ser Gly Arg Gly Glu Ala Glu Thr Arg Glu Cys Ile Tyr Tyr Asn Ala
  1               5                  10                  15

Asn Trp Glu Leu Glu Arg Thr Asn Gln Ser Gly Leu Glu Arg Cys Glu
             20                  25                  30

Gly Glu Gln Asp Lys Arg Leu His Cys Tyr Ala Ser Trp Ala Asn Ser
         35                  40                  45

Ser Gly Thr Ile Glu Leu Val Lys Lys Gly Cys Trp Leu Asp Asp Phe
     50                  55                  60

Asn Cys Tyr Asp Arg Gln Glu Cys Val Ala Thr Glu Glu Asn Pro Gln
 65                  70                  75                  80

Val Tyr Phe Cys Cys Cys Glu Gly Asn Phe Cys Asn Glu Arg Phe Thr
                 85                  90                  95

His Leu Pro Glu Ala
            100
```

```
<210> SEQ ID NO 19
<211> LENGTH: 1539
<212> TYPE: DNA
<213> ORGANISM: Homo sapiens
<220> FEATURE:
<223> OTHER INFORMATION: human ActRIIB (A64) precursor
```

<400> SEQUENCE: 19

```
atgacggcgc cctgggtggc cctcgccctc ctctggggat cgctgtggcc cggctctggg      60
cgtggggagg ctgagacacg ggagtgcatc tactacaacg ccaactggga gctggagcgc     120
accaaccaga gcggcctgga gcgctgcgaa ggcgagcagg acaagcggct gcactgctac     180
gcctcctggg ccaacagctc tggcaccatc gagctcgtga agaagggctg ctggctagat     240
gacttcaact gctacgatag gcaggagtgt gtggccactg aggagaaccc ccaggtgtac     300
ttctgctgct gtgaaggcaa cttctgcaac gagcgcttca ctcatttgcc agaggctggg     360
ggcccggaag tcacgtacga gccaccccg acagccccca ccctgctcac ggtgctggcc     420
tactcactgc tgcccatcgg gggccttttcc ctcatcgtcc tgctggcctt ttggatgtac     480
cggcatcgca agccccccta cggtcatgtg acatccatg aggaccctgg gcctccacca     540
ccatcccctc tggtgggcct gaagccactg cagctgctgg agatcaaggc tcggggcgc      600
tttggctgtg tctggaaggc ccagctcatg aatgactttg tagctgtcaa gatcttccca     660
ctccaggaca agcagtcgtg gcagagtgaa cgggagatct tcagcacacc tggcatgaag     720
cacgagaacc tgctacagtt cattgctgcc gagaagcgag gctccaacct cgaagtagag     780
ctgtggctca tcacggcctt ccatgacaag ggctccctca cggattacct caaggggaac     840
atcatcacat ggaacgaact gtgtcatgta gcagagacga tgtcacgagg cctctcatac     900
ctgcatgagg atgtgccctg gtgccgtggc gagggccaca gccgtctat gcccacagg      960
gactttaaaa gtaagaatgt attgctgaag agcgacctca cagccgtgct ggctgacttt    1020
ggcttggctg ttcgatttga gccagggaaa cctccagggg acacccacgg acaggtaggc    1080
acgagacggt acatggctcc tgaggtgctc gagggagcca tcaacttcca gagagatgcc    1140
ttcctgcgca ttgacatgta tgccatgggg ttggtgctgt gggagcttgt gtctcgctgc    1200
aaggctgcag acggacccgt ggatgagtac atgctgccct ttgaggaaga gattggccag    1260
caccttcgt tggaggagct gcaggaggtg gtggtgcaca gaagatgag gcccaccatt    1320
aaagatcact ggttgaaaca cccgggcctg gcccagcttt gtgtgaccat cgaggagtgc    1380
tgggaccatg atgcagaggc tcgcttgtcc gcgggctgtg tggaggagcg ggtgtccctg    1440
attcggaggt cggtcaacgg cactacctcg gactgtctcg tttccctggt gacctctgtc    1500
accaatgtgg acctgcccc taaagagtca agcatctaa                           1539
```

<210> SEQ ID NO 20
<211> LENGTH: 344
<212> TYPE: PRT
<213> ORGANISM: Artificial Sequence
<220> FEATURE:
<223> OTHER INFORMATION: Synthetic construct - fusion protein comprising
      a soluble extracellular domain of ActRIIB fused to an Fc domain

<400> SEQUENCE: 20

```
Ser Gly Arg Gly Glu Ala Glu Thr Arg Glu Cys Ile Tyr Tyr Asn Ala
  1               5                  10                  15
Asn Trp Glu Leu Glu Arg Thr Asn Gln Ser Gly Leu Glu Arg Cys Glu
             20                  25                  30
Gly Glu Gln Asp Lys Arg Leu His Cys Tyr Ala Ser Trp Ala Asn Ser
         35                  40                  45
Ser Gly Thr Ile Glu Leu Val Lys Lys Gly Cys Trp Leu Asp Asp Phe
     50                  55                  60
Asn Cys Tyr Asp Arg Gln Glu Cys Val Ala Thr Glu Glu Asn Pro Gln
 65                  70                  75                  80
```

```
Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 21
<211> LENGTH: 329
<212> TYPE: PRT
<213> ORGANISM: Artificial Sequence
<220> FEATURE:
<223> OTHER INFORMATION: Synthetic construct - fusion protein comprising
      a soluble extracellular domain of ActRIIB (A64) with the
      C-terminal 15 amino acids deleted fused to an Fc domain

<400> SEQUENCE: 21

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Ala Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80
```

```
Val Tyr Phe Cys Cys Cys Glu Gly Asn Phe Cys Asn Glu Arg Phe Thr
                85                  90                  95

His Leu Pro Glu Ala Gly Gly Thr His Thr Cys Pro Pro Cys Pro
            100                 105                 110

Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
            195                 200                 205

Ala Leu Pro Val Pro Ile Glu Lys Thr Ile Ser Lys Ala Lys Gly Gln
            210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 22
<211> LENGTH: 105
<212> TYPE: PRT
<213> ORGANISM: Artificial Sequence
<220> FEATURE:
<223> OTHER INFORMATION: human ActRIIB soluble (extracellular),
      processed polypeptide with the N-terminal 6 amino acids of the
      EC domain deleted and the C-terminal 5 amino acids of the EC
      domain deleted and with an L79D mutation

<400> SEQUENCE: 22

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
            35                  40                  45

Val Lys Lys Gly Cys Trp Asp Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95
```

Gly Pro Glu Val Thr Tyr Glu Pro Pro
                100             105

<210> SEQ ID NO 23
<211> LENGTH: 107
<212> TYPE: PRT
<213> ORGANISM: Artificial Sequence
<220> FEATURE:
<223> OTHER INFORMATION: human ActRIIB soluble (extracellular),
      processed polypeptide sequence with the N-terminal 6 amino acids
      of the EC domain deleted and the C-terminal 3 amino acids of the
      EC domain deleted and with an L79D mutatioN

<400> SEQUENCE: 23

Glu Thr Arg Glu Cys Ile Tyr Tyr Asn Ala Asn Trp Glu Leu Glu Arg
 1               5                  10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr
                100             105

<210> SEQ ID NO 24
<211> LENGTH: 360
<212> TYPE: PRT
<213> ORGANISM: Artificial Sequence
<220> FEATURE:
<223> OTHER INFORMATION: Unprocessed ActRIIB-Fc fusion protein with the
      N-terminal 6 amino acids of the EC domain deleted and the
      C-terminal 3 amino acids of the EC domain deleted and with an L79D
      mutation and with TPA leader sequence

<400> SEQUENCE: 24

Met Asp Ala Met Lys Arg Gly Leu Cys Cys Val Leu Leu Leu Cys Gly
 1               5                  10                  15

Ala Val Phe Val Ser Pro Gly Ala Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Cys Glu Gly Glu Gln Asp Lys Arg Leu His Cys Tyr Ala Ser Trp
    50                  55                  60

Arg Asn Ser Ser Gly Thr Ile Glu Leu Val Lys Lys Gly Cys Trp Asp
65                  70                  75                  80

Asp Asp Phe Asn Cys Tyr Asp Arg Gln Glu Cys Val Ala Thr Glu Glu
                85                  90                  95

Asn Pro Gln Val Tyr Phe Cys Cys Cys Glu Gly Asn Phe Cys Asn Glu
            100                 105                 110

Arg Phe Thr His Leu Pro Glu Ala Gly Gly Pro Glu Val Thr Tyr Glu
        115                 120                 125

Pro Pro Pro Thr Gly Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

```
Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
                180                 185                 190

Asp Gly Val Glu Val His Asn Ala Lys Thr Lys Pro Arg Glu Glu Gln
                195                 200                 205

Tyr Asn Ser Thr Tyr Arg Val Val Ser Val Leu Thr Val Leu His Gln
                210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
                260                 265                 270

Lys Asn Gln Val Ser Leu Thr Cys Leu Val Lys Gly Phe Tyr Pro Ser
                275                 280                 285

Asp Ile Ala Val Glu Trp Glu Ser Asn Gly Gln Pro Glu Asn Asn Tyr
                290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
                340                 345                 350

Ser Leu Ser Leu Ser Pro Gly Lys
                355                 360

<210> SEQ ID NO 25
<211> LENGTH: 335
<212> TYPE: PRT
<213> ORGANISM: Artificial Sequence
<220> FEATURE:
<223> OTHER INFORMATION: Processed ActRIIB-Fc fusion protein with the
      N-terminal 6 amino acids of the EC domain deleted and the
      C-terminal 3 amino acids of the EC domain deleted and with an
      L79D mutation

<400> SEQUENCE: 25

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
                20                  25                  30

Leu His Cys Tyr Ala Ser Trp Arg Asn Ser Ser Gly Thr Ile Glu Leu
                35                  40                  45

Val Lys Lys Gly Cys Trp Asp Asp Asp Phe Asn Cys Tyr Asp Arg Gln
50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
                100                 105                 110

Thr Cys Pro Pro Cys Pro Ala Pro Glu Leu Leu Gly Gly Pro Ser Val
                115                 120                 125

Phe Leu Phe Pro Pro Lys Pro Lys Asp Thr Leu Met Ile Ser Arg Thr
                130                 135                 140
```

```
Pro Glu Val Thr Cys Val Val Asp Val Ser His Glu Asp Pro Glu
145                 150                 155                 160

Val Lys Phe Asn Trp Tyr Val Asp Gly Val Glu Val His Asn Ala Lys
            165                 170                 175

Thr Lys Pro Arg Glu Glu Gln Tyr Asn Ser Thr Tyr Arg Val Val Ser
        180                 185                 190

Val Leu Thr Val Leu His Gln Asp Trp Leu Asn Gly Lys Glu Tyr Lys
            195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335

<210> SEQ ID NO 26
<211> LENGTH: 115
<212> TYPE: PRT
<213> ORGANISM: Homo sapiens
<220> FEATURE:
<223> OTHER INFORMATION: human ActRIIB soluble (extracellular)
      processed polypeptide

<400> SEQUENCE: 26

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 27
<211> LENGTH: 100
<212> TYPE: PRT
<213> ORGANISM: Artificial Sequence
<220> FEATURE:
<223> OTHER INFORMATION: human ActRIIB soluble (extracellular) processed
``` polypeptide sequence with the C-terminal 15 amino acids deleted

<400> SEQUENCE: 27

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
            100
```

<210> SEQ ID NO 28
<211> LENGTH: 512
<212> TYPE: PRT
<213> ORGANISM: Homo sapiens
<220> FEATURE:
<223> OTHER INFORMATION: human ActRIIB precursor protein

<400> SEQUENCE: 28

```
Met Thr Ala Pro Trp Val Ala Leu Ala Leu Leu Trp Gly Ser Leu Trp
1               5                   10                  15

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240
```

-continued

His Glu Asn Leu Leu Gln Phe Ile Ala Ala Glu Lys Arg Gly Ser Asn
             245                 250                 255

Leu Glu Val Glu Leu Trp Leu Ile Thr Ala Phe His Asp Lys Gly Ser
             260                 265                 270

Leu Thr Asp Tyr Leu Lys Gly Asn Ile Ile Thr Trp Asn Glu Leu Cys
             275                 280                 285

His Val Ala Glu Thr Met Ser Arg Gly Leu Ser Tyr Leu His Glu Asp
             290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
             325                 330                 335

Leu Ala Asp Phe Gly Leu Ala Val Arg Phe Glu Pro Gly Lys Pro Pro
             340                 345                 350

Gly Asp Thr His Gly Gln Val Gly Thr Arg Arg Tyr Met Ala Pro Glu
             355                 360                 365

Val Leu Glu Gly Ala Ile Asn Phe Gln Arg Asp Ala Phe Leu Arg Ile
             370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
             405                 410                 415

Glu Ile Gly Gln His Pro Ser Leu Glu Glu Leu Gln Glu Val Val Val
             420                 425                 430

His Lys Lys Met Arg Pro Thr Ile Lys Asp His Trp Leu Lys His Pro
             435                 440                 445

Gly Leu Ala Gln Leu Cys Val Thr Ile Glu Glu Cys Trp Asp His Asp
450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
             485                 490                 495

Val Thr Ser Val Thr Asn Val Asp Leu Pro Pro Lys Glu Ser Ser Ile
             500                 505                 510

<210> SEQ ID NO 29
<211> LENGTH: 116
<212> TYPE: PRT
<213> ORGANISM: Homo sapiens
<220> FEATURE:
<223> OTHER INFORMATION: human ActRIIB soluble (extracellular) processed
      polypeptide

<400> SEQUENCE: 29

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
             20                  25                  30

Gly Glu Gln Asp Lys Arg Leu His Cys Tyr Ala Ser Trp Arg Asn Ser
         35                  40                  45

Ser Gly Thr Ile Glu Leu Val Lys Lys Gly Cys Trp Leu Asp Asp Phe
     50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr

-continued

```
                 85                  90                  95

His Leu Pro Glu Ala Gly Gly Pro Glu Val Thr Tyr Glu Pro Pro Pro
            100                 105                 110

Thr Ala Pro Thr
        115

<210> SEQ ID NO 30
<211> LENGTH: 101
<212> TYPE: PRT
<213> ORGANISM: Artificial Sequence
<220> FEATURE:
<223> OTHER INFORMATION: human ActRIIB soluble (extracellular),
      processed polypeptide with the C-terminal 15 amino acids deleted

<400> SEQUENCE: 30

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala
            100

<210> SEQ ID NO 31
<211> LENGTH: 115
<212> TYPE: PRT
<213> ORGANISM: Homo sapiens
<220> FEATURE:
<223> OTHER INFORMATION: human ActRIIB soluble (extracellular),
      processed polypeptide

<400> SEQUENCE: 31

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 32
<211> LENGTH: 100
<212> TYPE: PRT
```

<213> ORGANISM: Artificial Sequence
<220> FEATURE:
<223> OTHER INFORMATION: human ActRIIB soluble (extracellular), processed polypeptide with the C-terminal 15 amino acids deleted

<400> SEQUENCE: 32

```
Gly Arg Gly Glu Ala Glu Thr Arg Glu Cys Ile Tyr Tyr Asn Ala Asn
  1               5                  10                  15

Trp Glu Leu Glu Arg Thr Asn Gln Ser Gly Leu Glu Arg Cys Glu Gly
             20                  25                  30

Glu Gln Asp Lys Arg Leu His Cys Tyr Ala Ser Trp Arg Asn Ser Ser
         35                  40                  45

Gly Thr Ile Glu Leu Val Lys Lys Gly Cys Trp Leu Asp Asp Phe Asn
 50                  55                  60

Cys Tyr Asp Arg Gln Glu Cys Val Ala Thr Glu Glu Asn Pro Gln Val
 65                  70                  75                  80

Tyr Phe Cys Cys Cys Glu Gly Asn Phe Cys Asn Glu Arg Phe Thr His
                 85                  90                  95

Leu Pro Glu Ala
            100
```

<210> SEQ ID NO 33
<211> LENGTH: 107
<212> TYPE: PRT
<213> ORGANISM: Artificial Sequence
<220> FEATURE:
<223> OTHER INFORMATION: human ActRIIB soluble (extracellular), processed polypeptide sequence with the N-terminal 6 amino acids of the EC domain deleted and the C-terminal 3 amino acids of the EC domain deleted and with an L79D mutation

<400> SEQUENCE: 33

```
Glu Thr Arg Glu Cys Ile Tyr Tyr Asn Ala Asn Trp Glu Leu Glu Arg
  1               5                  10                  15

Thr Asn Gln Ser Gly Leu Glu Arg Cys Glu Gly Glu Gln Asp Lys Arg
             20                  25                  30

Leu His Cys Tyr Ala Ser Trp Ala Asn Ser Ser Gly Thr Ile Glu Leu
         35                  40                  45

Val Lys Lys Gly Cys Trp Asp Asp Phe Asn Cys Tyr Asp Arg Gln
 50                  55                  60

Glu Cys Val Ala Thr Glu Glu Asn Pro Gln Val Tyr Phe Cys Cys Cys
 65                  70                  75                  80

Glu Gly Asn Phe Cys Asn Glu Arg Phe Thr His Leu Pro Glu Ala Gly
                 85                  90                  95

Gly Pro Glu Val Thr Tyr Glu Pro Pro Pro Thr
            100                 105
```

<210> SEQ ID NO 34
<211> LENGTH: 360
<212> TYPE: PRT
<213> ORGANISM: Artificial Sequence
<220> FEATURE:
<223> OTHER INFORMATION: Unprocessed ActRIIB-Fc fusion protein with the N-terminal 6 amino acids of the EC domain deleted and the C-terminal 3 amino acids of the EC domain deleted and with an L79D mutation and with TPA leader sequence

<400> SEQUENCE: 34

```
Met Asp Ala Met Lys Arg Gly Leu Cys Cys Val Leu Leu Leu Cys Gly
  1               5                  10                  15

Ala Val Phe Val Ser Pro Gly Ala Ala Glu Thr Arg Glu Cys Ile Tyr
```

```
              20                  25                  30
Tyr Asn Ala Asn Trp Glu Leu Glu Arg Thr Asn Gln Ser Gly Leu Glu
            35                  40                  45
Arg Cys Glu Gly Glu Gln Asp Lys Arg Leu His Cys Tyr Ala Ser Trp
        50                  55                  60
Ala Asn Ser Ser Gly Thr Ile Glu Leu Val Lys Lys Gly Cys Trp Asp
 65                  70                  75                  80
Asp Asp Phe Asn Cys Tyr Asp Arg Gln Glu Cys Val Ala Thr Glu Glu
                85                  90                  95
Asn Pro Gln Val Tyr Phe Cys Cys Cys Glu Gly Asn Phe Cys Asn Glu
            100                 105                 110
Arg Phe Thr His Leu Pro Glu Ala Gly Gly Pro Glu Val Thr Tyr Glu
        115                 120                 125
Pro Pro Pro Thr Gly Gly Gly Thr His Thr Cys Pro Pro Cys Pro Ala
    130                 135                 140
Pro Glu Leu Leu Gly Gly Pro Ser Val Phe Leu Phe Pro Pro Lys Pro
145                 150                 155                 160
Lys Asp Thr Leu Met Ile Ser Arg Thr Pro Glu Val Thr Cys Val Val
                165                 170                 175
Val Asp Val Ser His Glu Asp Pro Glu Val Lys Phe Asn Trp Tyr Val
            180                 185                 190
Asp Gly Val Glu Val His Asn Ala Lys Thr Lys Pro Arg Glu Glu Gln
        195                 200                 205
Tyr Asn Ser Thr Tyr Arg Val Val Ser Val Leu Thr Val Leu His Gln
    210                 215                 220
Asp Trp Leu Asn Gly Lys Glu Tyr Lys Cys Lys Val Ser Asn Lys Ala
225                 230                 235                 240
Leu Pro Ala Pro Ile Glu Lys Thr Ile Ser Lys Ala Lys Gly Gln Pro
                245                 250                 255
Arg Glu Pro Gln Val Tyr Thr Leu Pro Pro Ser Arg Glu Glu Met Thr
            260                 265                 270
Lys Asn Gln Val Ser Leu Thr Cys Leu Val Lys Gly Phe Tyr Pro Ser
        275                 280                 285
Asp Ile Ala Val Glu Trp Glu Ser Asn Gly Gln Pro Glu Asn Asn Tyr
    290                 295                 300
Lys Thr Thr Pro Pro Val Leu Asp Ser Asp Gly Ser Phe Phe Leu Tyr
305                 310                 315                 320
Ser Lys Leu Thr Val Asp Lys Ser Arg Trp Gln Gln Gly Asn Val Phe
                325                 330                 335
Ser Cys Ser Val Met His Glu Ala Leu His Asn His Tyr Thr Gln Lys
            340                 345                 350
Ser Leu Ser Leu Ser Pro Gly Lys
        355                 360

<210> SEQ ID NO 35
<211> LENGTH: 335
<212> TYPE: PRT
<213> ORGANISM: Artificial Sequence
<220> FEATURE:
<223> OTHER INFORMATION: Processed ActRIIB-Fc fusion protein with the
      N-terminal 6 amino acids of the EC domain deleted and the
      C-terminal 3 amino acids of the EC domain deleted and with an L79D
      mutation

<400> SEQUENCE: 35

Glu Thr Arg Glu Cys Ile Tyr Tyr Asn Ala Asn Trp Glu Leu Glu Arg
```

```
              1               5              10              15
            Thr Asn Gln Ser Gly Leu Glu Arg Cys Glu Gly Glu Gln Asp Lys Arg
                             20              25              30

Leu His Cys Tyr Ala Ser Trp Ala Asn Ser Ser Gly Thr Ile Glu Leu
                             35              40              45

Val Lys Lys Gly Cys Trp Asp Asp Phe Asn Cys Tyr Asp Arg Gln
             50              55              60

Glu Cys Val Ala Thr Glu Glu Asn Pro Gln Val Tyr Phe Cys Cys Cys
             65              70              75              80

Glu Gly Asn Phe Cys Asn Glu Arg Phe Thr His Leu Pro Glu Ala Gly
                             85              90              95

Gly Pro Glu Val Thr Tyr Glu Pro Pro Pro Thr Gly Gly Thr His
                            100             105             110

Thr Cys Pro Pro Cys Pro Ala Pro Glu Leu Leu Gly Gly Pro Ser Val
                            115             120             125

Phe Leu Phe Pro Pro Lys Pro Lys Asp Thr Leu Met Ile Ser Arg Thr
                            130             135             140

Pro Glu Val Thr Cys Val Val Asp Val Ser His Glu Asp Pro Glu
            145             150             155             160

Val Lys Phe Asn Trp Tyr Val Asp Gly Val Glu Val His Asn Ala Lys
                            165             170             175

Thr Lys Pro Arg Glu Glu Gln Tyr Asn Ser Thr Tyr Arg Val Val Ser
                            180             185             190

Val Leu Thr Val Leu His Gln Asp Trp Leu Asn Gly Lys Glu Tyr Lys
                            195             200             205

Cys Lys Val Ser Asn Lys Ala Leu Pro Ala Pro Ile Glu Lys Thr Ile
                            210             215             220

Ser Lys Ala Lys Gly Gln Pro Arg Glu Pro Gln Val Tyr Thr Leu Pro
            225             230             235             240

Pro Ser Arg Glu Glu Met Thr Lys Asn Gln Val Ser Leu Thr Cys Leu
                            245             250             255

Val Lys Gly Phe Tyr Pro Ser Asp Ile Ala Val Glu Trp Glu Ser Asn
                            260             265             270

Gly Gln Pro Glu Asn Asn Tyr Lys Thr Thr Pro Pro Val Leu Asp Ser
                            275             280             285

Asp Gly Ser Phe Phe Leu Tyr Ser Lys Leu Thr Val Asp Lys Ser Arg
                            290             295             300

Trp Gln Gln Gly Asn Val Phe Ser Cys Ser Val Met His Glu Ala Leu
            305             310             315             320

His Asn His Tyr Thr Gln Lys Ser Leu Ser Leu Ser Pro Gly Lys
                            325             330             335

<210> SEQ ID NO 36
<211> LENGTH: 115
<212> TYPE: PRT
<213> ORGANISM: Artificial Sequence
<220> FEATURE:
<223> OTHER INFORMATION: human ActRIIB soluble (extracellular),
      processed polypeptide sequence with L79D mutation

<400> SEQUENCE: 36

Gly Arg Gly Glu Ala Glu Thr Arg Glu Cys Ile Tyr Tyr Asn Ala Asn
  1               5              10              15

Trp Glu Leu Glu Arg Thr Asn Gln Ser Gly Leu Glu Arg Cys Glu Gly
                 20              25              30
```

```
Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Asp Asp Phe Asn
 50                  55                  60

Cys Tyr Asp Arg Gln Glu Cys Val Ala Thr Glu Glu Asn Pro Gln Val
 65                  70                  75                  80

Tyr Phe Cys Cys Cys Glu Gly Asn Phe Cys Asn Glu Arg Phe Thr His
                 85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 37
<211> LENGTH: 115
<212> TYPE: PRT
<213> ORGANISM: Artificial Sequence
<220> FEATURE:
<223> OTHER INFORMATION: human ActRIIB soluble (extracellular),
      processed polypeptide sequence with L79D mutation

<400> SEQUENCE: 37

Gly Arg Gly Glu Ala Glu Thr Arg Glu Cys Ile Tyr Tyr Asn Ala Asn
  1               5                  10                  15

Trp Glu Leu Glu Arg Thr Asn Gln Ser Gly Leu Glu Arg Cys Glu Gly
             20                  25                  30

Glu Gln Asp Lys Arg Leu His Cys Tyr Ala Ser Trp Ala Asn Ser Ser
            35                  40                  45

Gly Thr Ile Glu Leu Val Lys Lys Gly Cys Trp Asp Asp Phe Asn
 50                  55                  60

Cys Tyr Asp Arg Gln Glu Cys Val Ala Thr Glu Glu Asn Pro Gln Val
 65                  70                  75                  80

Tyr Phe Cys Cys Cys Glu Gly Asn Phe Cys Asn Glu Arg Phe Thr His
                 85                  90                  95

Leu Pro Glu Ala Gly Gly Pro Glu Val Thr Tyr Glu Pro Pro Pro Thr
            100                 105                 110

Ala Pro Thr
        115

<210> SEQ ID NO 38
<211> LENGTH: 343
<212> TYPE: PRT
<213> ORGANISM: Artificial Sequence
<220> FEATURE:
<223> OTHER INFORMATION: human ActRIIB soluble (extracellular),
      processed polypeptide sequence with L79D mutation fused to an Fc
      domain with a GGG linker

<400> SEQUENCE: 38

Gly Arg Gly Glu Ala Glu Thr Arg Glu Cys Ile Tyr Tyr Asn Ala Asn
  1               5                  10                  15

Trp Glu Leu Glu Arg Thr Asn Gln Ser Gly Leu Glu Arg Cys Glu Gly
             20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Asp Asp Phe Asn
 50                  55                  60

Cys Tyr Asp Arg Gln Glu Cys Val Ala Thr Glu Glu Asn Pro Gln Val
 65                  70                  75                  80
```

```
Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
            115                 120                 125

Glu Leu Leu Gly Gly Pro Ser Val Phe Leu Phe Pro Pro Lys Pro Lys
            130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
            195                 200                 205

Trp Leu Asn Gly Lys Glu Tyr Lys Cys Lys Val Ser Asn Lys Ala Leu
210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 39
<211> LENGTH: 343
<212> TYPE: PRT
<213> ORGANISM: Artificial Sequence
<220> FEATURE:
<223> OTHER INFORMATION: human ActRIIB soluble (extracellular),
      processed polypeptide sequence with L79D mutation fused to an Fc
      domain

<400> SEQUENCE: 39

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
        35                  40                  45

Gly Thr Ile Glu Leu Val Lys Lys Gly Cys Trp Asp Asp Asp Phe Asn
    50                  55                  60

Cys Tyr Asp Arg Gln Glu Cys Val Ala Thr Glu Glu Asn Pro Gln Val
65                  70                  75                  80
```

```
Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
            115                 120                 125

Glu Leu Leu Gly Gly Pro Ser Val Phe Leu Phe Pro Pro Lys Pro Lys
            130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
            195                 200                 205

Trp Leu Asn Gly Lys Glu Tyr Lys Cys Lys Val Ser Asn Lys Ala Leu
            210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 40
<211> LENGTH: 368
<212> TYPE: PRT
<213> ORGANISM: Artificial Sequence
<220> FEATURE:
<223> OTHER INFORMATION: human ActRIIB soluble (extracellular),
      processed polypeptide sequence with L79D mutation fused to an
      Fc domain and with TPA leader sequence

<400> SEQUENCE: 40

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Asp Asp Asp Phe Asn Cys Tyr Asp Arg Gln Glu Cys
```

```
            85                  90                  95
Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
            115                 120                 125

Glu Val Thr Tyr Glu Pro Pro Thr Ala Pro Thr Gly Gly Gly Thr
            130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
            165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
            195                 200                 205

Lys Thr Lys Pro Arg Glu Glu Gln Tyr Asn Ser Thr Tyr Arg Val Val
            210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
            245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
            275                 280                 285

Leu Val Lys Gly Phe Tyr Pro Ser Asp Ile Ala Val Glu Trp Glu Ser
            290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
            325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
            355                 360                 365

<210> SEQ ID NO 41
<211> LENGTH: 368
<212> TYPE: PRT
<213> ORGANISM: Artificial Sequence
<220> FEATURE:
<223> OTHER INFORMATION: human ActRIIB soluble (extracellular),
      processed polypeptide sequence with L79D mutation fused to an Fc
      domain and with TPA leader sequence

<400> SEQUENCE: 41

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
            35                  40                  45

Gln Ser Gly Leu Glu Arg Cys Glu Gly Glu Gln Asp Lys Arg Leu His
        50                  55                  60

Cys Tyr Ala Ser Trp Ala Asn Ser Ser Gly Thr Ile Glu Leu Val Lys
65              70                  75                  80
```

```
Lys Gly Cys Trp Asp Asp Phe Asn Cys Tyr Asp Arg Gln Glu Cys
            85                  90                  95

Val Ala Thr Glu Glu Asn Pro Gln Val Tyr Phe Cys Cys Glu Gly
            100                 105                 110

Asn Phe Cys Asn Glu Arg Phe Thr His Leu Pro Glu Ala Gly Gly Pro
            115                 120                 125

Glu Val Thr Tyr Glu Pro Pro Thr Ala Pro Thr Gly Gly Gly Thr
            130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
            195                 200                 205

Lys Thr Lys Pro Arg Glu Glu Gln Tyr Asn Ser Thr Tyr Arg Val Val
210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
                260                 265                 270

Pro Pro Ser Arg Glu Glu Met Thr Lys Asn Gln Val Ser Leu Thr Cys
            275                 280                 285

Leu Val Lys Gly Phe Tyr Pro Ser Asp Ile Ala Val Glu Trp Glu Ser
            290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
            355                 360                 365

<210> SEQ ID NO 42
<211> LENGTH: 141
<212> TYPE: PRT
<213> ORGANISM: Artificial Sequence
<220> FEATURE:
<223> OTHER INFORMATION: human ActRIIB soluble (extracellular),
      processed polypeptide having a variant C-terminal sequence

<400> SEQUENCE: 42

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
```

```
                65                  70                  75                  80
Tyr Phe Cys Cys Cys Glu Gly Asn Phe Cys Asn Glu Arg Phe Thr His
                    85                  90                  95

Leu Pro Glu Ala Gly Gly Pro Glu Gly Pro Trp Ala Ser Thr Thr Ile
                100                 105                 110

Pro Ser Gly Gly Pro Glu Ala Thr Ala Ala Gly Asp Gln Gly Ser
            115                 120                 125

Gly Ala Leu Trp Leu Cys Leu Glu Gly Pro Ala His Glu
        130                 135                 140

<210> SEQ ID NO 43
<211> LENGTH: 141
<212> TYPE: PRT
<213> ORGANISM: Artificial Sequence
<220> FEATURE:
<223> OTHER INFORMATION: human ActRIIB soluble (extracellular),
      processed polypeptide having a variant C-terminal sequence having
      an L79D mutation

<400> SEQUENCE: 43

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
                20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Asp Asp Asp Phe Asn
        50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                    85                  90                  95

Leu Pro Glu Ala Gly Gly Pro Glu Gly Pro Trp Ala Ser Thr Thr Ile
                100                 105                 110

Pro Ser Gly Gly Pro Glu Ala Thr Ala Ala Gly Asp Gln Gly Ser
            115                 120                 125

Gly Ala Leu Trp Leu Cys Leu Glu Gly Pro Ala His Glu
        130                 135                 140

<210> SEQ ID NO 44
<211> LENGTH: 370
<212> TYPE: PRT
<213> ORGANISM: Artificial Sequence
<220> FEATURE:
<223> OTHER INFORMATION: human ActRIIB soluble (extracellular),
      processed polypeptide sequence having a variant C-terminal
      sequence having an L79D mutation fused to an Fc domain with a TGGG
      linker

<400> SEQUENCE: 44

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
                20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Asp Asp Asp Phe Asn
        50                  55                  60

Cys Tyr Asp Arg Gln Glu Cys Val Ala Thr Glu Glu Asn Pro Gln Val
```

```
                65                  70                  75                  80
Tyr Phe Cys Cys Cys Glu Gly Asn Phe Cys Asn Glu Arg Phe Thr His
                        85                  90                  95
Leu Pro Glu Ala Gly Gly Pro Glu Gly Pro Trp Ala Ser Thr Thr Ile
                        100                 105                 110
Pro Ser Gly Gly Pro Glu Ala Thr Ala Ala Gly Asp Gln Gly Ser
                    115                 120                 125
Gly Ala Leu Trp Leu Cys Leu Glu Gly Pro Ala His Glu Thr Gly Gly
130                 135                 140
Gly Thr His Thr Cys Pro Pro Cys Pro Ala Pro Glu Leu Leu Gly Gly
145                 150                 155                 160
Pro Ser Val Phe Leu Phe Pro Pro Lys Pro Lys Asp Thr Leu Met Ile
                    165                 170                 175
Ser Arg Thr Pro Glu Val Thr Cys Val Val Val Asp Val Ser His Glu
                180                 185                 190
Asp Pro Glu Val Lys Phe Asn Trp Tyr Val Asp Gly Val Glu Val His
                195                 200                 205
Asn Ala Lys Thr Lys Pro Arg Glu Glu Gln Tyr Asn Ser Thr Tyr Arg
210                 215                 220
Val Val Ser Val Leu Thr Val Leu His Gln Asp Trp Leu Asn Gly Lys
225                 230                 235                 240
Glu Tyr Lys Cys Lys Val Ser Asn Lys Ala Leu Pro Ala Pro Ile Glu
                245                 250                 255
Lys Thr Ile Ser Lys Ala Lys Gly Gln Pro Arg Glu Pro Gln Val Tyr
                260                 265                 270
Thr Leu Pro Pro Ser Arg Glu Glu Met Thr Lys Asn Gln Val Ser Leu
            275                 280                 285
Thr Cys Leu Val Lys Gly Phe Tyr Pro Ser Asp Ile Ala Val Glu Trp
            290                 295                 300
Glu Ser Asn Gly Gln Pro Glu Asn Asn Tyr Lys Thr Thr Pro Val
305                 310                 315                 320
Leu Asp Ser Asp Gly Ser Phe Phe Leu Tyr Ser Lys Leu Thr Val Asp
                325                 330                 335
Lys Ser Arg Trp Gln Gln Gly Asn Val Phe Ser Cys Ser Val Met His
                340                 345                 350
Glu Ala Leu His Asn His Tyr Thr Gln Lys Ser Leu Ser Leu Ser Pro
                355                 360                 365
Gly Lys
    370
```

<210> SEQ ID NO 45
<211> LENGTH: 1083
<212> TYPE: DNA
<213> ORGANISM: Artificial Sequence
<220> FEATURE:
<223> OTHER INFORMATION: Unprocessed ActRIIB-Fc fusion protein with the
      N-terminal 6 amino acids of the EC domain deleted and the
      C-terminal 3 amino acids of the EC domain deleted and with an L79D
      mutation and with TPA leader sequence

<400> SEQUENCE: 45
atggatgcaa tgaagagagg gctctgctgt gtgctgctgc tgtgtggagc agtcttcgtt     60
tcgcccggcg ccgccgaaac ccgcgaatgt atttattaca atgctaattg ggaactcgaa    120
cggacgaacc aatccgggct cgaacggtgt gaggggggaac aggataaacg cctccattgc    180
tatgcgtcgt ggaggaactc ctccgggacg attgaactgg tcaagaaagg gtgctgggac    240

-continued

```
gacgatttca attgttatga ccgccaggaa tgtgtcgcga ccgaagagaa tccgcaggtc    300
tatttctgtt gttgcgaggg gaatttctgt aatgaacggt ttacccacct ccccgaagcc    360
ggcgggcccg aggtgaccta tgaacccccg cccaccggtg gtggaactca cacatgccca    420
ccgtgcccag cacctgaact cctgggggga ccgtcagtct tcctcttccc cccaaaaccc    480
aaggacaccc tcatgatctc ccggacccct gaggtcacat gcgtggtggt ggacgtgagc    540
cacgaagacc ctgaggtcaa gttcaactgg tacgtggacg gcgtggaggt gcataatgcc    600
aagacaaagc cgcgggagga gcagtacaac agcacgtacc gtgtggtcag cgtcctcacc    660
gtcctgcacc aggactggct gaatggcaag gagtacaagt gcaaggtctc caacaaagcc    720
ctcccagccc ccatcgagaa aaccatctcc aaagccaaag gcagccccg agaaccacag    780
gtgtacaccc tgcccccatc ccgggaggag atgaccaaga accaggtcag cctgacctgc    840
ctggtcaaag gcttctatcc cagcgacatc gccgtggagt gggagagcaa tgggcagccg    900
gagaacaact acaagaccac gcctcccgtg ctggactccg acggctcctt cttcctctat    960
agcaagctca ccgtggacaa gagcaggtgg cagcagggga acgtcttctc atgctccgtg   1020
atgcatgagg ctctgcacaa ccactacacg cagaagagcc tctccctgtc cccgggtaaa   1080
tga                                                                 1083
```

<210> SEQ ID NO 46
<211> LENGTH: 344
<212> TYPE: PRT
<213> ORGANISM: Artificial Sequence
<220> FEATURE:
<223> OTHER INFORMATION: fusion protein comprising a soluble
      extracellular domain of ActRIIB fused to an Fc domain

<400> SEQUENCE: 46

Ser Gly Arg Gly Glu Ala Glu Thr Arg Glu Cys Ile Tyr Tyr Asn Ala
 1               5                  10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln

```
                195                 200                 205
Asp Trp Leu Asn Gly Lys Glu Tyr Lys Cys Lys Val Ser Asn Lys Ala
    210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
                260                 265                 270

Asp Ile Ala Val Glu Trp Glu Ser Asn Gly Gln Pro Glu Asn Asn Tyr
                275                 280                 285

Lys Thr Thr Pro Pro Val Leu Asp Ser Asp Gly Ser Phe Phe Leu Tyr
                290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
                340

<210> SEQ ID NO 47
<211> LENGTH: 329
<212> TYPE: PRT
<213> ORGANISM: Artificial Sequence
<220> FEATURE:
<223> OTHER INFORMATION: fusion protein comprising a soluble
      extracellular domain of ActRIIB (R64) with the C-terminal 15
      amino acids deleted fused to an Fc domain

<400> SEQUENCE: 47

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
                20                  25                  30

Gly Glu Gln Asp Lys Arg Leu His Cys Tyr Ala Ser Trp Arg Asn Ser
            35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Thr His Thr Cys Pro Pro Cys Pro
                100                 105                 110

Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val
        130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205
```

```
Ala Leu Pro Val Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

<210> SEQ ID NO 48
<211> LENGTH: 407
<212> TYPE: PRT
<213> ORGANISM: Unknown
<220> FEATURE:
<223> OTHER INFORMATION: full-length, unprocessed precursor protein
      GDF11 (GDF11 preproprotein)

<400> SEQUENCE: 48

```
Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
            20                  25                  30

Ala Ala Ala Ala Ala Ala Ala Ala Gly Val Gly Gly Glu Arg Ser
        35                  40                  45

Ser Arg Pro Ala Pro Ser Val Ala Pro Glu Pro Asp Gly Cys Pro Val
    50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
            100                 105                 110

Ile Leu Asp Leu His Asp Phe Gln Gly Asp Ala Leu Gln Pro Glu Asp
        115                 120                 125

Phe Leu Glu Glu Asp Glu Tyr His Ala Thr Thr Glu Thr Val Ile Ser
130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
        195                 200                 205

Ala Gly Gly Gly Gly Gly Gly Arg Arg His Ile Arg Ile Arg Ser Leu
    210                 215                 220

Lys Ile Glu Leu His Ser Arg Ser Gly His Trp Gln Ser Ile Asp Phe
```

```
                    225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
                260                 265                 270

Ser Leu Gly Pro Gly Ala Glu Gly Leu His Pro Phe Met Glu Leu Arg
                275                 280                 285

Val Leu Glu Asn Thr Lys Arg Ser Arg Arg Asn Leu Gly Leu Asp Cys
            290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
                340                 345                 350

Tyr Pro His Thr His Leu Val Gln Gln Ala Asn Pro Arg Gly Ser Ala
                355                 360                 365

Gly Pro Cys Cys Thr Pro Thr Lys Met Ser Pro Ile Asn Met Leu Tyr
            370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405

<210> SEQ ID NO 49
<211> LENGTH: 1221
<212> TYPE: DNA
<213> ORGANISM: Unknown
<220> FEATURE:
<223> OTHER INFORMATION: full-length, unprocessed precursor protein
      GDF11 (GDF11 preproprotein)

<400> SEQUENCE: 49
atggtgctcg cggccccgct gctgctgggc ttcctgctcc tcgccctgga gctgcggccc      60 cgggggagg cggccgaggg ccccgcggcg gcggcgcgg cggcggcggc ggcggcagcg      120 gcggggtcg ggggagcg ctccagccgg ccagcccgt ccgtggcgcc cgagccggac      180
ggctgccccg tgtgcgttg gcggcagcac agccgcgagc tgcgcctaga gagcatcaag      240
tcgcagatct tgagcaaact gcggctcaag gaggcgccca catcagccg cgaggtggtg      300 aagcagctgc tgcccaaggc gccgccgctg cagcagatcc tggacctaca cgacttccag      360
ggcgacgcgc tgcagcccga ggacttcctg gaggaggacg agtaccacgc caccaccgag      420
accgtcatta gcatggccca ggagacggac ccagcagtac agacagatgg cagccctctc      480
tgctgccatt ttcacttcag ccccaaggtg atgttcacaa aggtactgaa ggcccagctg      540
tgggtgtacc tacggcctgt accccgccca gccacagtct acctgcagat cttgcgacta      600 aaaccctaa ctggggaagg gaccgcaggg ggagggggcg gaggccggcg tcacatccgt      660
atccgctcac tgaagattga gctgcactca cgctcaggcc attggcagag catcgacttc      720
aagcaagtgc tacacagctg gttccgccag ccacagagca actggggcat cgagatcaac      780
gcctttgatc ccagtggcac agacctggct gtcacctccc tggggccggg agccgagggg      840
ctgcatccat tcatggagct tcgagtccta gagaacacaa aacgttcccg gcggaacctg      900
ggtctggact cgacgagca ctcaagcgag tcccgctgct gccgatatcc cctcacagtg      960
gactttgagg cttttcggctg ggactggatc atcgcaccta gcgctacaa ggccaactac     1020
```

```
tgctccggcc agtgcgagta catgttcatg caaaaatatc cgcataccca tttggtgcag      1080
caggccaatc caagaggctc tgctgggccc tgttgtaccc ccaccaagat gtccccaatc      1140
aacatgctct acttcaatga caagcagcag attatctacg gcaagatccc tggcatggtg      1200
gtggatcgct gtggctgctc t                                                1221
```

<210> SEQ ID NO 50
<211> LENGTH: 274
<212> TYPE: PRT
<213> ORGANISM: Homo sapiens
<220> FEATURE:
<223> OTHER INFORMATION: GDF11 propeptide of human GDF11 protein

<400> SEQUENCE: 50

```
Ala Glu Gly Pro Ala Ala Ala Ala Ala Ala Ala Ala Ala Ala Ala Ala
  1               5                  10                  15

Ala Gly Val Gly Gly Glu Arg Ser Ser Arg Pro Ala Pro Ser Val Ala
                 20                  25                  30

Pro Glu Pro Asp Gly Cys Pro Val Cys Val Trp Arg Gln His Ser Arg
             35                  40                  45

Glu Leu Arg Leu Glu Ser Ile Lys Ser Gln Ile Leu Ser Lys Leu Arg
 50                  55                  60

Leu Lys Glu Ala Pro Asn Ile Ser Arg Glu Val Val Lys Gln Leu Leu
 65                  70                  75                  80

Pro Lys Ala Pro Pro Leu Gln Gln Ile Leu Asp Leu His Asp Phe Gln
                 85                  90                  95

Gly Asp Ala Leu Gln Pro Glu Asp Phe Leu Glu Glu Asp Glu Tyr His
            100                 105                 110

Ala Thr Thr Glu Thr Val Ile Ser Met Ala Gln Glu Thr Asp Pro Ala
            115                 120                 125

Val Gln Thr Asp Gly Ser Pro Leu Cys Cys His Phe His Phe Ser Pro
130                 135                 140

Lys Val Met Phe Thr Lys Val Leu Lys Ala Gln Leu Trp Val Tyr Leu
145                 150                 155                 160

Arg Pro Val Pro Arg Pro Ala Thr Val Tyr Leu Gln Ile Leu Arg Leu
                165                 170                 175

Lys Pro Leu Thr Gly Glu Gly Thr Ala Gly Gly Gly Gly Gly Gly Arg
            180                 185                 190

Arg His Ile Arg Ile Arg Ser Leu Lys Ile Glu Leu His Ser Arg Ser
            195                 200                 205

Gly His Trp Gln Ser Ile Asp Phe Lys Gln Val Leu His Ser Trp Phe
        210                 215                 220

Arg Gln Pro Gln Ser Asn Trp Gly Ile Glu Ile Asn Ala Phe Asp Pro
225                 230                 235                 240

Ser Gly Thr Asp Leu Ala Val Thr Ser Leu Gly Pro Gly Ala Glu Gly
                245                 250                 255

Leu His Pro Phe Met Glu Leu Arg Val Leu Glu Asn Thr Lys Arg Ser
            260                 265                 270

Arg Arg
```

-continued

```
<210> SEQ ID NO 51
<211> LENGTH: 822
<212> TYPE: DNA
<213> ORGANISM: Homo sapiens
<220> FEATURE:
<223> OTHER INFORMATION: GDF11 propeptide of human GDF11 protein

<400> SEQUENCE: 51
gccgagggcc ccgcggcggc ggcggcggcg gcggcggcgg cggcagcggc gggggtcggg      60
ggggagcgct ccagccggcc agccccgtcc gtggcgcccg agccggacgg ctgccccgtg     120
tgcgtttggc ggcagcacag ccgcgagctg cgcctagaga gcatcaagtc gcagatcttg     180
agcaaactgc ggctcaagga ggcgcccaac atcagccgcg aggtggtgaa gcagctgctg     240
cccaaggcgc cgccgctgca gcagatcctg gacctacacg acttccaggg cgacgcgctg     300
cagcccgagg acttcctgga ggaggacgag taccacgcca ccaccgagac cgtcattagc     360
atggcccagg agacggaccc agcagtacag acagatggca gccctctctg ctgccatttt     420
cacttcagcc ccaaggtgat gttcacaaag gtactgaagg cccagctgtg ggtgtaccta     480
cggcctgtac cccgcccagc cacagtctac ctgcagatct gcgactaaa  accctaact     540 ggggaaggga ccgcagggg  aggggcgga ggccggcgtc acatccgtat ccgctcactg     600
aagattgagc tgcactcacg ctcaggccat tggcagagca tcgacttcaa gcaagtgcta     660
cacagctggt ccgccagcc  acagagcaac tggggcatcg agatcaacgc ctttgatccc     720
agtggcacag acctggctgt cacctccctg gggccgggag ccgaggggct gcatccattc     780
atggagcttc gagtcctaga gaacacaaaa cgttcccggc gg                        822

<210> SEQ ID NO 52
<211> LENGTH: 109
<212> TYPE: PRT
<213> ORGANISM: Homo sapiens
<220> FEATURE:
<223> OTHER INFORMATION: Mature human GDF11 protein

<400> SEQUENCE: 52

Asn Leu Gly Leu Asp Cys Asp Glu His Ser Ser Glu Ser Arg Cys Cys
 1               5                  10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
        35                  40                  45

Tyr Met Phe Met Gln Lys Tyr Pro His Thr His Leu Val Gln Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
            100                 105

<210> SEQ ID NO 53
<211> LENGTH: 327
<212> TYPE: DNA
<213> ORGANISM: Homo sapiens
<220> FEATURE:
<223> OTHER INFORMATION: GDF11 propeptide of human GDF11 protein

<400> SEQUENCE: 53
aacctgggtc tggactgcga cgagcactca agcgagtccc gctgctgccg atatcccctc      60
```

```
acagtggact ttgaggcttt cggctgggac tggatcatcg cacctaagcg ctacaaggcc    120
aactactgct ccggccagtg cgagtacatg ttcatgcaaa aatatccgca tacccatttg    180
gtgcagcagg ccaatccaag aggctctgct gggccctgtt gtaccccac caagatgtcc    240 ccaatcaaca tgctctactt caatgacaag cagcagatta tctacggcaa gatccctggc    300
atggtggtgg atcgctgtgg ctgctct                                        327
```

What is claimed:

1. A method for treating vascular calcification in a subject in need thereof, wherein the method comprises administering a therapeutically effective amount of an ActRIIA inhibitor to the subject, wherein the ActRIIA inhibitor is a polypeptide comprising an amino acid sequence selected from the group consisting of:
 a. 90% identical to SEQ ID NO:2;
 b. 95% identical to SEQ ID NO:2;
 c. 98% identical to SEQ ID NO:2;
 d. SEQ ID NO:2;
 e. 90% identical to SEQ ID NO:3;
 f. 95% identical to SEQ ID NO:3;
 g. 98% identical to SEQ ID NO:3;
 h. SEQ ID NO:3;
 i. 90% identical to SEQ ID NO:6;
 j. 95% identical to SEQ ID NO:6;
 k. 98% identical to SEQ ID NO:6;
 l. SEQ ID NO:6;
 m. 90% identical to SEQ ID NO:7;
 n. 95% identical to SEQ ID NO:7;
 o. 98% identical to SEQ ID NO:7;
 p. SEQ ID NO:7;
 q. 90% identical to SEQ ID NO:12;
 r. 95% identical to SEQ ID NO:12;
 s. 98% identical to SEQ ID NO:12; and
 t. SEQ ID NO:12.

2. A method for reducing vascular calcium levels in a subject diagnosed with vascular calcification, wherein the method comprises administering a therapeutically effective amount of an ActRIIA inhibitor to the subject, wherein the ActRIIA inhibitor is a polypeptide comprising an amino acid sequence selected from the group consisting of:
 a. 90% identical to SEQ ID NO:2;
 b. 95% identical to SEQ ID NO:2;
 c. 98% identical to SEQ ID NO:2;
 d. SEQ ID NO:2;
 e. 90% identical to SEQ ID NO:3;
 f. 95% identical to SEQ ID NO:3;
 g. 98% identical to SEQ ID NO:3;
 h. SEQ ID NO:3;
 i. 90% identical to SEQ ID NO:6;
 j. 95% identical to SEQ ID NO:6;
 k. 98% identical to SEQ ID NO:6;
 l. SEQ ID NO:6;
 m. 90% identical to SEQ ID NO:7;
 n. 95% identical to SEQ ID NO:7;
 o. 98% identical to SEQ ID NO:7;
 p. SEQ ID NO:7;
 q. 90% identical to SEQ ID NO:12;
 r. 95% identical to SEQ ID NO:12;
 s. 98% identical to SEQ ID NO:12; and
 t. SEQ ID NO:12.

3. The method of claim 1, wherein the ActRIIA inhibitor is a polypeptide comprising the amino acid sequence of SEQ ID NO:7.

4. The method of claim 1, wherein the ActRIIA inhibitor is administered parentally.

5. The method of claim 1, wherein the subject is less than 18 years old.

6. The method of claim 1, wherein the method increases the height of the subject.

7. The method of claim 1, wherein the subject has end stage renal disease.

8. The method of claim 1, wherein the subject undergoes dialysis.

9. The method of claim 2, wherein the ActRIIA inhibitor is a polypeptide comprising the amino acid sequence of SEQ ID NO:7.

10. The method of claim 2, wherein the ActRIIA inhibitor is administered parentally.

11. The method of claim 2, wherein the subject is less than 18 years old.

12. The method of claim 2, wherein the method increases the height of the subject.

13. The method of claim 2, wherein the subject has end stage renal disease.

14. The method of claim 2, wherein the subject undergoes dialysis.

15. The method of claim 1, wherein the ActRIIA inhibitor is a polypeptide consisting of the amino acid sequence of SEQ ID NO:7.

16. The method of claim 2, wherein the ActRIIA inhibitor is a polypeptide consisting of the amino acid sequence of SEQ ID NO:7.

* * * * *